US012460221B2

(12) United States Patent
Senger et al.

(10) Patent No.: US 12,460,221 B2

(45) Date of Patent: Nov. 4, 2025

(54) METHOD FOR THE PRODUCTION OF HIGH LEVELS OF PUFA IN PLANTS

(71) Applicant: BASF PLANT SCIENCE COMPANY GMBH, Ludwigshafen (DE)

(72) Inventors: Toralf Senger, Research Triangle Park, NC (US); Hui Yang, Saskatoon (CA); Carl Andre, Research Triangle Park, NC (US); Patricia Vrinten, Saskatoon (CA)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 804 days.

(21) Appl. No.: 17/273,858

(22) PCT Filed: Sep. 6, 2019

(86) PCT No.: PCT/EP2019/073831

§ 371 (c)(1),
(2) Date: Mar. 5, 2021

(87) PCT Pub. No.: WO2020/049155

PCT Pub. Date: Mar. 12, 2020

(65) Prior Publication Data

US 2023/0183728 A1 Jun. 15, 2023

(30) Foreign Application Priority Data

Sep. 7, 2018 (EP) .................................... 18193296
Nov. 9, 2018 (EP) .................................... 18193841

(51) Int. Cl.

| | |
|---|---|
| ***C12N 15/82*** | (2006.01) |
| ***A23D 9/00*** | (2006.01) |
| ***A23L 33/115*** | (2016.01) |
| ***C07K 16/40*** | (2006.01) |
| ***C12N 9/12*** | (2006.01) |

(52) U.S. Cl.

CPC ........... *C12N 15/8247* (2013.01); *A23D 9/00* (2013.01); *A23L 33/115* (2016.08); *C07K 16/40* (2013.01); *C12N 9/1288* (2013.01); *C12N 15/8218* (2013.01); *C12Y 207/08002* (2013.01); *A23V 2002/00* (2013.01)

(58) Field of Classification Search

CPC .................................................. C12N 15/8247

See application file for complete search history.

(56) References Cited

U.S. PATENT DOCUMENTS 9,200,293 B2 * 12/2015 Browse .............. C12N 15/8247
2015/0143573 A1 * 5/2015 Denolf ............... C12N 15/8247
536/23.6

FOREIGN PATENT DOCUMENTS

| | | | |
|---|---|---|---|
| WO | WO-2006/100241 A2 | | 9/2006 |
| WO | WO-2009/111587 A2 | | 9/2009 |
| WO | WO-2013/078187 A1 | | 5/2013 |
| WO | WO-2014/006158 A1 | | 1/2014 |
| WO | WO-2014/006162 A1 | | 1/2014 |
| WO | WO 2016/075327 | * | 5/2016 |

OTHER PUBLICATIONS

Fourgoux-Nicol et al Plant Molecular Biology vol. 40, pp. 857-872 (Year: 1999).*

Bates, et al.,"Acyl Editing and Headgroup Exchange Are the Major Mechanisms That Direct Polyunsaturated Fatty Acid Flux into Triacylglycerols", Plant Physiology, vol. 160, Issue 3, Nov. 29, 2012, pp. 1530-1539.

Blasi, et al., "Study of Some Experimental Parameters in the Synthesis of Triacylglycerols with CLA Isomers and Structural Analysis", Journal of the American Oil Chemists' Society, vol. 86, Issue 6, May 6, 2009, pp. 531-537.

Cheng, et al., "Towards the production of high levels of eicosapentaenoic acid in transgenic plants: the effects of different host species, genes and promoters", Transgenic Research, vol. 19, Issue 2, Jul. 7, 2009, pp. 221-229.

Haslam, et al., "The modification of plant oil composition via metabolic engineering—better nutrition by design", Plant Biotechnology Journal, vol. 11, Issue 2, Oct. 16, 2012, pp. 157-168.

Hernandez-Martin, et al., "Enzymatic Re-esterification of Lower Glycerides from Soybean Oil with Conjugated Linoleic Acid (CLA)", Journal of Agricultural and Food Chemistry, vol. 57, Issue 2, Dec. 29, 2008, pp. 701-708.

Hirose, et al.,"Synthesis of triacylglycerol containing conjugated linoleic acid by esterification using two blended lipases", Journal of the American Oil Chemists' Society, vol. 83, Issue 1, Jan. 2006, pp. 35-38.

Hu, et al., "The Phosphatidylcholine Diacylglycerol Cholinephosphotransferase Is Required for Efficient Hydroxy Fatty Acid Accumulation in Transgenic Arabidopsis", Plant Physiology , vol. 158, Issue 4, Apr. 2012, pp. 1944-1954.

International Search Report and Written Opinion for PCT Patent Application No. PCT/EP2019/073831, Issued on Jan. 14, 2020.

Lager, et al., "Plant Acyl-CoA:Lysophosphatidylcholine Acyltransferases (LPCATs) Have Different Specificities in Their Forward and Reverse Reactions", Journal of Biological Chemistry, vol. 288, Issue 52, Dec. 27, 2013, pp. 36902-36914.

(Continued)

*Primary Examiner* — David H Kruse

(74) *Attorney, Agent, or Firm* — MARSHALL, GERSTEIN & BORUN LLP

(57) ABSTRACT

The present invention is concerned with materials and methods for the production of genetically modified plants, particularly where the plants are for the production of at least one unsaturated or polyunsaturated fatty acid. The invention is also concerned with identification of genes conveying an unsaturated fatty acid metabolic property to a plant or plant cell, and generally relates to the field of phosphotidylcholine:diacylglycerol cholinephosphotransferase (PDCT).

5 Claims, 14 Drawing Sheets

Figure 1A:
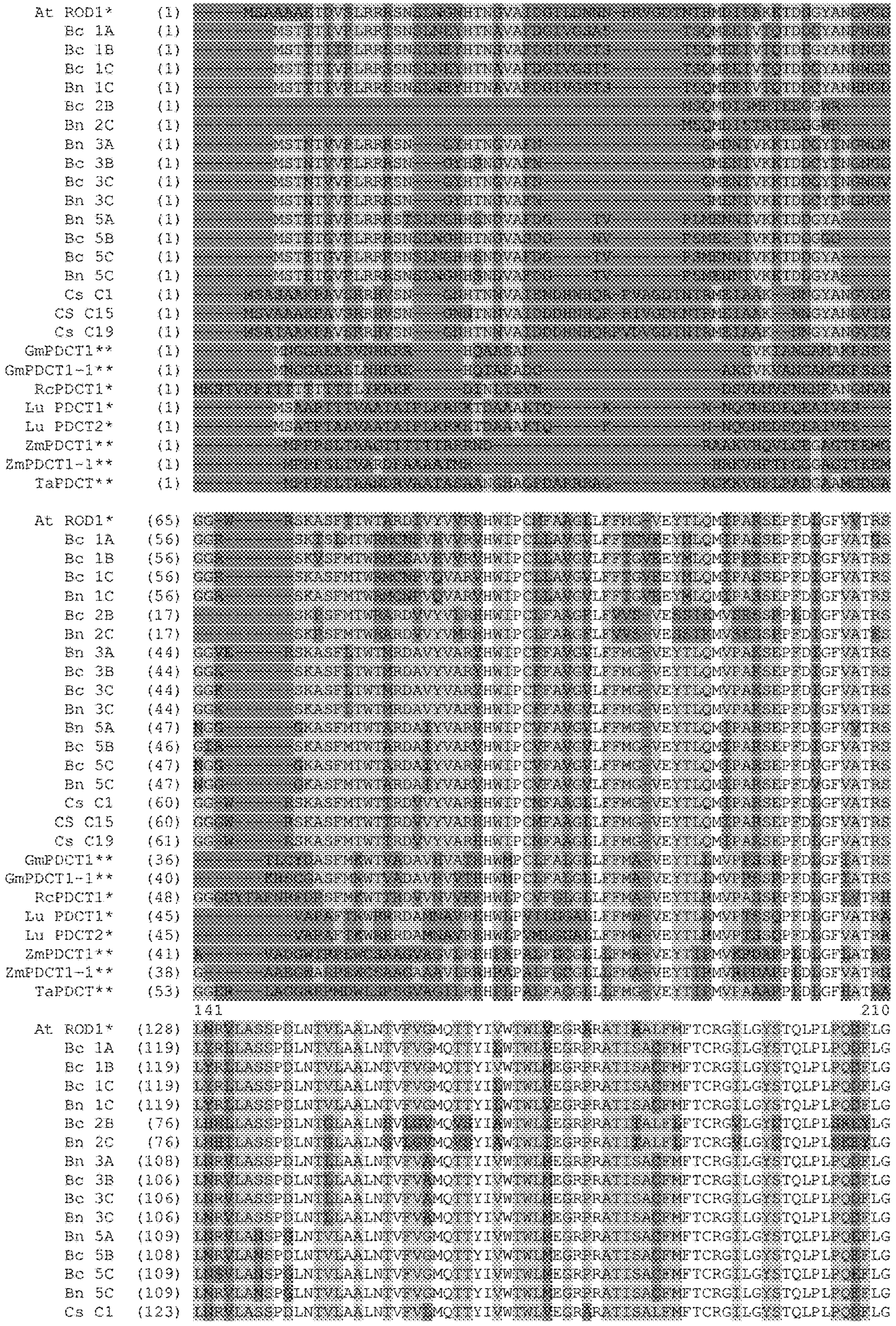

Specification includes a Sequence Listing.

(56) References Cited

OTHER PUBLICATIONS

Liu, et al., "Chapter 7: Evaluation of the seed oils from a canola plant genetically transformed to produce high levels of γ-linolenic acid", γ-Linolenic acid: recent advances in biotechnology and clinical applications, Second International Symposium on γ-Linolenic Acid, 91st AOCS Annual Meeting & Expo, Ed. Huang, et al., 2001, pp. 61-71.

Lu, et al., "An enzyme regulating triacylglycerol composition is encoded by the ROD1 gene of *Arabidopsis*", Proceedings of National Academy of Sciences, vol. 106, Issue 44, Nov. 3, 2009, pp. 18837-18842.

Petrie, et al., "Metabolic Engineering Plant Seeds with Fish Oil-Like Levels of DHA", PLoS One, vol. 7, Issue 11, Nov. 7, 2012, p. e49165 (pp. 1-7).

Ruiz-Lopez, et al., "Successful high?level accumulation of fish oil omega-3 long-chain polyunsaturated fatty acids in a transgenic oilseed crop", The Plant Journal, vol. 77, Issue 2, Nov. 8, 2013, pp. 198-208.

Swanson, et al., "Omega-3 Fatty Acids EPA and DHA: Health Benefits Throughout Life", Advances in Nutrition, vol. 3, Issue 1, Jan. 5, 2012, pp. 1-7.

Venegas-Calerón, et al., "An alternative to fish oils: Metabolic engineering of oil-seed crops to produce omega-3 long chain polyunsaturated fatty acids", Progress in Lipid Research, vol. 49, Issue 2, Apr. 2010, pp. 108-119.

Ursin, "Modification of Plant Lipids for Human Health: Development of Functional Land-Based Omega-3 Fatty Acids", The Journal of Nutrition, vol. 133, Issue 12, Dec. 1, 2003, pp. 4271-4274.

Wickramarathna, et al.,"Heterologous expression of flax Phospholipid: Diacylglycerol Cholinephosphotransferase (PDCT) increases polyunsaturated fatty acid content in yeast and *Arabidopsis* seeds", BMC Biotechnology, vol. 15, Issue 1, Article No. 63, Jun. 30, 2015, 15 pages.

Wu, et al., "Stepwise engineering to produce high yields of very long-chain polyunsaturated fatty acids in plants", Nature Biotechnology, vol. 23, Issue 8, Aug. 2005, pp. 1013-1017.

* cited by examiner

Alignment of PDCT protein sequences

FIG. 2

Alignment of N-terminal region of C. sativa sequences. All differences in the *C. satvia* proteins are within this region.

```
                1                                               70
Cs C1    (1) MSASAAKPAVSRRHVSNGNHTNNVAISNDHNHQRPV-AGDTNTRMEIAAKNNGYANGVSGGG-WRSKASF
CS C15   (1) MSVAAAKPAVSRRHVSNGNNTNNVAIDDDHNHQRSI-VGDKNTRMEIAAKNNGYANGV-GGGGWRSKASF
Cs C19   (1) MSATAAKPAVSRRHVSNGNHTNNVAIDDDHNHQRPVDVGDTNTRMEIAAKNNGYANGV-GGG-WRSKASF
```

Phylogenetic tree based on PDCT protein sequences.

Pathway and genes in fatty acid synthesis pathway in transgenic Arabidopsis plants.

Action of PDCT (Modified from Lu et al., 2009)

FIG. 7

Formula used for pathway step conversion efficiency Ceff $$C_{eff} = \frac{100}{S + P} \times P$$

| Pathway Step | Product Stream | pre-requisite of product stream | | | | | | | |
|---|---|---|---|---|---|---|---|---|---|
| d12Des | d12Des Product Stream 1 | 18:1n-9 | 18:1n-9 | 18:2n-6 | 18:3n-6 | 20:3n-6 | 20:4n-6 | 22:4n-6 | 22:5n-6 |
| | d12Des Product Stream 2 | 18:3n-3 from 18:2n-6 via d15Des | | 18:3n-3 | 18:4n-3 | 20:4n-3 | 20:5n-3 | 22:5n-3 | 22:6n-3 |
| | d12Des Product Stream 3 | 20:2n-6 from 18:2n-5 via d6Elo | | 20:2n-6 | | | | | |
| | d12Des Product Stream 4 | 20:3n-3 from 18:3n-3 via d6Elo | | 20:3n-3 | | | | | |
| d6Des | d12Des Product Stream 1 | 18:2n-6 | | 18:2n-6 | 18:3n-6 | 20:3n-6 | 20:4n-6 | 22:4n-6 | 22:5n-6 |
| | d12Des Product Stream 2 | 18:3n-3 produced by o3Des | | 18:3n-3 | 18:4n-3 | 20:4n-3 | 20:5n-3 | 22:5n-3 | 22:6n-3 |
| d6Elo | d6Elo Product Stream 1 | 18:3n-6 produced by d6Des | | | 18:3n-6 | 20:3n-6 | 20:4n-6 | 22:4n-6 | 22:5n-6 |
| | d6Elo Product Stream 2 | 18:4n-3 produced by d6Des or o3Des | | | 18:4n-3 | 20:4n-3 | 20:5n-3 | 22:5n-3 | 22:6n-3 |
| d5Des | d5Des Product Stream 1 | 20:3n-6 produced by d6Elo | | | | 20:3n-6 | 20:4n-6 | 22:4n-6 | 22:5n-6 |
| | d5Des Product Stream 2 | 20:4n-3 produced by d6Elo or o3Des | | | | 20:4n-3 | 20:5n-3 | 22:5n-3 | 22:6n-3 |
| d5Elo | d5Elo Product Stream 1 | 20:4n-6 produced by d5Des | | | | | 20:4n-6 | 22:4n-6 | 22:5n-6 |
| | d5Elo Product Stream 2 | 20:4n-3 produced by d5Des or o3Des | | | | | 20:5n-3 | 22:5n-3 | 22:6n-3 |
| d4Des | d4Des Product Stream 1 | 20:4n-6 produced by d5Des | | | | | | 22:4n-6 | 22:5n-6 |
| | d4Des Product Stream 2 | 20:4n-3 produced by d5Des or o3Des | | | | | | 22:5n-3 | 22:6n-3 |
| o3Des | | List of all o6Des Fatty acid substrates | 18:2n-6 | 18:3n-6 | 20:2n-6 | 20:3n-6 | 20:4n-6 | 22:4n-6 | 22:5n-6 |
| | | List of all o3Des Fatty acid products | 18:3n-3 | 18:4n-3 | 20:3n-3 | 20:4n-3 | 20:5n-3 | 22:5n-3 | 22:6n-3 |

FIG. 8

| Needle Protein Identity% Default settings | ATROD1 | BJROD1-A1 | BJROD1-A2 | BJROD1-A3 | BJROD1-B1 | BJROD1-B2 | BJROD1-B3 | BJROD1-B4 | BRROD1_SEQIDNO7 | CAMELINA_C1(80668) | CAMELINA_C15(45897) | CAMELINA_C19(65416) | CARINATA_1B | CARINATA_1C | CARINATA_2B | CARINATA_2C | CARINATA_3B | CARINATA_3C | CARINATA_5B | CARINATA_5C | GMROD1-1 | GMROD1-2 | LUPOCT1 | LUPOCT2 | NAPUS_1A | NAPUS_1C | NAPUS_2A | NAPUS_2C | NAPUS_3A | NAPUS_3C | NAPUS_5A | NAPUS_5C | OSROD1_SEQIDNO11 | RCPOCT | RCROD1_SEQIDNO9 | ZMROD1_GRMZM2G015040 | ZMROD1_GRMZM2G087896 |
|---|---|---|---|---|---|---|---|---|---|---|---|---|---|---|---|---|---|---|---|---|---|---|---|---|---|---|---|---|---|---|---|---|---|---|---|---|---|
| ATROD1 | ** | 73 | 76 | 73 | 79 | 78 | 74 | 56 | 79 | 86 | 86 | 86 | 74 | 74 | 56 | 56 | 79 | 79 | 81 | 80 | 61 | 58 | 55 | 54 | 73 | 74 | 56 | 55 | 73 | 73 | 80 | 80 | 46 | 59 | 59 | 44 | 43 |
| BJROD1-A1 | 73 | ** | 83 | 76 | 97 | 84 | 78 | 57 | 99 | 77 | 77 | 77 | 76 | 79 | 57 | 57 | 97 | 98 | 87 | 87 | 62 | 63 | 55 | 55 | 77 | 79 | 57 | 57 | 98 | 98 | 87 | 87 | 45 | 59 | 59 | 45 | 44 |
| BJROD1-A2 | 76 | 83 | ** | 77 | 83 | 87 | 78 | 55 | 83 | 72 | 72 | 73 | 76 | 78 | 55 | 55 | 83 | 83 | 87 | 93 | 62 | 58 | 52 | 52 | 77 | 78 | 55 | 55 | 82 | 83 | 95 | 94 | 42 | 60 | 60 | 45 | 46 |
| BJROD1-A3 | 73 | 76 | 77 | ** | 79 | 76 | 96 | 55 | 79 | 69 | 70 | 70 | 96 | 95 | 55 | 55 | 79 | 79 | 79 | 78 | 60 | 54 | 53 | 53 | 99 | 96 | 55 | 55 | 78 | 79 | 78 | 79 | 42 | 57 | 57 | 44 | 43 |
| BJROD1-B1 | 79 | 97 | 83 | 79 | ** | 83 | 79 | 57 | 98 | 77 | 76 | 76 | 79 | 79 | 57 | 57 | 99 | 98 | 87 | 87 | 62 | 63 | 54 | 54 | 78 | 79 | 57 | 56 | 97 | 98 | 87 | 87 | 44 | 61 | 61 | 46 | 44 |
| BJROD1-B2 | 78 | 84 | 87 | 76 | 83 | ** | 78 | 56 | 84 | 75 | 75 | 75 | 77 | 78 | 59 | 56 | 83 | 85 | 93 | 91 | 64 | 65 | 54 | 54 | 75 | 77 | 56 | 56 | 84 | 85 | 91 | 92 | 41 | 59 | 59 | 47 | 46 |
| BJROD1-B3 | 74 | 78 | 78 | 96 | 79 | 78 | ** | 56 | 79 | 70 | 70 | 71 | 99 | 95 | 55 | 56 | 79 | 79 | 80 | 79 | 62 | 53 | 53 | 54 | 95 | 96 | 56 | 56 | 78 | 79 | 79 | 79 | 43 | 58 | 58 | 44 | 45 |
| BJROD1-B4 | 56 | 57 | 55 | 55 | 57 | 53 | 56 | ** | 57 | 55 | 55 | 55 | 56 | 55 | 97 | 98 | 57 | 57 | 58 | 56 | 55 | 54 | 48 | 48 | 55 | 56 | ** | 99 | 57 | 57 | 56 | 58 | 38 | 52 | 52 | 45 | 45 |
| BRROD1_SEQIDNO7 | 79 | 99 | 83 | 79 | 98 | 84 | 79 | 57 | ** | 77 | 77 | 77 | 79 | 80 | 57 | 57 | 98 | 99 | 86 | 87 | 61 | 63 | 55 | 55 | 78 | 79 | 57 | 57 | 99 | 99 | 87 | 87 | 41 | 61 | 61 | 46 | 44 |
| CAMELINA_C1(80668) | 86 | 77 | 72 | 69 | 77 | 75 | 70 | 55 | 77 | ** | 97 | 98 | 70 | 71 | 55 | 55 | 77 | 77 | 77 | 76 | 61 | 60 | 55 | 55 | 69 | 71 | 55 | 55 | 77 | 77 | 76 | 76 | 44 | 55 | 55 | 45 | 47 |
| CAMELINA_C15(45897) | 86 | 77 | 72 | 70 | 76 | 75 | 70 | 55 | 77 | 97 | ** | 97 | 70 | 71 | 55 | 55 | 76 | 76 | 77 | 77 | 61 | 61 | 54 | 54 | 70 | 71 | 55 | 55 | 77 | 76 | 76 | 77 | 45 | 60 | 60 | 45 | 47 |
| CAMELINA_C19(65416) | 86 | 77 | 73 | 70 | 76 | 75 | 71 | 55 | 77 | 98 | 97 | ** | 71 | 72 | 55 | 55 | 76 | 77 | 77 | 76 | 60 | 61 | 53 | 55 | 70 | 71 | 55 | 55 | 77 | 77 | 76 | 76 | 44 | 60 | 60 | 44 | 48 |
| CARINATA_1B | 74 | 76 | 76 | 96 | 79 | 77 | 99 | 56 | 79 | 70 | 70 | 71 | ** | 94 | 56 | 57 | 79 | 79 | 80 | 79 | 61 | 55 | 54 | 55 | 95 | 95 | 56 | 56 | 76 | 79 | 79 | 79 | 42 | 58 | 58 | 44 | 45 |
| CARINATA_1C | 74 | 79 | 78 | 95 | 79 | 78 | 95 | 55 | 80 | 71 | 71 | 72 | 94 | ** | 55 | 56 | 80 | 80 | 80 | 79 | 60 | 53 | 53 | 54 | 96 | 99 | 55 | 55 | 79 | 80 | 79 | 80 | 42 | 58 | 58 | 43 | 43 |
| CARINATA_2B | 56 | 57 | 55 | 55 | 57 | 53 | 55 | 97 | 57 | 55 | 55 | 55 | 56 | 55 | ** | 99 | 57 | 57 | 58 | 56 | 56 | 55 | 49 | 49 | 55 | 56 | 97 | 97 | 57 | 57 | 56 | 58 | 38 | 52 | 52 | 45 | 44 |
| CARINATA_2C | 56 | 57 | 55 | 55 | 57 | 53 | 56 | 98 | 57 | 55 | 55 | 55 | 57 | 58 | 99 | ** | 57 | 57 | 58 | 56 | 55 | 54 | 49 | 49 | 55 | 56 | 98 | 97 | 57 | 57 | 56 | 56 | 38 | 52 | 52 | 45 | 46 |
| CARINATA_3B | 79 | 97 | 83 | 79 | 99 | 83 | 79 | 57 | 98 | 77 | 76 | 76 | 79 | 80 | 57 | 57 | ** | 98 | 87 | 87 | 62 | 63 | 54 | 54 | 78 | 80 | 57 | 57 | 97 | 98 | 87 | 87 | 44 | 61 | 61 | 46 | 44 |
| CARINATA_3C | 79 | 98 | 83 | 79 | 98 | 85 | 79 | 57 | 99 | 77 | 76 | 77 | 79 | 80 | 57 | 57 | 98 | ** | 87 | 87 | 62 | 63 | 55 | 55 | 78 | 80 | 57 | 56 | 98 | ** | 87 | 87 | 45 | 61 | 61 | 46 | 44 |
| CARINATA_5B | 81 | 87 | 83 | 79 | 87 | 93 | 80 | 58 | 86 | 77 | 77 | 77 | 80 | 80 | 58 | 59 | 87 | 87 | ** | 94 | 62 | 61 | 54 | 54 | 79 | 80 | 58 | 58 | 87 | 87 | 93 | 94 | 43 | 60 | 60 | 46 | 46 |
| CARINATA_5C | 80 | 87 | 93 | 78 | 87 | 91 | 79 | 58 | 87 | 76 | 77 | 76 | 79 | 79 | 58 | 58 | 87 | 87 | 94 | ** | 60 | 61 | 52 | 52 | 78 | 79 | 58 | 55 | 86 | 87 | 98 | ** | 43 | 60 | 60 | 46 | 45 |
| GMROD1-1 | 61 | 62 | 62 | 60 | 62 | 64 | 62 | 55 | 61 | 61 | 61 | 60 | 61 | 60 | 56 | 55 | 62 | 62 | 62 | 60 | ** | 66 | 60 | 60 | 61 | 60 | 55 | 55 | 61 | 62 | 62 | 60 | 47 | 68 | 68 | 51 | 53 |
| GMROD1-2 | 58 | 63 | 58 | 54 | 63 | 65 | 53 | 54 | 63 | 60 | 61 | 61 | 55 | 53 | 55 | 54 | 63 | 63 | 61 | 61 | 66 | ** | 56 | 56 | 54 | 53 | 54 | 53 | 63 | 63 | 61 | 61 | 47 | 59 | 59 | 51 | 49 |
| LUPOCT1 | 55 | 55 | 52 | 53 | 54 | 54 | 53 | 48 | 55 | 55 | 54 | 53 | 54 | 53 | 49 | 49 | 54 | 55 | 54 | 52 | 60 | 56 | ** | 99 | 53 | 53 | 48 | 48 | 55 | 55 | 52 | 52 | 46 | 59 | 59 | 48 | 49 |
| LUPOCT2 | 54 | 55 | 52 | 53 | 54 | 54 | 54 | 48 | 55 | 55 | 54 | 55 | 55 | 54 | 49 | 49 | 54 | 55 | 54 | 52 | 60 | 56 | 99 | ** | 54 | 54 | 48 | 48 | 55 | 55 | 52 | 52 | 46 | 59 | 59 | 48 | 49 |
| NAPUS_1A | 73 | 77 | 77 | 99 | 78 | 75 | 95 | 55 | 78 | 69 | 70 | 70 | 95 | 96 | 55 | 55 | 78 | 78 | 79 | 78 | 61 | 54 | 53 | 54 | ** | 97 | 55 | 55 | 78 | 78 | 78 | 78 | 42 | 57 | 57 | 44 | 43 |
| NAPUS_1C | 74 | 79 | 78 | 96 | 79 | 77 | 96 | 56 | 79 | 71 | 71 | 71 | 95 | 99 | 56 | 56 | 80 | 80 | 80 | 79 | 60 | 53 | 53 | 54 | 97 | ** | 56 | 55 | 79 | 80 | 79 | 79 | 42 | 58 | 58 | 43 | 43 |
| NAPUS_2A | 56 | 57 | 55 | 55 | 57 | 53 | 56 | ** | 57 | 55 | 55 | 55 | 56 | 55 | 97 | 98 | 57 | 57 | 58 | 56 | 55 | 54 | 48 | 48 | 55 | 56 | ** | ** | 57 | 57 | 56 | 56 | 38 | 52 | 52 | 45 | 46 |
| NAPUS_2C | 55 | 57 | 55 | 55 | 56 | 53 | 56 | 99 | 57 | 55 | 55 | 55 | 56 | 56 | 97 | 97 | 57 | 58 | 58 | 55 | 55 | 53 | 48 | 48 | 55 | 55 | ** | ** | 57 | 56 | 55 | 55 | 38 | 51 | 51 | 45 | 45 |
| NAPUS_3A | 79 | 98 | 82 | 78 | 97 | 84 | 78 | 57 | 99 | 77 | 77 | 77 | 78 | 79 | 57 | 57 | 97 | 98 | 87 | 86 | 61 | 63 | 55 | 55 | 78 | 79 | 57 | 57 | ** | 98 | 86 | 86 | 45 | 61 | 61 | 46 | 44 |
| NAPUS_3C | 79 | 98 | 83 | 79 | 98 | 85 | 79 | 57 | 99 | 77 | 76 | 77 | 79 | 80 | 57 | 57 | 98 | ** | 87 | 87 | 62 | 63 | 55 | 55 | 78 | 80 | 57 | 56 | 98 | ** | 87 | 87 | 45 | 61 | 61 | 46 | 44 |
| NAPUS_5A | 80 | 87 | 95 | 78 | 87 | 91 | 79 | 56 | 87 | 75 | 76 | 76 | 79 | 79 | 56 | 56 | 87 | 87 | 93 | 98 | 62 | 61 | 52 | 52 | 78 | 79 | 56 | 55 | 86 | 87 | ** | 98 | 42 | 60 | 60 | 45 | 46 |
| NAPUS_5C | 80 | 87 | 94 | 79 | 87 | 92 | 79 | 56 | 87 | 76 | 77 | 76 | 79 | 80 | 56 | 56 | 87 | 87 | 94 | ** | 60 | 61 | 52 | 52 | 78 | 79 | 56 | 55 | 86 | 87 | 98 | ** | 43 | 60 | 60 | 46 | 45 |
| OSROD1_SEQIDNO11 | 46 | 45 | 42 | 42 | 44 | 41 | 43 | 38 | 41 | 44 | 45 | 44 | 42 | 42 | 38 | 38 | 44 | 45 | 43 | 43 | 47 | 47 | 46 | 46 | 42 | 42 | 38 | 38 | 45 | 45 | 42 | 43 | ** | 49 | 49 | 69 | 63 |
| RCPOCT | 59 | 59 | 60 | 57 | 61 | 59 | 58 | 52 | 61 | 55 | 60 | 60 | 58 | 58 | 52 | 52 | 61 | 61 | 60 | 60 | 68 | 59 | 59 | 59 | 57 | 58 | 52 | 51 | 61 | 61 | 60 | 60 | 43 | ** | ** | 51 | 48 |
| RCROD1_SEQIDNO9 | 59 | 59 | 60 | 57 | 61 | 59 | 56 | 52 | 61 | 55 | 60 | 60 | 58 | 58 | 52 | 52 | 61 | 61 | 60 | 60 | 68 | 59 | 59 | 59 | 57 | 58 | 52 | 51 | 61 | 61 | 60 | 60 | 49 | ** | ** | 51 | 48 |
| ZMROD1_GRMZM2G015040 | 44 | 45 | 45 | 44 | 46 | 47 | 44 | 45 | 46 | 45 | 45 | 44 | 44 | 43 | 45 | 45 | 46 | 46 | 46 | 46 | 51 | 51 | 46 | 48 | 44 | 43 | 45 | 45 | 46 | 46 | 45 | 46 | 69 | 51 | 51 | ** | 84 |
| ZMROD1_GRMZM2G087896 | 43 | 44 | 46 | 43 | 44 | 46 | 45 | 44 | 44 | 47 | 47 | 48 | 45 | 43 | 44 | 45 | 44 | 44 | 46 | 45 | 53 | 49 | 48 | 49 | 43 | 43 | 44 | 44 | 44 | 44 | 46 | 45 | 63 | 48 | 48 | 84 | ** |

SEQUENCE LISTING

```
<160> NUMBER OF SEQ ID NOS: 109

<210> SEQ ID NO 1
<211> LENGTH: 870
<212> TYPE: DNA
<213> ORGANISM: Brassica napus

<400> SEQUENCE: 1

atgtcaacta caacaatcgt ccctctccgt cgcacttcta actctctcaa tgaataccac      60

actaacgcag tcgcctttga cggaatcgtc gggtcagcaa gtactagcca aatggaggag     120

attgttacgc aaaccgacga ctgctacgcc aaccccaacg gagatggagg gagaagcaag     180

acgtcgttaa tgacgtggag gatgtgcaat cctgtccacg tggtgagagt ccattggata     240

ccgtgtttgt tagcggtagg agttctgttc ttcacgtgcg tagaggagta catgctccag     300

atgattccgg cgagttctga gccgttcgat attggttttg tggcgacggg ctctctgtat     360

cgcctcttgg cttcttcacc ggatcttaat accgttttag ctgctctcaa cacggtgttt     420

gtagggatgc aaacgacgta tattttatgg acatggttgg tggaaggacg accacgagcg     480

accatctcgg cttgcttcat gtttacttgc cgtggcattc tgggttactc tactcagctc     540

cctcttcctc aggattttct aggatcaggg gtagattttc cggtaggaaa cgtctcgttc     600

ttcctcttct actcaggcca tgtcgcaggg tcgacgatag catccttgga tatgaggaga     660

atgaagaggt tgagacttgc cttgcttttt gacatcctca atgtattaca atcgatcagg     720
```

cttctcggga cgagaggaca atacacgatc gatctcgctg tcggagttgg cgctggggtt 780
ctctttgact cactggctgg aaaatacgaa gagatgatga gcaagagaca caatgtaggc 840
aatggtttta gtttgatttc gtctcgctag 870

<210> SEQ ID NO 2
<211> LENGTH: 289
<212> TYPE: PRT
<213> ORGANISM: Brassica napus

<400> SEQUENCE: 2

Met Ser Thr Thr Thr Ile Val Pro Leu Arg Arg Thr Ser Asn Ser Leu
1 5 10 15

Asn Glu Tyr His Thr Asn Ala Val Ala Phe Asp Gly Ile Val Gly Ser
20 25 30

Ala Ser Thr Ser Gln Met Glu Glu Ile Val Thr Gln Thr Asp Asp Cys
35 40 45

Tyr Ala Asn Pro Asn Gly Asp Gly Gly Arg Ser Lys Thr Ser Leu Met
50 55 60

Thr Trp Arg Met Cys Asn Pro Val His Val Val Arg Val His Trp Ile
65 70 75 80

Pro Cys Leu Leu Ala Val Gly Val Leu Phe Phe Thr Cys Val Glu Glu
85 90 95

Tyr Met Leu Gln Met Ile Pro Ala Ser Ser Glu Pro Phe Asp Ile Gly
100 105 110

Phe Val Ala Thr Gly Ser Leu Tyr Arg Leu Leu Ala Ser Ser Pro Asp
115 120 125

Leu Asn Thr Val Leu Ala Ala Leu Asn Thr Val Phe Val Gly Met Gln
130 135 140

Thr Thr Tyr Ile Leu Trp Thr Trp Leu Val Glu Gly Arg Pro Arg Ala
145 150 155 160

Thr Ile Ser Ala Cys Phe Met Phe Thr Cys Arg Gly Ile Leu Gly Tyr
165 170 175

Ser Thr Gln Leu Pro Leu Pro Gln Asp Phe Leu Gly Ser Gly Val Asp
180 185 190

Phe Pro Val Gly Asn Val Ser Phe Phe Leu Phe Tyr Ser Gly His Val
195 200 205

Ala Gly Ser Thr Ile Ala Ser Leu Asp Met Arg Arg Met Lys Arg Leu
210 215 220

Arg Leu Ala Leu Leu Phe Asp Ile Leu Asn Val Leu Gln Ser Ile Arg
225 230 235 240

Leu Leu Gly Thr Arg Gly Gln Tyr Thr Ile Asp Leu Ala Val Gly Val
245 250 255

Gly Ala Gly Val Leu Phe Asp Ser Leu Ala Gly Lys Tyr Glu Glu Met
260 265 270

Met Ser Lys Arg His Asn Val Gly Asn Gly Phe Ser Leu Ile Ser Ser
275 280 285

Arg

<210> SEQ ID NO 3
<211> LENGTH: 708
<212> TYPE: DNA
<213> ORGANISM: Brassica napus

<400> SEQUENCE: 3
atgtctcaaa tggacatttc tacgagaact gaggaaggag gatggagaag caagccttcg 60

```
ttcatgacgt ggagagcgcg cgacgttgtc tacgtgatga gacaccattg gataccgtgt    120

ctgttcgcgg ccggattctt gttcgtcgta agcgtggagt cctcgatcaa gatggtttcc    180

gagagttctc caccgttcga tattgggttt gtggccacgg agtctctgca tcatatcttg    240

gcttcttcac cggatctgaa caccggtttg gccgctctaa actcggtgtt aggagtgatg    300

caagtatcgt atattgcatg gacatggtta atagaaggac ggccacgagc caccatcacg    360

gctttattcc tcttcacttg tcgcggtgtt ctcggttact gtactcagct tcctctttca    420

aaggagtatc taggttcagc aatcgatttc ccgctaggaa acctgtcgtt cttctatttt    480

ttctcgggtc acgtggcagg cgcgaccatc gcatctttgg acatgaggag gatgcagagg    540

ttgagacttg cgatggtttt tgacatcctc aatgtactac agtcgatcag gctgctggcg    600

acgagaggac actacacgat cgatctcgca ggtggagttg ccgccgcgat tctctttgac    660

tcattggccg gcaagtacga agctaataca aggaagaggc aattgtag                 708
```

<210> SEQ ID NO 4
<211> LENGTH: 235
<212> TYPE: PRT
<213> ORGANISM: Brassica napus

<400> SEQUENCE: 4

```
Met Ser Gln Met Asp Ile Ser Thr Arg Thr Glu Glu Gly Gly Trp Arg
1               5                   10                  15

Ser Lys Pro Ser Phe Met Thr Trp Arg Ala Arg Asp Val Val Tyr Val
            20                  25                  30

Met Arg His His Trp Ile Pro Cys Leu Phe Ala Ala Gly Phe Leu Phe
        35                  40                  45

Val Val Ser Val Glu Ser Ser Ile Lys Met Val Ser Glu Ser Ser Pro
    50                  55                  60

Pro Phe Asp Ile Gly Phe Val Ala Thr Glu Ser Leu His His Ile Leu
65                  70                  75                  80

Ala Ser Ser Pro Asp Leu Asn Thr Gly Leu Ala Ala Leu Asn Ser Val
                85                  90                  95

Leu Gly Val Met Gln Val Ser Tyr Ile Ala Trp Thr Trp Leu Ile Glu
            100                 105                 110

Gly Arg Pro Arg Ala Thr Ile Thr Ala Leu Phe Leu Phe Thr Cys Arg
        115                 120                 125

Gly Val Leu Gly Tyr Cys Thr Gln Leu Pro Leu Ser Lys Glu Tyr Leu
    130                 135                 140

Gly Ser Ala Ile Asp Phe Pro Leu Gly Asn Leu Ser Phe Phe Tyr Phe
145                 150                 155                 160

Phe Ser Gly His Val Ala Gly Ala Thr Ile Ala Ser Leu Asp Met Arg
                165                 170                 175

Arg Met Gln Arg Leu Arg Leu Ala Met Val Phe Asp Ile Leu Asn Val
            180                 185                 190

Leu Gln Ser Ile Arg Leu Leu Ala Thr Arg Gly His Tyr Thr Ile Asp
        195                 200                 205

Leu Ala Gly Gly Val Ala Ala Ala Ile Leu Phe Asp Ser Leu Ala Gly
    210                 215                 220

Lys Tyr Glu Ala Asn Thr Arg Lys Arg Gln Leu
225                 230                 235
```

<210> SEQ ID NO 5
<211> LENGTH: 870

<212> TYPE: DNA
<213> ORGANISM: Brassica carinata

<400> SEQUENCE: 5
atgtcaacta caacaattat ccctctccgt cggagttcta actctctcaa tgaataccac 60
actaactcag tcgcctttga cggaatcgtc gggtcaacaa gtactagcca aatggaggag 120
attgttacgc aaacggacga aggctacgcc aaccccaacg gagatggagg gagaagcaag 180
gtgtcgttca tgacgtggag gatgtgcagt gctgtccacg tggtgagagt ccattggata 240
ccatgtttgt tagcggtagg agttctgttc ttcacggggg tggaggagta catgctccag 300
atgattcccc cgagttctga gccgttcgat attggttttg tggcgacgcg ctctctctat 360
cgcctcttgg cttcttcacc ggatcttaac accgttttag ccgctctcaa cacggtgttc 420
gtagggatgc aaacgacgta tattgtatgg acatggttga tggaaggacg accaagagcg 480
accatttcgg cttgcttcat gtttacctgt cgcggcattc ttggttactc tacgcagctc 540
cctcttcctc aggattttct aggatcaggg gtagattttc cggtaggaaa cgtctcgttc 600
ttcctcttct actcaggcca tgtggcaggg tcgacgatag catccttgga catgaggaga 660
atgaagaggt tgagactagc cttgcttttt gacatcctca atgtattaca atcgatcagg 720
cttctcggga cgagaggaca atacacgatc gatctcgctg tcggagttgg cgctggggtt 780
ctctttgact cactggctgg aaaatacgaa gagatgatga gcaagagaca caatgtaggc 840
aatggtttta gtttaatttc gactcgctag 870

<210> SEQ ID NO 6
<211> LENGTH: 289
<212> TYPE: PRT
<213> ORGANISM: Brassica carinata

<400> SEQUENCE: 6

Met Ser Thr Thr Thr Ile Ile Pro Leu Arg Arg Ser Ser Asn Ser Leu
1 5 10 15

Asn Glu Tyr His Thr Asn Ser Val Ala Phe Asp Gly Ile Val Gly Ser
20 25 30

Thr Ser Thr Ser Gln Met Glu Glu Ile Val Thr Gln Thr Asp Glu Gly
35 40 45

Tyr Ala Asn Pro Asn Gly Asp Gly Gly Arg Ser Lys Val Ser Phe Met
50 55 60

Thr Trp Arg Met Cys Ser Ala Val His Val Val Arg Val His Trp Ile
65 70 75 80

Pro Cys Leu Leu Ala Val Gly Val Leu Phe Phe Thr Gly Val Glu Glu
85 90 95

Tyr Met Leu Gln Met Ile Pro Pro Ser Ser Glu Pro Phe Asp Ile Gly
100 105 110

Phe Val Ala Thr Arg Ser Leu Tyr Arg Leu Leu Ala Ser Ser Pro Asp
115 120 125

Leu Asn Thr Val Leu Ala Ala Leu Asn Thr Val Phe Val Gly Met Gln
130 135 140

Thr Thr Tyr Ile Val Trp Thr Trp Leu Met Glu Gly Arg Pro Arg Ala
145 150 155 160

Thr Ile Ser Ala Cys Phe Met Phe Thr Cys Arg Gly Ile Leu Gly Tyr
165 170 175

Ser Thr Gln Leu Pro Leu Pro Gln Asp Phe Leu Gly Ser Gly Val Asp
180 185 190

```
Phe Pro Val Gly Asn Val Ser Phe Phe Leu Phe Tyr Ser Gly His Val
        195                 200                 205

Ala Gly Ser Thr Ile Ala Ser Leu Asp Met Arg Arg Met Lys Arg Leu
    210                 215                 220

Arg Leu Ala Leu Leu Phe Asp Ile Leu Asn Val Leu Gln Ser Ile Arg
225                 230                 235                 240

Leu Leu Gly Thr Arg Gly Gln Tyr Thr Ile Asp Leu Ala Val Gly Val
                245                 250                 255

Gly Ala Gly Val Leu Phe Asp Ser Leu Ala Gly Lys Tyr Glu Glu Met
            260                 265                 270

Met Ser Lys Arg His Asn Val Gly Asn Gly Phe Ser Leu Ile Ser Thr
        275                 280                 285

Arg


<210> SEQ ID NO 7
<211> LENGTH: 870
<212> TYPE: DNA
<213> ORGANISM: Brassica carinata

<400> SEQUENCE: 7

atgtcaacta caacaatcgt ccctctccgt cgcagttcta actctctcaa tgaataccac      60

actaacgcag tcgcctttga cggaatcgtc gggtcaacaa gtactagcca aatggaggag     120

attgttacgc aaaccgacga ctgctacgcc aatcacaacg gagatggagg gagaagcaag     180

gcatcgttta tgacgtggag gatgtgcaat cctgtccagg tggcgagagt ccattggata     240

ccgtgtttgc tagcggtagg agttctgttc ttcacgggcg tagaggagta catgctccag     300

atgattccgg cgagttctga gccgttcgat attggttttg tggcgacgcg ctctctgtat     360

cgactcttgg cttcttcacc ggatcttaat accgttttag ctgctctcaa cacggtgttt     420

gtagggatgc aaacgacgta tattttatgg acatggttgg tggaaggacg accacgagcg     480

accatctcgg cttgcttcat gtttacttgt cgtggcattc ttggttactc tactcagctc     540

cctcttcctc aggattttct aggatcaggg gtagattttc cggtaggaaa cgtctcgttc     600

ttcctcttct attctggcca cgtagccggt tcaatgatca catccttgga catgaggaga     660

atgcagaggt tgagactagc cttgcttttt gacatcctca atgtattaca atcgatcagg     720

cttctcggga cgagaggaca atacacgatc gatctcgctg tcggagttgg cgctggggtt     780

ctctttgact cattggccgg gaagtacgaa gagatgatga gcaagagacg caatgtaggc     840

aatggtttta gtttgatttc gtctcgctag                                      870


<210> SEQ ID NO 8
<211> LENGTH: 289
<212> TYPE: PRT
<213> ORGANISM: Brassica carinata

<400> SEQUENCE: 8

Met Ser Thr Thr Thr Ile Val Pro Leu Arg Arg Ser Ser Asn Ser Leu
1               5                   10                  15

Asn Glu Tyr His Thr Asn Ala Val Ala Phe Asp Gly Ile Val Gly Ser
            20                  25                  30

Thr Ser Thr Ser Gln Met Glu Glu Ile Val Thr Gln Thr Asp Asp Cys
        35                  40                  45

Tyr Ala Asn His Asn Gly Asp Gly Gly Arg Ser Lys Ala Ser Phe Met
    50                  55                  60

Thr Trp Arg Met Cys Asn Pro Val Gln Val Ala Arg Val His Trp Ile
```

```
65                  70                  75                  80

Pro Cys Leu Leu Ala Val Gly Val Leu Phe Phe Thr Gly Val Glu Glu
                85                  90                  95

Tyr Met Leu Gln Met Ile Pro Ala Ser Ser Glu Pro Phe Asp Ile Gly
            100                 105                 110

Phe Val Ala Thr Arg Ser Leu Tyr Arg Leu Leu Ala Ser Ser Pro Asp
        115                 120                 125

Leu Asn Thr Val Leu Ala Ala Leu Asn Thr Val Phe Val Gly Met Gln
    130                 135                 140

Thr Thr Tyr Ile Leu Trp Thr Trp Leu Val Glu Gly Arg Pro Arg Ala
145                 150                 155                 160

Thr Ile Ser Ala Cys Phe Met Phe Thr Cys Arg Gly Ile Leu Gly Tyr
                165                 170                 175

Ser Thr Gln Leu Pro Leu Pro Gln Asp Phe Leu Gly Ser Gly Val Asp
            180                 185                 190

Phe Pro Val Gly Asn Val Ser Phe Phe Leu Phe Tyr Ser Gly His Val
        195                 200                 205

Ala Gly Ser Met Ile Thr Ser Leu Asp Met Arg Arg Met Gln Arg Leu
    210                 215                 220

Arg Leu Ala Leu Leu Phe Asp Ile Leu Asn Val Leu Gln Ser Ile Arg
225                 230                 235                 240

Leu Leu Gly Thr Arg Gly Gln Tyr Thr Ile Asp Leu Ala Val Gly Val
                245                 250                 255

Gly Ala Gly Val Leu Phe Asp Ser Leu Ala Gly Lys Tyr Glu Glu Met
            260                 265                 270

Met Ser Lys Arg Arg Asn Val Gly Asn Gly Phe Ser Leu Ile Ser Ser
        275                 280                 285

Arg
```

<210> SEQ ID NO 9
<211> LENGTH: 708
<212> TYPE: DNA
<213> ORGANISM: Brassica carinata

<400> SEQUENCE: 9

```
atgtctcaaa tggacatttc tatgagaacg gaggaaggag gatggagaag caagccgtcg      60

tttatgacgt ggagagcgcg cgacgttgtc tacgtgttga gacaccattg gataccgtgt     120

ttgttcgcgg ccggattctt gttcgtcgta agcgtggagt cctcgatcaa gatggtttcc     180

gagagttctc cgccgctcga tattgggttt gtggccactc gctctctcca tcatctcttg     240

gcttcttcac cggatctgaa caccggtttg gccgctctaa actcggtgtt aggagtgatg     300

caagtatcgt atattgcatg gacatggtta atagaaggac ggccacgagc caccatcacg     360

gctttattcc tcttcacttg tcgcggcgtt ctcggttact gtactcagct ccctctttca     420

aaggagtatc taggatcagc aatcgatttc ccgctaggaa acctctcgtt cttctatttc     480

ttctcgggtc acgtggcagg cacgaccatc gcatctttgg acatgaggag aatgcagagg     540

ttgagacttg cgatggtttt tgacatcctc aatgtattac aatcgatcag gctgctagcg     600

acgagaggac actacacgat cgatctcgca ggtggagttg ccgccgcgat tctctttgac     660

tcattggccg gcaagtacga agcaagtaca agaaagaggc aattgtag                  708
```

<210> SEQ ID NO 10
<211> LENGTH: 235
<212> TYPE: PRT

<213> ORGANISM: Brassica carinata

<400> SEQUENCE: 10

Met Ser Gln Met Asp Ile Ser Met Arg Thr Glu Glu Gly Gly Trp Arg
1               5                   10                  15

Ser Lys Pro Ser Phe Met Thr Trp Arg Ala Arg Asp Val Val Tyr Val
            20                  25                  30

Leu Arg His His Trp Ile Pro Cys Leu Phe Ala Ala Gly Phe Leu Phe
        35                  40                  45

Val Val Ser Val Glu Ser Ser Ile Lys Met Val Ser Glu Ser Ser Pro
    50                  55                  60

Pro Leu Asp Ile Gly Phe Val Ala Thr Arg Ser Leu His His Leu Leu
65                  70                  75                  80

Ala Ser Ser Pro Asp Leu Asn Thr Gly Leu Ala Ala Leu Asn Ser Val
                85                  90                  95

Leu Gly Val Met Gln Val Ser Tyr Ile Ala Trp Thr Trp Leu Ile Glu
            100                 105                 110

Gly Arg Pro Arg Ala Thr Ile Thr Ala Leu Phe Leu Phe Thr Cys Arg
        115                 120                 125

Gly Val Leu Gly Tyr Cys Thr Gln Leu Pro Leu Ser Lys Glu Tyr Leu
    130                 135                 140

Gly Ser Ala Ile Asp Phe Pro Leu Gly Asn Leu Ser Phe Phe Tyr Phe
145                 150                 155                 160

Phe Ser Gly His Val Ala Gly Thr Thr Ile Ala Ser Leu Asp Met Arg
                165                 170                 175

Arg Met Gln Arg Leu Arg Leu Ala Met Val Phe Asp Ile Leu Asn Val
            180                 185                 190

Leu Gln Ser Ile Arg Leu Leu Ala Thr Arg Gly His Tyr Thr Ile Asp
        195                 200                 205

Leu Ala Gly Gly Val Ala Ala Ala Ile Leu Phe Asp Ser Leu Ala Gly
    210                 215                 220

Lys Tyr Glu Ala Ser Thr Arg Lys Arg Gln Leu
225                 230                 235

<210> SEQ ID NO 11
<211> LENGTH: 708
<212> TYPE: DNA
<213> ORGANISM: Brassica carinata

<400> SEQUENCE: 11
atgtctcaaa tggacatttc tacgagaacg gaggaaggag gatggagaag caagccgtcg 60
tttatgacgt ggagagcgcg cgacgttgtc tacgtgttga gacaccattg gataccgtgt 120
ttgttcgcgg ccggattctt gttcgtcgta agcgtggagt cctcgatcaa gatggtttcc 180
gagagttctc cgccgctcga tattgggttt gtggccactc gctctctcca tcatctcttg 240
gcttcttcac cggatctgaa caccggtttg gccgctctaa actcggtgtt aggagtgatg 300
caagtatcgt atattgcatg gacatggtta atagaaggac ggccacgagc caccatcacg 360
gctttattcc tcttcacttg tcgcggcgtt ctcggttact gtactcagct ccctctttca 420
aaggagtatc taggatcagc aatcgatttc ccgctaggaa acctctcgtt cttctatttc 480
ttctcgggtc acgtggcagg cacgaccatc gcatctttgg acatgaggag aatgcagagg 540
ttgagacttg cgatggtttt tgacatcctc aatgtattac aatcgatcag gctgctagcg 600
acgagaggac actacacgat cgatctcgca ggtggagttg ccgccgcgat tctctttgac 660
tcattggccg gcaagtacga agcaaataca agaaagaggc aattgtag 708

<210> SEQ ID NO 12
<211> LENGTH: 235
<212> TYPE: PRT
<213> ORGANISM: Brassica carinata

<400> SEQUENCE: 12

```
Met Ser Gln Met Asp Ile Ser Thr Arg Thr Glu Glu Gly Gly Trp Arg
1               5                   10                  15

Ser Lys Pro Ser Phe Met Thr Trp Arg Ala Arg Asp Val Val Tyr Val
            20                  25                  30

Leu Arg His His Trp Ile Pro Cys Leu Phe Ala Ala Gly Phe Leu Phe
        35                  40                  45

Val Val Ser Val Glu Ser Ser Ile Lys Met Val Ser Glu Ser Ser Pro
    50                  55                  60

Pro Leu Asp Ile Gly Phe Val Ala Thr Arg Ser Leu His His Leu Leu
65                  70                  75                  80

Ala Ser Ser Pro Asp Leu Asn Thr Gly Leu Ala Ala Leu Asn Ser Val
                85                  90                  95

Leu Gly Val Met Gln Val Ser Tyr Ile Ala Trp Thr Trp Leu Ile Glu
            100                 105                 110

Gly Arg Pro Arg Ala Thr Ile Thr Ala Leu Phe Leu Phe Thr Cys Arg
        115                 120                 125

Gly Val Leu Gly Tyr Cys Thr Gln Leu Pro Leu Ser Lys Glu Tyr Leu
    130                 135                 140

Gly Ser Ala Ile Asp Phe Pro Leu Gly Asn Leu Ser Phe Phe Tyr Phe
145                 150                 155                 160

Phe Ser Gly His Val Ala Gly Thr Thr Ile Ala Ser Leu Asp Met Arg
                165                 170                 175

Arg Met Gln Arg Leu Arg Leu Ala Met Val Phe Asp Ile Leu Asn Val
            180                 185                 190

Leu Gln Ser Ile Arg Leu Leu Ala Thr Arg Gly His Tyr Thr Ile Asp
        195                 200                 205

Leu Ala Gly Gly Val Ala Ala Ala Ile Leu Phe Asp Ser Leu Ala Gly
    210                 215                 220

Lys Tyr Glu Ala Asn Thr Arg Lys Arg Gln Leu
225                 230                 235
```

<210> SEQ ID NO 13
<211> LENGTH: 708
<212> TYPE: DNA
<213> ORGANISM: Brassica carinata

<400> SEQUENCE: 13

```
atgtctcaaa tggacatttc tacgagaact gaggaaggag gatggagaag caagccttcg     60

ttcatgacgt ggagagcgcg cgacgttgtc tacgtgatga gacaccattg gataccgtgt    120

ctgttcgcgg ccggattctt gttcgtcgta agcgtggagt cctcgatcaa gatggtttcc    180

gagagttctc caccgttcga tattgggttt gtggccacgg agtctctgca tcatatcttg    240

gcttcttcac cggatctgaa caccggtttg gccgctctaa actcggtgtt aggagtgatg    300

caagtatcgt atattgcatg gacatggtta atagaaggac ggccacgagc caccatcacg    360

gctttattcc tcttcacttg tcgcggcgtt ctcggttact gtacgcagct ccctctttca    420

aaggagtatc taggatcagc aatcgatttc ccgctaggaa acctctcgtt cttctatttt    480
```

```
ttctcgggtc acgtggcagg cacgaccatc gcatctttgg acatgaggag aatgcagagg    540

ttgagacttg cgatggtttt tgacatcctc aatgtattac agtcgatcag gctgcttgcg    600

acgagaggac actacacgat cgatctcgca ggtggagttg ccgccgcgat tctctttgac    660

tcattggccg gcaagtacga agcaaataca agaaagaggc aattgtag                 708
```

<210> SEQ ID NO 14
<211> LENGTH: 235
<212> TYPE: PRT
<213> ORGANISM: Brassica juncea

<400> SEQUENCE: 14

```
Met Ser Gln Met Asp Ile Ser Thr Arg Thr Glu Glu Gly Gly Trp Arg
1               5                   10                  15

Ser Lys Pro Ser Phe Met Thr Trp Arg Ala Arg Asp Val Val Tyr Val
            20                  25                  30

Met Arg His His Trp Ile Pro Cys Leu Phe Ala Ala Gly Phe Leu Phe
        35                  40                  45

Val Val Ser Val Glu Ser Ser Ile Lys Met Val Ser Glu Ser Ser Pro
    50                  55                  60

Pro Phe Asp Ile Gly Phe Val Ala Thr Glu Ser Leu His His Ile Leu
65                  70                  75                  80

Ala Ser Ser Pro Asp Leu Asn Thr Gly Leu Ala Ala Leu Asn Ser Val
                85                  90                  95

Leu Gly Val Met Gln Val Ser Tyr Ile Ala Trp Thr Trp Leu Ile Glu
            100                 105                 110

Gly Arg Pro Arg Ala Thr Ile Thr Ala Leu Phe Leu Phe Thr Cys Arg
        115                 120                 125

Gly Val Leu Gly Tyr Cys Thr Gln Leu Pro Leu Ser Lys Glu Tyr Leu
    130                 135                 140

Gly Ser Ala Ile Asp Phe Pro Leu Gly Asn Leu Ser Phe Phe Tyr Phe
145                 150                 155                 160

Phe Ser Gly His Val Ala Gly Thr Thr Ile Ala Ser Leu Asp Met Arg
                165                 170                 175

Arg Met Gln Arg Leu Arg Leu Ala Met Val Phe Asp Ile Leu Asn Val
            180                 185                 190

Leu Gln Ser Ile Arg Leu Leu Ala Thr Arg Gly His Tyr Thr Ile Asp
        195                 200                 205

Leu Ala Gly Gly Val Ala Ala Ala Ile Leu Phe Asp Ser Leu Ala Gly
    210                 215                 220

Lys Tyr Glu Ala Asn Thr Arg Lys Arg Gln Leu
225                 230                 235
```

<210> SEQ ID NO 15
<211> LENGTH: 870
<212> TYPE: DNA
<213> ORGANISM: Brassica juncea

<400> SEQUENCE: 15

```
atgtcaacta caacaatcgt ccctctccgt cgcacttcta actctctcaa tgaataccac     60

actaacgcag tcgcctttga cggaatcgtc gggtcagcaa gtactagcca aatggaggag    120

attgttacgc aaaccgacga ctgctacgcc aaccccaacg gagatggagg gagaagcaag    180

gtgtcgttaa tgacgtggag gatgtgcaat cctgtccacg tggtgagagt ccattggata    240

ccgtgtttgt tagcggtagg agttctgttc ttcacgtgcg tagaggagta catgctccag    300
```

-continued

```
atgattccgg cgagttctga gccgttcgat attggttttg tggcgacggg ctctctgtat    360

cgcctcttgg cttcttcacc ggatcttaat accgttttag ctgctctcaa cacggtgttt    420

gtagggatgc aaacgacgta tattgtatgg acatggttga tggaaggacg accacgagcg    480

accatctcgg cttgctttat gtttacttgc cgtggcattc tgggttactc tactcagctc    540

cctcttcctc aggattttct aggatcaggg gtagattttc cggtaggaaa cgtctcgttc    600

ttcctcttct actcaggcca tgtcgcaggg tcgacgatag catccttgga tatgaggaga    660

atgaagaggt tgagacttgc cttgcttttt gacatcctca atgtattaca atcgatcagg    720

cttctcggga cgagaggaca atacacgatc gatctcgctg tcggagttgg cgctggggtt    780

ctctttgact cactggctgg aaaatacgaa gagatgatga gcaagagaca caatgtaggc    840

aatggtttta gtttaatttc gactcgctag                                     870


<210> SEQ ID NO 16
<211> LENGTH: 289
<212> TYPE: PRT
<213> ORGANISM: Brassica juncea

<400> SEQUENCE: 16

Met Ser Thr Thr Thr Ile Val Pro Leu Arg Arg Thr Ser Asn Ser Leu
1               5                   10                  15

Asn Glu Tyr His Thr Asn Ala Val Ala Phe Asp Gly Ile Val Gly Ser
            20                  25                  30

Ala Ser Thr Ser Gln Met Glu Glu Ile Val Thr Gln Thr Asp Asp Cys
        35                  40                  45

Tyr Ala Asn Pro Asn Gly Asp Gly Gly Arg Ser Lys Val Ser Leu Met
    50                  55                  60

Thr Trp Arg Met Cys Asn Pro Val His Val Val Arg Val His Trp Ile
65                  70                  75                  80

Pro Cys Leu Leu Ala Val Gly Val Leu Phe Phe Thr Cys Val Glu Glu
                85                  90                  95

Tyr Met Leu Gln Met Ile Pro Ala Ser Ser Glu Pro Phe Asp Ile Gly
            100                 105                 110

Phe Val Ala Thr Gly Ser Leu Tyr Arg Leu Leu Ala Ser Ser Pro Asp
        115                 120                 125

Leu Asn Thr Val Leu Ala Ala Leu Asn Thr Val Phe Val Gly Met Gln
    130                 135                 140

Thr Thr Tyr Ile Val Trp Thr Trp Leu Met Glu Gly Arg Pro Arg Ala
145                 150                 155                 160

Thr Ile Ser Ala Cys Phe Met Phe Thr Cys Arg Gly Ile Leu Gly Tyr
                165                 170                 175

Ser Thr Gln Leu Pro Leu Pro Gln Asp Phe Leu Gly Ser Gly Val Asp
            180                 185                 190

Phe Pro Val Gly Asn Val Ser Phe Phe Leu Phe Tyr Ser Gly His Val
        195                 200                 205

Ala Gly Ser Thr Ile Ala Ser Leu Asp Met Arg Arg Met Lys Arg Leu
    210                 215                 220

Arg Leu Ala Leu Leu Phe Asp Ile Leu Asn Val Leu Gln Ser Ile Arg
225                 230                 235                 240

Leu Leu Gly Thr Arg Gly Gln Tyr Thr Ile Asp Leu Ala Val Gly Val
                245                 250                 255

Gly Ala Gly Val Leu Phe Asp Ser Leu Ala Gly Lys Tyr Glu Glu Met
            260                 265                 270
```

Met Ser Lys Arg His Asn Val Gly Asn Gly Phe Ser Leu Ile Ser Thr
275 280 285

Arg

<210> SEQ ID NO 17
<211> LENGTH: 849
<212> TYPE: DNA
<213> ORGANISM: Brassica napus

<400> SEQUENCE: 17
atgtcaacta ataccgtcgt ccctctccgt cgcagatcta acggatatca cactaacggc 60
gtggccttta acggaatgga taatattgtc aagaaaaccg acgactgcta caccaacggc 120
aacggcaacg gaggagtaga gagaagcaaa gcctcgtttc tgacatggac catgcgtgac 180
gctgtctacg tagcgagata ccattggata ccgtgtttct ttgcggtcgg agttctgttc 240
tttatggggg ttgagtacac gctccagatg gttccggcga agtctgagcc gttcgatatt 300
gggtttgtgg ccacgcgctc tctgaaccgc gtcttggcga gttcaccgga tcttaacacc 360
cttttagcgg ctctaaacac ggtattcgta gcgatgcaaa cgacgtatat tgtatggaca 420
tggttgatgg aaggaagacc acgagccact atctcggctt gcttcatgtt tacttgtcgc 480
ggcattcttg gttactctac tcagctccct ctaccacagg attttttagg atcaggagtt 540
gattttccgg tgggaaacgt ctcattcttc ctcttctatt ctggccacgt agccggttca 600
atgatcgcat ccttggacat gaggagaatg cagaggttga gactagcgat gctttttgac 660
atcctcaaca tattacaatc gatcagactg ctcgggacga gaggacacta cacgatcgat 720
cttgcggtcg gagttggcgc tggattctc tttgactcat tggccgggaa gtacgaagag 780
atgatgagca agagacacaa tttagccaat ggttttagtt tgatttctaa agactcgcta 840
gtcaattaa 849

<210> SEQ ID NO 18
<211> LENGTH: 282
<212> TYPE: PRT
<213> ORGANISM: Brassica napus

<400> SEQUENCE: 18

Met Ser Thr Asn Thr Val Val Pro Leu Arg Arg Arg Ser Asn Gly Tyr
1 5 10 15

His Thr Asn Gly Val Ala Phe Asn Gly Met Asp Asn Ile Val Lys Lys
20 25 30

Thr Asp Asp Cys Tyr Thr Asn Gly Asn Gly Asn Gly Gly Val Glu Arg
35 40 45

Ser Lys Ala Ser Phe Leu Thr Trp Thr Met Arg Asp Ala Val Tyr Val
50 55 60

Ala Arg Tyr His Trp Ile Pro Cys Phe Phe Ala Val Gly Val Leu Phe
65 70 75 80

Phe Met Gly Val Glu Tyr Thr Leu Gln Met Val Pro Ala Lys Ser Glu
85 90 95

Pro Phe Asp Ile Gly Phe Val Ala Thr Arg Ser Leu Asn Arg Val Leu
100 105 110

Ala Ser Ser Pro Asp Leu Asn Thr Leu Leu Ala Ala Leu Asn Thr Val
115 120 125

Phe Val Ala Met Gln Thr Thr Tyr Ile Val Trp Thr Trp Leu Met Glu
130 135 140

Gly Arg Pro Arg Ala Thr Ile Ser Ala Cys Phe Met Phe Thr Cys Arg

-continued 145 150 155 160

Gly Ile Leu Gly Tyr Ser Thr Gln Leu Pro Leu Pro Gln Asp Phe Leu
165 170 175

Gly Ser Gly Val Asp Phe Pro Val Gly Asn Val Ser Phe Phe Leu Phe
180 185 190

Tyr Ser Gly His Val Ala Gly Ser Met Ile Ala Ser Leu Asp Met Arg
195 200 205

Arg Met Gln Arg Leu Arg Leu Ala Met Leu Phe Asp Ile Leu Asn Ile
210 215 220

Leu Gln Ser Ile Arg Leu Leu Gly Thr Arg Gly His Tyr Thr Ile Asp
225 230 235 240

Leu Ala Val Gly Val Gly Ala Gly Ile Leu Phe Asp Ser Leu Ala Gly
245 250 255

Lys Tyr Glu Glu Met Met Ser Lys Arg His Asn Leu Ala Asn Gly Phe
260 265 270

Ser Leu Ile Ser Lys Asp Ser Leu Val Asn
275 280

<210> SEQ ID NO 19
<211> LENGTH: 852
<212> TYPE: DNA
<213> ORGANISM: Brassica napus

<400> SEQUENCE: 19
atgtcaactg aaactagcgt ccctctccgt cgcagatcta cctctcttaa cggacatcac 60
tctaacgacg tcgcctttga cggaaccgtc ccattaatgg agaacaacat tgttaagaaa 120
acagacgacg gctacgccaa tggaggagga aaggcgtcgt ttatgacatg gacggcgcgt 180
gacgctatct acgtggcgag agtccattgg ataccgtgtg tgttcgcggt tggagttctc 240
ttcttcatgg gcgtcgagta tacgcttcaa atgattcccg cgaggtctga gccgttcgat 300
attgggtttg tggtcacgcg ctctctgaac cgcgtcttgg caaattcacc gggtcttaac 360
accgttttag ccgcactaaa cacggtgttc gtagggatgc aaactacgta tattgtatgg 420
acatggttga tggaaggaag accacgagcc accatctcgg cttgcttcat gtttacttgt 480
cgcggtatcc ttggttactc tactcagctc cctctccctc aggagttttt aggatcagga 540
gtcgattttc ctgtgggaaa cgtctcattc ttccttttct actcgggtca cgtcgccggt 600
tcgatgatag catccttaga catgaggaga atgcagaggt tgagactagc aatgcttttt 660
gacatcctca atgtattaca atcgatacgg ctgctcggga cgagaggaca ttacaccatc 720
gatcttgcgg tcggagttgg cgctgggatt ctctttgact cgttggccgg gaagtacgaa 780
gagatgatga gcaaaagaca caatttaggc aatggtttta gtttgatttc taaagactcg 840
ctagacaatt aa 852

<210> SEQ ID NO 20
<211> LENGTH: 283
<212> TYPE: PRT
<213> ORGANISM: Brassica napus

<400> SEQUENCE: 20

Met Ser Thr Glu Thr Ser Val Pro Leu Arg Arg Arg Ser Thr Ser Leu
1 5 10 15

Asn Gly His His Ser Asn Asp Val Ala Phe Asp Gly Thr Val Pro Leu
20 25 30

Met Glu Asn Asn Ile Val Lys Lys Thr Asp Asp Gly Tyr Ala Asn Gly

```
        35                  40                  45

Gly Gly Lys Ala Ser Phe Met Thr Trp Thr Ala Arg Asp Ala Ile Tyr
    50                  55                  60

Val Ala Arg Val His Trp Ile Pro Cys Val Phe Ala Val Gly Val Leu
65                  70                  75                  80

Phe Phe Met Gly Val Glu Tyr Thr Leu Gln Met Ile Pro Ala Arg Ser
                85                  90                  95

Glu Pro Phe Asp Ile Gly Phe Val Val Thr Arg Ser Leu Asn Arg Val
            100                 105                 110

Leu Ala Asn Ser Pro Gly Leu Asn Thr Val Leu Ala Ala Leu Asn Thr
        115                 120                 125

Val Phe Val Gly Met Gln Thr Thr Tyr Ile Val Trp Thr Trp Leu Met
    130                 135                 140

Glu Gly Arg Pro Arg Ala Thr Ile Ser Ala Cys Phe Met Phe Thr Cys
145                 150                 155                 160

Arg Gly Ile Leu Gly Tyr Ser Thr Gln Leu Pro Leu Pro Gln Glu Phe
                165                 170                 175

Leu Gly Ser Gly Val Asp Phe Pro Val Gly Asn Val Ser Phe Phe Leu
            180                 185                 190

Phe Tyr Ser Gly His Val Ala Gly Ser Met Ile Ala Ser Leu Asp Met
        195                 200                 205

Arg Arg Met Gln Arg Leu Arg Leu Ala Met Leu Phe Asp Ile Leu Asn
    210                 215                 220

Val Leu Gln Ser Ile Arg Leu Leu Gly Thr Arg Gly His Tyr Thr Ile
225                 230                 235                 240

Asp Leu Ala Val Gly Val Gly Ala Gly Ile Leu Phe Asp Ser Leu Ala
                245                 250                 255

Gly Lys Tyr Glu Glu Met Met Ser Lys Arg His Asn Leu Gly Asn Gly
            260                 265                 270

Phe Ser Leu Ile Ser Lys Asp Ser Leu Asp Asn
        275                 280


<210> SEQ ID NO 21
<211> LENGTH: 843
<212> TYPE: DNA
<213> ORGANISM: Brassica carinata

<400> SEQUENCE: 21

atgtcaacta ataccgtcgt ccctctccgt cgcagatcta acggatatca cagtaacggc      60

gtggccttta acggaatgga gaacattgtc aagaaaacag acgactgcta caccaacggc     120

aacggaggag gagggaagag caaggcgtcg tttctgacat ggaccatgcg cgacgctgtc     180

tacgtggcga gataccattg gataccgtgt ttctttgcgg tcggagttct gttctttatg     240

ggcgttgagt atacgctcca gatggttccg gcgaagtctg agccgttcga tattgggttt     300

gtggccacgc gctctctgaa ccgcgtcttg gcgagttcac cggatcttaa caccctttta     360

gcggctctaa acacggtatt cgtagcgatg caaacgacgt atattgtatg gacatggttg     420

atggaaggaa gaccacgagc cactatctct gcttgcttta tgtttacttg tcgtggcatt     480

cttggttact ctactcagct ccctctccca caggattttt taggatcagg agttgatttt     540

ccagtgggaa acgtctcatt cttcctcttc tattctggtc acgtcgccgg ttcaatgatc     600

gcatccttgg acatgaggag aatgcggagg ttgagactag cgatgctttt tgacatcctc     660

aacgtattac aatctatcag gctgctcggg acaagaggac attacacgat tgatcttgcg     720
```

gtcggagttg gcgctgggat tctctttgac tctttggccg ggaagtacga agagatgatg 780
agcaagagac acaatttagc caatggtttt agtttgattt cgaaagaatc cctagtcaat 840
taa 843

<210> SEQ ID NO 22
<211> LENGTH: 280
<212> TYPE: PRT
<213> ORGANISM: Brassica carinata

<400> SEQUENCE: 22

Met Ser Thr Asn Thr Val Val Pro Leu Arg Arg Arg Ser Asn Gly Tyr
1 5 10 15

His Ser Asn Gly Val Ala Phe Asn Gly Met Glu Asn Ile Val Lys Lys
20 25 30

Thr Asp Asp Cys Tyr Thr Asn Gly Asn Gly Gly Gly Gly Lys Ser Lys
35 40 45

Ala Ser Phe Leu Thr Trp Thr Met Arg Asp Ala Val Tyr Val Ala Arg
50 55 60

Tyr His Trp Ile Pro Cys Phe Phe Ala Val Gly Val Leu Phe Phe Met
65 70 75 80

Gly Val Glu Tyr Thr Leu Gln Met Val Pro Ala Lys Ser Glu Pro Phe
85 90 95

Asp Ile Gly Phe Val Ala Thr Arg Ser Leu Asn Arg Val Leu Ala Ser
100 105 110

Ser Pro Asp Leu Asn Thr Leu Leu Ala Ala Leu Asn Thr Val Phe Val
115 120 125

Ala Met Gln Thr Thr Tyr Ile Val Trp Thr Trp Leu Met Glu Gly Arg
130 135 140

Pro Arg Ala Thr Ile Ser Ala Cys Phe Met Phe Thr Cys Arg Gly Ile
145 150 155 160

Leu Gly Tyr Ser Thr Gln Leu Pro Leu Pro Gln Asp Phe Leu Gly Ser
165 170 175

Gly Val Asp Phe Pro Val Gly Asn Val Ser Phe Phe Leu Phe Tyr Ser
180 185 190

Gly His Val Ala Gly Ser Met Ile Ala Ser Leu Asp Met Arg Arg Met
195 200 205

Arg Arg Leu Arg Leu Ala Met Leu Phe Asp Ile Leu Asn Val Leu Gln
210 215 220

Ser Ile Arg Leu Leu Gly Thr Arg Gly His Tyr Thr Ile Asp Leu Ala
225 230 235 240

Val Gly Val Gly Ala Gly Ile Leu Phe Asp Ser Leu Ala Gly Lys Tyr
245 250 255

Glu Glu Met Met Ser Lys Arg His Asn Leu Ala Asn Gly Phe Ser Leu
260 265 270

Ile Ser Lys Glu Ser Leu Val Asn
275 280

<210> SEQ ID NO 23
<211> LENGTH: 843
<212> TYPE: DNA
<213> ORGANISM: Brassica carinata

<400> SEQUENCE: 23
atgtcaacta ataccgtcgt ccctctccgt cgcagatcta acggatatca cactaacggc 60
gtggccttca acggaatgga gaacattgtc aagaaaaccg acgactgcta caccaatggc 120

```
aacggagtag gagggaagag caaggcgtcg tttctgacat ggaccatgcg tgacgctgtc    180

tacgtagcga gataccattg gataccgtgt ttctttgcgg tcggagttct gttctttatg    240

ggggttgagt acacgctcca gatggttccg gcgaagtctg agccgttcga tattgggttt    300

gtggccacgc gctctctgaa ccgcgtcttg gcgagttcac cggatcttaa caccctttta    360

gcggctctaa acacggtatt cgtagcgatg caaacgacgt atattgtatg gacatggttg    420

atggaaggaa gaccacgagc cactatctcg gcttgcttca tgtttacttg tcgcggtatt    480

cttggttact ctactcagct ccctctacca caggattttt taggatcagg agttgatttt    540

ccggtgggaa acgtctcatt cttcctcttc tattctggcc acgtagccgg ttcaatgatc    600

gcatccttgg acatgaggag aatgcagagg ttgagactag cgatgctttt tgacatcctc    660

aacatattac aatcgatcag gctgctcggg acgagaggac actacacgat cgatcttgcg    720

gtcggagttg gcgctgggat tctctttgac tcattggccg ggaagtacga agagatgatg    780

agcaagagac acaatttagc caatggtttt agtttgattt ctaaagactc gctagtcaat    840

taa                                                                  843
```

<210> SEQ ID NO 24
<211> LENGTH: 280
<212> TYPE: PRT
<213> ORGANISM: Brassica carinata

<400> SEQUENCE: 24

```
Met Ser Thr Asn Thr Val Val Pro Leu Arg Arg Arg Ser Asn Gly Tyr
1               5                   10                  15

His Thr Asn Gly Val Ala Phe Asn Gly Met Glu Asn Ile Val Lys Lys
            20                  25                  30

Thr Asp Asp Cys Tyr Thr Asn Gly Asn Gly Val Gly Gly Lys Ser Lys
        35                  40                  45

Ala Ser Phe Leu Thr Trp Thr Met Arg Asp Ala Val Tyr Val Ala Arg
    50                  55                  60

Tyr His Trp Ile Pro Cys Phe Phe Ala Val Gly Val Leu Phe Phe Met
65                  70                  75                  80

Gly Val Glu Tyr Thr Leu Gln Met Val Pro Ala Lys Ser Glu Pro Phe
                85                  90                  95

Asp Ile Gly Phe Val Ala Thr Arg Ser Leu Asn Arg Val Leu Ala Ser
            100                 105                 110

Ser Pro Asp Leu Asn Thr Leu Leu Ala Ala Leu Asn Thr Val Phe Val
        115                 120                 125

Ala Met Gln Thr Thr Tyr Ile Val Trp Thr Trp Leu Met Glu Gly Arg
    130                 135                 140

Pro Arg Ala Thr Ile Ser Ala Cys Phe Met Phe Thr Cys Arg Gly Ile
145                 150                 155                 160

Leu Gly Tyr Ser Thr Gln Leu Pro Leu Pro Gln Asp Phe Leu Gly Ser
                165                 170                 175

Gly Val Asp Phe Pro Val Gly Asn Val Ser Phe Phe Leu Phe Tyr Ser
            180                 185                 190

Gly His Val Ala Gly Ser Met Ile Ala Ser Leu Asp Met Arg Arg Met
        195                 200                 205

Gln Arg Leu Arg Leu Ala Met Leu Phe Asp Ile Leu Asn Ile Leu Gln
    210                 215                 220

Ser Ile Arg Leu Leu Gly Thr Arg Gly His Tyr Thr Ile Asp Leu Ala
225                 230                 235                 240
```

Val Gly Val Gly Ala Gly Ile Leu Phe Asp Ser Leu Ala Gly Lys Tyr
245 250 255

Glu Glu Met Met Ser Lys Arg His Asn Leu Ala Asn Gly Phe Ser Leu
260 265 270

Ile Ser Lys Asp Ser Leu Val Asn
275 280

<210> SEQ ID NO 25
<211> LENGTH: 849
<212> TYPE: DNA
<213> ORGANISM: Brassica carinata

<400> SEQUENCE: 25
atgtcaactg aaactggcgt ccctctccgt cgcagatcta actctcttaa cggacatcac 60
actaacggcg tcgcctctga cggaaacgtc ccatcaatgg agagcattgt taagagaaca 120
gacggaggag gaggagggat cagaagcaag gcgtcgttta tgacatggac ggcgcgtgac 180
gctatctacg tggcgagagt ccattggata ccgtgtgtgt tcgcggtcgg agttctgttc 240
ttcatgggcg tcgagtatac gcttcagatg attcccgcga ggtctgagcc gttcgatatt 300
gggttcgtgg ccacgcgctc tctgaaccgc gtcttggcaa actcaccgga tcttaacacc 360
gttttagccg cactaaacac ggttttcgta gggatgcaaa cgacgtatat tgtatggaca 420
tggttgatgg aaggacgacc acgagcgacc atctcggctt gctttatgtt tacttgtcgc 480
ggcattcttg gttactctac tcagcttcct ctccctcagg agtttttagg atcaggagtc 540
gattttccgg tgggaaacgt ctcattcttc ctcttctact cgggtcacgt cgccggttcc 600
atgatagcat ccttggacat gaggagaatg cagaggttga gactagcgat gctttttgac 660
atcctcaatg tactacaatc catcaggctg ctcgggacga gaggacatta caccatcgat 720
cttgcggtcg gagttggcgc tgggattctc tttgactcgt tggccgggaa gtacgaagag 780
atgatgaaca agagacacaa tttaggcaat ggttttagtt tgatttctaa agactcgcta 840
gtcaattaa 849

<210> SEQ ID NO 26
<211> LENGTH: 282
<212> TYPE: PRT
<213> ORGANISM: Brassica carinata

<400> SEQUENCE: 26

Met Ser Thr Glu Thr Gly Val Pro Leu Arg Arg Arg Ser Asn Ser Leu
1 5 10 15

Asn Gly His His Thr Asn Gly Val Ala Ser Asp Gly Asn Val Pro Ser
20 25 30

Met Glu Ser Ile Val Lys Arg Thr Asp Gly Gly Gly Gly Gly Ile Arg
35 40 45

Ser Lys Ala Ser Phe Met Thr Trp Thr Ala Arg Asp Ala Ile Tyr Val
50 55 60

Ala Arg Val His Trp Ile Pro Cys Val Phe Ala Val Gly Val Leu Phe
65 70 75 80

Phe Met Gly Val Glu Tyr Thr Leu Gln Met Ile Pro Ala Arg Ser Glu
85 90 95

Pro Phe Asp Ile Gly Phe Val Ala Thr Arg Ser Leu Asn Arg Val Leu
100 105 110

Ala Asn Ser Pro Asp Leu Asn Thr Val Leu Ala Ala Leu Asn Thr Val
115 120 125

```
Phe Val Gly Met Gln Thr Thr Tyr Ile Val Trp Thr Trp Leu Met Glu
    130                 135                 140

Gly Arg Pro Arg Ala Thr Ile Ser Ala Cys Phe Met Phe Thr Cys Arg
145                 150                 155                 160

Gly Ile Leu Gly Tyr Ser Thr Gln Leu Pro Leu Pro Gln Glu Phe Leu
                165                 170                 175

Gly Ser Gly Val Asp Phe Pro Val Gly Asn Val Ser Phe Phe Leu Phe
            180                 185                 190

Tyr Ser Gly His Val Ala Gly Ser Met Ile Ala Ser Leu Asp Met Arg
        195                 200                 205

Arg Met Gln Arg Leu Arg Leu Ala Met Leu Phe Asp Ile Leu Asn Val
    210                 215                 220

Leu Gln Ser Ile Arg Leu Leu Gly Thr Arg Gly His Tyr Thr Ile Asp
225                 230                 235                 240

Leu Ala Val Gly Val Gly Ala Gly Ile Leu Phe Asp Ser Leu Ala Gly
                245                 250                 255

Lys Tyr Glu Glu Met Met Asn Lys Arg His Asn Leu Gly Asn Gly Phe
            260                 265                 270

Ser Leu Ile Ser Lys Asp Ser Leu Val Asn
        275                 280
```

<210> SEQ ID NO 27
<211> LENGTH: 852
<212> TYPE: DNA
<213> ORGANISM: Brassica carinata

<400> SEQUENCE: 27

```
atgtcaactg aaactggcgt ccctctccgt cgcagatcta actctcttaa cggacatcac      60

tctaacgacg tcgcctttga cggaaccgtc ccatcaatgg agaacaacat tgttaagaaa     120

acagacgacg gctacgccaa tggaggagga aaggcgtcgt ttatgacatg gacggcgcgt     180

gacgctatct acgtggcgag agtccattgg ataccgtgtg tgttcgcggt tggagttctg     240

ttcttcatgg gcgtcgagta tacgcttcag atgattcccg cgaggtctga gccgttcgat     300

gttgggtttg tggccacgcg ctctctgaac agcgtcttgg caaattcacc gggtcttaac     360

accgttttag ccgcactaaa cacggtgttc gtagggatgc aaactacgta tattgtatgg     420

acatggttga tggaaggaag accacgagcc accatctcgg cttgcttcat gtttacttgt     480

cgcggtattc ttggttactc tactcagctc cctctccctc aggagttttt aggatcagga     540

gtcgattttc ctgtgggaaa cgtctcattc ttcctttttct actcgggtca cgtcgccggt     600

tcgatgatag catccttaga catgaggaga atgcagaggt tgagactagc aatgcttttt     660

gacatcctca atgtattaca atcgataagg ctgctcggga cgagaggaca ttacaccatc     720

gatcttgcgg tcggagttgg cgctgggatt ctctttgact cgttggccgg gaagtacgaa     780

gagatgatga gcaaaagaca caatttaggc aatggtttta gtttgatttc taaagactcg     840

ctagtcaatt aa                                                         852
```

<210> SEQ ID NO 28
<211> LENGTH: 283
<212> TYPE: PRT
<213> ORGANISM: Brassica carinata

<400> SEQUENCE: 28

```
Met Ser Thr Glu Thr Gly Val Pro Leu Arg Arg Arg Ser Asn Ser Leu
1               5                   10                  15
```

```
Asn Gly His His Ser Asn Asp Val Ala Phe Asp Gly Thr Val Pro Ser
            20                  25                  30

Met Glu Asn Asn Ile Val Lys Lys Thr Asp Asp Gly Tyr Ala Asn Gly
        35                  40                  45

Gly Gly Lys Ala Ser Phe Met Thr Trp Thr Ala Arg Asp Ala Ile Tyr
    50                  55                  60

Val Ala Arg Val His Trp Ile Pro Cys Val Phe Ala Val Gly Val Leu
65                  70                  75                  80

Phe Phe Met Gly Val Glu Tyr Thr Leu Gln Met Ile Pro Ala Arg Ser
                85                  90                  95

Glu Pro Phe Asp Val Gly Phe Val Ala Thr Arg Ser Leu Asn Ser Val
            100                 105                 110

Leu Ala Asn Ser Pro Gly Leu Asn Thr Val Leu Ala Ala Leu Asn Thr
        115                 120                 125

Val Phe Val Gly Met Gln Thr Thr Tyr Ile Val Trp Thr Trp Leu Met
    130                 135                 140

Glu Gly Arg Pro Arg Ala Thr Ile Ser Ala Cys Phe Met Phe Thr Cys
145                 150                 155                 160

Arg Gly Ile Leu Gly Tyr Ser Thr Gln Leu Pro Leu Pro Gln Glu Phe
                165                 170                 175

Leu Gly Ser Gly Val Asp Phe Pro Val Gly Asn Val Ser Phe Phe Leu
            180                 185                 190

Phe Tyr Ser Gly His Val Ala Gly Ser Met Ile Ala Ser Leu Asp Met
        195                 200                 205

Arg Arg Met Gln Arg Leu Arg Leu Ala Met Leu Phe Asp Ile Leu Asn
    210                 215                 220

Val Leu Gln Ser Ile Arg Leu Leu Gly Thr Arg Gly His Tyr Thr Ile
225                 230                 235                 240

Asp Leu Ala Val Gly Val Gly Ala Gly Ile Leu Phe Asp Ser Leu Ala
                245                 250                 255

Gly Lys Tyr Glu Glu Met Met Ser Lys Arg His Asn Leu Gly Asn Gly
            260                 265                 270

Phe Ser Leu Ile Ser Lys Asp Ser Leu Val Asn
        275                 280
```

<210> SEQ ID NO 29
<211> LENGTH: 818
<212> TYPE: DNA
<213> ORGANISM: Brassica juncea

<400> SEQUENCE: 29

```
atgtcaactg aaactagcgt ccctctccgt cgcagatcta cctctcttaa cggacatcac      60

tctaacgacg tcgcctttga cggaaccgtc ccattaatgg agaacaacat tgttaagaaa     120

acagacgacg gctacgccaa tggaggagga aaggcgtcgt ttatgacatg gacggcgcgt     180

gacgctatct acgtggcgag agtccattgg ataccgtgtg tgttcgcggt tggagttctc     240

ttcttcatgg gcgtcgagta tacgcttcaa atgattcccg cgaggtctga gccgttcgat     300

attgggtttg tggtcacgcg ctctctgaac cgcgtcttgg caaattcacc ggctcttaac     360

accgttttag ccgcactaaa cacggtgttc gtagggatgc aaactacgta tattgtatgg     420

acatggttga tggaaggaag accacgggcc accatctcgg cttgcttcat gtttacttgt     480

cgcgactcta cccagcttcc tctccctcag gagtttttag gatcaggagt cgattttccg     540

gtgggaaacg tctcattctt cctcttctac tcgggtcacg tcgccggttc catgatagca     600
```

```
tccttggaca tgaggagaat gcagaggttg agactagcga tgctttttga catcctcaat    660

gtactacaat ccatcaggct gctcgggacg agaggacatt acaccatcga tcttgcggtc    720

ggagttggcg ctgggattct ctttgactcg ttggccggga agtacgaaga gatgatgagc    780

aaaagacaca atttaggcaa tggttttagt ttgatttc                            818
```

<210> SEQ ID NO 30
<211> LENGTH: 272
<212> TYPE: PRT
<213> ORGANISM: Brassica juncea

<400> SEQUENCE: 30

```
Met Ser Thr Glu Thr Ser Val Pro Leu Arg Arg Arg Ser Thr Ser Leu
1               5                   10                  15

Asn Gly His His Ser Asn Asp Val Ala Phe Asp Gly Thr Val Pro Leu
            20                  25                  30

Met Glu Asn Asn Ile Val Lys Lys Thr Asp Asp Gly Tyr Ala Asn Gly
        35                  40                  45

Gly Gly Lys Ala Ser Phe Met Thr Trp Thr Ala Arg Asp Ala Ile Tyr
    50                  55                  60

Val Ala Arg Val His Trp Ile Pro Cys Val Phe Ala Val Gly Val Leu
65                  70                  75                  80

Phe Phe Met Gly Val Glu Tyr Thr Leu Gln Met Ile Pro Ala Arg Ser
                85                  90                  95

Glu Pro Phe Asp Ile Gly Phe Val Val Thr Arg Ser Leu Asn Arg Val
            100                 105                 110

Leu Ala Asn Ser Pro Ala Leu Asn Thr Val Leu Ala Ala Leu Asn Thr
        115                 120                 125

Val Phe Val Gly Met Gln Thr Thr Tyr Ile Val Trp Thr Trp Leu Met
    130                 135                 140

Glu Gly Arg Pro Arg Ala Thr Ile Ser Ala Cys Phe Met Phe Thr Cys
145                 150                 155                 160

Arg Asp Ser Thr Gln Leu Pro Leu Pro Gln Glu Phe Leu Gly Ser Gly
                165                 170                 175

Val Asp Phe Pro Val Gly Asn Val Ser Phe Phe Leu Phe Tyr Ser Gly
            180                 185                 190

His Val Ala Gly Ser Met Ile Ala Ser Leu Asp Met Arg Arg Met Gln
        195                 200                 205

Arg Leu Arg Leu Ala Met Leu Phe Asp Ile Leu Asn Val Leu Gln Ser
    210                 215                 220

Ile Arg Leu Leu Gly Thr Arg Gly His Tyr Thr Ile Asp Leu Ala Val
225                 230                 235                 240

Gly Val Gly Ala Gly Ile Leu Phe Asp Ser Leu Ala Gly Lys Tyr Glu
                245                 250                 255

Glu Met Met Ser Lys Arg His Asn Leu Gly Asn Gly Phe Ser Leu Ile
            260                 265                 270
```

<210> SEQ ID NO 31
<211> LENGTH: 807
<212> TYPE: DNA
<213> ORGANISM: Brassica juncea

<400> SEQUENCE: 31

```
atgtcaactg aaactggcgt ccctctccgt cgcagatcta actctcttaa cggacatcac     60

actaacggcg tcgcctctga cggaacaaac gtcccattaa tggagaaggc gtcgtttatg    120
```

```
acatggacgg cgcgtgacgc tatctacgtg gcgagagtcc attggatacc gtgtgtgttc    180

gcggtcggag ttctgttctt catgggcgtc gagtatacgc ttcagatgat tcccgcgagg    240

tctgagccgt tcgatattgg gttcgtggcc acgcgctctc tgaatcgcgt cttggcagat    300

tcaccggatc ttaacaccgt tttagctgca ctaaacacgg ttttcgtagg gatgcaaact    360

acgtatattg tatggacatg gttgatggaa ggaagaccac gggccaccat ctcggcttgc    420

ttcatgttta cttgtcgcgg tattcttggt tactctactc agctccctct ccctcaggag    480

tttttaggat caggagtcga ttttccggtg ggaaacgtct cattcttcct cttctactcg    540

ggtcacgtcg ccggttccat gatagcatcc ttggacatga ggagaatgca gaggttgaga    600

ctagcgatgc tttttgacat cctcaatgta ctacaatcca tcaggctgct cgggacgaga    660

ggacattaca ccatcgatct tgcggtcgga gttggcgctg ggattctctt tgactcgttg    720

gccgggaagt acgaagagat gatgagcaaa agacacaatt taggcaatgg ttttagtttg    780

atttctaaag actcgctagt caattaa                                          807
```

```
<210> SEQ ID NO 32
<211> LENGTH: 268
<212> TYPE: PRT
<213> ORGANISM: Brassica juncea

<400> SEQUENCE: 32

Met Ser Thr Glu Thr Gly Val Pro Leu Arg Arg Arg Ser Asn Ser Leu
1               5                   10                  15

Asn Gly His His Thr Asn Gly Val Ala Ser Asp Gly Thr Asn Val Pro
            20                  25                  30

Leu Met Glu Lys Ala Ser Phe Met Thr Trp Thr Ala Arg Asp Ala Ile
        35                  40                  45

Tyr Val Ala Arg Val His Trp Ile Pro Cys Val Phe Ala Val Gly Val
    50                  55                  60

Leu Phe Phe Met Gly Val Glu Tyr Thr Leu Gln Met Ile Pro Ala Arg
65                  70                  75                  80

Ser Glu Pro Phe Asp Ile Gly Phe Val Ala Thr Arg Ser Leu Asn Arg
                85                  90                  95

Val Leu Ala Asp Ser Pro Asp Leu Asn Thr Val Leu Ala Ala Leu Asn
            100                 105                 110

Thr Val Phe Val Gly Met Gln Thr Thr Tyr Ile Val Trp Thr Trp Leu
        115                 120                 125

Met Glu Gly Arg Pro Arg Ala Thr Ile Ser Ala Cys Phe Met Phe Thr
    130                 135                 140

Cys Arg Gly Ile Leu Gly Tyr Ser Thr Gln Leu Pro Leu Pro Gln Glu
145                 150                 155                 160

Phe Leu Gly Ser Gly Val Asp Phe Pro Val Gly Asn Val Ser Phe Phe
                165                 170                 175

Leu Phe Tyr Ser Gly His Val Ala Gly Ser Met Ile Ala Ser Leu Asp
            180                 185                 190

Met Arg Arg Met Gln Arg Leu Arg Leu Ala Met Leu Phe Asp Ile Leu
        195                 200                 205

Asn Val Leu Gln Ser Ile Arg Leu Leu Gly Thr Arg Gly His Tyr Thr
    210                 215                 220

Ile Asp Leu Ala Val Gly Val Gly Ala Gly Ile Leu Phe Asp Ser Leu
225                 230                 235                 240

Ala Gly Lys Tyr Glu Glu Met Met Ser Lys Arg His Asn Leu Gly Asn
```

-continued

```
                245                 250                 255

Gly Phe Ser Leu Ile Ser Lys Asp Ser Leu Val Asn
            260                 265


<210> SEQ ID NO 33
<211> LENGTH: 894
<212> TYPE: DNA
<213> ORGANISM: Camelina sativa

<400> SEQUENCE: 33

atgtcagtcg ccgcagctaa acccgccgtc tctcgccgtc acgtatctaa cggaaacaac      60

actaacaacg tcgccattga cgacgatcac aaccaccaac gccgcatcgt cggagataaa     120

aacactcgaa tggagatcgc tgctaagaac aacggctacg ccaacggtgt catcggagga     180

ggaggatgga ggagcaaggc gtcgttcatg acgtggacga cgcgtgacgt tgtctacgtg     240

gcgagacacc attggatacc gtgcatgttc gctgccgggc ttttgttctt catgggggtc     300

gagtacacgc tccagatgat tcccgcgaga tctgagccgt tcgatcttgg gttcgtggcc     360

acgcgctctt tgaatcgcgt cttagcatct tccccggatc ttaacaccgt tttagccgca     420

ctaaacacgg tgttcgtatt gatgcaaaca acgtatattg tatggacatg gttagtggaa     480

ggacgagcac gagcaaccat ctcggcttta ttcatgttca cgtgtcgggg cattctcggc     540

tactctactc agcttcctct ccctcaggat tttttaggat caggagttga ttttccagtg     600

ggaaacgtct ctttcttcct cttcttctcg ggccacgttg ccggctcgat gatcgcatca     660

ctggacatga ggagaatgca gaggtttaag ctggcgaggg tttttgacat cctcaatgta     720

ttacaatcga tcaggctgct cggtacaaga ggacactaca ccatcgacct tgcggttgga     780

gttggcgctg ggattctctt tgactcactg gccgggaagt acgaagagat gagcagaaga     840

caccacctag gaactggttt tagtttgata tcgaaagact ctctagtcaa ttaa           894


<210> SEQ ID NO 34
<211> LENGTH: 297
<212> TYPE: PRT
<213> ORGANISM: Camelina sativa

<400> SEQUENCE: 34

Met Ser Val Ala Ala Ala Lys Pro Ala Val Ser Arg Arg His Val Ser
1               5                   10                  15

Asn Gly Asn Asn Thr Asn Asn Val Ala Ile Asp Asp Asp His Asn His
            20                  25                  30

Gln Arg Arg Ile Val Gly Asp Lys Asn Thr Arg Met Glu Ile Ala Ala
        35                  40                  45

Lys Asn Asn Gly Tyr Ala Asn Gly Val Ile Gly Gly Gly Gly Trp Arg
    50                  55                  60

Ser Lys Ala Ser Phe Met Thr Trp Thr Thr Arg Asp Val Val Tyr Val
65                  70                  75                  80

Ala Arg His His Trp Ile Pro Cys Met Phe Ala Ala Gly Leu Leu Phe
                85                  90                  95

Phe Met Gly Val Glu Tyr Thr Leu Gln Met Ile Pro Ala Arg Ser Glu
            100                 105                 110

Pro Phe Asp Leu Gly Phe Val Ala Thr Arg Ser Leu Asn Arg Val Leu
        115                 120                 125

Ala Ser Ser Pro Asp Leu Asn Thr Val Leu Ala Ala Leu Asn Thr Val
    130                 135                 140

Phe Val Leu Met Gln Thr Thr Tyr Ile Val Trp Thr Trp Leu Val Glu
```

```
145                 150                 155                 160

Gly Arg Ala Arg Ala Thr Ile Ser Ala Leu Phe Met Phe Thr Cys Arg
                165                 170                 175

Gly Ile Leu Gly Tyr Ser Thr Gln Leu Pro Leu Pro Gln Asp Phe Leu
            180                 185                 190

Gly Ser Gly Val Asp Phe Pro Val Gly Asn Val Ser Phe Phe Leu Phe
        195                 200                 205

Phe Ser Gly His Val Ala Gly Ser Met Ile Ala Ser Leu Asp Met Arg
    210                 215                 220

Arg Met Gln Arg Phe Lys Leu Ala Arg Val Phe Asp Ile Leu Asn Val
225                 230                 235                 240

Leu Gln Ser Ile Arg Leu Leu Gly Thr Arg Gly His Tyr Thr Ile Asp
                245                 250                 255

Leu Ala Val Gly Val Gly Ala Gly Ile Leu Phe Asp Ser Leu Ala Gly
            260                 265                 270

Lys Tyr Glu Glu Met Ser Arg Arg His His Leu Gly Thr Gly Phe Ser
        275                 280                 285

Leu Ile Ser Lys Asp Ser Leu Val Asn
    290                 295


<210> SEQ ID NO 35
<211> LENGTH: 894
<212> TYPE: DNA
<213> ORGANISM: Camelina sativa

<400> SEQUENCE: 35

atgtcagcca ccgcagctaa acccgctgtc tctcgccgtc acgtatctaa cggaaaccac     60

actaacaacg tcgccattga cgacgatcac aaccaccaac gccccgtcga cgtcggagat    120

acaaacactc gaatggagat cgctgctaag aacaacggct acgccaacgg tgtcatcgga    180

ggaggatgga ggagcaaggc gtcgttcatg acgtggacga cgcgtgacgt tgtctacgtg    240

gcgagacacc attggatacc gtgcatgttc gctgccgggc ttttgttctt catgggggtc    300

gagtacacgc tccagatgat acccgcgaga tctgagccgt tcgatcttgg gtttgtagcc    360

acgcgctctt tgaatcgcgt cttagcatct tccccggatc taaacactgt tctagccgca    420

ctaaacacgg tgttcgtatt gatgcaaaca acgtatattg tatggacatg gttagtggaa    480

ggacgagcac gagcaaccat ctcggcttta ttcatgttca cgtgtcgcgg cattctcggc    540

tactctactc agcttcctct ccctcaggat tttttaggat caggagttga ttttccggtg    600

ggaaacgtct ctttcttcct cttcttctcg ggccacgttg ccggctcgat gatcgcatcg    660

ttggacatga ggagaatgca gaggtttaag ctggcgaggg tttttgacat cctcaatgta    720

ttacaatcga tcaggctgct cggtacaaga ggacactaca ccatcgacct tgcggttgga    780

gttggcgctg ggattctttt tgactcactg gccggaaagt acgaagagat gagcagaaga    840

caccacctag gaactggttt tagtttgata tcgaaagact ctctagtcaa ttaa          894


<210> SEQ ID NO 36
<211> LENGTH: 297
<212> TYPE: PRT
<213> ORGANISM: Camelina sativa

<400> SEQUENCE: 36

Met Ser Ala Thr Ala Ala Lys Pro Ala Val Ser Arg Arg His Val Ser
1               5                   10                  15

Asn Gly Asn His Thr Asn Asn Val Ala Ile Asp Asp Asp His Asn His
```

```
            20                  25                  30

Gln Arg Pro Val Asp Val Gly Asp Thr Asn Thr Arg Met Glu Ile Ala
        35                  40                  45

Ala Lys Asn Asn Gly Tyr Ala Asn Gly Val Ile Gly Gly Gly Trp Arg
    50                  55                  60

Ser Lys Ala Ser Phe Met Thr Trp Thr Thr Arg Asp Val Val Tyr Val
65                  70                  75                  80

Ala Arg His His Trp Ile Pro Cys Met Phe Ala Ala Gly Leu Leu Phe
                85                  90                  95

Phe Met Gly Val Glu Tyr Thr Leu Gln Met Ile Pro Ala Arg Ser Glu
            100                 105                 110

Pro Phe Asp Leu Gly Phe Val Ala Thr Arg Ser Leu Asn Arg Val Leu
        115                 120                 125

Ala Ser Ser Pro Asp Leu Asn Thr Val Leu Ala Ala Leu Asn Thr Val
    130                 135                 140

Phe Val Leu Met Gln Thr Thr Tyr Ile Val Trp Thr Trp Leu Val Glu
145                 150                 155                 160

Gly Arg Ala Arg Ala Thr Ile Ser Ala Leu Phe Met Phe Thr Cys Arg
                165                 170                 175

Gly Ile Leu Gly Tyr Ser Thr Gln Leu Pro Leu Pro Gln Asp Phe Leu
            180                 185                 190

Gly Ser Gly Val Asp Phe Pro Val Gly Asn Val Ser Phe Phe Leu Phe
        195                 200                 205

Phe Ser Gly His Val Ala Gly Ser Met Ile Ala Ser Leu Asp Met Arg
    210                 215                 220

Arg Met Gln Arg Phe Lys Leu Ala Arg Val Phe Asp Ile Leu Asn Val
225                 230                 235                 240

Leu Gln Ser Ile Arg Leu Leu Gly Thr Arg Gly His Tyr Thr Ile Asp
                245                 250                 255

Leu Ala Val Gly Val Gly Ala Gly Ile Leu Phe Asp Ser Leu Ala Gly
            260                 265                 270

Lys Tyr Glu Glu Met Ser Arg Arg His His Leu Gly Thr Gly Phe Ser
        275                 280                 285

Leu Ile Ser Lys Asp Ser Leu Val Asn
    290                 295


<210> SEQ ID NO 37
<211> LENGTH: 891
<212> TYPE: DNA
<213> ORGANISM: Camelina sativa

<400> SEQUENCE: 37

atgtcagcct ccgcagctaa acccgccgtc tctcgccgtc acgtatctaa cggaaaccac      60

actaacaacg tcgccattga gaacgatcac aaccaccaac gccccgtcgc cggagataca     120

aacactcgaa tggagatcgc tgctaagaac aacggctacg ccaacggtgt cggaggagga     180

ggatggagga gcaaggcgtc gttcatgacg tggacgacgc gtgacgttgt ctacgtggcg     240

agacaccatt ggataccgtg catgttcgct gccgggcttt tgttcttcat gggggtcgag     300

tacacgctcc agatgatacc cgcgagatct gaaccgttcg atcttgggtt tgtggccacg     360

cgctctttaa atcgcgtctt agcatcttcc ccggatctaa acactgttct agccgcacta     420

aacacggtgt tcgtattgat gcaaacaacg tatattgtat ggacatggtt agtggaagga     480

cgagcacgag caaccatctc ggctttattc atgttcacgt gtcgcggcat tctcggctac     540
```

-continued tctactcagc ttcctctccc tcaggatttt ttaggatcag gagttgattt tccggtggga 600
aacgtctctt tcttcctctt cttctcgggc cacgttgccg gctcgatgat cgcatcgttg 660
gacatgagga gaatgcaaag gtttaagctg gcgagggttt ttgacatcct caatgtatta 720
caatcgatca ggctgctcgg tacaagagga cactacacca tcgaccttgc ggttggagtt 780
ggcgctggga ttctctttga ctcactggcc gggaagtacg aagagatgag cagaagacac 840
cacctaggaa ctggttttag tttgatatcg aaagactctc tagtcaatta a 891

<210> SEQ ID NO 38
<211> LENGTH: 296
<212> TYPE: PRT
<213> ORGANISM: Camelina sativa

<400> SEQUENCE: 38

```
Met Ser Ala Ser Ala Ala Lys Pro Ala Val Ser Arg Arg His Val Ser
1               5                   10                  15

Asn Gly Asn His Thr Asn Asn Val Ala Ile Glu Asn Asp His Asn His
            20                  25                  30

Gln Arg Pro Val Ala Gly Asp Thr Asn Thr Arg Met Glu Ile Ala Ala
        35                  40                  45

Lys Asn Asn Gly Tyr Ala Asn Gly Val Gly Gly Gly Gly Trp Arg Ser
    50                  55                  60

Lys Ala Ser Phe Met Thr Trp Thr Thr Arg Asp Val Val Tyr Val Ala
65                  70                  75                  80

Arg His His Trp Ile Pro Cys Met Phe Ala Ala Gly Leu Leu Phe Phe
                85                  90                  95

Met Gly Val Glu Tyr Thr Leu Gln Met Ile Pro Ala Arg Ser Glu Pro
            100                 105                 110

Phe Asp Leu Gly Phe Val Ala Thr Arg Ser Leu Asn Arg Val Leu Ala
        115                 120                 125

Ser Ser Pro Asp Leu Asn Thr Val Leu Ala Ala Leu Asn Thr Val Phe
    130                 135                 140

Val Leu Met Gln Thr Thr Tyr Ile Val Trp Thr Trp Leu Val Glu Gly
145                 150                 155                 160

Arg Ala Arg Ala Thr Ile Ser Ala Leu Phe Met Phe Thr Cys Arg Gly
                165                 170                 175

Ile Leu Gly Tyr Ser Thr Gln Leu Pro Leu Pro Gln Asp Phe Leu Gly
            180                 185                 190

Ser Gly Val Asp Phe Pro Val Gly Asn Val Ser Phe Phe Leu Phe Phe
        195                 200                 205

Ser Gly His Val Ala Gly Ser Met Ile Ala Ser Leu Asp Met Arg Arg
    210                 215                 220

Met Gln Arg Phe Lys Leu Ala Arg Val Phe Asp Ile Leu Asn Val Leu
225                 230                 235                 240

Gln Ser Ile Arg Leu Leu Gly Thr Arg Gly His Tyr Thr Ile Asp Leu
                245                 250                 255

Ala Val Gly Val Gly Ala Gly Ile Leu Phe Asp Ser Leu Ala Gly Lys
            260                 265                 270

Tyr Glu Glu Met Ser Arg Arg His His Leu Gly Thr Gly Phe Ser Leu
        275                 280                 285

Ile Ser Lys Asp Ser Leu Val Asn
    290                 295
```

<210> SEQ ID NO 39

<211> LENGTH: 870
<212> TYPE: DNA
<213> ORGANISM: Brassica juncea

<400> SEQUENCE: 39
atgtcaacta caacaatcgt ccctctccgt cggagttcta actctctcaa tgaataccac 60
actaacgcag tcgcctttga cggaatcgtc gggtcaacaa gtactagcca aatggaggag 120
attgttacgc aaatggacga aggctacgcc aaccccaacg gagatggagg gagaagcaag 180
gtgtcgttca tgacgtggag gatgtgcagt gctgtccacg tggtgagagt ccactggata 240
ccgtgtttgt tagcggtagg agttctgttc ttcacggggg tggaggagta catgctccag 300
atgattcccc cgagttctga gccgttcgat attggttttg tggcgacgcg ctctctctat 360
cgcctcttgg cttcttcacc ggatctcaac accgttttag ccgctctcaa cacggtgttc 420
gtagggatgc aaacgacgta tattgtatgg acatggttga tggaaggacg accacgagcg 480
accatctcgg cttgctttat gtttacatgt cgtggcattc ttggttactc tactcagctc 540
cctcttcctc aggatttttct aggatcaggg gtagactttc ctgtaggaaa cgtctccttc 600
ttcctcttct actcaggcca tgtggcaggg tcgacgatag catccttgga catgaggaga 660
atgaagaggt tgagactagc cttgcttttt gacatcctca atgtattaca atcgatcagg 720
cttctcggga cgagaggaca atacacgatc gatctcgctg tcggagttgg cgctggggtt 780
ctctttgact cactggctgg aaaatacgaa gagatgatga gcaagagaca caatgtaggc 840
aatggtttta gtttgatttc gtctcgctag 870

<210> SEQ ID NO 40
<211> LENGTH: 289
<212> TYPE: PRT
<213> ORGANISM: Brassica juncea

<400> SEQUENCE: 40

Met Ser Thr Thr Thr Ile Val Pro Leu Arg Arg Ser Ser Asn Ser Leu
1 5 10 15

Asn Glu Tyr His Thr Asn Ala Val Ala Phe Asp Gly Ile Val Gly Ser
20 25 30

Thr Ser Thr Ser Gln Met Glu Glu Ile Val Thr Gln Met Asp Glu Gly
35 40 45

Tyr Ala Asn Pro Asn Gly Asp Gly Gly Arg Ser Lys Val Ser Phe Met
50 55 60

Thr Trp Arg Met Cys Ser Ala Val His Val Val Arg Val His Trp Ile
65 70 75 80

Pro Cys Leu Leu Ala Val Gly Val Leu Phe Phe Thr Gly Val Glu Glu
85 90 95

Tyr Met Leu Gln Met Ile Pro Pro Ser Ser Glu Pro Phe Asp Ile Gly
100 105 110

Phe Val Ala Thr Arg Ser Leu Tyr Arg Leu Leu Ala Ser Ser Pro Asp
115 120 125

Leu Asn Thr Val Leu Ala Ala Leu Asn Thr Val Phe Val Gly Met Gln
130 135 140

Thr Thr Tyr Ile Val Trp Thr Trp Leu Met Glu Gly Arg Pro Arg Ala
145 150 155 160

Thr Ile Ser Ala Cys Phe Met Phe Thr Cys Arg Gly Ile Leu Gly Tyr
165 170 175

Ser Thr Gln Leu Pro Leu Pro Gln Asp Phe Leu Gly Ser Gly Val Asp
180 185 190

Phe Pro Val Gly Asn Val Ser Phe Phe Leu Phe Tyr Ser Gly His Val
195 200 205

Ala Gly Ser Thr Ile Ala Ser Leu Asp Met Arg Arg Met Lys Arg Leu
210 215 220

Arg Leu Ala Leu Leu Phe Asp Ile Leu Asn Val Leu Gln Ser Ile Arg
225 230 235 240

Leu Leu Gly Thr Arg Gly Gln Tyr Thr Ile Asp Leu Ala Val Gly Val
245 250 255

Gly Ala Gly Val Leu Phe Asp Ser Leu Ala Gly Lys Tyr Glu Glu Met
260 265 270

Met Ser Lys Arg His Asn Val Gly Asn Gly Phe Ser Leu Ile Ser Ser
275 280 285

Arg

<210> SEQ ID NO 41
<211> LENGTH: 870
<212> TYPE: DNA
<213> ORGANISM: Brassica napus

<400> SEQUENCE: 41
atgtcaacta caacaatcgt ccctctccgt cgcagttcta actctctcaa tgaataccac 60
actaacgcag tcgcctttga cggaatcgtc gggtcaacaa gtactagcca aatggaggag 120
attgttacgc aaaccgacga ctgctacgcc aatcacaacg gagatggagg gagaagcaag 180
gcatcgttta tgacgtggag gatgtgcaat cctgtccagg tggcgagagt ccattggata 240
ccgtgtttgc tagcggtagg agttctgttc ttcacgggcg tagaggagta catgctccag 300
atgattccgg cgagttctga gccgttcgat attggttttg tggcgacgcg ctctctgtat 360
cgactcttgg cttcttcacc ggatcttaat accgttttag ctgctctcaa cacggtgttt 420
gtagggatgc aaacgacgta tattttatgg acatggttgg tggaaggacg accacgagcg 480
accatctcgg cttgcttcat gtttacttgt cgtggcattc ttggttactc tactcagctc 540
cctcttcctc aggattttct aggatcaggg gtagattttc cggtaggaaa cgtctcgttc 600
ttcctcttct actcaggcca tgtcgcaggg tcgacgatag catccttgga tatgaggaga 660
atgaagaggt tgagactagc cttgcttttt gacatcctca atgtattaca atcgatcagg 720
cttctcggga cgagaggaca atacacgatc gatctcgctg tcggagttgg cgctggggtt 780
ctctttgact cactggctgg aaaatacgaa gagatgatga gcaagagacg caatgtaggc 840
aatggtttta gtttgatttc gtctcgctag 870

<210> SEQ ID NO 42
<211> LENGTH: 289
<212> TYPE: PRT
<213> ORGANISM: Brassica napus

<400> SEQUENCE: 42

Met Ser Thr Thr Thr Ile Val Pro Leu Arg Arg Ser Ser Asn Ser Leu
1 5 10 15

Asn Glu Tyr His Thr Asn Ala Val Ala Phe Asp Gly Ile Val Gly Ser
20 25 30

Thr Ser Thr Ser Gln Met Glu Glu Ile Val Thr Gln Thr Asp Asp Cys
35 40 45

Tyr Ala Asn His Asn Gly Asp Gly Gly Arg Ser Lys Ala Ser Phe Met
50 55 60

Thr Trp Arg Met Cys Asn Pro Val Gln Val Ala Arg Val His Trp Ile
65 70 75 80

Pro Cys Leu Leu Ala Val Gly Val Leu Phe Phe Thr Gly Val Glu Glu
85 90 95

Tyr Met Leu Gln Met Ile Pro Ala Ser Ser Glu Pro Phe Asp Ile Gly
100 105 110

Phe Val Ala Thr Arg Ser Leu Tyr Arg Leu Leu Ala Ser Ser Pro Asp
115 120 125

Leu Asn Thr Val Leu Ala Ala Leu Asn Thr Val Phe Val Gly Met Gln
130 135 140

Thr Thr Tyr Ile Leu Trp Thr Trp Leu Val Glu Gly Arg Pro Arg Ala
145 150 155 160

Thr Ile Ser Ala Cys Phe Met Phe Thr Cys Arg Gly Ile Leu Gly Tyr
165 170 175

Ser Thr Gln Leu Pro Leu Pro Gln Asp Phe Leu Gly Ser Gly Val Asp
180 185 190

Phe Pro Val Gly Asn Val Ser Phe Phe Leu Phe Tyr Ser Gly His Val
195 200 205

Ala Gly Ser Thr Ile Ala Ser Leu Asp Met Arg Arg Met Lys Arg Leu
210 215 220

Arg Leu Ala Leu Leu Phe Asp Ile Leu Asn Val Leu Gln Ser Ile Arg
225 230 235 240

Leu Leu Gly Thr Arg Gly Gln Tyr Thr Ile Asp Leu Ala Val Gly Val
245 250 255

Gly Ala Gly Val Leu Phe Asp Ser Leu Ala Gly Lys Tyr Glu Glu Met
260 265 270

Met Ser Lys Arg Arg Asn Val Gly Asn Gly Phe Ser Leu Ile Ser Ser
275 280 285

Arg

<210> SEQ ID NO 43
<211> LENGTH: 708
<212> TYPE: DNA
<213> ORGANISM: Brassica napus

<400> SEQUENCE: 43
atgtctcaaa tggacatttc tacgagaact gaggaaggag gatggagaag caagccttcg 60
tttatgacgt ggagagcgcg cgacgttgtc tacgtgatga gacaccattg gataccgtgt 120
ctgttcgcgg ccggattctt gttcgtcgta agcgtggagt cctcgatcaa gatggtttcc 180
gagagttctc caccgttcga tattgggttt gtggccacgg agtctctgca tcatatcttg 240
gcttcttcac cggatctgaa caccggtttg gccgctctaa actcggtgtt aggagtgatg 300
caagtatcgt atattgcatg gacatggtta atagaaggac ggccccgagc caccatcacg 360
gctttattcc tcttcacttg tcgcggtgtt ctcggttact gtactcagct ccctctttca 420
aaggagtatc taggatcagc aatcgatttc ccgctaggaa atctctcgtt cttctatttt 480
ttctcgggtc acgtggcagg cgcgaccatc gcatctttgg acatgaggag gatgcagagg 540
ttgagatttg cgatggtttt tgacatcctc aatgtattac agtcgatcag gctgcttgcg 600
acgagaggac actacacgat cgatctcgca ggtggagttg ccgctgcgat tctctttgac 660
tcattggccg gaaagtacga agctaataca agaaagaggc aattgtag 708

<210> SEQ ID NO 44
<211> LENGTH: 235

<212> TYPE: PRT
<213> ORGANISM: Brassica napus

<400> SEQUENCE: 44

Met Ser Gln Met Asp Ile Ser Thr Arg Thr Glu Glu Gly Gly Trp Arg
1 5 10 15

Ser Lys Pro Ser Phe Met Thr Trp Arg Ala Arg Asp Val Val Tyr Val
20 25 30

Met Arg His His Trp Ile Pro Cys Leu Phe Ala Ala Gly Phe Leu Phe
35 40 45

Val Val Ser Val Glu Ser Ser Ile Lys Met Val Ser Glu Ser Ser Pro
50 55 60

Pro Phe Asp Ile Gly Phe Val Ala Thr Glu Ser Leu His His Ile Leu
65 70 75 80

Ala Ser Ser Pro Asp Leu Asn Thr Gly Leu Ala Ala Leu Asn Ser Val
85 90 95

Leu Gly Val Met Gln Val Ser Tyr Ile Ala Trp Thr Trp Leu Ile Glu
100 105 110

Gly Arg Pro Arg Ala Thr Ile Thr Ala Leu Phe Leu Phe Thr Cys Arg
115 120 125

Gly Val Leu Gly Tyr Cys Thr Gln Leu Pro Leu Ser Lys Glu Tyr Leu
130 135 140

Gly Ser Ala Ile Asp Phe Pro Leu Gly Asn Leu Ser Phe Phe Tyr Phe
145 150 155 160

Phe Ser Gly His Val Ala Gly Ala Thr Ile Ala Ser Leu Asp Met Arg
165 170 175

Arg Met Gln Arg Leu Arg Phe Ala Met Val Phe Asp Ile Leu Asn Val
180 185 190

Leu Gln Ser Ile Arg Leu Leu Ala Thr Arg Gly His Tyr Thr Ile Asp
195 200 205

Leu Ala Gly Gly Val Ala Ala Ile Leu Phe Asp Ser Leu Ala Gly
210 215 220

Lys Tyr Glu Ala Asn Thr Arg Lys Arg Gln Leu
225 230 235

<210> SEQ ID NO 45
<211> LENGTH: 870
<212> TYPE: DNA
<213> ORGANISM: Artificial Sequence
<220> FEATURE:
<223> OTHER INFORMATION: Consensus PDCT1

<400> SEQUENCE: 45
atgtcaacta caacaatcgt ccctctccgt cgcagttcta actctctcaa tgaataccac 60
actaacgcag tcgcctttga cggaatcgtc gggtcaacaa gtactagcca aatggaggag 120
attgttacgc aaaccgacga aggctacgcc aaccccaacg gagatggagg gagaagcaag 180
ccttcgttta tgacgtggag gatgtgcgac gttgtctacg tggtgagagt ccattggata 240
ccgtgtttgt tagcggtagg agttctgttc ttcacgagcg tggaggagta catgctccag 300
atgattcccg agagttctga gccgttcgat attggttttg tggcgacgcg ctctctgtat 360
cgtctcttgg cttcttcacc ggatcttaac accgttttag ccgctctcaa cacggtgttt 420
gtagggatgc aaacgacgta tattgcatgg acatggttga tagaaggacg accacgagcg 480
accatctcgg cttgcttcat gtttacttgt cgcggcattc tcggttactc tactcagctc 540
cctcttcctc aggattttct aggatcaggg gtagattttc cggtaggaaa cgtctcgttc 600

```
ttcctcttct actcaggcca cgtggcaggg tcgacgatcg catccttgga catgaggaga    660

atgcagaggt tgagacttgc cttgcttttt gacatcctca atgtattaca atcgatcagg    720

cttctcggga cgagaggaca atacacgatc gatctcgctg tcggagttgg cgctggggtt    780

ctctttgact cattggccgg aaagtacgaa gagatgatga gcaagagaca aaatgtaggc    840

aatggtttta gtttgatttc gtctcgctag                                     870
```

<210> SEQ ID NO 46
<211> LENGTH: 289
<212> TYPE: PRT
<213> ORGANISM: Artificial Sequence
<220> FEATURE:
<223> OTHER INFORMATION: Consensus PDCT1

<400> SEQUENCE: 46

```
Met Ser Thr Thr Thr Ile Val Pro Leu Arg Arg Ser Ser Asn Ser Leu
1               5                   10                  15

Asn Glu Tyr His Thr Asn Ala Val Ala Phe Asp Gly Ile Val Gly Ser
            20                  25                  30

Thr Ser Thr Ser Gln Met Glu Glu Ile Val Thr Gln Thr Asp Glu Gly
        35                  40                  45

Tyr Ala Asn Pro Asn Gly Asp Gly Gly Arg Ser Lys Pro Ser Phe Met
    50                  55                  60

Thr Trp Arg Met Cys Asp Val Val Tyr Val Val Arg Val His Trp Ile
65                  70                  75                  80

Pro Cys Leu Leu Ala Val Gly Val Leu Phe Phe Thr Ser Val Glu Glu
                85                  90                  95

Tyr Met Leu Gln Met Ile Pro Glu Ser Ser Glu Pro Phe Asp Ile Gly
            100                 105                 110

Phe Val Ala Thr Arg Ser Leu Tyr Arg Leu Leu Ala Ser Ser Pro Asp
        115                 120                 125

Leu Asn Thr Val Leu Ala Ala Leu Asn Thr Val Phe Val Gly Met Gln
    130                 135                 140

Thr Thr Tyr Ile Ala Trp Thr Trp Leu Ile Glu Gly Arg Pro Arg Ala
145                 150                 155                 160

Thr Ile Ser Ala Cys Phe Met Phe Thr Cys Arg Gly Ile Leu Gly Tyr
                165                 170                 175

Ser Thr Gln Leu Pro Leu Pro Gln Asp Phe Leu Gly Ser Gly Val Asp
            180                 185                 190

Phe Pro Val Gly Asn Val Ser Phe Phe Leu Phe Tyr Ser Gly His Val
        195                 200                 205

Ala Gly Ser Thr Ile Ala Ser Leu Asp Met Arg Arg Met Gln Arg Leu
    210                 215                 220

Arg Leu Ala Leu Leu Phe Asp Ile Leu Asn Val Leu Gln Ser Ile Arg
225                 230                 235                 240

Leu Leu Gly Thr Arg Gly Gln Tyr Thr Ile Asp Leu Ala Val Gly Val
                245                 250                 255

Gly Ala Gly Val Leu Phe Asp Ser Leu Ala Gly Lys Tyr Glu Glu Met
            260                 265                 270

Met Ser Lys Arg Gln Asn Val Gly Asn Gly Phe Ser Leu Ile Ser Ser
        275                 280                 285

Arg
```

<210> SEQ ID NO 47

-continued

<211> LENGTH: 894
<212> TYPE: DNA
<213> ORGANISM: Artificial Sequence
<220> FEATURE:
<223> OTHER INFORMATION: Consensus PDCT19

<400> SEQUENCE: 47

```
atgtcagcct ccgcagctaa acccgctgtc tctcgccgtc acgtatctaa cggaaaccac     60

actaacaacg tcgccattga cgacgatcac aaccaccaac gccccgtcga cgccggagat    120

acaaacactc gaatggagat cgctgctaag aacaacggct acgccaacgg tgtcggagga    180

ggaggatgga ggagcaaggc gtcgttcatg acgtggacga cgcgtgacgt tgtctacgtg    240

gcgagacacc attggatacc gtgcatgttc gctgccgggc ttttgttctt catgggggtc    300

gagtacacgc tccagatgat acccgcgaga tctgagccgt tcgatcttgg gtttgtagcc    360

acgcgctctt tgaatcgcgt cttagcatct tccccggatc taaacactgt tctagccgca    420

ctaaacacgg tgttcgtatt gatgcaaaca acgtatattg tatggacatg gttagtggaa    480

ggacgagcac gagcaaccat ctcggcttta ttcatgttca cgtgtcgcgg cattctcggc    540

tactctactc agcttcctct ccctcaggat tttttaggat caggagttga ttttccggtg    600

ggaaacgtct ctttcttcct cttcttctcg ggccacgttg ccggctcgat gatcgcatcg    660

ttggacatga ggagaatgca gaggtttaag ctggcgaggg tttttgacat cctcaatgta    720

ttacaatcga tcaggctgct cggtacaaga ggacactaca ccatcgacct tgcggttgga    780

gttggcgctg ggattctttt tgactcactg gccggaaagt acgaagagat gagcagaaga    840

caccacctag gaactggttt tagtttgata tcgaaagact ctctagtcaa ttaa          894
```

<210> SEQ ID NO 48
<211> LENGTH: 297
<212> TYPE: PRT
<213> ORGANISM: Artificial Sequence
<220> FEATURE:
<223> OTHER INFORMATION: Consensus PDCT19

<400> SEQUENCE: 48

```
Met Ser Ala Ser Ala Ala Lys Pro Ala Val Ser Arg Arg His Val Ser
1               5                   10                  15

Asn Gly Asn His Thr Asn Asn Val Ala Ile Asp Asp Asp His Asn His
            20                  25                  30

Gln Arg Pro Val Asp Ala Gly Asp Thr Asn Thr Arg Met Glu Ile Ala
        35                  40                  45

Ala Lys Asn Asn Gly Tyr Ala Asn Gly Val Gly Gly Gly Gly Trp Arg
    50                  55                  60

Ser Lys Ala Ser Phe Met Thr Trp Thr Thr Arg Asp Val Val Tyr Val
65                  70                  75                  80

Ala Arg His His Trp Ile Pro Cys Met Phe Ala Ala Gly Leu Leu Phe
                85                  90                  95

Phe Met Gly Val Glu Tyr Thr Leu Gln Met Ile Pro Ala Arg Ser Glu
            100                 105                 110

Pro Phe Asp Leu Gly Phe Val Ala Thr Arg Ser Leu Asn Arg Val Leu
        115                 120                 125

Ala Ser Ser Pro Asp Leu Asn Thr Val Leu Ala Ala Leu Asn Thr Val
    130                 135                 140

Phe Val Leu Met Gln Thr Thr Tyr Ile Val Trp Thr Trp Leu Val Glu
145                 150                 155                 160

Gly Arg Ala Arg Ala Thr Ile Ser Ala Leu Phe Met Phe Thr Cys Arg
```

-continued

```
                165                 170                 175

Gly Ile Leu Gly Tyr Ser Thr Gln Leu Pro Leu Pro Gln Asp Phe Leu
            180                 185                 190

Gly Ser Gly Val Asp Phe Pro Val Gly Asn Val Ser Phe Phe Leu Phe
        195                 200                 205

Phe Ser Gly His Val Ala Gly Ser Met Ile Ala Ser Leu Asp Met Arg
    210                 215                 220

Arg Met Gln Arg Phe Lys Leu Ala Arg Val Phe Asp Ile Leu Asn Val
225                 230                 235                 240

Leu Gln Ser Ile Arg Leu Leu Gly Thr Arg Gly His Tyr Thr Ile Asp
                245                 250                 255

Leu Ala Val Gly Val Gly Ala Gly Ile Leu Phe Asp Ser Leu Ala Gly
            260                 265                 270

Lys Tyr Glu Glu Met Ser Arg Arg His His Leu Gly Thr Gly Phe Ser
        275                 280                 285

Leu Ile Ser Lys Asp Ser Leu Val Asn
    290                 295


<210> SEQ ID NO 49
<211> LENGTH: 843
<212> TYPE: DNA
<213> ORGANISM: Brassica juncea
<220> FEATURE:
<221> NAME/KEY: misc_feature
<222> LOCATION: (476)..(477)
<223> OTHER INFORMATION: n is a or g or c or t

<400> SEQUENCE: 49

atgtcaacta ataccgtcgt ccctctccgt cgcagatcta acggatatca cagtaacggc     60

gtggccttta acggaatgga gaacattgtc aagaaaacag acgactgcta caccaacggc    120

aacggaggag gagggaagag caaggcgtcg tttctgacat ggaccatgcg cgacgctgtc    180

tacgtggcga gataccattg gataccgtgt ttctttgcgg tcggagttct gttctttatg    240

ggcgttgagt atacgctcca gatggttccg gcgaagtctg agccgttcga tattgggttt    300

gtggccacgc gctctctgaa ccgcgtcttg gcgagttcac cggatcttaa caccctttta    360

gcggctctaa acacggtatt cgtagcgatg caaacgacgt atattgtatg gacatggttg    420

atggaaggaa gaccacgagc cactatctct gcttgcttta tgtttacttg tcgcgnnatt    480

cttggttact ctactcagct ccctctccca caggattttt taggatcagg agttgatttt    540

ccagtgggaa acgtctcatt cttcctcttc tattctggtc acgtcgccgg ttcaatgatc    600

gcatccttgg acatgaggag aatgcggagg ttgagactag cgatgctttt tgacatcctc    660

aacgtattac aatctatcag gctgctcggg acaagaggac attacacgat tgatcttgcg    720

gtcggagttg gcgctgggat tctctttgac tctttggccg ggaagtacga agagatgatg    780

agcaagagac acaatttagc caatggtttt agtttgattt cgaaagactc gctagtcaat    840

taa                                                                  843


<210> SEQ ID NO 50
<211> LENGTH: 280
<212> TYPE: PRT
<213> ORGANISM: Brassica juncea
<220> FEATURE:
<221> NAME/KEY: MISC_FEATURE
<222> LOCATION: (159)..(159)
<223> OTHER INFORMATION: Xaa is Val or Ala or Asp or Glu or Gly

<400> SEQUENCE: 50
```

-continued

```
Met Ser Thr Asn Thr Val Val Pro Leu Arg Arg Arg Ser Asn Gly Tyr
1               5                   10                  15

His Ser Asn Gly Val Ala Phe Asn Gly Met Glu Asn Ile Val Lys Lys
            20                  25                  30

Thr Asp Asp Cys Tyr Thr Asn Gly Asn Gly Gly Gly Gly Lys Ser Lys
        35                  40                  45

Ala Ser Phe Leu Thr Trp Thr Met Arg Asp Ala Val Tyr Val Ala Arg
    50                  55                  60

Tyr His Trp Ile Pro Cys Phe Phe Ala Val Gly Val Leu Phe Phe Met
65                  70                  75                  80

Gly Val Glu Tyr Thr Leu Gln Met Val Pro Ala Lys Ser Glu Pro Phe
                85                  90                  95

Asp Ile Gly Phe Val Ala Thr Arg Ser Leu Asn Arg Val Leu Ala Ser
            100                 105                 110

Ser Pro Asp Leu Asn Thr Leu Leu Ala Ala Leu Asn Thr Val Phe Val
        115                 120                 125

Ala Met Gln Thr Thr Tyr Ile Val Trp Thr Trp Leu Met Glu Gly Arg
    130                 135                 140

Pro Arg Ala Thr Ile Ser Ala Cys Phe Met Phe Thr Cys Arg Xaa Ile
145                 150                 155                 160

Leu Gly Tyr Ser Thr Gln Leu Pro Leu Pro Gln Asp Phe Leu Gly Ser
                165                 170                 175

Gly Val Asp Phe Pro Val Gly Asn Val Ser Phe Phe Leu Phe Tyr Ser
            180                 185                 190

Gly His Val Ala Gly Ser Met Ile Ala Ser Leu Asp Met Arg Arg Met
        195                 200                 205

Arg Arg Leu Arg Leu Ala Met Leu Phe Asp Ile Leu Asn Val Leu Gln
    210                 215                 220

Ser Ile Arg Leu Leu Gly Thr Arg Gly His Tyr Thr Ile Asp Leu Ala
225                 230                 235                 240

Val Gly Val Gly Ala Gly Ile Leu Phe Asp Ser Leu Ala Gly Lys Tyr
                245                 250                 255

Glu Glu Met Met Ser Lys Arg His Asn Leu Ala Asn Gly Phe Ser Leu
            260                 265                 270

Ile Ser Lys Asp Ser Leu Val Asn
        275                 280


<210> SEQ ID NO 51
<211> LENGTH: 843
<212> TYPE: DNA
<213> ORGANISM: Brassica juncea

<400> SEQUENCE: 51

atgtcaacta ataccgtcgt ccctctccgt cgcagatcta acggaaatca cactaacggc     60

gaggccttta acggaatgga gaacattgtc aagaaaaccg acgactgcta caccaacggc    120

aacggaggag tagagagaag caaagcctcg tttctgacat ggaccatgcg tgacgctgtc    180

tacgtagcga gataccattg gataccgtgt ttctttgcgg tcggagttct gttctttatg    240

ggggttgagt acacgctcca gatggttccg gcgaagtctg agccgttcga tattgggttt    300

gtggccacgc gctctctgaa ccgcgtcttg gcgagttcac cggatcttaa caccctttta    360

gcggctctaa acacggtatt cgtagcgatg caaacgacgt atattgtatg gacatggttg    420

atggaaggaa gaccacgagc cactatctcg gcttgcttca tgtttacttg tcgcggcatt    480
```

```
cttggttact ctactcagct ccctctacca caggattttt taggatcagg agttgatttt    540

ccggtgggaa acgtctcatt cttcctcttc tattctggcc acgtagccgg ttcaatgatc    600

gcatccttgg acatgaggag aatgcagagg ttgagactag cgatgctttt tgacatcctc    660

aacatattac aatcgatcag actgctcggg acgagaggac actacacgat cgatcttgcg    720

gtcggagttg gcgctgggat tctctttgac tcattggccg ggaagtacga agagatgatg    780

agcaagagac acaatttagc caatggtttt agtttgattt ctaaagactc gctagtcaat    840

taa                                                                  843
```

```
<210> SEQ ID NO 52
<211> LENGTH: 280
<212> TYPE: PRT
<213> ORGANISM: Brassica juncea

<400> SEQUENCE: 52

Met Ser Thr Asn Thr Val Val Pro Leu Arg Arg Arg Ser Asn Gly Asn
1               5                   10                  15

His Thr Asn Gly Glu Ala Phe Asn Gly Met Glu Asn Ile Val Lys Lys
            20                  25                  30

Thr Asp Asp Cys Tyr Thr Asn Gly Asn Gly Gly Val Glu Arg Ser Lys
        35                  40                  45

Ala Ser Phe Leu Thr Trp Thr Met Arg Asp Ala Val Tyr Val Ala Arg
    50                  55                  60

Tyr His Trp Ile Pro Cys Phe Phe Ala Val Gly Val Leu Phe Phe Met
65                  70                  75                  80

Gly Val Glu Tyr Thr Leu Gln Met Val Pro Ala Lys Ser Glu Pro Phe
                85                  90                  95

Asp Ile Gly Phe Val Ala Thr Arg Ser Leu Asn Arg Val Leu Ala Ser
            100                 105                 110

Ser Pro Asp Leu Asn Thr Leu Leu Ala Ala Leu Asn Thr Val Phe Val
        115                 120                 125

Ala Met Gln Thr Thr Tyr Ile Val Trp Thr Trp Leu Met Glu Gly Arg
    130                 135                 140

Pro Arg Ala Thr Ile Ser Ala Cys Phe Met Phe Thr Cys Arg Gly Ile
145                 150                 155                 160

Leu Gly Tyr Ser Thr Gln Leu Pro Leu Pro Gln Asp Phe Leu Gly Ser
                165                 170                 175

Gly Val Asp Phe Pro Val Gly Asn Val Ser Phe Phe Leu Phe Tyr Ser
            180                 185                 190

Gly His Val Ala Gly Ser Met Ile Ala Ser Leu Asp Met Arg Arg Met
        195                 200                 205

Gln Arg Leu Arg Leu Ala Met Leu Phe Asp Ile Leu Asn Ile Leu Gln
    210                 215                 220

Ser Ile Arg Leu Leu Gly Thr Arg Gly His Tyr Thr Ile Asp Leu Ala
225                 230                 235                 240

Val Gly Val Gly Ala Gly Ile Leu Phe Asp Ser Leu Ala Gly Lys Tyr
                245                 250                 255

Glu Glu Met Met Ser Lys Arg His Asn Leu Ala Asn Gly Phe Ser Leu
            260                 265                 270

Ile Ser Lys Asp Ser Leu Val Asn
        275                 280


<210> SEQ ID NO 53
<211> LENGTH: 843
```

<212> TYPE: DNA
<213> ORGANISM: Brassica rapa

<400> SEQUENCE: 53

```
atgtcaacta ataccgtcgt ccctctccgt cgcagatcta acggatatca cactaacggc     60

gtggccttta acggaatgga gaacattgtc aagaaaaccg acgactgcta caccaacggc    120

aacggaggag tagagagaag caaagcctcg tttctgacat ggaccatgcg tgacgctgtc    180

tacgtagcga gataccattg gataccgtgt ttctttgcgg tcggagttct gttctttatg    240

ggggttgagt acacgctcca gatggttccg gcgaagtctg agccgttcga tattgggttt    300

gtggccacgc gctctctgaa ccgcgtcttg gcgagttcac cggatcttaa caccctttta    360

gcggctctaa acacggtatt cgtagcgatg cagacgacgt atattgtatg gacatggttg    420

atggaaggaa gaccacgagc cactatctcg gcttgcttca tgtttacttg tcgcggcatt    480

cttggttact ctactcagct ccctctacca caggattttt taggatcagg agttgatttt    540

ccggtgggaa acgtctcatt cttcctcttc tattctggcc acgtagccgg ttcaatgatc    600

gcatccttgg acatgaggag aatgcagagg ttgagactag cgatgctttt tgacatcctc    660

aacatattac aatcgatcag actgctcggg acgagaggac actacacgat cgatcttgcg    720

gtcggagttg gcgctgggat tctctttgac tcattggccg ggaagtacga agagatgatg    780

agcaagagac acaatttagc caatggtttt agtttgattt ctaaagactc gctagtcaat    840

taa                                                                  843
```

<210> SEQ ID NO 54
<211> LENGTH: 280
<212> TYPE: PRT
<213> ORGANISM: Brassica rapa

<400> SEQUENCE: 54

```
Met Ser Thr Asn Thr Val Val Pro Leu Arg Arg Arg Ser Asn Gly Tyr
1               5                   10                  15

His Thr Asn Gly Val Ala Phe Asn Gly Met Glu Asn Ile Val Lys Lys
            20                  25                  30

Thr Asp Asp Cys Tyr Thr Asn Gly Asn Gly Gly Val Glu Arg Ser Lys
        35                  40                  45

Ala Ser Phe Leu Thr Trp Thr Met Arg Asp Ala Val Tyr Val Ala Arg
    50                  55                  60

Tyr His Trp Ile Pro Cys Phe Phe Ala Val Gly Val Leu Phe Phe Met
65                  70                  75                  80

Gly Val Glu Tyr Thr Leu Gln Met Val Pro Ala Lys Ser Glu Pro Phe
                85                  90                  95

Asp Ile Gly Phe Val Ala Thr Arg Ser Leu Asn Arg Val Leu Ala Ser
            100                 105                 110

Ser Pro Asp Leu Asn Thr Leu Leu Ala Ala Leu Asn Thr Val Phe Val
        115                 120                 125

Ala Met Gln Thr Thr Tyr Ile Val Trp Thr Trp Leu Met Glu Gly Arg
    130                 135                 140

Pro Arg Ala Thr Ile Ser Ala Cys Phe Met Phe Thr Cys Arg Gly Ile
145                 150                 155                 160

Leu Gly Tyr Ser Thr Gln Leu Pro Leu Pro Gln Asp Phe Leu Gly Ser
                165                 170                 175

Gly Val Asp Phe Pro Val Gly Asn Val Ser Phe Phe Leu Phe Tyr Ser
            180                 185                 190
```

```
Gly His Val Ala Gly Ser Met Ile Ala Ser Leu Asp Met Arg Arg Met
        195                 200                 205

Gln Arg Leu Arg Leu Ala Met Leu Phe Asp Ile Leu Asn Ile Leu Gln
    210                 215                 220

Ser Ile Arg Leu Leu Gly Thr Arg Gly His Tyr Thr Ile Asp Leu Ala
225                 230                 235                 240

Val Gly Val Gly Ala Gly Ile Leu Phe Asp Ser Leu Ala Gly Lys Tyr
                245                 250                 255

Glu Glu Met Met Ser Lys Arg His Asn Leu Ala Asn Gly Phe Ser Leu
            260                 265                 270

Ile Ser Lys Asp Ser Leu Val Asn
        275                 280
```

<210> SEQ ID NO 55
<211> LENGTH: 852
<212> TYPE: DNA
<213> ORGANISM: Brassica napus

<400> SEQUENCE: 55

```
atgtcaactg aaactggcgt ccctctccgt cgcagatcta actctcttaa cggacatcac      60

tctaacgacg tcgcctttga cggaaccgtc ccatcaatgg agaacaacat tgttaagaaa     120

acagacgacg gctacgccaa tggaggagga aaggcgtcgt ttatgacatg gacggcgcgt     180

gacgctatct acgtggcgag agtccattgg ataccgtgtg tgttcgcggt tggagttctg     240

ttcttcatgg gcgtcgagta tacgcttcag atgattcccg cgaggtctga gccgttcgat     300

gttgggtttg tggccacgcg ctctctgaac cgcgtcttgg caaattcacc gggtcttaac     360

accgttttag ccgcactaaa cacggtgttc gtagggatgc aaactacgta tattgtatgg     420

acatggttga tggaaggaag accacgagcc accatctcgg cttgcttcat gtttacttgt     480

cgcggtattc ttggttactc tactcagctc cctctccctc aggagttttt aggatcagga     540

gtcgattttc ctgtgggaaa cgtctcattc ttccttttct actcgggtca cgtcgccggt     600

tcgatgatag catccttaga catgaggaga atgcagaggt tgagactagc aatgcttttt     660

gacatcctca atgttttaca atcgataagg ctgctcggga cgagaggaca ttacaccatc     720

gatcttgcgg tcggagttgg cgctgggatt ctctttgact cgttggccgg gaagtacgaa     780

gagatgatga gcaaaagaca caatttaggc aatggtttta gtttgatttc taaagactcg     840

ctagtcaatt aa                                                         852
```

<210> SEQ ID NO 56
<211> LENGTH: 283
<212> TYPE: PRT
<213> ORGANISM: Brassica napus

<400> SEQUENCE: 56

```
Met Ser Thr Glu Thr Gly Val Pro Leu Arg Arg Arg Ser Asn Ser Leu
1               5                   10                  15

Asn Gly His His Ser Asn Asp Val Ala Phe Asp Gly Thr Val Pro Ser
            20                  25                  30

Met Glu Asn Asn Ile Val Lys Lys Thr Asp Asp Gly Tyr Ala Asn Gly
        35                  40                  45

Gly Gly Lys Ala Ser Phe Met Thr Trp Thr Ala Arg Asp Ala Ile Tyr
    50                  55                  60

Val Ala Arg Val His Trp Ile Pro Cys Val Phe Ala Val Gly Val Leu
65                  70                  75                  80
```

-continued

```
Phe Phe Met Gly Val Glu Tyr Thr Leu Gln Met Ile Pro Ala Arg Ser
                85                  90                  95

Glu Pro Phe Asp Val Gly Phe Val Ala Thr Arg Ser Leu Asn Arg Val
            100                 105                 110

Leu Ala Asn Ser Pro Gly Leu Asn Thr Val Leu Ala Ala Leu Asn Thr
        115                 120                 125

Val Phe Val Gly Met Gln Thr Thr Tyr Ile Val Trp Thr Trp Leu Met
    130                 135                 140

Glu Gly Arg Pro Arg Ala Thr Ile Ser Ala Cys Phe Met Phe Thr Cys
145                 150                 155                 160

Arg Gly Ile Leu Gly Tyr Ser Thr Gln Leu Pro Leu Pro Gln Glu Phe
                165                 170                 175

Leu Gly Ser Gly Val Asp Phe Pro Val Gly Asn Val Ser Phe Phe Leu
            180                 185                 190

Phe Tyr Ser Gly His Val Ala Gly Ser Met Ile Ala Ser Leu Asp Met
        195                 200                 205

Arg Arg Met Gln Arg Leu Arg Leu Ala Met Leu Phe Asp Ile Leu Asn
    210                 215                 220

Val Leu Gln Ser Ile Arg Leu Leu Gly Thr Arg Gly His Tyr Thr Ile
225                 230                 235                 240

Asp Leu Ala Val Gly Val Gly Ala Gly Ile Leu Phe Asp Ser Leu Ala
                245                 250                 255

Gly Lys Tyr Glu Glu Met Met Ser Lys Arg His Asn Leu Gly Asn Gly
            260                 265                 270

Phe Ser Leu Ile Ser Lys Asp Ser Leu Val Asn
        275                 280
```

<210> SEQ ID NO 57
<211> LENGTH: 843
<212> TYPE: DNA
<213> ORGANISM: Brassica napus

<400> SEQUENCE: 57

```
atgtcaacta ataccgtcgt ccctctccgt cgcagatcta acggatatca cactaacggc      60

gtggccttca acggaatgga gaacattgtc aagaaaaccg acgactgcta caccaatggc     120

aacggagtag gagggaagag caaggcgtcg tttctgacat ggaccatgcg tgacgctgtc     180

tacgtagcga gataccattg gataccgtgt ttctttgcgg tcggagttct gttctttatg     240

ggggttgagt acacgctcca gatggttccg gcgaagtctg agccgttcga tattgggttt     300

gtggccacgc gctctctgaa ccgcgtcttg gcgagttcac cggatcttaa cacccttttg     360

gcggctctaa acacggtatt cgtagcgatg caaacgacgt atattgtatg gacatggttg     420

atggaaggaa gaccacgagc cactatctcg gcttgcttca tgtttacttg tcgcggtatt     480

cttggttact ctactcagct ccctctacca caggattttt taggatcagg agttgatttt     540

ccggtgggaa acgtctcatt cttcctcttc tattctggcc acgtagccgg ttcaatgatc     600

gcatccttgg acatgaggag aatgcagagg ttgagactag cgatgctttt tgacatcctc     660

aacatattac aatcgatcag gctgctcggg acgagaggac actacacgat cgatcttgcg     720

gtcggagttg gcgctgggat tctctttgac tcattggccg ggaagtacga agagatgatg     780

agcaagagac acaatttagc caatggtttt agtttgattt ctaaagactc gctagtcaat     840

taa                                                                   843
```

<210> SEQ ID NO 58

<211> LENGTH: 280
<212> TYPE: PRT
<213> ORGANISM: Brassica napus

<400> SEQUENCE: 58

Met Ser Thr Asn Thr Val Val Pro Leu Arg Arg Arg Ser Asn Gly Tyr
1 5 10 15

His Thr Asn Gly Val Ala Phe Asn Gly Met Glu Asn Ile Val Lys Lys
20 25 30

Thr Asp Asp Cys Tyr Thr Asn Gly Asn Gly Val Gly Gly Lys Ser Lys
35 40 45

Ala Ser Phe Leu Thr Trp Thr Met Arg Asp Ala Val Tyr Val Ala Arg
50 55 60

Tyr His Trp Ile Pro Cys Phe Phe Ala Val Gly Val Leu Phe Phe Met
65 70 75 80

Gly Val Glu Tyr Thr Leu Gln Met Val Pro Ala Lys Ser Glu Pro Phe
85 90 95

Asp Ile Gly Phe Val Ala Thr Arg Ser Leu Asn Arg Val Leu Ala Ser
100 105 110

Ser Pro Asp Leu Asn Thr Leu Leu Ala Ala Leu Asn Thr Val Phe Val
115 120 125

Ala Met Gln Thr Thr Tyr Ile Val Trp Thr Trp Leu Met Glu Gly Arg
130 135 140

Pro Arg Ala Thr Ile Ser Ala Cys Phe Met Phe Thr Cys Arg Gly Ile
145 150 155 160

Leu Gly Tyr Ser Thr Gln Leu Pro Leu Pro Gln Asp Phe Leu Gly Ser
165 170 175

Gly Val Asp Phe Pro Val Gly Asn Val Ser Phe Phe Leu Phe Tyr Ser
180 185 190

Gly His Val Ala Gly Ser Met Ile Ala Ser Leu Asp Met Arg Arg Met
195 200 205

Gln Arg Leu Arg Leu Ala Met Leu Phe Asp Ile Leu Asn Ile Leu Gln
210 215 220

Ser Ile Arg Leu Leu Gly Thr Arg Gly His Tyr Thr Ile Asp Leu Ala
225 230 235 240

Val Gly Val Gly Ala Gly Ile Leu Phe Asp Ser Leu Ala Gly Lys Tyr
245 250 255

Glu Glu Met Met Ser Lys Arg His Asn Leu Ala Asn Gly Phe Ser Leu
260 265 270

Ile Ser Lys Asp Ser Leu Val Asn
275 280

<210> SEQ ID NO 59
<211> LENGTH: 843
<212> TYPE: DNA
<213> ORGANISM: Artificial Sequence
<220> FEATURE:
<223> OTHER INFORMATION: Consensus PDCT3/5

<400> SEQUENCE: 59
atgtcaacta ataccgtcgt ccctctccgt cgcagatcta acggacatca cactaacggc 60
gtggccttta acggaatgga gaacattgtc aagaaaacag acgactgcta caccaatggc 120
aacggaggag gagggaagag caaggcgtcg tttctgacat ggaccatgcg tgacgctgtc 180
tacgtggcga gataccattg gataccgtgt ttctttgcgg tcggagttct gttctttatg 240
ggcgttgagt atacgctcca gatggttccg gcgaagtctg agccgttcga tattgggttt 300

```
gtggccacgc gctctctgaa ccgcgtcttg gcgagttcac cggatcttaa caccctttta    360

gcggctctaa acacggtatt cgtagcgatg caaacgacgt atattgtatg gacatggttg    420

atggaaggaa gaccacgagc cactatctcg gcttgcttca tgtttacttg tcgcggtatt    480

cttggttact ctactcagct ccctctccca caggattttt taggatcagg agttgatttt    540

ccggtgggaa acgtctcatt cttcctcttc tattctggtc acgtcgccgg ttcaatgatc    600

gcatccttgg acatgaggag aatgcagagg ttgagactag cgatgctttt tgacatcctc    660

aacgtattac aatcgatcag gctgctcggg acgagaggac attacacgat cgatcttgcg    720

gtcggagttg gcgctgggat tctctttgac tcgttggccg ggaagtacga agagatgatg    780

agcaagagac acaatttagc caatggtttt agtttgattt ctaaagactc gctagtcaat    840

taa                                                                  843
```

<210> SEQ ID NO 60
<211> LENGTH: 280
<212> TYPE: PRT
<213> ORGANISM: Artificial Sequence
<220> FEATURE:
<223> OTHER INFORMATION: Consensus PDCT3/5

<400> SEQUENCE: 60

```
Met Ser Thr Asn Thr Val Val Pro Leu Arg Arg Arg Ser Asn Gly His
1               5                   10                  15

His Thr Asn Gly Val Ala Phe Asn Gly Met Glu Asn Ile Val Lys Lys
            20                  25                  30

Thr Asp Asp Cys Tyr Thr Asn Gly Asn Gly Gly Gly Gly Lys Ser Lys
        35                  40                  45

Ala Ser Phe Leu Thr Trp Thr Met Arg Asp Ala Val Tyr Val Ala Arg
    50                  55                  60

Tyr His Trp Ile Pro Cys Phe Phe Ala Val Gly Val Leu Phe Phe Met
65                  70                  75                  80

Gly Val Glu Tyr Thr Leu Gln Met Val Pro Ala Lys Ser Glu Pro Phe
                85                  90                  95

Asp Ile Gly Phe Val Ala Thr Arg Ser Leu Asn Arg Val Leu Ala Ser
            100                 105                 110

Ser Pro Asp Leu Asn Thr Leu Leu Ala Ala Leu Asn Thr Val Phe Val
        115                 120                 125

Ala Met Gln Thr Thr Tyr Ile Val Trp Thr Trp Leu Met Glu Gly Arg
    130                 135                 140

Pro Arg Ala Thr Ile Ser Ala Cys Phe Met Phe Thr Cys Arg Gly Ile
145                 150                 155                 160

Leu Gly Tyr Ser Thr Gln Leu Pro Leu Pro Gln Asp Phe Leu Gly Ser
                165                 170                 175

Gly Val Asp Phe Pro Val Gly Asn Val Ser Phe Phe Leu Phe Tyr Ser
            180                 185                 190

Gly His Val Ala Gly Ser Met Ile Ala Ser Leu Asp Met Arg Arg Met
        195                 200                 205

Gln Arg Leu Arg Leu Ala Met Leu Phe Asp Ile Leu Asn Val Leu Gln
    210                 215                 220

Ser Ile Arg Leu Leu Gly Thr Arg Gly His Tyr Thr Ile Asp Leu Ala
225                 230                 235                 240

Val Gly Val Gly Ala Gly Ile Leu Phe Asp Ser Leu Ala Gly Lys Tyr
                245                 250                 255
```

-continued

```
Glu Glu Met Met Ser Lys Arg His Asn Leu Ala Asn Gly Phe Ser Leu
            260                 265                 270

Ile Ser Lys Asp Ser Leu Val Asn
        275                 280


<210> SEQ ID NO 61
<211> LENGTH: 906
<212> TYPE: DNA
<213> ORGANISM: Arabidopsis thaliana

<400> SEQUENCE: 61

atgtcagccg ccgcagctga aaccgacgtc tctctccgtc gcagatctaa ctctcttaac      60

ggaaaccaca ctaacggcgt cgccattgac ggaaccctag acaacaacaa ccgtcgcgtc     120

ggagatacaa acactcacat ggatatatct gctaagaaaa ctgacaacgg ctacgccaat     180

ggtgtcggag gaggaggatg gagaagcaaa gcgtcgttca cgacgtggac ggcgcgtgat     240

atcgtctacg tggtgagata ccattggata ccgtgcatgt tcgctgccgg acttctgttc     300

ttcatgggcg tggagtacac gcttcagatg attcccgcga gatctgagcc gttcgatctt     360

gggtttgtgg tcacgcgctc tttgaatcgc gtattagcat cttcaccgga tcttaacact     420

gttttagccg cactaaacac ggtgttcgta gggatgcaaa caacgtatat tgtatggaca     480

tggttagtgg aaggacgagc acgagccacc atcgcggctt tattcatgtt cacttgtcgc     540

ggcattctcg gctactctac tcagcttcct ctccctcagg actttctagg atcaggggtt     600

gattttccgg tgggaaatgt ctctttcttc ctcttcttct ctggccatgt cgccggctcg     660

atgatcgcat cattggacat gagaagaatg cagaggttga gacttgcaat ggtctttgac     720

atcctcaatg tattacagtc gatcagactg ctcggtacaa gaggacatta cacaatcgac     780

cttgcggttg gagttggcgc tgggattctc ttcgactcat tggccggaaa gtacgaagag     840

atgatgagca agagacattt aggcactggt tttagtttga tttcgaaaga ctctctagtc     900

aattaa                                                                906


<210> SEQ ID NO 62
<211> LENGTH: 301
<212> TYPE: PRT
<213> ORGANISM: Arabidopsis thaliana

<400> SEQUENCE: 62

Met Ser Ala Ala Ala Ala Glu Thr Asp Val Ser Leu Arg Arg Arg Ser
1               5                   10                  15

Asn Ser Leu Asn Gly Asn His Thr Asn Gly Val Ala Ile Asp Gly Thr
            20                  25                  30

Leu Asp Asn Asn Asn Arg Arg Val Gly Asp Thr Asn Thr His Met Asp
        35                  40                  45

Ile Ser Ala Lys Lys Thr Asp Asn Gly Tyr Ala Asn Gly Val Gly Gly
    50                  55                  60

Gly Gly Trp Arg Ser Lys Ala Ser Phe Thr Thr Trp Thr Ala Arg Asp
65                  70                  75                  80

Ile Val Tyr Val Val Arg Tyr His Trp Ile Pro Cys Met Phe Ala Ala
                85                  90                  95

Gly Leu Leu Phe Phe Met Gly Val Glu Tyr Thr Leu Gln Met Ile Pro
            100                 105                 110

Ala Arg Ser Glu Pro Phe Asp Leu Gly Phe Val Val Thr Arg Ser Leu
        115                 120                 125

Asn Arg Val Leu Ala Ser Ser Pro Asp Leu Asn Thr Val Leu Ala Ala
```

-continued

```
    130                 135                 140

Leu Asn Thr Val Phe Val Gly Met Gln Thr Thr Tyr Ile Val Trp Thr
145                 150                 155                 160

Trp Leu Val Glu Gly Arg Ala Arg Ala Thr Ile Ala Ala Leu Phe Met
                165                 170                 175

Phe Thr Cys Arg Gly Ile Leu Gly Tyr Ser Thr Gln Leu Pro Leu Pro
            180                 185                 190

Gln Asp Phe Leu Gly Ser Gly Val Asp Phe Pro Val Gly Asn Val Ser
        195                 200                 205

Phe Phe Leu Phe Phe Ser Gly His Val Ala Gly Ser Met Ile Ala Ser
    210                 215                 220

Leu Asp Met Arg Arg Met Gln Arg Leu Arg Leu Ala Met Val Phe Asp
225                 230                 235                 240

Ile Leu Asn Val Leu Gln Ser Ile Arg Leu Leu Gly Thr Arg Gly His
                245                 250                 255

Tyr Thr Ile Asp Leu Ala Val Gly Val Gly Ala Gly Ile Leu Phe Asp
            260                 265                 270

Ser Leu Ala Gly Lys Tyr Glu Glu Met Met Ser Lys Arg His Leu Gly
        275                 280                 285

Thr Gly Phe Ser Leu Ile Ser Lys Asp Ser Leu Val Asn
    290                 295                 300
```

<210> SEQ ID NO 63
<211> LENGTH: 804
<212> TYPE: DNA
<213> ORGANISM: Glycine max

<400> SEQUENCE: 63

```
atgaatggcg gcgctgaggc ctccctcaat cacaggcgca aacaccaaac agctcccgcc      60

gacggcgcta aaggcgttaa ggtagcaaac ggagccatgg ggaagccgtc ctcttccaag     120

cactcctgcg gcgcgtcgtt catgaaatgg accgtggctg acgctgtcca cgtggtgacg     180

caccattgga tgccgtgctt gttcgcattg gggcttctct tcttcatggc cgtggagtac     240

acgcttctca tggtgccgcc gtcgtcgccg cccttcgacc ttggcttcat cgccacacgc     300

tccctccacg cgctcctcga gtcgtcgccg aatctcaaca cgctcttcgc cgggctcaat     360

acggtgtttg tggggatgca aacgagttat atcttatgga cgtggctgat tgaaggacgc     420

cccagagcca caatttcagc attgttcatg ttcacatgcc gtgggatttt aggctactcc     480

acccagctcc cattgcctca ggggtttttg ggctcgggtg tggacttccc tgttgggaac     540

gtgtcttttt tcttgttttt ttctgggcac gttgcagggt cagtgattgc ttcattggac     600

atgaggagga tgcagaggtg ggaactggct tggacttttg atgtgctcaa tgttttgcaa     660

gctgtgaggt tgctgggtac aagaggccat tacactattg atttggccgt aggggttggt     720

gctggaattc tctttgattc tttagctggc aagtacgaag atagcaaaag gaatggtgct     780

ctcaaacaca atttgattgc gtga                                            804
```

<210> SEQ ID NO 64
<211> LENGTH: 267
<212> TYPE: PRT
<213> ORGANISM: Glycine max

<400> SEQUENCE: 64

```
Met Asn Gly Gly Ala Glu Ala Ser Leu Asn His Arg Arg Lys His Gln
1               5                   10                  15
```

-continued

```
Thr Ala Pro Ala Asp Gly Ala Lys Gly Val Lys Val Ala Asn Gly Ala
            20                  25                  30

Met Gly Lys Pro Ser Ser Ser Lys His Ser Cys Gly Ala Ser Phe Met
        35                  40                  45

Lys Trp Thr Val Ala Asp Ala Val His Val Val Thr His His Trp Met
    50                  55                  60

Pro Cys Leu Phe Ala Leu Gly Leu Leu Phe Phe Met Ala Val Glu Tyr
65                  70                  75                  80

Thr Leu Leu Met Val Pro Pro Ser Ser Pro Pro Phe Asp Leu Gly Phe
                85                  90                  95

Ile Ala Thr Arg Ser Leu His Ala Leu Leu Glu Ser Ser Pro Asn Leu
            100                 105                 110

Asn Thr Leu Phe Ala Gly Leu Asn Thr Val Phe Val Gly Met Gln Thr
        115                 120                 125

Ser Tyr Ile Leu Trp Thr Trp Leu Ile Glu Gly Arg Pro Arg Ala Thr
    130                 135                 140

Ile Ser Ala Leu Phe Met Phe Thr Cys Arg Gly Ile Leu Gly Tyr Ser
145                 150                 155                 160

Thr Gln Leu Pro Leu Pro Gln Gly Phe Leu Gly Ser Gly Val Asp Phe
                165                 170                 175

Pro Val Gly Asn Val Ser Phe Phe Leu Phe Phe Ser Gly His Val Ala
            180                 185                 190

Gly Ser Val Ile Ala Ser Leu Asp Met Arg Arg Met Gln Arg Trp Glu
        195                 200                 205

Leu Ala Trp Thr Phe Asp Val Leu Asn Val Leu Gln Ala Val Arg Leu
    210                 215                 220

Leu Gly Thr Arg Gly His Tyr Thr Ile Asp Leu Ala Val Gly Val Gly
225                 230                 235                 240

Ala Gly Ile Leu Phe Asp Ser Leu Ala Gly Lys Tyr Glu Asp Ser Lys
                245                 250                 255

Arg Asn Gly Ala Leu Lys His Asn Leu Ile Ala
            260                 265
```

<210> SEQ ID NO 65
<211> LENGTH: 840
<212> TYPE: DNA
<213> ORGANISM: Glycine max

<400> SEQUENCE: 65

```
atgaacggcg gcgctgaggc ctccgtcaat cacaggcgca gacaccaagc agcttccgct      60

aacggcgtta agatagcaaa cggggccatg gcgaagccgt cctcgacgct ctgctacgac     120

gcctcgttca tgaaatggac cgtggcggat gctgtccacg tggcgacgca tcattggatg     180

ccgtgcttat tcgcattagg gcttctcttc ttcatggccg tggaatacac gctcctcatg     240

gttccgccgt cgtcgccgcc tttcgatctg ggcttcattg ccacgcgttc cctccacgca     300

ctcctcgagt catcgccgaa tctcaacacg ctcttcgccg ggctcaatac ggtgtttgtg     360

gggatgcaaa cgagttatat cttatggacg tggctgattg aaggacgccc cagagccacg     420

atttcagcat tgttcatgtt cacatgccgt ggaattttag ggtactccac ccagctccca     480

ttgcctcagg gatttttggg ctcgggtgtg gatttcccag ttgggaacgt gtcgtttttc     540

ttgttttttt cggggcatgt tgcgggttca gtgattgctt ccttggacat gaggaggatg     600

cagaggtggg aactggcttg gacttttgat gtgctcaatg ttttgcaagc tgtgaggttg     660

ctgggtacaa gaggacatta cactattgat ttggccgtag ggttggtgc tggaattctc      720
```

tttgattctt tagctggcaa gtacgaagat agcaaaagga atgctgctct atccacaacc 780
cacagagcac aatttgattg cgtcaacaat gtggatatag ctaaaaaaat taacaaatga 840

<210> SEQ ID NO 66
<211> LENGTH: 279
<212> TYPE: PRT
<213> ORGANISM: Glycine max

<400> SEQUENCE: 66

Met Asn Gly Gly Ala Glu Ala Ser Val Asn His Arg Arg Arg His Gln
1 5 10 15

Ala Ala Ser Ala Asn Gly Val Lys Ile Ala Asn Gly Ala Met Ala Lys
20 25 30

Pro Ser Ser Thr Leu Cys Tyr Asp Ala Ser Phe Met Lys Trp Thr Val
35 40 45

Ala Asp Ala Val His Val Ala Thr His His Trp Met Pro Cys Leu Phe
50 55 60

Ala Leu Gly Leu Leu Phe Phe Met Ala Val Glu Tyr Thr Leu Leu Met
65 70 75 80

Val Pro Pro Ser Ser Pro Pro Phe Asp Leu Gly Phe Ile Ala Thr Arg
85 90 95

Ser Leu His Ala Leu Leu Glu Ser Ser Pro Asn Leu Asn Thr Leu Phe
100 105 110

Ala Gly Leu Asn Thr Val Phe Val Gly Met Gln Thr Ser Tyr Ile Leu
115 120 125

Trp Thr Trp Leu Ile Glu Gly Arg Pro Arg Ala Thr Ile Ser Ala Leu
130 135 140

Phe Met Phe Thr Cys Arg Gly Ile Leu Gly Tyr Ser Thr Gln Leu Pro
145 150 155 160

Leu Pro Gln Gly Phe Leu Gly Ser Gly Val Asp Phe Pro Val Gly Asn
165 170 175

Val Ser Phe Phe Leu Phe Phe Ser Gly His Val Ala Gly Ser Val Ile
180 185 190

Ala Ser Leu Asp Met Arg Arg Met Gln Arg Trp Glu Leu Ala Trp Thr
195 200 205

Phe Asp Val Leu Asn Val Leu Gln Ala Val Arg Leu Leu Gly Thr Arg
210 215 220

Gly His Tyr Thr Ile Asp Leu Ala Val Gly Val Gly Ala Gly Ile Leu
225 230 235 240

Phe Asp Ser Leu Ala Gly Lys Tyr Glu Asp Ser Lys Arg Asn Ala Ala
245 250 255

Leu Ser Thr Thr His Arg Ala Gln Phe Asp Cys Val Asn Asn Val Asp
260 265 270

Ile Ala Lys Lys Ile Asn Lys
275

<210> SEQ ID NO 67
<211> LENGTH: 858
<212> TYPE: DNA
<213> ORGANISM: Ricinus communis

<400> SEQUENCE: 67
atgaaatcca ccgtccctcc caccaccaca accacaacca caactactct ttacaagcgc 60
aagaaagaca tcaacttgac ctccgtcaac gacagtgttg acatggttag caacaagaac 120

-continued

```
tttgctaacg gtaatgttaa tggtggtggg ggctacactg cttttaatag gtttgaccca    180

tcgttcatga aatggacgac tcatgatgtg gtcaatgtag tcaagtttca ttggttaccg    240

tgtgtttttg gacttgggtt gctattcttt atggccgttg aatacactct tcgcatggtt    300

ccggcttctt ctccgccttt tgatttgggg tttctggtta cgcgccacct tcatctcttg    360

ctttcttctt ggccggcgct caacactttg ttggcttttc ttaatacggt gtttgttttg    420

atgcaaaccg catatatatt gtggacgtgg ctaatagagg gcagaccaag agctacaatt    480

tcggctttat tcatgttcac ttgccgtggg attcttggct actccactca gcttccactt    540

cctgagggat ttctgggatc aggagttgat tttccagtag gaaatgtgtc attcttcctg    600

tttttctccg gccatgtcgc ggggtctgtg atagcatcgc tcgatatgag aagaatgcag    660

agatgggaat tggcatggac atatgatgtg cttaatgttc tacaagctgt gaggctacta    720

ggcactagag gccactatac aatcgactta gcaactggtg taggtgctgg cattctgttt    780

gattcacttg cggggaaata tgaagagagc aagagaaaac aggctgttgt tgctaaagag    840

tcttctttgt ttagttaa                                                  858


<210> SEQ ID NO 68
<211> LENGTH: 285
<212> TYPE: PRT
<213> ORGANISM: Ricinus communis

<400> SEQUENCE: 68

Met Lys Ser Thr Val Pro Pro Thr Thr Thr Thr Thr Thr Thr Thr Thr
1               5                   10                  15

Leu Tyr Lys Arg Lys Lys Asp Ile Asn Leu Thr Ser Val Asn Asp Ser
            20                  25                  30

Val Asp Met Val Ser Asn Lys Asn Phe Ala Asn Gly Asn Val Asn Gly
        35                  40                  45

Gly Gly Gly Tyr Thr Ala Phe Asn Arg Phe Asp Pro Ser Phe Met Lys
    50                  55                  60

Trp Thr Thr His Asp Val Val Asn Val Val Lys Phe His Trp Leu Pro
65                  70                  75                  80

Cys Val Phe Gly Leu Gly Leu Leu Phe Phe Met Ala Val Glu Tyr Thr
                85                  90                  95

Leu Arg Met Val Pro Ala Ser Ser Pro Pro Phe Asp Leu Gly Phe Leu
            100                 105                 110

Val Thr Arg His Leu His Leu Leu Leu Ser Ser Trp Pro Ala Leu Asn
        115                 120                 125

Thr Leu Leu Ala Phe Leu Asn Thr Val Phe Val Leu Met Gln Thr Ala
    130                 135                 140

Tyr Ile Leu Trp Thr Trp Leu Ile Glu Gly Arg Pro Arg Ala Thr Ile
145                 150                 155                 160

Ser Ala Leu Phe Met Phe Thr Cys Arg Gly Ile Leu Gly Tyr Ser Thr
                165                 170                 175

Gln Leu Pro Leu Pro Glu Gly Phe Leu Gly Ser Gly Val Asp Phe Pro
            180                 185                 190

Val Gly Asn Val Ser Phe Phe Leu Phe Phe Ser Gly His Val Ala Gly
        195                 200                 205

Ser Val Ile Ala Ser Leu Asp Met Arg Arg Met Gln Arg Trp Glu Leu
    210                 215                 220

Ala Trp Thr Tyr Asp Val Leu Asn Val Leu Gln Ala Val Arg Leu Leu
225                 230                 235                 240
```

-continued

```
Gly Thr Arg Gly His Tyr Thr Ile Asp Leu Ala Thr Gly Val Gly Ala
                245                 250                 255

Gly Ile Leu Phe Asp Ser Leu Ala Gly Lys Tyr Glu Glu Ser Lys Arg
            260                 265                 270

Lys Gln Ala Val Val Ala Lys Glu Ser Ser Leu Phe Ser
        275                 280                 285
```

<210> SEQ ID NO 69
<211> LENGTH: 858
<212> TYPE: DNA
<213> ORGANISM: Ricinus communis

<400> SEQUENCE: 69

```
atgaaatcca ccgtccctcc caccaccaca accacaacca caactactct ttacaagcgc      60

aagaaagaca tcaacttgac ctccgtcaac gacagtgttg acatggttag caacaagaac     120

tttgctaacg gtaatgttaa tggtggtggg ggctacactg cttttaatag gtttgaccca     180

tcgttcatga aatggacgac tcatgatgtg gtcaatgtag tcaagtttca ttggttaccg     240

tgtgtttttg gacttgggtt gctattcttt atggccgttg aatacactct tcgcatggtt     300

ccggcttctt ctccgccttt tgatttgggg tttctggtta cgcgccacct tcatctcttg     360

ctttcttctt ggccggcgct caacactttg ttggcttttc ttaatacggt gtttgttttg     420

atgcaaaccg catatatatt gtggacgtgg ctaatagagg gcagaccaag agctacaatt     480

tcggctttat tcatgttcac ttgccgtggg attcttggct actccactca gcttccactt     540

cctgagggat ttctgggatc aggagttgat tttccagtag gaaatgtgtc attcttcctg     600

tttttctccg gccatgtcgc ggggtctgtg atagcatcgc tcgatatgag aagaatgcag     660

agatgggaat tggcatggac atatgatgtg cttaatgttc tacaagctgt gaggctacta     720

ggcactagag gccactatac aatcgactta gcaactggtg taggtgctgg cattctgttt     780

gattcacttg cggggaaata tgaagagagc aagagaaaac aggctgttgt tgctaaagag     840

tcttctttgt ttagttaa                                                   858
```

<210> SEQ ID NO 70
<211> LENGTH: 285
<212> TYPE: PRT
<213> ORGANISM: Ricinus communis

<400> SEQUENCE: 70

```
Met Lys Ser Thr Val Pro Pro Thr Thr Thr Thr Thr Thr Thr Thr Thr
1               5                   10                  15

Leu Tyr Lys Arg Lys Lys Asp Ile Asn Leu Thr Ser Val Asn Asp Ser
            20                  25                  30

Val Asp Met Val Ser Asn Lys Asn Phe Ala Asn Gly Asn Val Asn Gly
        35                  40                  45

Gly Gly Gly Tyr Thr Ala Phe Asn Arg Phe Asp Pro Ser Phe Met Lys
    50                  55                  60

Trp Thr Thr His Asp Val Val Asn Val Val Lys Phe His Trp Leu Pro
65                  70                  75                  80

Cys Val Phe Gly Leu Gly Leu Leu Phe Phe Met Ala Val Glu Tyr Thr
                85                  90                  95

Leu Arg Met Val Pro Ala Ser Ser Pro Pro Phe Asp Leu Gly Phe Leu
            100                 105                 110

Val Thr Arg His Leu His Leu Leu Leu Ser Ser Trp Pro Ala Leu Asn
        115                 120                 125
```

-continued

```
Thr Leu Leu Ala Phe Leu Asn Thr Val Phe Val Leu Met Gln Thr Ala
    130                 135                 140

Tyr Ile Leu Trp Thr Trp Leu Ile Glu Gly Arg Pro Arg Ala Thr Ile
145                 150                 155                 160

Ser Ala Leu Phe Met Phe Thr Cys Arg Gly Ile Leu Gly Tyr Ser Thr
                165                 170                 175

Gln Leu Pro Leu Pro Glu Gly Phe Leu Gly Ser Gly Val Asp Phe Pro
            180                 185                 190

Val Gly Asn Val Ser Phe Phe Leu Phe Phe Ser Gly His Val Ala Gly
        195                 200                 205

Ser Val Ile Ala Ser Leu Asp Met Arg Arg Met Gln Arg Trp Glu Leu
    210                 215                 220

Ala Trp Thr Tyr Asp Val Leu Asn Val Leu Gln Ala Val Arg Leu Leu
225                 230                 235                 240

Gly Thr Arg Gly His Tyr Thr Ile Asp Leu Ala Thr Gly Val Gly Ala
                245                 250                 255

Gly Ile Leu Phe Asp Ser Leu Ala Gly Lys Tyr Glu Glu Ser Lys Arg
            260                 265                 270

Lys Gln Ala Val Val Ala Lys Glu Ser Ser Leu Phe Ser
        275                 280                 285
```

<210> SEQ ID NO 71
<211> LENGTH: 831
<212> TYPE: DNA
<213> ORGANISM: Linum usitatissimum

<400> SEQUENCE: 71

```
atgtctgccg cacccaccac caccgtggca gccaccgcca ttccgttgaa gcgcaagaaa      60

acggatgctg ctgctaaaac acagaaaaac aaccagggaa atgaggacga acaggaggca     120

atagtggaga gcgtggcgcc ggcgtttacg aaatggagga ggagagatgc gatgaatgcg     180

gttagggagc attggttgcc tgtcatattg ggaggtgccc tgttgttttt catgtgggtt     240

gagtacaccc tcaggatggt cccgacctcc tcacaaccct ttgatttagg gttcgtggcc     300

acccgagctc tccatcgcct tctttcttcc tcgccggagc tcaactccgt cctcgccgct     360

ctcaacacgg tgttcgtggg aatgcagaca agctacatac tgtggacgtt tgtggtggag     420

ggaaggggga gacccactat ctctgcactt ttcatgttca cttgccgtgg aattcttggc     480

tattccactc agcttcctct ccccgaggga tatttggggt cgggagtgga cttcccagta     540

gggaacgtgt cgtttttcct gttcttctcc gggcacgtgg cgggatcagt aatagcatca     600

caggatatga ggagaatgca aaggtgggag cttgccttgg gatttgaatt cctcaacgcc     660

ttacaagtgg tcaggctact cgccaccaga ggtcactaca ccattgattt ggccgctggt     720

tatgccgccg gtctactctt tgactcactt gccggacgtt atctccaaac caagaccgcc     780

actgctgctg ctcttcttac cacttctccc agaaaatttg tcaccaacta g              831
```

<210> SEQ ID NO 72
<211> LENGTH: 276
<212> TYPE: PRT
<213> ORGANISM: Linum usitatissimum

<400> SEQUENCE: 72

```
Met Ser Ala Ala Pro Thr Thr Thr Val Ala Ala Thr Ala Ile Pro Leu
1               5                   10                  15

Lys Arg Lys Lys Thr Asp Ala Ala Ala Lys Thr Gln Lys Asn Asn Gln
            20                  25                  30
```

```
Gly Asn Glu Asp Glu Gln Glu Ala Ile Val Glu Ser Val Ala Pro Ala
        35                  40                  45

Phe Thr Lys Trp Arg Arg Arg Asp Ala Met Asn Ala Val Arg Glu His
    50                  55                  60

Trp Leu Pro Val Ile Leu Gly Gly Ala Leu Leu Phe Phe Met Trp Val
65                  70                  75                  80

Glu Tyr Thr Leu Arg Met Val Pro Thr Ser Ser Gln Pro Phe Asp Leu
                85                  90                  95

Gly Phe Val Ala Thr Arg Ala Leu His Arg Leu Leu Ser Ser Ser Pro
            100                 105                 110

Glu Leu Asn Ser Val Leu Ala Ala Leu Asn Thr Val Phe Val Gly Met
        115                 120                 125

Gln Thr Ser Tyr Ile Leu Trp Thr Phe Val Val Glu Gly Arg Gly Arg
    130                 135                 140

Pro Thr Ile Ser Ala Leu Phe Met Phe Thr Cys Arg Gly Ile Leu Gly
145                 150                 155                 160

Tyr Ser Thr Gln Leu Pro Leu Pro Glu Gly Tyr Leu Gly Ser Gly Val
                165                 170                 175

Asp Phe Pro Val Gly Asn Val Ser Phe Phe Leu Phe Phe Ser Gly His
            180                 185                 190

Val Ala Gly Ser Val Ile Ala Ser Gln Asp Met Arg Arg Met Gln Arg
        195                 200                 205

Trp Glu Leu Ala Leu Gly Phe Glu Phe Leu Asn Ala Leu Gln Val Val
    210                 215                 220

Arg Leu Leu Ala Thr Arg Gly His Tyr Thr Ile Asp Leu Ala Ala Gly
225                 230                 235                 240

Tyr Ala Ala Gly Leu Leu Phe Asp Ser Leu Ala Gly Arg Tyr Leu Gln
                245                 250                 255

Thr Lys Thr Ala Thr Ala Ala Ala Leu Leu Thr Thr Ser Pro Arg Lys
            260                 265                 270

Phe Val Thr Asn
        275
```

<210> SEQ ID NO 73
<211> LENGTH: 831
<212> TYPE: DNA
<213> ORGANISM: Linum usitatissimum

<400> SEQUENCE: 73

```
atgtctgcca cacccaccgc cgccgtggca gccaccgcca ttccgttgaa gcgcaagaaa     60

acggatgctg ctgctaaaac acagaaaaac aaccagggaa atgaggacga acaggaggca    120

atagtggaga gcgtggcgcc ggcgtttacg aaatggagga ggagagatgc gatgaatgcg    180

gtcagggagc attggttgcc tgtcatgttg ggaggtgccc tgttgttttt catgtgggtt    240

gagtacaccc tcaggatggt cccgacctcc tcacagccct ttgatttagg gttcgtggcc    300

acccgagctc tccatcgcct tctttcttcc tcgccggagc tcaactccgt cctcgccgct    360

ctcaacacgg tgttcgtggg aatgcagaca agctacatat tgtggacgtt tgtggtggag    420

ggaaggggga gacccactat ctctgcactt ttcatgttca cttgccgtgg aattcttggc    480

tattccactc agcttcctct cccagaggga tatttggggt cgggagtgga cttcccagta    540

gggaacgtgt cgtttttcct ctttttctcg ggacacgtgg cgggatcagt gatagcatca    600

caggatatga ggagaatgca aaggtgggag ctggccttgg gatttgaatt cctcaacgcc    660
```

ttacaagtag tcaggctact cgccaccaga ggtcactaca ccattgattt ggccgccggt 720
tatgccgccg gtctgctctt tgactcactt gccggacgtt acctccaaac caagaccgcc 780
actgctgctg ctcttcttac cacctctccc agaaaatttg tcaccaacta g 831

<210> SEQ ID NO 74
<211> LENGTH: 276
<212> TYPE: PRT
<213> ORGANISM: Linum usitatissimum

<400> SEQUENCE: 74

Met Ser Ala Thr Pro Thr Ala Ala Val Ala Ala Thr Ala Ile Pro Leu
1 5 10 15

Lys Arg Lys Lys Thr Asp Ala Ala Ala Lys Thr Gln Lys Asn Asn Gln
20 25 30

Gly Asn Glu Asp Glu Gln Glu Ala Ile Val Glu Ser Val Ala Pro Ala
35 40 45

Phe Thr Lys Trp Arg Arg Arg Asp Ala Met Asn Ala Val Arg Glu His
50 55 60

Trp Leu Pro Val Met Leu Gly Gly Ala Leu Leu Phe Phe Met Trp Val
65 70 75 80

Glu Tyr Thr Leu Arg Met Val Pro Thr Ser Ser Gln Pro Phe Asp Leu
85 90 95

Gly Phe Val Ala Thr Arg Ala Leu His Arg Leu Leu Ser Ser Ser Pro
100 105 110

Glu Leu Asn Ser Val Leu Ala Ala Leu Asn Thr Val Phe Val Gly Met
115 120 125

Gln Thr Ser Tyr Ile Leu Trp Thr Phe Val Val Glu Gly Arg Gly Arg
130 135 140

Pro Thr Ile Ser Ala Leu Phe Met Phe Thr Cys Arg Gly Ile Leu Gly
145 150 155 160

Tyr Ser Thr Gln Leu Pro Leu Pro Glu Gly Tyr Leu Gly Ser Gly Val
165 170 175

Asp Phe Pro Val Gly Asn Val Ser Phe Phe Leu Phe Phe Ser Gly His
180 185 190

Val Ala Gly Ser Val Ile Ala Ser Gln Asp Met Arg Arg Met Gln Arg
195 200 205

Trp Glu Leu Ala Leu Gly Phe Glu Phe Leu Asn Ala Leu Gln Val Val
210 215 220

Arg Leu Leu Ala Thr Arg Gly His Tyr Thr Ile Asp Leu Ala Ala Gly
225 230 235 240

Tyr Ala Ala Gly Leu Leu Phe Asp Ser Leu Ala Gly Arg Tyr Leu Gln
245 250 255

Thr Lys Thr Ala Thr Ala Ala Ala Leu Leu Thr Thr Ser Pro Arg Lys
260 265 270

Phe Val Thr Asn
275

<210> SEQ ID NO 75
<211> LENGTH: 924
<212> TYPE: DNA
<213> ORGANISM: Oryza sativa

<400> SEQUENCE: 75
atgccgccgc cgccgccgcc cagcctcacg gccaacaccg catcctccat gggcaacgcc 60
gaggccgtcg tggtgctgcc cgcgaacggc ggcgcgcggc ggcgcgccga caaggtcgtc 120

```
caccccggcgc cgatgccgga cagagcagct ggtggcgcga tggagaggga aggcggcggc    180

gtcggcggcg gcggcgaggt gggtgggtgg aggaggccgg agtggtgctc ggcggcgggg    240

gtggcggggg tcctgcggcg gcacccggcg gcggcggcgt tcgggtgcgg gctgctgctg    300

ttcatggccg tggagtacac catccccatg gtgccgcccg ccgcgccgcc ggtcgacctc    360

ggcttcgccg ccaccgccgc gctccacgcc gggatcgccg cccgcccatg gctcaactcg    420

ctcctcgccg cgctcaacac ggtgttcgtg gcgatgcagg cggcgtacat cctgtgggcg    480

atcctcggcg agggccggcc gcgcgccgcc gtggcggcga tgatgatgtt cacctgccgc    540

ggcgcgctcg gctgcgccac gcagctgccg ctgccggccg agttcctggg ctccggcatg    600

gacttccccg tcggcaacgt ctccttcttc ctcttcttct ccggccacgt cgccggcgcg    660

gtgatcgccg ccgaggacat gcgccgcgcg gggcgccgcg gcatggcgcg cctctacgac    720

gcgctcaacc tgctccaggg cgtcaggctg ctcgcctgca ggggccacta caccatcgac    780

ctcgccgtcg gcgtcggcgc cggcctcctc ttcgacatgc tcgccggcag gtacctggac    840

ggcaagaaca ccgtcgacgg cggcgccgcc gtggcgccgg ggagccggtg ctgcagctgc    900

cacaaggctc tcttgtcaca gtag                                            924
```

<210> SEQ ID NO 76
<211> LENGTH: 307
<212> TYPE: PRT
<213> ORGANISM: Oryza sativa

<400> SEQUENCE: 76

```
Met Pro Pro Pro Pro Pro Pro Ser Leu Thr Ala Asn Thr Ala Ser Ser
1               5                   10                  15

Met Gly Asn Ala Glu Ala Val Val Val Leu Pro Ala Asn Gly Gly Ala
            20                  25                  30

Arg Arg Arg Ala Asp Lys Val Val His Pro Ala Pro Met Pro Asp Arg
        35                  40                  45

Ala Ala Gly Gly Ala Met Glu Arg Glu Gly Gly Gly Val Gly Gly Gly
    50                  55                  60

Gly Glu Val Gly Gly Trp Arg Arg Pro Glu Trp Cys Ser Ala Ala Gly
65                  70                  75                  80

Val Ala Gly Val Leu Arg Arg His Pro Ala Ala Ala Ala Phe Gly Cys
                85                  90                  95

Gly Leu Leu Leu Phe Met Ala Val Glu Tyr Thr Ile Pro Met Val Pro
            100                 105                 110

Pro Ala Ala Pro Pro Val Asp Leu Gly Phe Ala Ala Thr Ala Ala Leu
        115                 120                 125

His Ala Gly Ile Ala Ala Arg Pro Trp Leu Asn Ser Leu Leu Ala Ala
    130                 135                 140

Leu Asn Thr Val Phe Val Ala Met Gln Ala Ala Tyr Ile Leu Trp Ala
145                 150                 155                 160

Ile Leu Gly Glu Gly Arg Pro Arg Ala Ala Val Ala Ala Met Met Met
                165                 170                 175

Phe Thr Cys Arg Gly Ala Leu Gly Cys Ala Thr Gln Leu Pro Leu Pro
            180                 185                 190

Ala Glu Phe Leu Gly Ser Gly Met Asp Phe Pro Val Gly Asn Val Ser
        195                 200                 205

Phe Phe Leu Phe Phe Ser Gly His Val Ala Gly Ala Val Ile Ala Ala
    210                 215                 220
```

-continued

```
Glu Asp Met Arg Arg Ala Gly Arg Arg Gly Met Ala Arg Leu Tyr Asp
225                 230                 235                 240

Ala Leu Asn Leu Leu Gln Gly Val Arg Leu Leu Ala Cys Arg Gly His
                245                 250                 255

Tyr Thr Ile Asp Leu Ala Val Gly Val Gly Ala Gly Leu Leu Phe Asp
            260                 265                 270

Met Leu Ala Gly Arg Tyr Leu Asp Gly Lys Asn Thr Val Asp Gly Gly
        275                 280                 285

Ala Ala Val Ala Pro Gly Ser Arg Cys Cys Ser Cys His Lys Ala Leu
    290                 295                 300

Leu Ser Gln
305
```

<210> SEQ ID NO 77
<211> LENGTH: 849
<212> TYPE: DNA
<213> ORGANISM: Zea mays
<220> FEATURE:
<221> NAME/KEY: misc_feature
<222> LOCATION: (726)..(726)
<223> OTHER INFORMATION: s is g or c

<400> SEQUENCE: 77

```
atgccgccgc ccagcctcac cgccgccggc accaccacca ccacaacccg ccgccgcaac      60

gaccgagccg cgaaggtcca ccaggtactg ggcgaaggcg cggggacgga ggagatgggc     120

gcggtggcgg acgggtggac gcggcccgag tggtgctcgg cggcgggcgt cgcgggcgtg     180

ctgcggcggc acccggcgcc cgcgctcttc gggtgcggcc tcctgctctt catggccgtc     240

gagtacacca tccccatggt caagccggac gcgccgccgc tcgacctagg cttcctcgcc     300

accgcgggca tgcacgccgc catcgccgcg aggccctggc ttaactcgct cctcgccgcg     360

ctcaacacgg tcttcgtcgc gatgcaggcg gcgtacatcc tgtgggccat cctcgccgag     420

cagcggccgc gcgcggccgt cgccgcgctc atgatgttca cttgccgggg cgtgctgggc     480

tgcgccaccc agctcccgct gccggaggag ttcctgggct ccgggatgga cttccccgtg     540

ggcaacgtct ccttcttcct cttcttctcg ggccacgtcg cgggcgcggt gatcgcggcg     600

gccgacatgc ggcgcgaggg gcggctggcg ctggcgcgcc tcttcgactc gctcaacgtg     660

ctccaggtgg tcaggctgct cgcgtgcagg ggacactaca ccattgacct ggctgttggc     720

gttggsgcgg gcatcctctt cgacacgctc tccggatggt acttcgacgc caagaacggc     780

gatagcagca acgcaccgga gaagcagtgc cggagctgcc agtgccacaa ggccctcctt     840

tcacactag                                                             849
```

<210> SEQ ID NO 78
<211> LENGTH: 282
<212> TYPE: PRT
<213> ORGANISM: Zea mays

<400> SEQUENCE: 78

```
Met Pro Pro Pro Ser Leu Thr Ala Ala Gly Thr Thr Thr Thr Thr Thr
1               5                   10                  15

Arg Arg Arg Asn Asp Arg Ala Ala Lys Val His Gln Val Leu Gly Glu
            20                  25                  30

Gly Ala Gly Thr Glu Glu Met Gly Ala Val Ala Asp Gly Trp Thr Arg
        35                  40                  45

Pro Glu Trp Cys Ser Ala Ala Gly Val Ala Gly Val Leu Arg Arg His
    50                  55                  60
```

```
Pro Ala Pro Ala Leu Phe Gly Cys Gly Leu Leu Leu Phe Met Ala Val
65                  70                  75                  80

Glu Tyr Thr Ile Pro Met Val Lys Pro Asp Ala Pro Pro Leu Asp Leu
                85                  90                  95

Gly Phe Leu Ala Thr Ala Gly Met His Ala Ala Ile Ala Ala Arg Pro
            100                 105                 110

Trp Leu Asn Ser Leu Leu Ala Ala Leu Asn Thr Val Phe Val Ala Met
        115                 120                 125

Gln Ala Ala Tyr Ile Leu Trp Ala Ile Leu Ala Glu Gln Arg Pro Arg
    130                 135                 140

Ala Ala Val Ala Ala Leu Met Met Phe Thr Cys Arg Gly Val Leu Gly
145                 150                 155                 160

Cys Ala Thr Gln Leu Pro Leu Pro Glu Glu Phe Leu Gly Ser Gly Met
                165                 170                 175

Asp Phe Pro Val Gly Asn Val Ser Phe Phe Leu Phe Phe Ser Gly His
            180                 185                 190

Val Ala Gly Ala Val Ile Ala Ala Ala Asp Met Arg Arg Glu Gly Arg
        195                 200                 205

Leu Ala Leu Ala Arg Leu Phe Asp Ser Leu Asn Val Leu Gln Val Val
    210                 215                 220

Arg Leu Leu Ala Cys Arg Gly His Tyr Thr Ile Asp Leu Ala Val Gly
225                 230                 235                 240

Val Gly Ala Gly Ile Leu Phe Asp Thr Leu Ser Gly Trp Tyr Phe Asp
                245                 250                 255

Ala Lys Asn Gly Asp Ser Ser Asn Ala Pro Glu Lys Gln Cys Arg Ser
            260                 265                 270

Cys Gln Cys His Lys Ala Leu Leu Ser His
        275                 280
```

<210> SEQ ID NO 79
<211> LENGTH: 825
<212> TYPE: DNA
<213> ORGANISM: Zea mays
<220> FEATURE:
<221> NAME/KEY: misc_feature
<222> LOCATION: (412)..(412)
<223> OTHER INFORMATION: m is a or c
<220> FEATURE:
<221> NAME/KEY: misc_feature
<222> LOCATION: (635)..(635)
<223> OTHER INFORMATION: w is a or t

<400> SEQUENCE: 79

```
atgccgccgc ccagcctcac cgtggcgcgc gacccggccg ccgccgccac cacgcggcac     60

cgcaaggtcc acccgacgcc gggcggaggc gcagggacga cgaaggagat gggcgcggcg    120

gaggggtggg cgcggcccga gtggtgctcg gcggcgggcg ccgcggccgt gctgcggcgg    180

cacccggcgc ccgcgctctt cgggtgcggc ctcctgctct tcatggccgt cgagtacacc    240

atccccatgg tcaggccgga cgcgccgccg ctcgacctgg gcttcgtcgc caccaggggc    300

ttgcacgccg ccgtcgccgc gaggccctgg ctcaactcgc tcctcgccgc gctcaacacg    360

gtcttcgtcg cgatgcaggc ggcgtacatc ctgtgggcca tcctcggcga gmagcggccg    420

cgcgccgccg tcgccacgct catgatgttc acctgccggg gcgcgctggg ctgcgccacc    480

cagctcccgc tgccggagga gttcctgggg tccgggatgg acttccccgt gggcaacgtc    540

tccttcttcc tcttcttctc gggccacgtc gcgggcgcgg tcatcgcggc cgccgacatg    600
```

-continued

```
cgccgcgagg gccggctggc gctggcgcgc ctctwcgacg cgctcaacgc gctccagggg    660

gtcaggctgc tggcgtgcag gggacactac accatcgacc tggccgtcgg tgtcggagcg    720

gggatcctct tcgatacgct ctccggatgg tacttccacg ccaagaacgc accggagaag    780

cactgccgca gctgccagtg ccacaaggct ctcctttcac gctag                    825
```

<210> SEQ ID NO 80
<211> LENGTH: 274
<212> TYPE: PRT
<213> ORGANISM: Zea mays
<220> FEATURE:
<221> NAME/KEY: MISC_FEATURE
<222> LOCATION: (138)..(138)
<223> OTHER INFORMATION: Xaa is Lys or Gln
<220> FEATURE:
<221> NAME/KEY: MISC_FEATURE
<222> LOCATION: (212)..(212)
<223> OTHER INFORMATION: Xaa is Tyr or Phe

<400> SEQUENCE: 80

```
Met Pro Pro Pro Ser Leu Thr Val Ala Arg Asp Pro Ala Ala Ala Ala
1               5                   10                  15

Thr Thr Arg His Arg Lys Val His Pro Thr Pro Gly Gly Gly Ala Gly
            20                  25                  30

Thr Thr Lys Glu Met Gly Ala Ala Glu Gly Trp Ala Arg Pro Glu Trp
        35                  40                  45

Cys Ser Ala Ala Gly Ala Ala Ala Val Leu Arg Arg His Pro Ala Pro
    50                  55                  60

Ala Leu Phe Gly Cys Gly Leu Leu Leu Phe Met Ala Val Glu Tyr Thr
65                  70                  75                  80

Ile Pro Met Val Arg Pro Asp Ala Pro Pro Leu Asp Leu Gly Phe Val
                85                  90                  95

Ala Thr Arg Gly Leu His Ala Ala Val Ala Ala Arg Pro Trp Leu Asn
            100                 105                 110

Ser Leu Leu Ala Ala Leu Asn Thr Val Phe Val Ala Met Gln Ala Ala
        115                 120                 125

Tyr Ile Leu Trp Ala Ile Leu Gly Glu Xaa Arg Pro Arg Ala Ala Val
    130                 135                 140

Ala Thr Leu Met Met Phe Thr Cys Arg Gly Ala Leu Gly Cys Ala Thr
145                 150                 155                 160

Gln Leu Pro Leu Pro Glu Glu Phe Leu Gly Ser Gly Met Asp Phe Pro
                165                 170                 175

Val Gly Asn Val Ser Phe Phe Leu Phe Phe Ser Gly His Val Ala Gly
            180                 185                 190

Ala Val Ile Ala Ala Ala Asp Met Arg Arg Glu Gly Arg Leu Ala Leu
        195                 200                 205

Ala Arg Leu Xaa Asp Ala Leu Asn Ala Leu Gln Gly Val Arg Leu Leu
    210                 215                 220

Ala Cys Arg Gly His Tyr Thr Ile Asp Leu Ala Val Gly Val Gly Ala
225                 230                 235                 240

Gly Ile Leu Phe Asp Thr Leu Ser Gly Trp Tyr Phe His Ala Lys Asn
                245                 250                 255

Ala Pro Glu Lys His Cys Arg Ser Cys Gln Cys His Lys Ala Leu Leu
            260                 265                 270

Ser Arg
```

<210> SEQ ID NO 81

<211> LENGTH: 301
<212> TYPE: PRT
<213> ORGANISM: Artificial Sequence
<220> FEATURE:
<223> OTHER INFORMATION: At ROD1

<400> SEQUENCE: 81

```
Met Ser Ala Ala Ala Ala Glu Thr Asp Val Ser Leu Arg Arg Arg Ser
1               5                   10                  15

Asn Ser Leu Asn Gly Asn His Thr Asn Gly Val Ala Ile Asp Gly Thr
            20                  25                  30

Leu Asp Asn Asn Asn Arg Arg Val Gly Asp Thr Asn Thr His Met Asp
        35                  40                  45

Ile Ser Ala Lys Lys Thr Asp Asn Gly Tyr Ala Asn Gly Val Gly Gly
    50                  55                  60

Gly Gly Trp Arg Ser Lys Ala Ser Phe Thr Thr Trp Thr Ala Arg Asp
65                  70                  75                  80

Ile Val Tyr Val Val Arg Tyr His Trp Ile Pro Cys Met Phe Ala Ala
                85                  90                  95

Gly Leu Leu Phe Phe Met Gly Val Glu Tyr Thr Leu Gln Met Ile Pro
            100                 105                 110

Ala Arg Ser Glu Pro Phe Asp Leu Gly Phe Val Val Thr Arg Ser Leu
        115                 120                 125

Asn Arg Val Leu Ala Ser Ser Pro Asp Leu Asn Thr Val Leu Ala Ala
    130                 135                 140

Leu Asn Thr Val Phe Val Gly Met Gln Thr Thr Tyr Ile Val Trp Thr
145                 150                 155                 160

Trp Leu Val Glu Gly Arg Ala Arg Ala Thr Ile Ala Ala Leu Phe Met
                165                 170                 175

Phe Thr Cys Arg Gly Ile Leu Gly Tyr Ser Thr Gln Leu Pro Leu Pro
            180                 185                 190

Gln Asp Phe Leu Gly Ser Gly Val Asp Phe Pro Val Gly Asn Val Ser
        195                 200                 205

Phe Phe Leu Phe Phe Ser Gly His Val Ala Gly Ser Met Ile Ala Ser
    210                 215                 220

Leu Asp Met Arg Arg Met Gln Arg Leu Arg Leu Ala Met Val Phe Asp
225                 230                 235                 240

Ile Leu Asn Val Leu Gln Ser Ile Arg Leu Leu Gly Thr Arg Gly His
                245                 250                 255

Tyr Thr Ile Asp Leu Ala Val Gly Val Gly Ala Gly Ile Leu Phe Asp
            260                 265                 270

Ser Leu Ala Gly Lys Tyr Glu Glu Met Met Ser Lys Arg His Leu Gly
        275                 280                 285

Thr Gly Phe Ser Leu Ile Ser Lys Asp Ser Leu Val Asn
    290                 295                 300
```

<210> SEQ ID NO 82
<211> LENGTH: 289
<212> TYPE: PRT
<213> ORGANISM: Artificial Sequence
<220> FEATURE:
<223> OTHER INFORMATION: Bc 1A

<400> SEQUENCE: 82

```
Met Ser Thr Thr Thr Ile Val Pro Leu Arg Arg Thr Ser Asn Ser Leu
1               5                   10                  15

Asn Glu Tyr His Thr Asn Ala Val Ala Phe Asp Gly Ile Val Gly Ser
```

```
            20                  25                  30

Ala Ser Thr Ser Gln Met Glu Glu Ile Val Thr Gln Thr Asp Asp Cys
        35                  40                  45

Tyr Ala Asn Pro Asn Gly Asp Gly Gly Arg Ser Lys Thr Ser Leu Met
    50                  55                  60

Thr Trp Arg Met Cys Asn Pro Val His Val Val Arg Val His Trp Ile
65                  70                  75                  80

Pro Cys Leu Leu Ala Val Gly Val Leu Phe Phe Thr Cys Val Glu Glu
                85                  90                  95

Tyr Met Leu Gln Met Ile Pro Ala Ser Ser Glu Pro Phe Asp Ile Gly
            100                 105                 110

Phe Val Ala Thr Gly Ser Leu Tyr Arg Leu Leu Ala Ser Ser Pro Asp
        115                 120                 125

Leu Asn Thr Val Leu Ala Ala Leu Asn Thr Val Phe Val Gly Met Gln
    130                 135                 140

Thr Thr Tyr Ile Leu Trp Thr Trp Leu Val Glu Gly Arg Pro Arg Ala
145                 150                 155                 160

Thr Ile Ser Ala Cys Phe Met Phe Thr Cys Arg Gly Ile Leu Gly Tyr
                165                 170                 175

Ser Thr Gln Leu Pro Leu Pro Gln Asp Phe Leu Gly Ser Gly Val Asp
            180                 185                 190

Phe Pro Val Gly Asn Val Ser Phe Phe Leu Phe Tyr Ser Gly His Val
        195                 200                 205

Ala Gly Ser Thr Ile Ala Ser Leu Asp Met Arg Arg Met Lys Arg Leu
    210                 215                 220

Arg Leu Ala Leu Leu Phe Asp Ile Leu Asn Val Leu Gln Ser Ile Arg
225                 230                 235                 240

Leu Leu Gly Thr Arg Gly Gln Tyr Thr Ile Asp Leu Ala Val Gly Val
                245                 250                 255

Gly Ala Gly Val Leu Phe Asp Ser Leu Ala Gly Lys Tyr Glu Glu Met
            260                 265                 270

Met Ser Lys Arg His Asn Val Gly Asn Gly Phe Ser Leu Ile Ser Ser
        275                 280                 285

Arg


<210> SEQ ID NO 83
<211> LENGTH: 290
<212> TYPE: PRT
<213> ORGANISM: Artificial Sequence
<220> FEATURE:
<223> OTHER INFORMATION: Bc 1B

<400> SEQUENCE: 83

Met Ser Thr Thr Thr Ile Ile Pro Leu Arg Arg Ser Ser Asn Ser Leu
1               5                   10                  15

Asn Glu Tyr His Thr Asn Ser Val Ala Phe Asp Gly Ile Val Gly Ser
            20                  25                  30

Thr Ser Thr Ser Gln Met Glu Glu Ile Val Thr Gln Thr Asp Glu Gly
        35                  40                  45

Tyr Ala Asn Pro Asn Gly Asp Gly Gly Arg Ser Lys Val Ser Phe Met
    50                  55                  60

Thr Trp Arg Met Cys Ser Ala Val His Val Val Arg Val His Trp Ile
65                  70                  75                  80

Pro Cys Leu Leu Ala Val Gly Val Leu Phe Phe Thr Gly Val Glu Glu
                85                  90                  95
```

-continued

```
Tyr Met Leu Gln Met Ile Pro Pro Ser Ser Glu Pro Phe Asp Ile Gly
            100                 105                 110

Phe Val Ala Thr Arg Ser Leu Tyr Arg Leu Leu Ala Ser Ser Pro Asp
        115                 120                 125

Leu Asn Thr Val Leu Ala Ala Leu Asn Thr Val Phe Val Gly Met Gln
    130                 135                 140

Thr Thr Tyr Ile Val Trp Thr Trp Leu Met Glu Gly Arg Pro Arg Ala
145                 150                 155                 160

Thr Ile Ser Ala Cys Phe Met Phe Thr Cys Arg Gly Ile Leu Gly Tyr
                165                 170                 175

Ser Thr Gln Leu Pro Leu Pro Gln Asp Phe Leu Gly Ser Gly Val Asp
            180                 185                 190

Phe Pro Val Gly Asn Val Ser Phe Phe Leu Phe Tyr Ser Gly His Val
        195                 200                 205

Ala Gly Ser Thr Ile Ala Ser Leu Asp Met Arg Arg Met Lys Arg Leu
    210                 215                 220

Arg Leu Ala Ala Leu Leu Phe Asp Ile Leu Asn Val Leu Gln Ser Ile
225                 230                 235                 240

Arg Leu Leu Gly Thr Arg Gly Gln Tyr Thr Ile Asp Leu Ala Val Gly
                245                 250                 255

Val Gly Ala Gly Val Leu Phe Asp Ser Leu Ala Gly Lys Tyr Glu Glu
            260                 265                 270

Met Met Ser Lys Arg His Asn Val Gly Asn Gly Phe Ser Leu Ile Ser
        275                 280                 285

Thr Arg
    290
```

<210> SEQ ID NO 84
<211> LENGTH: 289
<212> TYPE: PRT
<213> ORGANISM: Artificial Sequence
<220> FEATURE:
<223> OTHER INFORMATION: Bc 1C

<400> SEQUENCE: 84

```
Met Ser Thr Thr Thr Ile Val Pro Leu Arg Arg Ser Ser Asn Ser Leu
1               5                   10                  15

Asn Glu Tyr His Thr Asn Ala Val Ala Phe Asp Gly Ile Val Gly Ser
            20                  25                  30

Thr Ser Thr Ser Gln Met Glu Glu Ile Val Thr Gln Thr Asp Asp Cys
        35                  40                  45

Tyr Ala Asn His Asn Gly Asp Gly Gly Arg Ser Lys Ala Ser Phe Met
    50                  55                  60

Thr Trp Arg Met Cys Asn Pro Val Gln Val Ala Arg Val His Trp Ile
65                  70                  75                  80

Pro Cys Leu Leu Ala Val Gly Val Leu Phe Phe Thr Gly Val Glu Glu
                85                  90                  95

Tyr Met Leu Gln Met Ile Pro Ala Ser Ser Glu Pro Phe Asp Ile Gly
            100                 105                 110

Phe Val Ala Thr Arg Ser Leu Tyr Arg Leu Leu Ala Ser Ser Pro Asp
        115                 120                 125

Leu Asn Thr Val Leu Ala Ala Leu Asn Thr Val Phe Val Gly Met Gln
    130                 135                 140

Thr Thr Tyr Ile Leu Trp Thr Trp Leu Val Glu Gly Arg Pro Arg Ala
145                 150                 155                 160
```

-continued

```
Thr Ile Ser Ala Cys Phe Met Phe Thr Cys Arg Gly Ile Leu Gly Tyr
                165                 170                 175

Ser Thr Gln Leu Pro Leu Pro Gln Asp Phe Leu Gly Ser Gly Val Asp
            180                 185                 190

Phe Pro Val Gly Asn Val Ser Phe Phe Leu Phe Tyr Ser Gly His Val
        195                 200                 205

Ala Gly Ser Met Ile Thr Ser Leu Asp Met Arg Arg Met Gln Arg Leu
    210                 215                 220

Arg Leu Ala Leu Leu Phe Asp Ile Leu Asn Val Leu Gln Ser Ile Arg
225                 230                 235                 240

Leu Leu Gly Thr Arg Gly Gln Tyr Thr Ile Asp Leu Ala Val Gly Val
                245                 250                 255

Gly Ala Gly Val Leu Phe Asp Ser Leu Ala Gly Lys Tyr Glu Glu Met
            260                 265                 270

Met Ser Lys Arg Arg Asn Val Gly Asn Gly Phe Ser Leu Ile Ser Ser
        275                 280                 285

Arg


<210> SEQ ID NO 85
<211> LENGTH: 289
<212> TYPE: PRT
<213> ORGANISM: Artificial Sequence
<220> FEATURE:
<223> OTHER INFORMATION: Bn 1C

<400> SEQUENCE: 85

Met Ser Thr Thr Thr Ile Val Pro Leu Arg Arg Ser Ser Asn Ser Leu
1               5                   10                  15

Asn Glu Tyr His Thr Asn Ala Val Ala Phe Asp Gly Ile Val Gly Ser
            20                  25                  30

Thr Ser Thr Ser Gln Met Glu Glu Ile Val Thr Gln Thr Asp Asp Cys
        35                  40                  45

Tyr Ala Asn His Asn Gly Asp Gly Gly Arg Ser Lys Ala Ser Phe Met
    50                  55                  60

Thr Trp Arg Met Cys Asn Pro Val Gln Val Ala Arg Val His Trp Ile
65                  70                  75                  80

Pro Cys Leu Leu Ala Val Gly Val Leu Phe Phe Thr Gly Val Glu Glu
                85                  90                  95

Tyr Met Leu Gln Met Ile Pro Ala Ser Ser Glu Pro Phe Asp Ile Gly
            100                 105                 110

Phe Val Ala Thr Arg Ser Leu Tyr Arg Leu Leu Ala Ser Ser Pro Asp
        115                 120                 125

Leu Asn Thr Val Leu Ala Ala Leu Asn Thr Val Phe Val Gly Met Gln
    130                 135                 140

Thr Thr Tyr Ile Leu Trp Thr Trp Leu Val Glu Gly Arg Pro Arg Ala
145                 150                 155                 160

Thr Ile Ser Ala Cys Phe Met Phe Thr Cys Arg Gly Ile Leu Gly Tyr
                165                 170                 175

Ser Thr Gln Leu Pro Leu Pro Gln Asp Phe Leu Gly Ser Gly Val Asp
            180                 185                 190

Phe Pro Val Gly Asn Val Ser Phe Phe Leu Phe Tyr Ser Gly His Val
        195                 200                 205

Ala Gly Ser Thr Ile Ala Ser Leu Asp Met Arg Arg Met Lys Arg Leu
    210                 215                 220
```

```
Arg Leu Ala Leu Leu Phe Asp Ile Leu Asn Val Leu Gln Ser Ile Arg
225                 230                 235                 240

Leu Leu Gly Thr Arg Gly Gln Tyr Thr Ile Asp Leu Ala Val Gly Val
                245                 250                 255

Gly Ala Gly Val Leu Phe Asp Ser Leu Ala Gly Lys Tyr Glu Glu Met
            260                 265                 270

Met Ser Lys Arg Arg Asn Val Gly Asn Gly Phe Ser Leu Ile Ser Ser
        275                 280                 285

Arg
```

<210> SEQ ID NO 86
<211> LENGTH: 235
<212> TYPE: PRT
<213> ORGANISM: Artificial Sequence
<220> FEATURE:
<223> OTHER INFORMATION: Bc 2B

<400> SEQUENCE: 86

```
Met Ser Gln Met Asp Ile Ser Met Arg Thr Glu Glu Gly Gly Trp Arg
1               5                   10                  15

Ser Lys Pro Ser Phe Met Thr Trp Arg Ala Arg Asp Val Val Tyr Val
            20                  25                  30

Leu Arg His His Trp Ile Pro Cys Leu Phe Ala Ala Gly Phe Leu Phe
        35                  40                  45

Val Val Ser Val Glu Ser Ser Ile Lys Met Val Ser Glu Ser Ser Pro
    50                  55                  60

Pro Leu Asp Ile Gly Phe Val Ala Thr Arg Ser Leu His His Leu Leu
65                  70                  75                  80

Ala Ser Ser Pro Asp Leu Asn Thr Gly Leu Ala Ala Leu Asn Ser Val
                85                  90                  95

Leu Gly Val Met Gln Val Ser Tyr Ile Ala Trp Thr Trp Leu Ile Glu
            100                 105                 110

Gly Arg Pro Arg Ala Thr Ile Thr Ala Leu Phe Leu Phe Thr Cys Arg
        115                 120                 125

Gly Val Leu Gly Tyr Cys Thr Gln Leu Pro Leu Ser Lys Glu Tyr Leu
    130                 135                 140

Gly Ser Ala Ile Asp Phe Pro Leu Gly Asn Leu Ser Phe Phe Tyr Phe
145                 150                 155                 160

Phe Ser Gly His Val Ala Gly Thr Thr Ile Ala Ser Leu Asp Met Arg
                165                 170                 175

Arg Met Gln Arg Leu Arg Leu Ala Met Val Phe Asp Ile Leu Asn Val
            180                 185                 190

Leu Gln Ser Ile Arg Leu Leu Ala Thr Arg Gly His Tyr Thr Ile Asp
        195                 200                 205

Leu Ala Gly Gly Val Ala Ala Ala Ile Leu Phe Asp Ser Leu Ala Gly
    210                 215                 220

Lys Tyr Glu Ala Asn Thr Arg Lys Arg Gln Leu
225                 230                 235
```

<210> SEQ ID NO 87
<211> LENGTH: 235
<212> TYPE: PRT
<213> ORGANISM: Artificial Sequence
<220> FEATURE:
<223> OTHER INFORMATION: Bn 2C

<400> SEQUENCE: 87

```
Met Ser Gln Met Asp Ile Ser Thr Arg Thr Glu Glu Gly Gly Trp Arg
1               5                   10                  15

Ser Lys Pro Ser Phe Met Thr Trp Arg Ala Arg Asp Val Val Tyr Val
            20                  25                  30

Met Arg His His Trp Ile Pro Cys Leu Phe Ala Ala Gly Phe Leu Phe
        35                  40                  45

Val Val Ser Val Glu Ser Ser Ile Lys Met Val Ser Glu Ser Ser Pro
    50                  55                  60

Pro Phe Asp Ile Gly Phe Val Ala Thr Glu Ser Leu His His Ile Leu
65                  70                  75                  80

Ala Ser Ser Pro Asp Leu Asn Thr Gly Leu Ala Ala Leu Asn Ser Val
                85                  90                  95

Leu Gly Val Met Gln Val Ser Tyr Ile Ala Trp Thr Trp Leu Ile Glu
            100                 105                 110

Gly Arg Pro Arg Ala Thr Ile Thr Ala Leu Phe Leu Phe Thr Cys Arg
        115                 120                 125

Gly Val Leu Gly Tyr Cys Thr Gln Leu Pro Leu Ser Lys Glu Tyr Leu
    130                 135                 140

Gly Ser Ala Ile Asp Phe Pro Leu Gly Asn Leu Ser Phe Phe Tyr Phe
145                 150                 155                 160

Phe Ser Gly His Val Ala Gly Thr Thr Ile Ala Ser Leu Asp Met Arg
                165                 170                 175

Arg Met Gln Arg Leu Arg Leu Ala Met Val Phe Asp Ile Leu Asn Val
            180                 185                 190

Leu Gln Ser Ile Arg Leu Leu Ala Thr Arg Gly His Tyr Thr Ile Asp
        195                 200                 205

Leu Ala Gly Gly Val Ala Ala Ile Leu Phe Asp Ser Leu Ala Gly
    210                 215                 220

Lys Tyr Glu Ala Asn Thr Arg Lys Arg Gln Leu
225                 230                 235
```

<210> SEQ ID NO 88
<211> LENGTH: 282
<212> TYPE: PRT
<213> ORGANISM: Artificial Sequence
<220> FEATURE:
<223> OTHER INFORMATION: Bn 3A

<400> SEQUENCE: 88

```
Met Ser Thr Asn Thr Val Val Pro Leu Arg Arg Arg Ser Asn Gly Tyr
1               5                   10                  15

His Thr Asn Gly Val Ala Phe Asn Gly Met Asp Asn Ile Val Lys Lys
            20                  25                  30

Thr Asp Asp Cys Tyr Thr Asn Gly Asn Gly Asn Gly Gly Val Glu Arg
        35                  40                  45

Ser Lys Ala Ser Phe Leu Thr Trp Thr Met Arg Asp Ala Val Tyr Val
    50                  55                  60

Ala Arg Tyr His Trp Ile Pro Cys Phe Phe Ala Val Gly Val Leu Phe
65                  70                  75                  80

Phe Met Gly Val Glu Tyr Thr Leu Gln Met Val Pro Ala Lys Ser Glu
                85                  90                  95

Pro Phe Asp Ile Gly Phe Val Ala Thr Arg Ser Leu Asn Arg Val Leu
            100                 105                 110

Ala Ser Ser Pro Asp Leu Asn Thr Leu Leu Ala Ala Leu Asn Thr Val
        115                 120                 125
```

-continued

Phe Val Ala Met Gln Thr Thr Tyr Ile Val Trp Thr Trp Leu Met Glu
130 135 140

Gly Arg Pro Arg Ala Thr Ile Ser Ala Cys Phe Met Phe Thr Cys Arg
145 150 155 160

Gly Ile Leu Gly Tyr Ser Thr Gln Leu Pro Leu Pro Gln Asp Phe Leu
165 170 175

Gly Ser Gly Val Asp Phe Pro Val Gly Asn Val Ser Phe Phe Leu Phe
180 185 190

Tyr Ser Gly His Val Ala Gly Ser Met Ile Ala Ser Leu Asp Met Arg
195 200 205

Arg Met Gln Arg Leu Arg Leu Ala Met Leu Phe Asp Ile Leu Asn Ile
210 215 220

Leu Gln Ser Ile Arg Leu Leu Gly Thr Arg Gly His Tyr Thr Ile Asp
225 230 235 240

Leu Ala Val Gly Val Gly Ala Gly Ile Leu Phe Asp Ser Leu Ala Gly
245 250 255

Lys Tyr Glu Glu Met Met Ser Lys Arg His Asn Leu Ala Asn Gly Phe
260 265 270

Ser Leu Ile Ser Lys Asp Ser Leu Val Asn
275 280

<210> SEQ ID NO 89
<211> LENGTH: 280
<212> TYPE: PRT
<213> ORGANISM: Artificial Sequence
<220> FEATURE:
<223> OTHER INFORMATION: Bc 3B

<400> SEQUENCE: 89

Met Ser Thr Asn Thr Val Val Pro Leu Arg Arg Arg Ser Asn Gly Tyr
1 5 10 15

His Ser Asn Gly Val Ala Phe Asn Gly Met Glu Asn Ile Val Lys Lys
20 25 30

Thr Asp Asp Cys Tyr Thr Asn Gly Asn Gly Gly Gly Gly Lys Ser Lys
35 40 45

Ala Ser Phe Leu Thr Trp Thr Met Arg Asp Ala Val Tyr Val Ala Arg
50 55 60

Tyr His Trp Ile Pro Cys Phe Phe Ala Val Gly Val Leu Phe Phe Met
65 70 75 80

Gly Val Glu Tyr Thr Leu Gln Met Val Pro Ala Lys Ser Glu Pro Phe
85 90 95

Asp Ile Gly Phe Val Ala Thr Arg Ser Leu Asn Arg Val Leu Ala Ser
100 105 110

Ser Pro Asp Leu Asn Thr Leu Leu Ala Ala Leu Asn Thr Val Phe Val
115 120 125

Ala Met Gln Thr Thr Tyr Ile Val Trp Thr Trp Leu Met Glu Gly Arg
130 135 140

Pro Arg Ala Thr Ile Ser Ala Cys Phe Met Phe Thr Cys Arg Gly Ile
145 150 155 160

Leu Gly Tyr Ser Thr Gln Leu Pro Leu Pro Gln Asp Phe Leu Gly Ser
165 170 175

Gly Val Asp Phe Pro Val Gly Asn Val Ser Phe Phe Leu Phe Tyr Ser
180 185 190

Gly His Val Ala Gly Ser Met Ile Ala Ser Leu Asp Met Arg Arg Met
195 200 205

-continued

```
Arg Arg Leu Arg Leu Ala Met Leu Phe Asp Ile Leu Asn Val Leu Gln
    210                 215                 220

Ser Ile Arg Leu Leu Gly Thr Arg Gly His Tyr Thr Ile Asp Leu Ala
225                 230                 235                 240

Val Gly Val Gly Ala Gly Ile Leu Phe Asp Ser Leu Ala Gly Lys Tyr
                245                 250                 255

Glu Glu Met Met Ser Lys Arg His Asn Leu Ala Asn Gly Phe Ser Leu
            260                 265                 270

Ile Ser Lys Glu Ser Leu Val Asn
        275                 280


<210> SEQ ID NO 90
<211> LENGTH: 280
<212> TYPE: PRT
<213> ORGANISM: Artificial Sequence
<220> FEATURE:
<223> OTHER INFORMATION: Bc 3C

<400> SEQUENCE: 90

Met Ser Thr Asn Thr Val Val Pro Leu Arg Arg Arg Ser Asn Gly Tyr
1               5                   10                  15

His Thr Asn Gly Val Ala Phe Asn Gly Met Glu Asn Ile Val Lys Lys
            20                  25                  30

Thr Asp Asp Cys Tyr Thr Asn Gly Asn Gly Val Gly Gly Lys Ser Lys
        35                  40                  45

Ala Ser Phe Leu Thr Trp Thr Met Arg Asp Ala Val Tyr Val Ala Arg
    50                  55                  60

Tyr His Trp Ile Pro Cys Phe Phe Ala Val Gly Val Leu Phe Phe Met
65                  70                  75                  80

Gly Val Glu Tyr Thr Leu Gln Met Val Pro Ala Lys Ser Glu Pro Phe
                85                  90                  95

Asp Ile Gly Phe Val Ala Thr Arg Ser Leu Asn Arg Val Leu Ala Ser
            100                 105                 110

Ser Pro Asp Leu Asn Thr Leu Leu Ala Ala Leu Asn Thr Val Phe Val
        115                 120                 125

Ala Met Gln Thr Thr Tyr Ile Val Trp Thr Trp Leu Met Glu Gly Arg
    130                 135                 140

Pro Arg Ala Thr Ile Ser Ala Cys Phe Met Phe Thr Cys Arg Gly Ile
145                 150                 155                 160

Leu Gly Tyr Ser Thr Gln Leu Pro Leu Pro Gln Asp Phe Leu Gly Ser
                165                 170                 175

Gly Val Asp Phe Pro Val Gly Asn Val Ser Phe Phe Leu Phe Tyr Ser
            180                 185                 190

Gly His Val Ala Gly Ser Met Ile Ala Ser Leu Asp Met Arg Arg Met
        195                 200                 205

Gln Arg Leu Arg Leu Ala Met Leu Phe Asp Ile Leu Asn Ile Leu Gln
    210                 215                 220

Ser Ile Arg Leu Leu Gly Thr Arg Gly His Tyr Thr Ile Asp Leu Ala
225                 230                 235                 240

Val Gly Val Gly Ala Gly Ile Leu Phe Asp Ser Leu Ala Gly Lys Tyr
                245                 250                 255

Glu Glu Met Met Ser Lys Arg His Asn Leu Ala Asn Gly Phe Ser Leu
            260                 265                 270

Ile Ser Lys Asp Ser Leu Val Asn
        275                 280
```

<210> SEQ ID NO 91
<211> LENGTH: 280
<212> TYPE: PRT
<213> ORGANISM: Artificial Sequence
<220> FEATURE:
<223> OTHER INFORMATION: Bn 3C

<400> SEQUENCE: 91

```
Met Ser Thr Asn Thr Val Val Pro Leu Arg Arg Arg Ser Asn Gly Tyr
1               5                   10                  15

His Thr Asn Gly Val Ala Phe Asn Gly Met Glu Asn Ile Val Lys Lys
            20                  25                  30

Thr Asp Asp Cys Tyr Thr Asn Gly Asn Gly Val Gly Gly Lys Ser Lys
        35                  40                  45

Ala Ser Phe Leu Thr Trp Thr Met Arg Asp Ala Val Tyr Val Ala Arg
    50                  55                  60

Tyr His Trp Ile Pro Cys Phe Phe Ala Val Gly Val Leu Phe Phe Met
65                  70                  75                  80

Gly Val Glu Tyr Thr Leu Gln Met Val Pro Ala Lys Ser Glu Pro Phe
                85                  90                  95

Asp Ile Gly Phe Val Ala Thr Arg Ser Leu Asn Arg Val Leu Ala Ser
            100                 105                 110

Ser Pro Asp Leu Asn Thr Leu Leu Ala Ala Leu Asn Thr Val Phe Val
        115                 120                 125

Ala Met Gln Thr Thr Tyr Ile Val Trp Thr Trp Leu Met Glu Gly Arg
    130                 135                 140

Pro Arg Ala Thr Ile Ser Ala Cys Phe Met Phe Thr Cys Arg Gly Ile
145                 150                 155                 160

Leu Gly Tyr Ser Thr Gln Leu Pro Leu Pro Gln Asp Phe Leu Gly Ser
                165                 170                 175

Gly Val Asp Phe Pro Val Gly Asn Val Ser Phe Phe Leu Phe Tyr Ser
            180                 185                 190

Gly His Val Ala Gly Ser Met Ile Ala Ser Leu Asp Met Arg Arg Met
        195                 200                 205

Gln Arg Leu Arg Leu Ala Met Leu Phe Asp Ile Leu Asn Ile Leu Gln
    210                 215                 220

Ser Ile Arg Leu Leu Gly Thr Arg Gly His Tyr Thr Ile Asp Leu Ala
225                 230                 235                 240

Val Gly Val Gly Ala Gly Ile Leu Phe Asp Ser Leu Ala Gly Lys Tyr
                245                 250                 255

Glu Glu Met Met Ser Lys Arg His Asn Leu Ala Asn Gly Phe Ser Leu
            260                 265                 270

Ile Ser Lys Asp Ser Leu Val Asn
        275                 280
```

<210> SEQ ID NO 92
<211> LENGTH: 283
<212> TYPE: PRT
<213> ORGANISM: Artificial Sequence
<220> FEATURE:
<223> OTHER INFORMATION: Bn 5A

<400> SEQUENCE: 92

```
Met Ser Thr Glu Thr Ser Val Pro Leu Arg Arg Arg Ser Thr Ser Leu
1               5                   10                  15

Asn Gly His His Ser Asn Asp Val Ala Phe Asp Gly Thr Val Pro Leu
            20                  25                  30
```

```
Met Glu Asn Asn Ile Val Lys Lys Thr Asp Asp Gly Tyr Ala Asn Gly
        35                  40                  45

Gly Gly Lys Ala Ser Phe Met Thr Trp Thr Ala Arg Asp Ala Ile Tyr
    50                  55                  60

Val Ala Arg Val His Trp Ile Pro Cys Val Phe Ala Val Gly Val Leu
65                  70                  75                  80

Phe Phe Met Gly Val Glu Tyr Thr Leu Gln Met Ile Pro Ala Arg Ser
                85                  90                  95

Glu Pro Phe Asp Ile Gly Phe Val Val Thr Arg Ser Leu Asn Arg Val
            100                 105                 110

Leu Ala Asn Ser Pro Gly Leu Asn Thr Val Leu Ala Ala Leu Asn Thr
        115                 120                 125

Val Phe Val Gly Met Gln Thr Thr Tyr Ile Val Trp Thr Trp Leu Met
    130                 135                 140

Glu Gly Arg Pro Arg Ala Thr Ile Ser Ala Cys Phe Met Phe Thr Cys
145                 150                 155                 160

Arg Gly Ile Leu Gly Tyr Ser Thr Gln Leu Pro Leu Pro Gln Glu Phe
                165                 170                 175

Leu Gly Ser Gly Val Asp Phe Pro Val Gly Asn Val Ser Phe Phe Leu
            180                 185                 190

Phe Tyr Ser Gly His Val Ala Gly Ser Met Ile Ala Ser Leu Asp Met
        195                 200                 205

Arg Arg Met Gln Arg Leu Arg Leu Ala Met Leu Phe Asp Ile Leu Asn
    210                 215                 220

Val Leu Gln Ser Ile Arg Leu Leu Gly Thr Arg Gly His Tyr Thr Ile
225                 230                 235                 240

Asp Leu Ala Val Gly Val Gly Ala Gly Ile Leu Phe Asp Ser Leu Ala
                245                 250                 255

Gly Lys Tyr Glu Glu Met Met Ser Lys Arg His Asn Leu Gly Asn Gly
            260                 265                 270

Phe Ser Leu Ile Ser Lys Asp Ser Leu Asp Asn
        275                 280


<210> SEQ ID NO 93
<211> LENGTH: 282
<212> TYPE: PRT
<213> ORGANISM: Artificial Sequence
<220> FEATURE:
<223> OTHER INFORMATION: Bc 5B

<400> SEQUENCE: 93

Met Ser Thr Glu Thr Gly Val Pro Leu Arg Arg Arg Ser Asn Ser Leu
1               5                   10                  15

Asn Gly His His Thr Asn Gly Val Ala Ser Asp Gly Asn Val Pro Ser
            20                  25                  30

Met Glu Ser Ile Val Lys Arg Thr Asp Gly Gly Gly Gly Gly Ile Arg
        35                  40                  45

Ser Lys Ala Ser Phe Met Thr Trp Thr Ala Arg Asp Ala Ile Tyr Val
    50                  55                  60

Ala Arg Val His Trp Ile Pro Cys Val Phe Ala Val Gly Val Leu Phe
65                  70                  75                  80

Phe Met Gly Val Glu Tyr Thr Leu Gln Met Ile Pro Ala Arg Ser Glu
                85                  90                  95

Pro Phe Asp Ile Gly Phe Val Ala Thr Arg Ser Leu Asn Arg Val Leu
            100                 105                 110
```

```
Ala Asn Ser Pro Asp Leu Asn Thr Val Leu Ala Ala Leu Asn Thr Val
        115                 120                 125

Phe Val Gly Met Gln Thr Thr Tyr Ile Val Trp Thr Trp Leu Met Glu
    130                 135                 140

Gly Arg Pro Arg Ala Thr Ile Ser Ala Cys Phe Met Phe Thr Cys Arg
145                 150                 155                 160

Gly Ile Leu Gly Tyr Ser Thr Gln Leu Pro Leu Pro Gln Glu Phe Leu
                165                 170                 175

Gly Ser Gly Val Asp Phe Pro Val Gly Asn Val Ser Phe Phe Leu Phe
            180                 185                 190

Tyr Ser Gly His Val Ala Gly Ser Met Ile Ala Ser Leu Asp Met Arg
        195                 200                 205

Arg Met Gln Arg Leu Arg Leu Ala Met Leu Phe Asp Ile Leu Asn Val
    210                 215                 220

Leu Gln Ser Ile Arg Leu Leu Gly Thr Arg Gly His Tyr Thr Ile Asp
225                 230                 235                 240

Leu Ala Val Gly Val Gly Ala Gly Ile Leu Phe Asp Ser Leu Ala Gly
                245                 250                 255

Lys Tyr Glu Glu Met Met Asn Lys Arg His Asn Leu Gly Asn Gly Phe
            260                 265                 270

Ser Leu Ile Ser Lys Asp Ser Leu Val Asn
        275                 280


<210> SEQ ID NO 94
<211> LENGTH: 283
<212> TYPE: PRT
<213> ORGANISM: Artificial Sequence
<220> FEATURE:
<223> OTHER INFORMATION: Bc 5C

<400> SEQUENCE: 94

Met Ser Thr Glu Thr Gly Val Pro Leu Arg Arg Arg Ser Asn Ser Leu
1               5                   10                  15

Asn Gly His His Ser Asn Asp Val Ala Phe Asp Gly Thr Val Pro Ser
            20                  25                  30

Met Glu Asn Asn Ile Val Lys Lys Thr Asp Asp Gly Tyr Ala Asn Gly
        35                  40                  45

Gly Gly Lys Ala Ser Phe Met Thr Trp Thr Ala Arg Asp Ala Ile Tyr
    50                  55                  60

Val Ala Arg Val His Trp Ile Pro Cys Val Phe Ala Val Gly Val Leu
65                  70                  75                  80

Phe Phe Met Gly Val Glu Tyr Thr Leu Gln Met Ile Pro Ala Arg Ser
                85                  90                  95

Glu Pro Phe Asp Val Gly Phe Val Ala Thr Arg Ser Leu Asn Ser Val
            100                 105                 110

Leu Ala Asn Ser Pro Gly Leu Asn Thr Val Leu Ala Ala Leu Asn Thr
        115                 120                 125

Val Phe Val Gly Met Gln Thr Thr Tyr Ile Val Trp Thr Trp Leu Met
    130                 135                 140

Glu Gly Arg Pro Arg Ala Thr Ile Ser Ala Cys Phe Met Phe Thr Cys
145                 150                 155                 160

Arg Gly Ile Leu Gly Tyr Ser Thr Gln Leu Pro Leu Pro Gln Glu Phe
                165                 170                 175

Leu Gly Ser Gly Val Asp Phe Pro Val Gly Asn Val Ser Phe Phe Leu
            180                 185                 190
```

```
Phe Tyr Ser Gly His Val Ala Gly Ser Met Ile Ala Ser Leu Asp Met
        195                 200                 205

Arg Arg Met Gln Arg Leu Arg Leu Ala Met Leu Phe Asp Ile Leu Asn
    210                 215                 220

Val Leu Gln Ser Ile Arg Leu Leu Gly Thr Arg Gly His Tyr Thr Ile
225                 230                 235                 240

Asp Leu Ala Val Gly Val Gly Ala Gly Ile Leu Phe Asp Ser Leu Ala
                245                 250                 255

Gly Lys Tyr Glu Glu Met Met Ser Lys Arg His Asn Leu Gly Asn Gly
            260                 265                 270

Phe Ser Leu Ile Ser Lys Asp Ser Leu Val Asn
        275                 280
```

<210> SEQ ID NO 95
<211> LENGTH: 283
<212> TYPE: PRT
<213> ORGANISM: Artificial Sequence
<220> FEATURE:
<223> OTHER INFORMATION: Bn 5C

<400> SEQUENCE: 95

```
Met Ser Thr Glu Thr Gly Val Pro Leu Arg Arg Arg Ser Asn Ser Leu
1               5                   10                  15

Asn Gly His His Ser Asn Asp Val Ala Phe Asp Gly Thr Val Pro Ser
            20                  25                  30

Met Glu Asn Asn Ile Val Lys Lys Thr Asp Asp Gly Tyr Ala Asn Gly
        35                  40                  45

Gly Gly Lys Ala Ser Phe Met Thr Trp Thr Ala Arg Asp Ala Ile Tyr
    50                  55                  60

Val Ala Arg Val His Trp Ile Pro Cys Val Phe Ala Val Gly Val Leu
65                  70                  75                  80

Phe Phe Met Gly Val Glu Tyr Thr Leu Gln Met Ile Pro Ala Arg Ser
                85                  90                  95

Glu Pro Phe Asp Val Gly Phe Val Ala Thr Arg Ser Leu Asn Arg Val
            100                 105                 110

Leu Ala Asn Ser Pro Gly Leu Asn Thr Val Leu Ala Ala Leu Asn Thr
        115                 120                 125

Val Phe Val Gly Met Gln Thr Thr Tyr Ile Val Trp Thr Trp Leu Met
    130                 135                 140

Glu Gly Arg Pro Arg Ala Thr Ile Ser Ala Cys Phe Met Phe Thr Cys
145                 150                 155                 160

Arg Gly Ile Leu Gly Tyr Ser Thr Gln Leu Pro Leu Pro Gln Glu Phe
                165                 170                 175

Leu Gly Ser Gly Val Asp Phe Pro Val Gly Asn Val Ser Phe Phe Leu
            180                 185                 190

Phe Tyr Ser Gly His Val Ala Gly Ser Met Ile Ala Ser Leu Asp Met
        195                 200                 205

Arg Arg Met Gln Arg Leu Arg Leu Ala Met Leu Phe Asp Ile Leu Asn
    210                 215                 220

Val Leu Gln Ser Ile Arg Leu Leu Gly Thr Arg Gly His Tyr Thr Ile
225                 230                 235                 240

Asp Leu Ala Val Gly Val Gly Ala Gly Ile Leu Phe Asp Ser Leu Ala
                245                 250                 255

Gly Lys Tyr Glu Glu Met Met Ser Lys Arg His Asn Leu Gly Asn Gly
            260                 265                 270
```

```
Phe Ser Leu Ile Ser Lys Asp Ser Leu Val Asn
        275                 280


<210> SEQ ID NO 96
<211> LENGTH: 296
<212> TYPE: PRT
<213> ORGANISM: Artificial Sequence
<220> FEATURE:
<223> OTHER INFORMATION: Cs C1

<400> SEQUENCE: 96

Met Ser Ala Ser Ala Ala Lys Pro Ala Val Ser Arg Arg His Val Ser
1               5                   10                  15

Asn Gly Asn His Thr Asn Asn Val Ala Ile Glu Asn Asp His Asn His
            20                  25                  30

Gln Arg Pro Val Ala Gly Asp Thr Asn Thr Arg Met Glu Ile Ala Ala
        35                  40                  45

Lys Asn Asn Gly Tyr Ala Asn Gly Val Gly Gly Gly Gly Trp Arg Ser
    50                  55                  60

Lys Ala Ser Phe Met Thr Trp Thr Thr Arg Asp Val Val Tyr Val Ala
65                  70                  75                  80

Arg His His Trp Ile Pro Cys Met Phe Ala Ala Gly Leu Leu Phe Phe
                85                  90                  95

Met Gly Val Glu Tyr Thr Leu Gln Met Ile Pro Ala Arg Ser Glu Pro
            100                 105                 110

Phe Asp Leu Gly Phe Val Ala Thr Arg Ser Leu Asn Arg Val Leu Ala
        115                 120                 125

Ser Ser Pro Asp Leu Asn Thr Val Leu Ala Ala Leu Asn Thr Val Phe
    130                 135                 140

Val Leu Met Gln Thr Thr Tyr Ile Val Trp Thr Trp Leu Val Glu Gly
145                 150                 155                 160

Arg Ala Arg Ala Thr Ile Ser Ala Leu Phe Met Phe Thr Cys Arg Gly
                165                 170                 175

Ile Leu Gly Tyr Ser Thr Gln Leu Pro Leu Pro Gln Asp Phe Leu Gly
            180                 185                 190

Ser Gly Val Asp Phe Pro Val Gly Asn Val Ser Phe Phe Leu Phe Phe
        195                 200                 205

Ser Gly His Val Ala Gly Ser Met Ile Ala Ser Leu Asp Met Arg Arg
    210                 215                 220

Met Gln Arg Phe Lys Leu Ala Arg Val Phe Asp Ile Leu Asn Val Leu
225                 230                 235                 240

Gln Ser Ile Arg Leu Leu Gly Thr Arg Gly His Tyr Thr Ile Asp Leu
                245                 250                 255

Ala Val Gly Val Gly Ala Gly Ile Leu Phe Asp Ser Leu Ala Gly Lys
            260                 265                 270

Tyr Glu Glu Met Ser Arg Arg His His Leu Gly Thr Gly Phe Ser Leu
        275                 280                 285

Ile Ser Lys Asp Ser Leu Val Asn
    290                 295


<210> SEQ ID NO 97
<211> LENGTH: 297
<212> TYPE: PRT
<213> ORGANISM: Artificial Sequence
<220> FEATURE:
<223> OTHER INFORMATION: CS C15
```

<400> SEQUENCE: 97

Met Ser Val Ala Ala Ala Lys Pro Ala Val Ser Arg Arg His Val Ser
1               5                   10                  15

Asn Gly Asn Asn Thr Asn Asn Val Ala Ile Asp Asp Asp His Asn His
            20                  25                  30

Gln Arg Arg Ile Val Gly Asp Lys Asn Thr Arg Met Glu Ile Ala Ala
        35                  40                  45

Lys Asn Asn Gly Tyr Ala Asn Gly Val Ile Gly Gly Gly Gly Trp Arg
    50                  55                  60

Ser Lys Ala Ser Phe Met Thr Trp Thr Thr Arg Asp Val Val Tyr Val
65                  70                  75                  80

Ala Arg His His Trp Ile Pro Cys Met Phe Ala Ala Gly Leu Leu Phe
                85                  90                  95

Phe Met Gly Val Glu Tyr Thr Leu Gln Met Ile Pro Ala Arg Ser Glu
            100                 105                 110

Pro Phe Asp Leu Gly Phe Val Ala Thr Arg Ser Leu Asn Arg Val Leu
        115                 120                 125

Ala Ser Ser Pro Asp Leu Asn Thr Val Leu Ala Ala Leu Asn Thr Val
    130                 135                 140

Phe Val Leu Met Gln Thr Thr Tyr Ile Val Trp Thr Trp Leu Val Glu
145                 150                 155                 160

Gly Arg Ala Arg Ala Thr Ile Ser Ala Leu Phe Met Phe Thr Cys Arg
                165                 170                 175

Gly Ile Leu Gly Tyr Ser Thr Gln Leu Pro Leu Pro Gln Asp Phe Leu
            180                 185                 190

Gly Ser Gly Val Asp Phe Pro Val Gly Asn Val Ser Phe Phe Leu Phe
        195                 200                 205

Phe Ser Gly His Val Ala Gly Ser Met Ile Ala Ser Leu Asp Met Arg
    210                 215                 220

Arg Met Gln Arg Phe Lys Leu Ala Arg Val Phe Asp Ile Leu Asn Val
225                 230                 235                 240

Leu Gln Ser Ile Arg Leu Leu Gly Thr Arg Gly His Tyr Thr Ile Asp
                245                 250                 255

Leu Ala Val Gly Val Gly Ala Gly Ile Leu Phe Asp Ser Leu Ala Gly
            260                 265                 270

Lys Tyr Glu Glu Met Ser Arg Arg His His Leu Gly Thr Gly Phe Ser
        275                 280                 285

Leu Ile Ser Lys Asp Ser Leu Val Asn
    290                 295

<210> SEQ ID NO 98
<211> LENGTH: 297
<212> TYPE: PRT
<213> ORGANISM: Artificial Sequence
<220> FEATURE:
<223> OTHER INFORMATION: Cs C19

<400> SEQUENCE: 98

Met Ser Ala Thr Ala Ala Lys Pro Ala Val Ser Arg Arg His Val Ser
1               5                   10                  15

Asn Gly Asn His Thr Asn Asn Val Ala Ile Asp Asp Asp His Asn His
            20                  25                  30

Gln Arg Pro Val Asp Val Gly Asp Thr Asn Thr Arg Met Glu Ile Ala
        35                  40                  45

Ala Lys Asn Asn Gly Tyr Ala Asn Gly Val Ile Gly Gly Gly Trp Arg

```
    50                  55                  60

Ser Lys Ala Ser Phe Met Thr Trp Thr Thr Arg Asp Val Val Tyr Val
65                  70                  75                  80

Ala Arg His His Trp Ile Pro Cys Met Phe Ala Ala Gly Leu Leu Phe
                85                  90                  95

Phe Met Gly Val Glu Tyr Thr Leu Gln Met Ile Pro Ala Arg Ser Glu
            100                 105                 110

Pro Phe Asp Leu Gly Phe Val Ala Thr Arg Ser Leu Asn Arg Val Leu
        115                 120                 125

Ala Ser Ser Pro Asp Leu Asn Thr Val Leu Ala Ala Leu Asn Thr Val
    130                 135                 140

Phe Val Leu Met Gln Thr Thr Tyr Ile Val Trp Thr Trp Leu Val Glu
145                 150                 155                 160

Gly Arg Ala Arg Ala Thr Ile Ser Ala Leu Phe Met Phe Thr Cys Arg
                165                 170                 175

Gly Ile Leu Gly Tyr Ser Thr Gln Leu Pro Leu Pro Gln Asp Phe Leu
            180                 185                 190

Gly Ser Gly Val Asp Phe Pro Val Gly Asn Val Ser Phe Phe Leu Phe
        195                 200                 205

Phe Ser Gly His Val Ala Gly Ser Met Ile Ala Ser Leu Asp Met Arg
    210                 215                 220

Arg Met Gln Arg Phe Lys Leu Ala Arg Val Phe Asp Ile Leu Asn Val
225                 230                 235                 240

Leu Gln Ser Ile Arg Leu Leu Gly Thr Arg Gly His Tyr Thr Ile Asp
                245                 250                 255

Leu Ala Val Gly Val Gly Ala Gly Ile Leu Phe Asp Ser Leu Ala Gly
            260                 265                 270

Lys Tyr Glu Glu Met Ser Arg Arg His His Leu Gly Thr Gly Phe Ser
        275                 280                 285

Leu Ile Ser Lys Asp Ser Leu Val Asn
    290                 295


<210> SEQ ID NO 99
<211> LENGTH: 279
<212> TYPE: PRT
<213> ORGANISM: Artificial Sequence
<220> FEATURE:
<223> OTHER INFORMATION: GmPDCT1

<400> SEQUENCE: 99

Met Asn Gly Gly Ala Glu Ala Ser Val Asn His Arg Arg Arg His Gln
1               5                   10                  15

Ala Ala Ser Ala Asn Gly Val Lys Ile Ala Asn Gly Ala Met Ala Lys
            20                  25                  30

Pro Ser Ser Thr Leu Cys Tyr Asp Ala Ser Phe Met Lys Trp Thr Val
        35                  40                  45

Ala Asp Ala Val His Val Ala Thr His His Trp Met Pro Cys Leu Phe
    50                  55                  60

Ala Leu Gly Leu Leu Phe Phe Met Ala Val Glu Tyr Thr Leu Leu Met
65                  70                  75                  80

Val Pro Pro Ser Ser Pro Pro Phe Asp Leu Gly Phe Ile Ala Thr Arg
                85                  90                  95

Ser Leu His Ala Leu Leu Glu Ser Ser Pro Asn Leu Asn Thr Leu Phe
            100                 105                 110

Ala Gly Leu Asn Thr Val Phe Val Gly Met Gln Thr Ser Tyr Ile Leu
```

```
        115                 120                 125

Trp Thr Trp Leu Ile Glu Gly Arg Pro Arg Ala Thr Ile Ser Ala Leu
    130                 135                 140

Gly Met Phe Thr Cys Arg Gly Ile Leu Gly Tyr Ser Thr Gln Leu Pro
145                 150                 155                 160

Leu Pro Gln Gly Phe Leu Gly Ser Gly Val Asp Phe Pro Val Gly Asn
                165                 170                 175

Val Ser Phe Phe Leu Phe Phe Ser Gly His Val Ala Gly Ser Val Ile
            180                 185                 190

Ala Ser Leu Asp Met Arg Arg Met Gln Arg Trp Glu Leu Ala Trp Thr
        195                 200                 205

Phe Asp Val Leu Asn Val Leu Gln Ala Val Arg Leu Leu Gly Thr Arg
    210                 215                 220

Gly His Tyr Thr Ile Asp Leu Ala Val Gly Val Gly Ala Gly Ile Leu
225                 230                 235                 240

Phe Asp Ser Leu Ala Gly Lys Tyr Glu Asp Ser Lys Arg Asn Ala Ala
                245                 250                 255

Leu Ser Thr Thr His Arg Ala Gln Phe Asp Cys Val Asn Asn Val Asp
            260                 265                 270

Ile Ala Lys Lys Ile Asn Lys
        275


<210> SEQ ID NO 100
<211> LENGTH: 267
<212> TYPE: PRT
<213> ORGANISM: Artificial Sequence
<220> FEATURE:
<223> OTHER INFORMATION: GmPDCT1-1

<400> SEQUENCE: 100

Met Asn Gly Gly Ala Glu Ala Ser Leu Asn His Arg Arg Lys His Gln
1               5                   10                  15

Thr Ala Pro Ala Asp Gly Ala Lys Gly Val Lys Val Ala Asn Gly Ala
            20                  25                  30

Met Gly Lys Pro Ser Ser Ser Lys His Ser Cys Gly Ala Ser Phe Met
        35                  40                  45

Lys Trp Thr Val Ala Asp Ala Val His Val Val Thr His His Trp Met
    50                  55                  60

Pro Cys Leu Phe Ala Leu Gly Leu Leu Phe Phe Met Ala Val Glu Tyr
65                  70                  75                  80

Thr Leu Leu Met Val Pro Pro Ser Ser Pro Pro Phe Asp Leu Gly Phe
                85                  90                  95

Ile Ala Thr Arg Ser Leu His Ala Leu Leu Glu Ser Ser Pro Asn Leu
            100                 105                 110

Asn Thr Leu Phe Ala Gly Leu Asn Thr Val Phe Val Gly Met Gln Thr
        115                 120                 125

Ser Tyr Ile Leu Trp Thr Trp Leu Ile Glu Gly Arg Pro Arg Ala Thr
    130                 135                 140

Ile Ser Ala Leu Phe Met Phe Thr Cys Arg Gly Ile Leu Gly Tyr Ser
145                 150                 155                 160

Thr Gln Leu Pro Leu Pro Gln Gly Phe Leu Gly Ser Gly Val Asp Phe
                165                 170                 175

Pro Val Gly Asn Val Ser Phe Phe Leu Phe Phe Ser Gly His Val Ala
            180                 185                 190

Gly Ser Val Ile Ala Ser Leu Asp Met Arg Arg Met Gln Arg Trp Glu
```

```
        195                 200                 205

Leu Ala Trp Thr Phe Asp Val Leu Asn Val Leu Gln Ala Val Arg Leu
    210                 215                 220

Leu Gly Thr Arg Gly His Tyr Thr Ile Asp Leu Ala Val Gly Val Gly
225                 230                 235                 240

Ala Gly Ile Leu Phe Asp Ser Leu Ala Gly Lys Tyr Glu Asp Ser Lys
                245                 250                 255

Arg Asn Gly Ala Leu Lys His Asn Leu Ile Ala
            260                 265


<210> SEQ ID NO 101
<211> LENGTH: 285
<212> TYPE: PRT
<213> ORGANISM: Artificial Sequence
<220> FEATURE:
<223> OTHER INFORMATION: RcPDCT1

<400> SEQUENCE: 101

Met Lys Ser Thr Val Pro Pro Thr Thr Thr Thr Thr Thr Thr Thr Thr
1               5                   10                  15

Leu Tyr Lys Arg Lys Lys Asp Ile Asn Leu Thr Ser Val Asn Asp Ser
            20                  25                  30

Val Asp Met Val Ser Asn Lys Asn Phe Ala Asn Gly Asn Val Asn Gly
        35                  40                  45

Gly Gly Gly Tyr Thr Ala Phe Asn Arg Phe Asp Pro Ser Phe Met Lys
    50                  55                  60

Trp Thr Thr His Asp Val Val Asn Val Val Lys Phe His Trp Leu Pro
65                  70                  75                  80

Cys Val Phe Gly Leu Gly Leu Leu Phe Phe Met Ala Val Glu Tyr Thr
                85                  90                  95

Leu Arg Met Val Pro Ala Ser Ser Pro Pro Phe Asp Leu Gly Phe Leu
            100                 105                 110

Val Thr Arg His Leu His Leu Leu Leu Ser Ser Trp Pro Ala Leu Asn
        115                 120                 125

Thr Leu Leu Ala Phe Leu Asn Thr Val Phe Val Leu Met Gln Thr Ala
    130                 135                 140

Tyr Ile Leu Trp Thr Trp Leu Ile Glu Gly Arg Pro Arg Ala Thr Ile
145                 150                 155                 160

Ser Ala Leu Phe Met Phe Thr Cys Arg Gly Ile Leu Gly Tyr Ser Thr
                165                 170                 175

Gln Leu Pro Leu Pro Glu Gly Phe Leu Gly Ser Gly Val Asp Phe Pro
            180                 185                 190

Val Gly Asn Val Ser Phe Phe Leu Phe Phe Ser Gly His Val Ala Gly
        195                 200                 205

Ser Val Ile Ala Ser Leu Asp Met Arg Arg Met Gln Arg Trp Glu Leu
    210                 215                 220

Ala Trp Thr Tyr Asp Val Leu Asn Val Leu Gln Ala Val Arg Leu Leu
225                 230                 235                 240

Gly Thr Arg Gly His Tyr Thr Ile Asp Leu Ala Thr Gly Val Gly Ala
                245                 250                 255

Gly Ile Leu Phe Asp Ser Leu Ala Gly Lys Tyr Glu Glu Ser Lys Arg
            260                 265                 270

Lys Gln Ala Val Val Ala Lys Glu Ser Ser Leu Phe Ser
        275                 280                 285
```

<210> SEQ ID NO 102
<211> LENGTH: 276
<212> TYPE: PRT
<213> ORGANISM: Artificial Sequence
<220> FEATURE:
<223> OTHER INFORMATION: Lu PDCT1

<400> SEQUENCE: 102

```
Met Ser Ala Ala Pro Thr Thr Thr Val Ala Ala Thr Ala Ile Pro Leu
1               5                   10                  15

Lys Arg Lys Lys Thr Asp Ala Ala Ala Lys Thr Gln Lys Asn Asn Gln
            20                  25                  30

Gly Asn Glu Asp Glu Gln Glu Ala Ile Val Glu Ser Val Ala Pro Ala
        35                  40                  45

Phe Thr Lys Trp Arg Arg Arg Asp Ala Met Asn Ala Val Arg Glu His
    50                  55                  60

Trp Leu Pro Val Ile Leu Gly Gly Ala Leu Leu Phe Phe Met Trp Val
65                  70                  75                  80

Glu Tyr Thr Leu Arg Met Val Pro Thr Ser Ser Gln Pro Phe Asp Leu
                85                  90                  95

Gly Phe Val Ala Thr Arg Ala Leu His Arg Leu Leu Ser Ser Ser Pro
            100                 105                 110

Glu Leu Asn Ser Val Leu Ala Ala Leu Asn Thr Val Phe Val Gly Met
        115                 120                 125

Gln Thr Ser Tyr Ile Leu Trp Thr Phe Val Val Glu Gly Arg Gly Arg
    130                 135                 140

Pro Thr Ile Ser Ala Leu Phe Met Phe Thr Cys Arg Gly Ile Leu Gly
145                 150                 155                 160

Tyr Ser Thr Gln Leu Pro Leu Pro Glu Gly Tyr Leu Gly Ser Gly Val
                165                 170                 175

Asp Phe Pro Val Gly Asn Val Ser Phe Phe Leu Phe Phe Ser Gly His
            180                 185                 190

Val Ala Gly Ser Val Ile Ala Ser Gln Asp Met Arg Arg Met Gln Arg
        195                 200                 205

Trp Glu Leu Ala Leu Gly Phe Glu Phe Leu Asn Ala Leu Gln Val Val
    210                 215                 220

Arg Leu Leu Ala Thr Arg Gly His Tyr Thr Ile Asp Leu Ala Ala Gly
225                 230                 235                 240

Tyr Ala Ala Gly Leu Leu Phe Asp Ser Leu Ala Gly Arg Tyr Leu Gln
                245                 250                 255

Thr Lys Thr Ala Thr Ala Ala Ala Leu Leu Thr Thr Ser Pro Arg Lys
            260                 265                 270

Phe Val Thr Asn
        275
```

<210> SEQ ID NO 103
<211> LENGTH: 276
<212> TYPE: PRT
<213> ORGANISM: Artificial Sequence
<220> FEATURE:
<223> OTHER INFORMATION: Lu PDCT2

<400> SEQUENCE: 103

```
Met Ser Ala Thr Pro Thr Ala Ala Val Ala Ala Thr Ala Ile Pro Leu
1               5                   10                  15

Lys Arg Lys Lys Thr Asp Ala Ala Ala Lys Thr Gln Lys Asn Asn Gln
            20                  25                  30
```

```
Gly Asn Glu Asp Glu Gln Glu Ala Ile Val Glu Ser Val Ala Pro Ala
        35                  40                  45

Phe Thr Lys Trp Arg Arg Arg Asp Ala Met Asn Ala Val Arg Glu His
    50                  55                  60

Trp Leu Pro Val Met Leu Gly Gly Ala Leu Leu Phe Phe Met Trp Val
65                  70                  75                  80

Glu Tyr Thr Leu Arg Met Val Pro Thr Ser Ser Gln Pro Phe Asp Leu
                85                  90                  95

Gly Phe Val Ala Thr Arg Ala Leu His Arg Leu Leu Ser Ser Ser Pro
            100                 105                 110

Glu Leu Asn Ser Val Leu Ala Ala Leu Asn Thr Val Phe Val Gly Met
        115                 120                 125

Gln Thr Ser Tyr Ile Leu Trp Thr Phe Val Val Glu Gly Arg Gly Arg
    130                 135                 140

Pro Thr Ile Ser Ala Leu Phe Met Phe Thr Cys Arg Gly Ile Leu Gly
145                 150                 155                 160

Tyr Ser Thr Gln Leu Pro Leu Pro Glu Gly Tyr Leu Gly Ser Gly Val
                165                 170                 175

Asp Phe Pro Val Gly Asn Val Ser Phe Phe Leu Phe Phe Ser Gly His
            180                 185                 190

Val Ala Gly Ser Val Ile Ala Ser Gln Asp Met Arg Arg Met Gln Arg
        195                 200                 205

Trp Glu Leu Ala Leu Gly Phe Glu Phe Leu Asn Ala Leu Gln Val Val
    210                 215                 220

Arg Leu Leu Ala Thr Arg Gly His Tyr Thr Ile Asp Leu Ala Ala Gly
225                 230                 235                 240

Tyr Ala Ala Gly Leu Leu Phe Asp Ser Leu Ala Gly Arg Tyr Leu Gln
                245                 250                 255

Thr Lys Thr Ala Thr Ala Ala Ala Leu Leu Thr Thr Ser Pro Arg Lys
            260                 265                 270

Phe Val Thr Asn
        275


<210> SEQ ID NO 104
<211> LENGTH: 282
<212> TYPE: PRT
<213> ORGANISM: Artificial Sequence
<220> FEATURE:
<223> OTHER INFORMATION: ZmPDCT1

<400> SEQUENCE: 104

Met Pro Pro Pro Ser Leu Thr Ala Ala Gly Thr Thr Thr Thr Thr Thr
1               5                   10                  15

Arg Arg Arg Asn Asp Arg Ala Ala Lys Val His Gln Val Leu Gly Glu
            20                  25                  30

Gly Ala Gly Thr Glu Glu Met Gly Ala Val Ala Asp Gly Trp Thr Arg
        35                  40                  45

Pro Glu Trp Cys Ser Ala Ala Gly Val Ala Gly Val Leu Arg Arg His
    50                  55                  60

Pro Ala Pro Ala Leu Phe Gly Cys Gly Leu Leu Leu Phe Met Ala Val
65                  70                  75                  80

Glu Tyr Thr Ile Pro Met Val Lys Pro Asp Ala Pro Pro Leu Asp Leu
                85                  90                  95

Gly Phe Leu Ala Thr Ala Gly Met His Ala Ala Ile Ala Ala Arg Pro
            100                 105                 110
```

-continued

```
Trp Leu Asn Ser Leu Leu Ala Ala Leu Asn Thr Val Phe Val Ala Met
        115                 120                 125

Gln Ala Ala Tyr Ile Leu Trp Ala Ile Leu Ala Glu Gln Arg Pro Arg
    130                 135                 140

Ala Ala Val Ala Ala Leu Met Met Phe Thr Cys Arg Gly Val Leu Gly
145                 150                 155                 160

Cys Ala Thr Gln Leu Pro Leu Pro Glu Glu Phe Leu Gly Ser Gly Met
                165                 170                 175

Asp Phe Pro Val Gly Asn Val Ser Phe Phe Leu Phe Phe Ser Gly His
            180                 185                 190

Val Ala Gly Ala Val Ile Ala Ala Ala Asp Met Arg Arg Glu Gly Arg
        195                 200                 205

Leu Ala Pro Ala Arg Leu Phe Asp Ser Leu Asn Val Leu Gln Val Val
    210                 215                 220

Arg Leu Leu Ala Cys Arg Gly His Tyr Thr Ile Asp Leu Ala Val Gly
225                 230                 235                 240

Val Gly Ala Gly Ile Leu Phe Asp Thr Leu Ser Gly Trp Tyr Phe Asp
                245                 250                 255

Ala Lys Asn Gly Asp Ser Ser Asn Ala Pro Glu Lys Gln Cys Arg Ser
            260                 265                 270

Cys Gln Cys His Lys Ala Leu Leu Ser His
        275                 280


<210> SEQ ID NO 105
<211> LENGTH: 274
<212> TYPE: PRT
<213> ORGANISM: Artificial Sequence
<220> FEATURE:
<223> OTHER INFORMATION: ZmPDCT1-1

<400> SEQUENCE: 105

Met Pro Pro Pro Ser Leu Thr Val Ala Arg Asp Pro Ala Ala Ala Ala
1               5                   10                  15

Thr Met Arg His Arg Lys Val His Pro Thr Pro Gly Gly Gly Ala Gly
            20                  25                  30

Thr Thr Lys Glu Met Gly Ala Ala Glu Gly Trp Ala Arg Pro Glu Trp
        35                  40                  45

Cys Ser Ala Ala Gly Ala Ala Ala Val Leu Arg Arg His Pro Ala Pro
    50                  55                  60

Ala Leu Phe Gly Cys Gly Leu Leu Leu Phe Met Ala Val Glu Tyr Thr
65                  70                  75                  80

Ile Pro Met Val Arg Pro Asp Ala Pro Pro Leu Asp Leu Gly Phe Val
                85                  90                  95

Ala Thr Arg Gly Leu His Ala Ala Val Ala Ala Arg Pro Trp Leu Asn
            100                 105                 110

Ser Leu Leu Ala Ala Leu Asn Thr Val Phe Val Ala Met Gln Ala Ala
        115                 120                 125

Tyr Ile Leu Trp Ala Ile Leu Gly Glu Gln Arg Pro Arg Ala Ala Val
    130                 135                 140

Ala Thr Leu Met Met Phe Thr Cys Arg Gly Ala Leu Gly Cys Ala Thr
145                 150                 155                 160

Gln Leu Pro Leu Pro Glu Glu Phe Leu Gly Ser Gly Met Asp Phe Pro
                165                 170                 175

Val Gly Asn Val Ser Phe Phe Leu Phe Phe Ser Gly His Val Ala Gly
            180                 185                 190
```

```
Ala Val Ile Ala Ala Ala Asp Met Arg Arg Glu Gly Arg Leu Ala Leu
        195                 200                 205

Ala Arg Leu Tyr Asp Ala Leu Asn Ala Leu Gln Gly Val Arg Leu Leu
    210                 215                 220

Ala Cys Arg Gly His Tyr Thr Ile Asp Leu Ala Val Gly Val Gly Ala
225                 230                 235                 240

Gly Ile Leu Phe Asp Thr Leu Ser Gly Trp Tyr Phe His Ala Lys Asn
                245                 250                 255

Ala Pro Glu Lys His Cys Arg Ser Cys Gln Cys His Lys Ala Leu Leu
            260                 265                 270

Ser Arg


<210> SEQ ID NO 106
<211> LENGTH: 297
<212> TYPE: PRT
<213> ORGANISM: Artificial Sequence
<220> FEATURE:
<223> OTHER INFORMATION: TaPDCT

<400> SEQUENCE: 106

Met Pro Pro Pro Ser Leu Thr Ala Ala Asn Asp Arg Val Ala Ala Thr
1               5                   10                  15

Ala Ser Ala Ala Asn Gly His Ala Gly Pro Asp Ala Arg Arg Arg Ala
            20                  25                  30

Gly Lys Gly Lys Lys Val His Pro Leu Pro Ala Asp Gly Ala Ala Met
        35                  40                  45

Gly Asp Gly Ala Gly Gly Glu Arg Leu Ala Gly Gly Arg Arg Pro Met
    50                  55                  60

Asp Trp Leu Ser Pro Ser Gly Val Ala Gly Ile Leu Arg Arg His Pro
65                  70                  75                  80

Leu Pro Ala Leu Phe Ala Cys Gly Leu Leu Leu Phe Met Gly Val Glu
                85                  90                  95

Tyr Thr Ile Pro Met Val Pro Ala Ala Ala Pro Pro Leu Asp Leu Gly
            100                 105                 110

Phe His Ala Thr Ala Ala Met His Ala Gly Ile Ala Ala Arg Pro Trp
        115                 120                 125

Leu Asn Ser Leu Leu Ala Ala Leu Asn Thr Val Phe Val Ala Met Gln
    130                 135                 140

Ala Ala Tyr Ile Leu Trp Ala Val Leu Ala Glu Gln Arg Pro Arg Ala
145                 150                 155                 160

Ala Ile Ala Thr Leu Met Met Phe Thr Cys Arg Gly Leu Leu Gly Cys
                165                 170                 175

Ser Thr Gln Leu Pro Leu Pro Ala Glu Phe Leu Gly Ser Gly Met Asp
            180                 185                 190

Phe Pro Val Gly Asn Val Ser Phe Phe Leu Phe Tyr Ser Gly His Val
        195                 200                 205

Ala Gly Ala Val Ile Ala Ser Ile Asp Met Arg Arg Val Gly Arg Arg
    210                 215                 220

Arg Leu Ala Val Leu Tyr Asp Thr Leu Asn Leu Leu Gln Phe Val Arg
225                 230                 235                 240

Leu Leu Ala Cys Arg Gly His Tyr Thr Ile Asp Leu Ala Val Gly Val
                245                 250                 255

Gly Ala Gly Leu Val Phe Asp Met Leu Ala Gly Trp Tyr Leu Asp Ser
            260                 265                 270

Lys Asn Ile Asp Ser Gly Asp Asn Arg Cys Cys Ser Ser Cys Gln Lys
```

```
        275                 280                 285

Ala Leu Val Ser Gln Lys Leu Thr Ser
    290                 295


<210> SEQ ID NO 107
<211> LENGTH: 68
<212> TYPE: PRT
<213> ORGANISM: Camelina sativa

<400> SEQUENCE: 107

Met Ser Ala Ser Ala Ala Lys Pro Ala Val Ser Arg Arg His Val Ser
1               5                   10                  15

Asn Gly Asn His Thr Asn Asn Val Ala Ile Glu Asn Asp His Asn His
            20                  25                  30

Gln Arg Pro Val Ala Gly Asp Thr Asn Thr Arg Met Glu Ile Ala Ala
        35                  40                  45

Lys Asn Asn Gly Tyr Ala Asn Gly Val Gly Gly Gly Gly Trp Arg Ser
    50                  55                  60

Lys Ala Ser Phe
65


<210> SEQ ID NO 108
<211> LENGTH: 69
<212> TYPE: PRT
<213> ORGANISM: Camelina sativa

<400> SEQUENCE: 108

Met Ser Val Ala Ala Ala Lys Pro Ala Val Ser Arg Arg His Val Ser
1               5                   10                  15

Asn Gly Asn Asn Thr Asn Asn Val Ala Ile Asp Asp Asp His Asn His
            20                  25                  30

Gln Arg Arg Ile Val Gly Asp Lys Asn Thr Arg Met Glu Ile Ala Ala
        35                  40                  45

Lys Asn Asn Gly Tyr Ala Asn Gly Val Ile Gly Gly Gly Gly Trp Arg
    50                  55                  60

Ser Lys Ala Ser Phe
65


<210> SEQ ID NO 109
<211> LENGTH: 69
<212> TYPE: PRT
<213> ORGANISM: Camelina sativa

<400> SEQUENCE: 109

Met Ser Ala Thr Ala Ala Lys Pro Ala Val Ser Arg Arg His Val Ser
1               5                   10                  15

Asn Gly Asn His Thr Asn Asn Val Ala Ile Asp Asp Asp His Asn His
            20                  25                  30

Gln Arg Pro Val Asp Val Gly Asp Thr Asn Thr Arg Met Glu Ile Ala
        35                  40                  45

Ala Lys Asn Asn Gly Tyr Ala Asn Gly Val Ile Gly Gly Gly Trp Arg
    50                  55                  60

Ser Lys Ala Ser Phe
65
```

METHOD FOR THE PRODUCTION OF HIGH LEVELS OF PUFA IN PLANTS

This application is a National Stage application of International Application No. PCT/EP2019/073831, filed Sep. 6, 2019, which claims priority to European Patent Application No. 18193296.3, filed Sep. 7, 2018 and European Patent Application No. 18193841.6, filed Sep. 11, 2018.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "180951_SeqListing.txt", which was created on Jun. 24, 2024 and is 213,979 bytes in size. The subject matter of the Sequence Listing is incorporated herein in its entirety by reference.

The present invention is concerned with materials and methods for the production of genetically modified plants, particularly where the plants are for the production of at least one unsaturated or polyunsaturated fatty acid. The invention is also concerned with identification of genes conveying an unsaturated fatty acid metabolic property to a plant or plant cell, and generally relates to the field of phosphotidylcholine:diacylglycerol cholinephosphotransferase (PDCT).

Very long chain polyunsaturated fatty acids (VLC-PUFAs), such as arachidonic acid (ARA; 20:4 ω6), eicosapentaenoic acid (EPA; 20:5ω3) and docosahexaenoic acid (DHA; 22:6ω3), have demonstrable benefits for human health (Swanson et al., 2012; Haslam et al., 2013), but humans are unable to synthesize these fatty acids in sufficient quantities. Transgenic oilseed crops are an alternative source for VLC-PUFAs: such systems minimally require two desaturation steps and one elongation to convert plant-derived linoleic acid (LA; 18:2 ω6) and ALA to VLC-PUFAs (Venegas-Caleron et al., 2010).

In the production of unusual fatty acids in plants, improving the flux of fatty acids through pools such as acyl-CoA PC, DAG and TAG is of particular interest (Wu et al., 2005;)

*Brassica carinata* has been shown to have potential as a host plant for VLC-PUFA production (Cheng at al., 2010). Ruiz-Lopez et al (2014) demonstrated that *Camelina sativa* also functions well as a host plant, and were able to demonstrate production of VLC-PUFA levels similar to those found in fish oils. *Brassica juncea* (Wu et al 2005), and *Brassica napus* has also been used as a host plant by various groups for the production of various fatty acids, including VLC-PUFAs, γ-linolenic acid (GLA), and stearidonic acid (SDA) (Petrie et al, 2014; Ursin et al, 2003, Liu et al, 2001).

Differences in VLC-PUFA production have been observed among these plants when enzymes involved in EPA and DHA biosynthesis (and their various pre-cursors) have been ectopically expressed, which may be partly due to differences in endogenous enzymes functioning in the fatty acid synthesis pathway (Cheng et al, 2010). Such differences may be reflected in the fatty acid profile of these plants; for example, *Camelina* seed oil is high in ALA (18:3), with levels of around 30% (Iskandarov et al. 2014, while *B. napus* generally has levels around 10% (Singer et al. 2014) and *B. carinata* seed oil averages 18% (Genet et al. 2004). A better understanding of the endogenous metabolism that impacts the production of EPA and DHA will lead to strategies to improve the production of these fatty acids in any host plant.

The identification of the phosphotidylcholine:diacylglycerol cholinephosphotransferase (PDCT) encoded by the

*Arabidopsis* (*Arabidopsis thaliana*) ROD1 gene (Lu et al., 2009) led to an improved understanding of the incorporation of polyunsaturated fatty acids (PUFAs) into triacylglycerols (TAGs). PDCT acts through the exchange of phosphocholine headgroups between de-novo synthesized diacylglycerols (DAG) and phosphatidylcholine (PC); PC can then be converted back to DAG and sequentially to TAG (Lu et al., 2009). Such exchanges contribute significantly to the flux of PUFAs into the TAG pool in *Arabidopsis* seeds (Bates et al., 2012).

To make possible the fortification of food and/or of feed with polyunsaturated omega-3-fatty acids, there is still a great need for a simple, inexpensive process for the production of each of the aforementioned long chain polyunsaturated fatty acids, especially in eukaryotic systems.

The invention is thus concerned with providing a reliable source for easy manufacture of VLC-PUFAs. To this end the invention is also concerned with providing plants reliably producing VLC-PUFAS, preferably EPA and/or DHA. The invention is also concerned with providing means and methods for obtaining, improving and farming such plants, and also with VLC-PUFA containing oil obtainable from such plants, particularly from the seeds thereof. Also, the invention provides uses for such plants and parts thereof.

The complementation of *Arabidopsis* rod1 mutants with flax PDCT (Wickramarathna et al., 2015) and castor PDCT (Hu et al., 2012) restored the fatty acid profiles of *Arabidopsis* seeds, showed that PDCT from different species function through similar mechanisms.

*B. napus, B. carinata*, and *C. sativa* are polyploid species, each having more than one copy of the PDCT gene. Differences in the PDCT genes within and between these three species may effect the production of polyunsaturated fatty acids in transgenic plants. Using *Arabidopsis* as a model system to examine the influence of PDCTs from *B. napus, B. carinata*, and *C. sativa* on the production of PUFAs in seeds it was found that individual PDCTs have distinct functional properties that influence the production of PUFAs in seeds.

It has now surprisingly been found that the reduced activity, e.g. a reduced expression of the phosphotidylcholine:diacylglycerol cholinephosphotransferase (PDCT) of the present invention, e.g. of a PDCT3 or a PDCT5, in a plant or a part thereof, a plant cell or plant seed results in an increase in the delta-6 elongase conversion efficiency in the oil crop plant, plant cell, plant seed, or a part thereof, the activity of one or more PDCT selected from the group consisting of:

(a) PDCT3 and/or PDCT5 having at least 80% sequence identity with SEQ ID NO: 18, 20, 22, 24, 26, 28, 30, 32, 50, 52, 54, 56, 58, and/or 60;

(b) PDCT3 and/or PDCT5 encoded by a polynucleotide having at least 80% sequence identity with SEQ ID NO: 17, 19, 21, 23, 27, 29, 31, 49, 51, 53, 55, and/or 57;

(c) PDCT3 and/or PDCT5 encoded by one or more polynucleotides that hybridize under high stringency conditions with (i) a polynucleotide that encodes the amino acid sequence of SEQ ID NO: 18, 20, 22, 24, 26, 28, 30, 32, 50, 52, 54, 56, 58, and/or 60, or (ii) the full-length complement of (i);

(d) variants of the PDCT3 and/or PDCT5 of SEQ ID NO: 18, 20, 22, 24, 26, 28, 30, 32, 50, 52, 54, 56, 58, and/or 60, comprising a substitution, preferably a conservative substitution, deletion, and/or insertion at one or more positions and having PDCT3 and/or PDCT5 activity;

(e) PDCT3 and/or PDCT5 encoded by a polynucleotide that differs from SEQ ID NO: 17, 19, 21, 23, 27, 29, 31, 49, 51, 53, 55, and/or 57 due to the degeneracy of the genetic code; and (f) fragments of the PDCT3 and/or PDCT5 of (a), (b), (c), (d) or (e) having PDCT3 and/or PDCT5 activity.

FIGURES

Figure 1B:
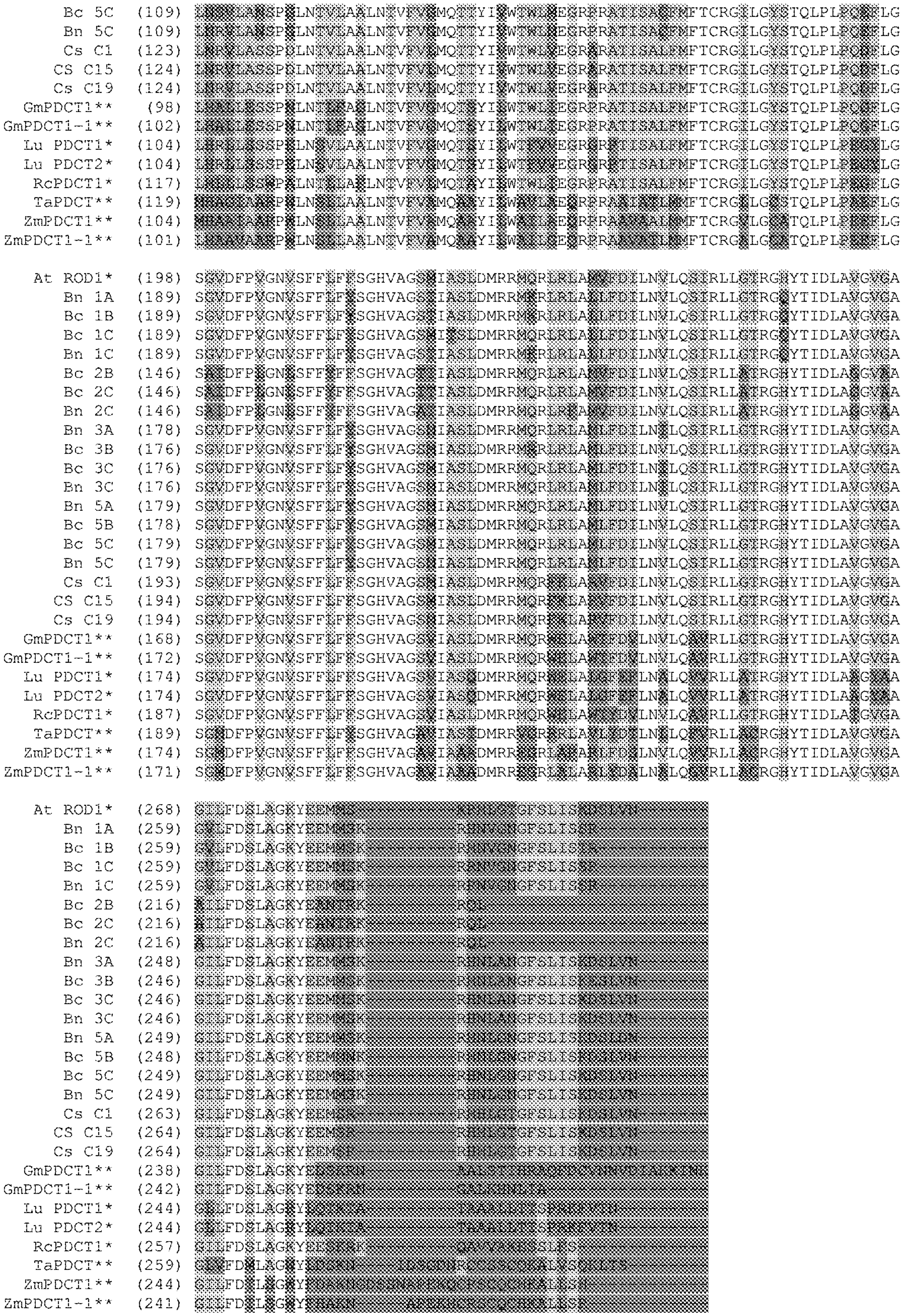

FIG. 1A and FIG. 1B Alignment of PDCT protein sequences: At ROD1* (SEQ ID NO: 81), Bc 1A (SEQ ID NO: 82), Bc 1B (SEQ ID NO: 83), Bc 1C (SEQ ID NO: 84), Bn 1C (SEQ ID NO: 85), Bc 2B (SEQ ID NO: 86), Bn 2C (SEQ ID NO: 87), Bn 3A (SEQ ID NO: 88), Bc 3B (SEQ ID NO: 89), Bc 3C (SEQ ID NO: 90), Bn 3C (SEQ ID NO: 91), Bn 5A (SEQ ID NO: 92), BC 5B (SEQ ID NO: 93), Bc 5C (SEQ ID NO: 94), Bn 5C (SEQ ID NO: 95), Cs C1 (SEQ ID NO: 96), Cs C15 (SEQ ID NO: 97), Cs C19 (SEQ ID NO: 98), GmPDCT1 (SEQ ID NO: 99), GmPDCT1-1 (SEQ ID NO: 100), RcPDCT1* (SEQ ID NO: 101), Lu PDCT1* (SEQ ID NO: 102), Lu PDCT2* (SEQ ID NO: 103), ZmPDCT1 (SEQ ID NO: 104), ZmPDCT1-1 (SEQ ID NO: 105), TaPDCT** (SEQ ID NO: 106).

Legend: At: *Arabidopsis thaliana*, Bn: *Brassica napus*, Bc: *Brassica carinata*, Cs: *Camelina sativa*, Gm: *Glycine max*, Lu: *Linum usitatissimum*, Rc: *Ricinus communis*, Ta: *Triticum aestivum*, Zm: *Zea mays*.

*activity demonstrated in other studies proteins selected based on homology in BLAST searches of NCBI databases, activity not demonstrated Color setup: Non-similar, weakly similar: dark grey, conserved: light grey, blocks of similar: medium grey, identical: white FIG. 2** Alignment of N-terminal region of *C. sativa* sequences: Cs C1 (SEQ ID NO: 107), CS C15 (SEQ ID NO: 108), Cs C19 (SEQ ID NO: 109). All differences in the *C. sativa* proteins are within this region.

Figure 3:
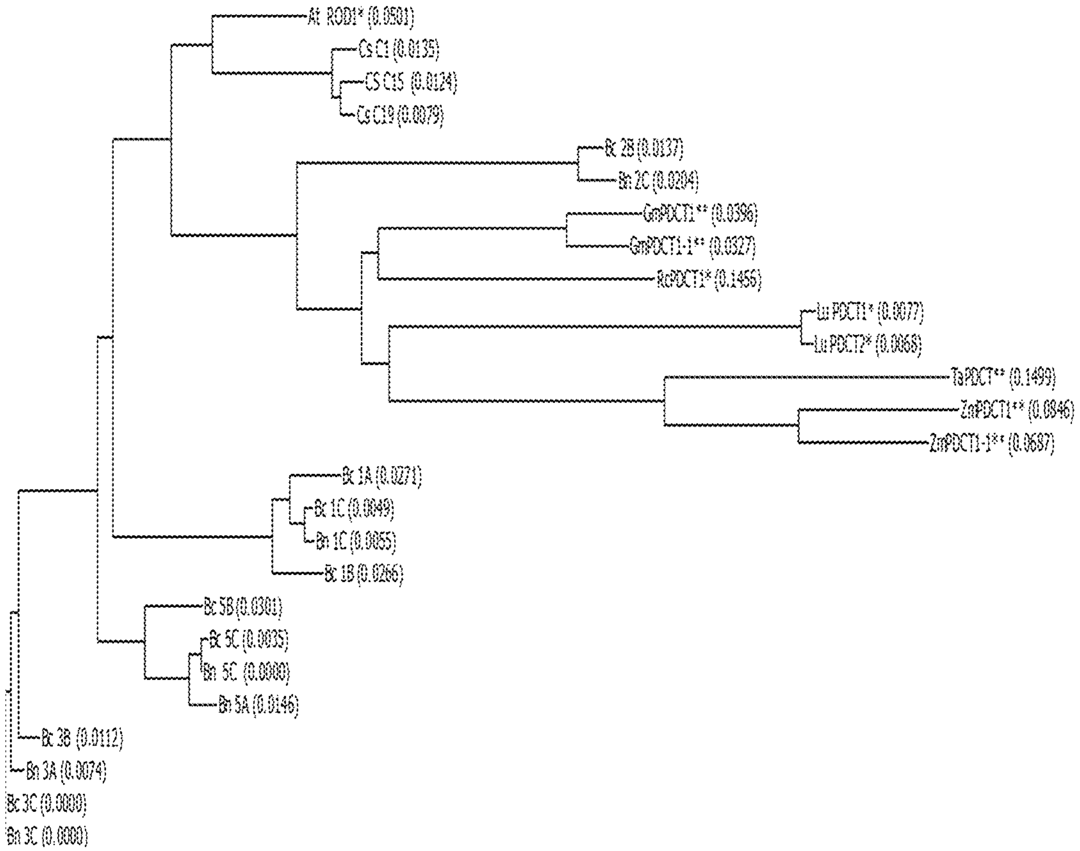

Color setup: Non-similar, weakly similar: dark grey, conserved: light grey, blocks of similar: medium grey, identical: white FIG. 3 Phylogenetic tree based on PDCT protein sequences.

Legend: At: *Arabidopsis thaliana*, Bn: *Brassica napus*, Bc: *Brassica carinata*, Cs: *Camelina sativa*, Gm: *Glycine max*, Lu: *Linum usitatissimum*, Rc: *Ricinus communis*, Ta: *Triticum aestivum*, Zm: *Zea mays*.

Figure 4:
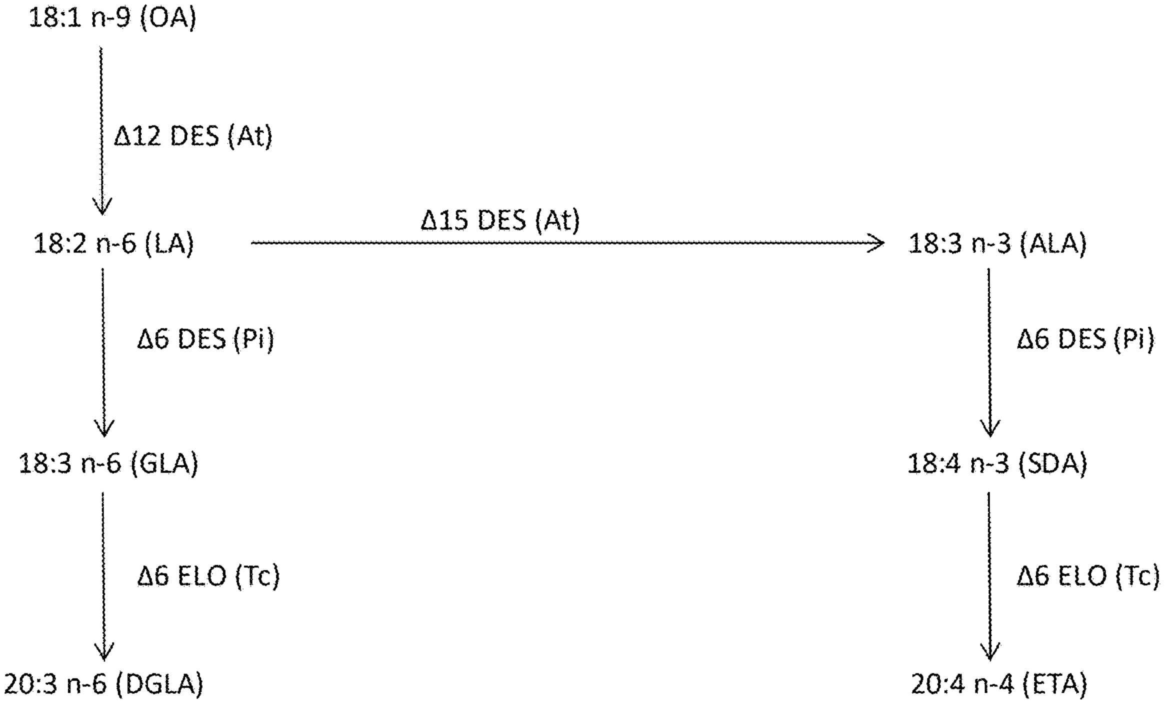

*activity demonstrated in other studies proteins selected based on homology in BLAST searches of NCBI databases, activity not demonstrated FIG. 4**. Pathway and genes in fatty acid synthesis pathway in transgenic *Arabidopsis* plants.

Figure 5:
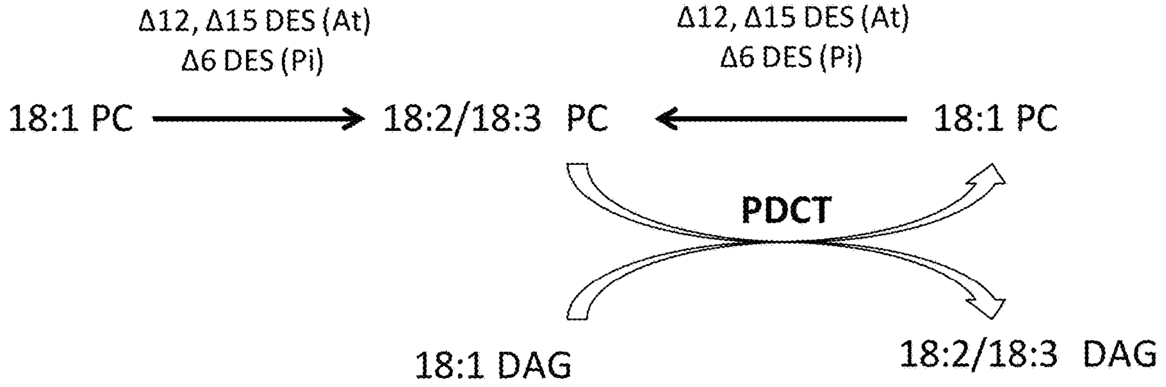

FIG. 5. Action of PDCT (Modified from Lu et al., 2009)

FIG. 6A-FIG. 6F Phylogenetic trees of PDCT proteins.

FIG. 7 describes the formulas to calculate pathway step conversion efficiencies. S: substrate of pathway step.

P: product of pathway step. Product was always the sum of the immediate product of the conversion at this pathway step, and all downstream products that passed this pathway step in order to be formed. E.g. DHA (22: 6n-3 does possess a double bond that was a result of the delta-12-desaturation of oleic acid (18: 1n-9) to linoleic acid (18: 2n-6).

FIG. 8:

Needle Matrix of PCDT sequences

FIG. 9A-FIG. 9F:

Conversion efficiencies of desaturases

Further, according to this invention, a PDCT is considered as a "PDCT3" or a "PDCT5" if in an functionality assay comprising the expression the PDCT in *A. thaliana* ROD1 k.o. mutant expressing a delta 6 elongase and a delta 6 desaturase and the PDCT having phosphotidylcholine:diacylglycerol cholinephosphotransferase (PDCT) activity, and whereby the conversion rate of a delta 6 elongase is decreased. Preferably, also the ETA level is reduced. Preferably the PDCT3 and/or PDCT5 has 80% or higher identity to 17, 19, 21, 23, 27, 29, 31, 49, 51, 53, 55, and/or 57. Preferably a PDCT3 has an identity of at least 80% to SEQ ID NO. 18, 22, or 24. Preferably, a PDCT5 has an identity of at least 80% to SEQ ID NO. 20, 26 or 28. For example, the Delta-6 desaturase uses phospholipids activated fatty acids as substrate.

Further, it was found that the a reduced expression of the phosphotidylcholine:diacylglycerol cholinephosphotransferase (PDCT) of the present invention, e.g. of a PDCT3 or a PDCT5 as described herein, allows to increase the level of ETA in an oil crop plant, plant cell, or seed, that produces vlcPUFA and expresses a Delta-6 elongase and/or a Delta-6 desaturase.

For example, phospholipid-dependent desaturase is also expressed in the plant, e.g. a phospholipid-dependent Delta-6 Desaturase. Further, in the method of the invention a Acyl-CoA dependent desaturase can be expressed, for example a Delta-6 desaturase that uses Acyl-CoA activated fatty acids as substrate.

It was also found that the a reduced expression of the phosphotidylcholine:diacylglycerol cholinephosphotransferase (PDCT) of the present invention, e.g. of a PDCT3 or a PDCT5 as described herein, allows reducing the level of alpha-linolenic acid (ALA), preferably also from GLA and/or SDA, in an oil crop plant that produces alpha-linolenic acid, GLA and SDA and expresses a Delta-6 elongase and/or a Delta-6 desaturase, compared to a control, in the oil crop plant, plant cell, plant seed, or a part thereof.

Likewise, it was also found that the a reduced expression of the phosphotidylcholine:diacylglycerol cholinephosphotransferase (PDCT) of the present invention, e.g. of a PDCT3 or a PDCT5 as described herein, allows reducing the level of 18:1 fatty acids in an oil crop plant that produces ETA and expresses preferably a Delta-6 elongase and Delta-6 desaturase, compared to a control, in the oil crop plant, plant cell, plant seed, or a part thereof.

Accordingly, the present invention relates also to a method to produce a plant or a part thereof, the plant cell, and/or the plant seed that comprises an oil that is characterized by an i. Increased ETA level ii. Reduced ALA level, iii. Reduced GLA level, iv. The level of the 18:2 fatty acid fraction in % (w/w) in the triacylglycerol (TAG) composition is higher than the 18:2 fatty acid level in % (w/w) in the diacylglyerol (DAG) fraction, v. The level of the 20:1 fatty acid in % (w/w) in the diacylglyerol fraction is higher than the 20:1 fatty acid level in % (w/w) in the triacylglycerol fraction vi. The level of the 22:1 fatty acid in % (w/w) in the diacylglyerol (DAG) fraction is higher than the 22:1 level in % (w/w) in the triacylglycerol fraction and/or vii. Reduced SDA level, and/or viii. Reduced 18:1 fatty acid level;

compared to a control, and, optionally, comprising the further step of isolating the oil from the plant or a part thereof, the plant cell, and/or the plant seed. Preferably, the oil is isolated from the plant or plant part, e.g. the seed.

Accordingly, for example, the plant, plant cell and/or the seed is expressing a Delta-6 desaturase and/or a Delta-6 elongase.

The invention also provides an improved method for the production of ALA, GLA and/or SDA in a plant, plant cell, seed or a part thereof, which comprises providing a plant, seed, or plant cell capable to produce ALA, GLA and/or SDA and the plant, seed, and/or plant cell functionally expressing:

at least a nucleic acid sequence which encodes a Delta-12 desaturase activity at least a nucleic acid sequence which encodes an Omega 3 desaturase activity, at least a nucleic acid sequence which encodes a Delta-6-desaturase activity, and at least a nucleic acid sequence which encodes a Delta-6 elongase activity, and at least a nucleic acid sequence which encodes a Delta-5 desaturase activity, and at least a nucleic acid sequence which encodes a Delta-5 elongase activity, and at least a nucleic acid sequence which encodes a Delta-4 desaturase activity, and whereby preferably, at least one desaturase uses Acyl-CoA as a substrate, and whereby the plant has a reduced activity of one or more PDCT of the invention, e.g. PDCT3 or PDCT5.

Thus, the present invention provides a method of the invention comprising providing or producing a plant, a part thereof, a plant cell, and/or plant seed with an reduced activity of one or more PDCT selected from the group consisting of:

(a) PDCT3 and/or PDCT5 having at least 80% sequence identity with SEQ ID NO: 18, 20, 22, 24, 26, 28, 30, 32, 50, 52, 54, 56, 58, and/or 60;

(b) PDCT3 and/or PDCT5 encoded by a polynucleotide having at least 80% sequence identity with SEQ ID NO: 17, 19, 21, 23, 27, 29, 31, 49, 51, 53, 55, and/or 57;

(c) PDCT3 and/or PDCT5 encoded by one or more polynucleotides that hybridize under high stringency conditions with (i) a polynucleotide that encodes the amino acid sequence of SEQ ID NO: 18, 20, 22, 24, 26, 28, 30, 32, 50, 52, 54, 56, 58, and/or 60, or (ii) the full-length complement of (i);

(d) variants of the PDCT3 and/or PDCT5 of SEQ ID NO: 18, 20, 22, 24, 26, 28, 30, 32, 50, 52, 54, 56, 58, and/or 60, comprising a substitution, preferably a conservative substitution, deletion, and/or insertion at one or more positions and having PDCT3 and/or PDCT5 activity;

(e) PDCT3 and/or PDCT5 encoded by a polynucleotide that differs from SEQ ID NO: 17, 19, 21, 23, 27, 29, 31, 49, 51, 53, 55, and/or 57 due to the degeneracy of the genetic code; and (f) fragments of the PDCT3 and/or PDCT5 of (a), (b), (c), (d) or (e) having PDCT3 and/or PDCT5 activity.

According to the invention, the activity of a PDCT3 and/or PDCT5 is decrease in the method of the invention, e.g. by expression of any expression reducing or inhibiting agent, like a transcription factors, ribozyme, microRNA, or antisense molecule, or by integrating into the genes or regulatory elements that encodes or regulate the expression or activity of the PDCT3 or PDCT5 a sequence or mutating the genes or regulatory elements that encode or regulate the expression or activity of a PDCT3 and/or a PDCT 5, whereby the measures results in the inhibition of an active PDCT3 or PDCT5 or results in a reduced or no expression of a polypeptide from that gene or results in the expression of an inactive polypeptide form the gene that encodes for a PDCT3 or PDCT5.

Thus, according to method of the invention depleting, inhibiting, reducing or decreasing or blocking the activity of at least one PDCT3 and/or PDCT5 in the plant, plant cell or seed used in the method of the invention is independent on the method that is used to achieve the decrease, depletion, inhibition, reduction or block of the activity.

Any measure that results in an expression of an inactive polypeptide or in no expression after an insertion or a mutation of a sequence into the gene encoding the PDCT3 or PDCT5 in a wild type or control is called herein "knock out".

The person skilled in the art is well aware that already the mutation of one amino acid in a polypeptide or the insertion of one base into a gene can lead to an decrease or a complete inhibition of the activity of a polypeptide in a cell, plant or a seed.

Thus, the method of the invention generally relates to decreasing or blocking the activity of at least one PDCT3 and/or PDCT5 independent on the method that is used to achieve the decrease or block of the activity.

Accordingly, the term "reduced" in context of the activity or expression of a PDCT3 and/or PDCT5 means herein that the activity of the PDCT3 and/or PDCT5 in a plant, cell, seed or a part thereof is reduced, repressed blocked, depleted, decreased or inhibited compared to a control as described herein. For example, in the assay described herein no or a reduced PDCT3 and/or PDCT5 activity can be measured. For example, the term "reduced" also encompasses a mutation or a knock out of a gene encoding the PDCT3 or PDCT5 in a plant, plant cell or seed. Thus, the term "reduced" also comprises the mutation or knock out of the PDCT3 and/or 5 of an oil seed crop producing PUFA, e.g. a *B. napus, B. carinata, B. rapa, C. sativa* or *B. juncea* or the expression of antisense RNA, ribozyme or microRNA molecules that target for the PDCT3 and/or PDCT5 in said plants, e.g. genes comprising the *B. napus, C. sativa* or *B. juncea* sequences as shown in the sequence listing According to this invention, the PDCT3 and/or PDCT5 activity is reduced, blocked, depleted, decreased or inhibited in *B. carinata* by reducing, blocking, depleting, decreasing or inhibiting the endogenous *B. carinata* gene as shown in the examples, tables and figures, e.g. in Table 5.

According to this invention, the PDCT3 and/or PDCT5 activity is reduced, blocked, depleted, decreased or inhibited in *B. juncea* by reducing, blocking, depleting, decreasing or inhibiting the endogenous *B. juncea* gene as shown in the examples, tables and figures, e.g. in Table 5.

According to this invention, the PDCT3 and/or PDCT5 activity is reduced, blocked, depleted, decreased or inhibited in *B. napus* by reducing, blocking, depleting, decreasing or inhibiting the endogenous *B. napus* gene as shown in the examples, tables and figures, e.g. in Table 5.

According to this invention, the PDCT3 and/or PDCT5 activity is reduced, blocked, depleted, decreased or inhibited in *C. sativa* by reducing, blocking, depleting, decreasing or inhibiting the endogenous *C. sativa* gene.

For example, the method of the invention comprises reducing, inhibiting, repressing, decreasing or deleting of an expression product of a nucleic acid molecule comprising a nucleic acid molecule as depicted in (a) to (f) above, e.g. a polypeptide having a PDCT3 and/or PDCT5 activity.

Accordingly, the present invention also relates to a method that comprises further at least one step selected from the group consisting of:

a) introducing of a nucleic acid molecule encoding a ribonucleic acid sequence, which is able to form a double-stranded ribonucleic acid molecule, whereby a fragment of at least 17 nt of said double-stranded ribonucleic acid molecule has a homology of at least 50%, preferably 60%, 70%, 80%, 90%, 95%, 97%, 98%, 99%, to a nucleic acid molecule selected from the group of aa) an isolated nucleic acid molecule as characterized above;

ab) an isolated nucleic acid molecule encoding a PDCT3 and/or PDCT5, wherein nucleic acid molecule is selected from the group consisting of:

ac) an isolated nucleic acid molecule encoding a (a) PDCT3 and/or PDCT5 having at least 80% sequence identity with SEQ ID NO: 18, 20, 22, 24, 26, 28, 30, 32, 50, 52, 54, 56, 58, and/or 60;

(b) PDCT3 and/or PDCT5 encoded by a polynucleotide having at least 80% sequence identity with SEQ ID NO: 17, 19, 21, 23, 27, 29, 31, 49, 51, 53, 55, and/or 57;

(c) PDCT3 and/or PDCT5 encoded by one or more polynucleotides that hybridize under high stringency conditions with (i) a polynucleotide that encodes the amino acid sequence of SEQ ID NO: 18, 20, 22, 24, 26, 28, 30, 32, 50, 52, 54, 56, 58, and/or 60, or (ii) the full-length complement of (i);

(d) variants of the PDCT3 and/or PDCT5 of SEQ ID NO: 18, 20, 22, 24, 26, 28, 30, 32, 50, 52, 54, 56, 58, and/or 60, comprising a substitution, preferably a conservative substitution, deletion, and/or insertion at one or more positions and having PDCT3 and/or PDCT5 activity;

(e) PDCT3 and/or PDCT5 encoded by a polynucleotide that differs from SEQ ID NO: 17, 19, 21, 23, 27, 29, 31, 49, 51, 53, 55, and/or 57 due to the degeneracy of the genetic code; and (f) fragments of the PDCT3 and/or PDCT5 of (a), (b), (c), (d) or (e) having PDCT3 and/or PDCT5 activity.

Thus, the reduction of the PDCT can be achieved by for example by:

b) introducing an RNAi, snRNA, dsRNA, siRNA, miRNA, ta-siRNA, cosuppression molecule, ribozyme, or antisense nucleic acid molecule, whereby the RNAi, snRNA, dsRNA, siRNA, miRNA, ta-siRNA, cosuppression molecule, ribozyme, or antisense nucleic acid molecule comprises a fragment of at least 17 nt with a homology of at least 50%, preferably 60%, 70%, 80%, 90%, 95%, 97%, 98%, 99%, to a nucleic acid molecule selected from the group defined in section (a)

c) introducing of a ribozyme which specifically cleaves a nucleic acid molecule selected from the group defined in section (a);

d) introducing of the RNAi, snRNA, dsRNA, siRNA, miRNA, ta-siRNA, cosuppression molecule, ribozyme, or antisense nucleic acid molecule characterized in (b) and the ribozyme characterized in (c);

e) introducing of a sense nucleic acid molecule conferring the expression of a nucleic acid molecule comprising a nucleic acid molecule selected from the group defined herein above or defined in section (ab) or (ac) above or a nucleic acid molecule encoding a polypeptide having at least 50% identity with the amino acid sequence of the polypeptide encoded by the nucleic acid molecule mentioned in section (a) to (c) and having a PDCT3 and/or PDCT5 activity for inducing a co-suppression of the endogenous expression product;

f) introducing a nucleic acid molecule conferring the expression of a dominant-negative mutant of a protein having the activity of a protein and having a PDCT3 and/or PDCT5 activity or comprising a polypeptide being encoded by a nucleic acid molecule as characterized herein above;

g) introducing a nucleic acid molecule encoding a factor, which binds to a nucleic acid molecule comprising a nucleic acid molecule selected from the group defined herein above or defined in section (ab) or (ac) of this claim conferring the expression of a protein having the activity of a protein encoded by a nucleic acid molecule as characterized herein above;

h) introducing a viral nucleic acid molecule conferring the decline of a RNA molecule comprising a nucleic acid molecule selected from the group defined herein above or defined in section (ab) or (ac) of this claim conferring the expression of a protein encoded by a nucleic acid molecule as characterized herein above;

i) introducing a nucleic acid construct capable to recombine with and silence, inactivate, repress or reduces the activity of an endogenous gene comprising a nucleic acid molecule selected from the group defined herein above or defined in section (ab) or (ac) of this claim conferring the expression of a protein encoded by a nucleic acid molecule as characterized herein above;

j) introducing a non-silent mutation in an endogenous gene comprising a nucleic acid molecule selected from the group defined herein above or defined in section (ab) or (ac) of this claim; and k) introducing an expression construct conferring the expression of nucleic acid molecule characterized in any one of (a) to (i).

Further, examples and methods how to reduce the activity of a PCDT are for example also described in WO2014/006158, for example, a reduction of activity of a PDCT mach be achieved by introducing mutations, such as: (a) a "missense mutation", which is a change in the nucleic acid sequence that results in the substitution of an amino acid for another amino acid; (b) a "nonsense mutation" or "STOP codon mutation", which is a change in the nucleic acid sequence that results in the introduction of a premature STOP codon and thus the termination of translation (resulting in a truncated protein); plant genes contain the translation stop codons "TGA" (UGA in RNA), "TAA" (UAA in RNA) and "TAG" (UAG in RNA); thus any nucleotide substitution, insertion, deletion which results in one of these codons to be in the mature mRNA being translated (in the reading frame) will terminate translation; (c) an "insertion mutation" of one or more amino acids, due to one or more codons having been added in the coding sequence of the nucleic acid; (d) a "deletion mutation" of one or more amino acids, due to one or more codons having been deleted in the coding sequence of the nucleic acid; WO 2014/006158 PCT/EP2013/064186 (e) a "frameshift mutation", resulting in the nucleic acid sequence being translated in a different frame downstream of the mutation. A frameshift mutation can have various causes, such as the insertion, deletion or duplication of one or more nucleotides; (f) a splice site mutation, resulting in altered splicing, which results in an altered mRNA processing and, consequently, in an altered encoded protein which contains either deletions, substitutions or insertions of various lengths, possibly combined with premature translation termination. Methods for gene targeting can be found in, for example, WO 2006/105946 or WO2009/002150.

DNA and the proteins that they encoded can be modified using various techniques known in molecular biology to generate variant proteins or enzymes with new or altered properties. For example, random PCR mutagenesis, see, e.g., Rice (1992) Proc. Natl. Acad. Sci. USA 89:5467-5471; or, combinatorial multiple cassette mutagenesis, see, e.g., Crameri (1995) Biotechniques 18:194-196.

Alternatively, nucleic acids, e.g., genes, can be reassembled after random, or "stochastic," fragmentation, see, e.g., U.S. Pat. Nos. 6,291,242; 6,287,862; 6,287,861; 5,955, 358; 5,830,721; 5,824,514; 5,811,238; 5,605,793.

Alternatively, modifications, additions or deletions are introduced by error-prone PCR, shuffling, site-directed mutagenesis, assembly PCR, sexual PCR mutagenesis, in vivo mutagenesis (phage-assisted continuous evolution, in vivo continuous evolution), cassette mutagenesis, recursive ensemble mutagenesis, exponential ensemble mutagenesis, site-specific mutagenesis, gene reassembly, gene site saturation mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

Alternatively, "gene site saturation mutagenesis" or "GSSM" includes a method that uses degenerate oligonucleotide primers to introduce point mutations into a polynucleotide, as described in detail in U.S. Pat. Nos. 6,171,820 and 6,764,835.

Alternatively, Synthetic Ligation Reassembly (SLR) includes methods of ligating oligonucleotide building blocks together non-stochastically (as disclosed in, e.g., U.S. Pat. No. 6,537,776).

Alternatively, Tailored multi-site combinatorial assembly ("TMSCA") is a method of producing a plurality of progeny polynucleotides having different combinations of various mutations at multiple sites by using at least two mutagenic non-overlapping oligonucleotide primers in a single reaction. (as described in PCT Pub. No. WO 2009/018449).

Further, the activity or expression of a PGCT according to the invention can be amended, in particular reduced by gene editing or genome editing methods. Gene editing or genome editing is a type of genetic engineering in which DNA is inserted, replaced, or removed from a genome and which can be obtained by using a variety of techniques such as "gene shuffling" or "directed evolution" consisting of iterations of DNA shuffling followed by appropriate screening and/or selection to generate variants of nucleic acids or portions thereof encoding proteins having a modified biological activity (Castle et al., (2004) Science 304 (5674): 1151-4; U.S. Pat. Nos. 5,811,238 and 6,395,547), or with "T-DNA activation" tagging (Hayashi et al. Science (1992) 1350-1353), where the resulting transgenic organisms show dominant phenotypes due to modified expression of genes close to the introduced promoter, or with "TILLING" (Targeted Induced Local Lesions In Genomes) and refers to a mutagenesis technology useful to generate and/or identify nucleic acids encoding proteins with modified expression and/or activity. TILLING also allows selection of organisms carrying such mutant variants. Methods for TILLING are well known in the art (McCallum et al., (2000) Nat Biotechnol 18: 455-457; reviewed by Stemple (2004) Nat Rev Genet 5 (2): 145-50). Another technique uses artificially engineered nucleases like Zinc finger nucleases, Transcription Activator-Like Effector Nucleases (TALENs), the CRISPR/Cas system, and engineered meganuclease such as re-engineered homing endonucleases (Esvelt, K M.; Wang, H H. (2013), Mol Syst Biol 9 (1): 641; Tan, W S. et al. (2012), Adv Genet 80:37-97; Puchta, H.; Fauser, F. (2013), Int. J. Dev. Biol 57: 629-637).

For example, in the process of the invention, a fragment of at least 17 bp of a 3'- or 5'-nucleic acid sequence of a sequences comprising a nucleic acid molecule selected from the group defined herein above or defined in section (ab) or (ac) above with an identity of at least 50%, preferably 60%, 70%, 80%, 90%, 95%, 97%, 98%, 99%, is used for the reduction of the nucleic acid molecule characterized above or the polypeptide encoded by said nucleic acid molecule.

Likewise, in the process of the invention, the reduction or deletion is caused by applying a chemical compound the non-human-organism.

Optionally, the method of the invention comprises the step of isolating the oil from the plant, plant seed or plant cell.

The present invention provides also a method comprising providing or producing a plant, a part thereof, a plant cell, and/or plant seed with an increased activity or de novo expression of one or more PDCT selected from the group consisting of:

(a) a PDCT1 having at least 80% sequence identity with SEQ ID NO: 2, 4, 6, 8, 10, 12, 14, 16, 40, 42, 44, and/or 46;

(b) a PDCT1 encoded by a polynucleotide having at least 80% sequence identity with SEQ ID NO 1, 3, 5, 7, 9, 11, 13, 15, 39, 41, 43, and/or 45;

(c) a PDCT1 encoded by a polynucleotide that hybridizes under high stringency conditions with (i) a polynucleotide that encodes the amino acid sequence of SEQ ID NO: 2, 4, 6, 8, 10, 12, 14, 16, 40, 42, 44, and/or 46, or (ii) the full-length complement of (i);

(d) a variant of the PDCT1 of SEQ ID NO: 2, 4, 6, 8, 10, 12, 14, 16, 40, 42, 44, and/or 46 comprising a substitution, preferably a conservative substitution, deletion, and/or insertion at one or more positions and having PDCT1 activity;

(e) a PDCT1 encoded by a polynucleotide that differs from SEQ ID NO 1, 3, 5, 7, 9, 11, 13, 15, 39, 41, 43, and/or 45 due to the degeneracy of the genetic code; and (f) a fragment of the PDCT1 of (a), (b), (c), (d) or (e) having PDCT1 activity;

Thus, by making use of the PDCT1 as shown herein, it is possible to improve the conversion efficiency of a Delta-6 elongase in plants, and to produce plants with an increased conversion rate of oleic acid to combined level C18 to C22 fatty acids in the cell and/or seed, and thus, to increase the production of PUFAs in a plant, cell or seed compared to a control that does not express the PDCT1 or does have a reduced activity compared to the cell, plant or seed used in the method of the invention.

According to this invention, a PDCT is considered as a "PDCT1" if in an functionality assay comprising the expression the PDCT in *A. thaliana* expressing a delta 6 elongase and a delta 6 desaturase and the PDCT having phosphotidylcholine:diacylglycerol cholinephosphotransferase (PDCT) activity, whereby the conversion rate of a delta 6 elongase is increased. Preferably the total PUFA level is increased. Preferably the PDCT1 has 80% or higher identity to SEQ ID NO. 2, and/or 4, preferably also to 6, 8, 10 and/or 12. Even more preferred is an identity of 80% also to 14 or 16. For example, the Delta-6 desaturase is phospholipid-dependent.

According to the invention, the activity of a PDCT19 can be increase, e.g. by de novo expression, for example after transformation with a corresponding expression construct, or by increasing the endogenous activity. Thus, the method of the invention comprises also increasing the activity of at least one PDCT19 in the plant, plant cell or plant seed, whereby the PDCT19 is selected from:

(a) a PDCT19 having at least 80% sequence identity with SEQ ID NO: 36, 38, and/or 48;

(b) a PDCT19 encoded by a polynucleotide having at least 80% sequence identity with SEQ ID NO: 35, 37, and/or 47;

(c) a PDCT19 encoded by a polynucleotide that hybridizes under high stringency conditions with (i) a polynucleotide that encodes the amino acid sequence of SEQ ID NO: 36, 38, and/or 48, or (ii) the full-length complement of (i);

(d) a variant of the PDCT19 of SEQ ID NO: 36, 38, and/or 48 comprising a substitution, preferably a conservative substitution, deletion, and/or insertion at one or more positions and having PDCT19 activity;

(e) a PDCT19 encoded by a polynucleotide that differs from SEQ ID NO: 35, 37, and/or 47 due to the degeneracy of the genetic code; and (f) a fragment of the PDCT19 of (a), (b), (c), (d) or (e) having PDCT19 activity.

Thus, by making use of the PDCT19 as shown herein, it is possible to improve the conversion efficiency of a Delta-6 desaturase in plants, produce plants wherein the combined ALA and LA level is less than the level of C18, C20 and C22 in the cell and/or seed, and thus, to increase the production of PUFAs in a plant, cell or seed compared to a control that does not express PDCT19 or does have a reduced activity compared to the cell, plant or seed used in the method of the invention.

Accordingly, a phosphotidylcholine:diacylglycerol cholinephosphotransferase (PDCT) enzyme is considered as a PDCT activity of the invention or "PDCT19" if has a phosphotidylcholine:diacylglycerol cholinephosphotransferase (PDCT) activity and further in a functionality assay comprising the expression of the PDCT in an *A. thaliana* ROD1 mutant expressing a delta 6 elongase and a delta 6 desaturase the ALA and LA level is less than the level of C18, C20 and C22 PUFAs. Preferably, the conversion rate of a delta 6 desaturase being increased. An example for a corresponding functionality test is shown in the examples. Such an activity herein is described as "PDCT19 activity". Preferably the PDCT19 has 80% or higher identity to SEQ ID NO. 36, 38 or 44. Preferably, the PDCT is not a *Camelina* C15 polypeptide, e.g. as shown in SEQ ID NO: 34. For example, the Delta-6 desaturase is phospholipid-dependent.

Preferably, the plant, plant cell and/or the seed is expressing a Delta-6 desaturase and/or Delta-6 elongase.

In one embodiment, in the method of the invention, the plant, plant cell, and/or seed, for example, expresses one or more Acyl-CoA dependent desaturase, e.g. an Acyl-CoA dependent Delta-4 desaturase, Delta-5 desaturase, Delta-6 Desaturase, Delta-12 Desaturase, and/or Omega-3 desaturase, for example a Acyl-CoA dependent Delta-6 desaturase as described herein.

Further, in the method of the invention, the plant, plant cell, and/or seed, for example, expresses one or more phospholipid dependent desaturases.

Thus, in the method of the invention, the plant, plant cell and/or seed, for example expresses Delta-4 desaturase, Delta-5 desaturase, Delta-6 Desaturase, Delta-12 Desaturase, and/or Omega-3 desaturase, whereby one or more desaturases use Acyl-CoA-activated fatty acids as substrate, and/or whereby one or more desaturases uses phospholipid activated fatty acids as substrate. Thus, in the method of the invention, the plant, plant cell and/or seed, for example expresses one or more Delta-4 desaturase, Delta-5 desaturase, Delta-6 Desaturase, Delta-12 Desaturase, and/or Omega-3 desaturase, that use Acyl-CoA-activated fatty acids as substrate, and one or more Delta-4 desaturase, Delta-5 desaturase, Delta-6 Desaturase, Delta-12 Desaturase, and/or Omega-3 desaturase, that use phospholipid-activated fatty acids as substrate Thus, by making use of method of the present invention it is possible to improve the conversion efficiency of a Delta-6 elongase in a plant, plant cell, plant seed or a part thereof and to produce plants with an increased level of ETA in the plant, plant cell, plant seed and/or part thereof, and thus, to increase the production of PUFAs in plant, plant cell, plant seed and/or part thereof compared to a control that does not have an reduced activity if the PDCT described herein, e.g. the PDCT3 and/or PDCT5 or does have a reduced activity compared to the cell, plant or seed used in the method of the invention.

Accordingly, the present invention relates to a method for increasing the Delta-6 elongase conversion efficiency in oil crop plant that produces vlcPUFA and expresses a Delta-6 elongase, even more preferred is the expression of Delta-6 elongase and a Delta-6 desaturase, e.g. a Acyl-CoA dependent Delta-6 desaturase, wherein the method comprises decreasing, compared to a control, in the oil crop plant, plant cell, plant seed, or a part thereof, the activity of said PDCT3 or PDCT5.

For example, the method of the invention relates to a method for increasing the Delta-6 elongase conversion efficiency in a *B. napus* cell, plant or seed, that produces ETA, comprising decreasing, compared to a control, in the *B. napus* plant, plant cell, plant seed, or a part thereof, the activity of one or more PDCT selected from the group consisting of:

(a) a PDCT3 having at least 80% sequence identity with SEQ ID NO: 18;

(b) a PDCT5 having at least 80% sequence identity with SEQ ID NO: 20;

(c) a PDCT3 encoded by a polynucleotide having at least 80% sequence identity with SEQ ID NO: 17;

(d) a PDCT5 encoded by a polynucleotide having at least 80% sequence identity with SEQ ID NO: 19

(e) a PDCT3 and/or PDCT5 encoded by one or more polynucleotides that hybridizes under high stringency conditions with (i) a polynucleotide that encodes the amino acid sequence of SEQ ID NO: 18 and/or 20, or (ii) the full-length complement of (i);

(f) variants of the PDCT3 and/or PDCT5 of SEQ ID NO: 18 and/or 20, comprising a substitution, preferably a conservative substitution, deletion, and/or insertion at one or more positions and having PDCT3 or PDCT5 activity;

(g) a PDCT3 encoded by a polynucleotide that differs from SEQ ID NO: 17 due to the degeneracy of the genetic code;

(h a PDCT5 encoded by a polynucleotide that differs from SEQ ID NO: 19 due to the degeneracy of the genetic code and (i) fragments of the PDCT3 and/or PDCT5 of (a), (b), (c), (d), (e), (f), (g), or (h) having PDCT3 and/or PDCT5 activity Further, the invention thus relates to a method for increasing the Delta 6 elongase conversion efficiency in a *B. carinata* cell, plant or seed that produces ETA, comprising decreasing, compared to a control, in the *B. carinata* plant, plant cell, plant seed, or a part thereof, the activity of one or more PDCT selected from the group consisting of:

(a) a PDCT3 having at least 90% sequence identity with SEQ ID NO: 22 or 24;

(b) a PDCT5 having at least 90% sequence identity with SEQ ID NO: 26 or 28;

(c) a PDCT3 encoded by a polynucleotide having at least 90% sequence identity with SEQ ID NO: 21 or 23;

(d) a PDCT5 encoded by a polynucleotide having at least 90% sequence identity with SEQ ID NO: 25 or 27, (e) PDCT3 and/or PDCT5 encoded by one or more polynucleotides that hybridize under high stringency conditions with (i) a polynucleotide that encodes the amino acid sequence of SEQ ID NO: 20 and/or 22, and/or 24 and/or 26, or (ii) the full-length complement of (i);

(f) variants of the PDCT3 and/or PDCT5 of SEQ ID NO: 20 and/or 22, and/or 24 and/or 26, comprising a substitution, preferably a conservative substitution, deletion, and/or insertion at one or more positions and having PDCT3 and/or PDCT5 activity;

(g) a PDCT3 encoded by a polynucleotide that differs from SEQ ID NO: 21 or 23 due to the degeneracy of the genetic code;

(h) a PDCT5 encoded by a polynucleotide that differs from SEQ ID NO: 25 or 27 due to the degeneracy of the genetic code and (e) fragments of the PDCT3 and/or PDCT5 of (a), (b), (c), (d), (e), (f), (g), or (h) having PDCT3 and/or PDCT5 activity Further, the invention relates to a method for increasing the Delta-6 elongase conversion efficiency in a *B. juncea* cell, plant or seed that produces ETA, comprising decreasing, compared to a control, in the *B. juncea* plant, plant cell, plant seed, or a part thereof, the activity of one or more PDCT selected from the group consisting of:

(a) a PDCT3 and/or PDCT5 having at least 90% sequence identity with SEQ ID NO: 30, 32, 50 52 and/or 54;

(b) a PDCT3 and/or PDCT5 encoded by a polynucleotide having at least 90% sequence identity with SEQ ID NO: 29, 31, 49, 51 and/or 53;

(c) PDCT3 and/or PDCT5 encoded by one or more polynucleotides that hybridize under high stringency conditions with (i) a polynucleotide that encodes the amino acid sequence of SEQ ID NO: 30, 32, 50 52 and/or 54, or (ii) the full-length complement of (i);

(d) variants of the PDCT3 and/or PDCT5 of SEQ ID NO: 30, 32, 50 52 and/or 54, comprising a substitution, preferably a conservative substitution, deletion, and/or insertion at one or more positions and having PDCT3 and/or PDCT5 activity;

(e) a PDCT3 and/or PDCT5 encoded by a polynucleotide that differs from SEQ ID NO: 29, 31, 49, 51 and/or 53 due to the degeneracy of the genetic code; and (f) fragments of the PDCT3 and/or PDCT5 of (a), (b), (c), (d), or (e) having PDCT3 and/or PDCT5 activity.

Further, the present invention relates to a method for the production of a plant, a part thereof, a plant cell, plant seed and/or plant seed comprising an oil wherein the level of the 18:2 fatty acid fraction in % (w/w) in the triacylglycerol (TAG) composition is higher than the 18:2 fatty acid level in % (w/w) in the diacylglyerol (DAG) fraction, comprising decreasing, compared to a control, in the oil crop plant, plant cell, plant seed, or a part thereof, the activity of one or more PDCT selected from the group consisting of:

(a) PDCT3 and/or PDCT5 having at least 80% sequence identity with SEQ ID NO: 18, 20, 22, 24, 26, 28, 30, 32, 50, 52, 54, 56, 58, and/or 60;

(b) PDCT3 and/or PDCT5 encoded by a polynucleotide having at least 80% sequence identity with SEQ ID NO: 17, 19, 21, 23, 27, 29, 31, 49, 51, 53, 55, 57 and/or 59;

(c) PDCT3 and/or PDCT5 encoded by one or more polynucleotides that hybridize under high stringency conditions with (i) a polynucleotide that encodes the amino acid sequence of SEQ ID NO: 18, 20, 22, 24, 26, 28, 30, 32, 50, 52, 54, 56, 58, and/or 60, or (ii) the full-length complement of (i);

(d) variants of the PDCT3 and/or PDCT5 of SEQ ID NO: 18, 20, 22, 24, 26, 28, 30, 32, 50, 52, 54, 56, 58, and/or 60, comprising a substitution, preferably a conservative substitution, deletion, and/or insertion at one or more positions and having PDCT3 and/or PDCT5 activity;

(e) PDCT3 and/or PDCT5 encoded by a polynucleotide that differs from SEQ ID NO: 17, 19, 21, 23, 27, 29, 31, 49, 51, 53, 55, 57 and/or 59 due to the degeneracy of the genetic code; and (f) fragments of the PDCT3 and/or PDCT5 of (a), (b), (c), (d) or (e) having PDCT3 and/or PDCT5 activity.

Optionally, the seed oil is isolated.

Further, the present invention relates to a method for the production of a composition, e.g. an oil, comprising the fatty acid 20:0 in a plant, or part thereof, like a plant cell, and/or part seed, or part thereof, wherein the level of the 20:0 fatty acid fraction in % (w/w) in the diacylglyerol fraction is higher than the 20:0 fatty acid level in % (w/w) in the triacylglycerol fraction, comprising, providing a plant cable to produce the 20:0 fatty acid and having a decreased activity or expression of one or more PDCT compared to the wild type, the PDCT selected from the group consisting of:

(a) PDCT3 and/or PDCT5 having at least 80% sequence identity with SEQ ID NO: 18, 20, 22, 24, 26, 28, 30, 32, 50, 52, 54, 56, 58, and/or 60;

(b) PDCT3 and/or PDCT5 encoded by a polynucleotide having at least 80% sequence identity with SEQ ID NO: 17, 19, 21, 23, 27, 29, 31, 49, 51, 53, 55, 57 and/or 59;

(c) PDCT3 and/or PDCT5 encoded by one or more polynucleotides that hybridize under high stringency conditions with (i) a polynucleotide that encodes the amino acid sequence of SEQ ID NO: 18, 20, 22, 24, 26, 28, 30, 32, 50, 52, 54, 56, 58, and/or 60, or (ii) the full-length complement of (i);

(d) variants of the PDCT3 and/or PDCT5 of SEQ ID NO: 18, 20, 22, 24, 26, 28, 30, 32, 50, 52, 54, 56, 58, and/or 60, comprising a substitution, preferably a conservative substitution, deletion, and/or insertion at one or more positions and having PDCT3 and/or PDCT5 activity;

(e) PDCT3 and/or PDCT5 encoded by a polynucleotide that differs from SEQ ID NO: 17, 19, 21, 23, 27, 29, 31, 49, 51, 53, 55, 57 and/or 59 due to the degeneracy of the genetic code; and (f) fragments of the PDCT3 and/or PDCT5 of (a), (b), (c), (d) or (e) having PDCT3 and/or PDCT5 activity.

Further, the present invention relates to a method for the production of a composition, e.g. an oil, comprising the 22:1 fatty acid in a plant, or part thereof, like a plant cell, and/or part seed, or part thereof, wherein the level of the 22:1 fatty acid in % (w/w) in the diacylglyerol (DAG) fraction is higher than the 22:1 level in % (w/w) in the triacylglycerol fraction, comprising, providing a plant cable to produce 22:1 and having a decreased activity or expression of one or more PDCT compared to the wild type, the PDCT selected from the group consisting of:

(a) PDCT3 and/or PDCT5 having at least 80% sequence identity with SEQ ID NO: 18, 20, 22, 24, 26, 28, 30, 32, 50, 52, 54, 56, 58, and/or 60;

(b) PDCT3 and/or PDCT5 encoded by a polynucleotide having at least 80% sequence identity with SEQ ID NO: 17, 19, 21, 23, 27, 29, 31, 49, 51, 53, 55, 57 and/or 59;

(c) PDCT3 and/or PDCT5 encoded by one or more polynucleotides that hybridize under high stringency conditions with (i) a polynucleotide that encodes the amino acid sequence of SEQ ID NO: 18, 20, 22, 24, 26, 28, 30, 32, 50, 52, 54, 56, 58, and/or 60, or (ii) the full-length complement of (i);

(d) variants of the PDCT3 and/or PDCT5 of SEQ ID NO: 18, 20, 22, 24, 26, 28, 30, 32, 50, 52, 54, 56, 58, and/or 60, comprising a substitution, preferably a conservative substitution, deletion, and/or insertion at one or more positions and having PDCT3 and/or PDCT5 activity;

(e) PDCT3 and/or PDCT5 encoded by a polynucleotide that differs from SEQ ID NO: 17, 19, 21, 23, 27, 29, 31, 49, 51, 53, 55, 57 and/or 59 due to the degeneracy of the genetic code; and (f) fragments of the PDCT3 and/or PDCT5 of (a), (b), (c), (d) or (e) having PDCT3 and/or PDCT5 activity.

It was found that the expression of the PDCT of the invention influences the trafficking of the fatty acids between different lipid pools. Increasing the activity of the polynucleotide of the invention, e.g. by overexpression the gene in seed, for example after transformation of a plant with the nucleotide sequences or constructs described herein, the ratio between the fatty acid in the TAG pool and the DAG pools changes compared to the control like a plant expressing only the natural occurring PDCT. For example, the fatty acid compositions are isolated from immature seeds, e.g. expressing a delta-6-desaturase and a delta-6-elongase. The level of 18:2 fatty acid is higher in the TAG fraction than in the DAG fraction if the expression of the PDCT3_5 or the sequences described herein is suppressed or reduced, whereas in the control the level of 18:2 is higher in the DAG fraction than in the TAG fraction. For example, the level of 18:2 fatty acid in the triacylglycerol fraction is more than 110% and less than 300% of the fatty acid level of the 18:2 fatty acid in the diacylglyerol fraction for example, 120%, 130%, 150%, 180%, or more, for example, between 130% and 180%. It was found that in the control, the level of 18:2 fatty acid in the triacylglycerol composition is less than 65% of the 18:2 fatty acid level in the diacylglyerol fraction. The ratio of the fatty acids in the different pools may be determined as described in the examples.

The level of 20:0 fatty acid is lower in the TAG fraction than in the DAG fraction if the expression of the PDCT3_5 or the sequences described herein is suppressed or reduced, whereas in the control the level of 20:0 is lower in the DAG fraction than in the TAG fraction. The level of 20:0 in the triacylglycerol fraction is more than 120% of the level of the 20:0 fatty acid in the diacylglyerol fraction, e.g. 150%, 180%, 200% or more, for example, between 150% and 200%, e.g. less than 500, 400%, 350% or 300%. It was found that in the control, the level of 20:0 fatty acid in the triacylglycerol fraction is less than 80% of level of the 20:0 fatty acid in the diacylglyerol fraction. The ratio of the fatty acids in the different pools may be determined as described in the examples.

The level of 22:1 fatty acid is lower in the TAG fraction than in the DAG fraction if the expression of the PDCT3_5 or the sequences described herein is suppressed or reduced, whereas in the control the level of 22:1 is about the same in the DAG fraction as in the TAG fraction. The level of 22:1 in the TAG fraction is more than 110% of the level of the 22:1 fatty acid level in the DAG fraction, e.g. 150%, 200%, 250%, 300%, 400%, 500%, 600%, 700%, 800% or 900% or more, for example, between 200% and 900%, e.g. less than 1500%, e.g. 1000% or less. It was found that in the control, the level of 22:1 fatty acid in the TAG fraction is about the same as the SDA level in the DAG fraction. The ratio of the fatty acids in the different pools may be determined as described in the examples.

For example, the plant used in the methods of the invention is also expressing a delta-6-elongase, as described herein and/or a delta-6-elongase, as described herein. Further, the plant the part thereof can have an increased total PUFA content as described herein. In one embodiment, the plant or plant part, e.g. the seed, comprises an oil or fatty acid composition with an increased DPA, DHA and/or EPA content as described herein.

In one embodiment, the present invention relates to an oil derived from a plant or a plant seed, that capable to produce EPA, and for example also DHA, and that expresses a delta 6 elongase and has reduced or no PDCT3 and/or PDCT5 activity, e.g. a plant as described herein, with one or more, e.g. all of the following features compared to the oil of a control plant:

i. Increased ETA level
ii. Reduced ALA level,
iii. Reduced GLA level
iv. Reduced SDA level,
v. the level of the 18:2 fatty acid fraction in % (w/w) in the triacylglycerol (TAG) composition is higher than the 18:2 fatty acid level in % (w/w) in the diacylglyerol (DAG) fraction,
vi. the level of the 20:0 fatty acid in % (w/w) in the diacylglyerol fraction is higher than the 20:0 fatty acid level in % (w/w) in the triacylglycerol fraction
vii. wherein the level of the 22:1 fatty acid in % (w/w) in the diacylglyerol (DAG) fraction is higher than the SDA level in % (w/w) in the triacylglycerol fraction and/or
viii. Reduced 18:1 fatty acid level.

For example, the level of 18:2 fatty acid in the triacylglycerol fraction is more than 110% and less than 300% of the fatty acid level of the 18:2 fatty acid in the diacylglyerol fraction for example, 120%, 130%, 150%, 180%, or more, for example, between 130% and 180%; and/or the level of 20:0 in the triacylglycerol fraction is more than 120% of the level of the 20:0 fatty acid in the diacylglyerol fraction, e.g. 150%, 180%, 200% or more, for example, between 150% and 200%, e.g. less than 500, 400%, 350% or 300%, and/or the level of 22:1 in the TAG fraction is more than 110% of the level of the 22:1 fatty acid level in the DAG fraction, e.g. 150%, 200%, 250%, 300%, 400%, 500%, 600%, 700%, 800% or 900% or more, for example, between 200% and 900%, e.g. less than 1500%, e.g. 1000% or less. For example, the level of 18:2 fatty acid in the triacylglycerol fraction is more than 110% and less than 180% of the fatty acid level of the 18:2 fatty acid in the diacylglyerol fraction; and/or the level of 20:0 in the triacylglycerol fraction is between 120% and 200% of the level of the 20:0 fatty acid in the diacylglyerol fraction, and/or the level of 22:1 in the TAG fraction is between 110% and 400% of the level of the 22:1 fatty acid level in the DAG fraction.

Figure 6A:
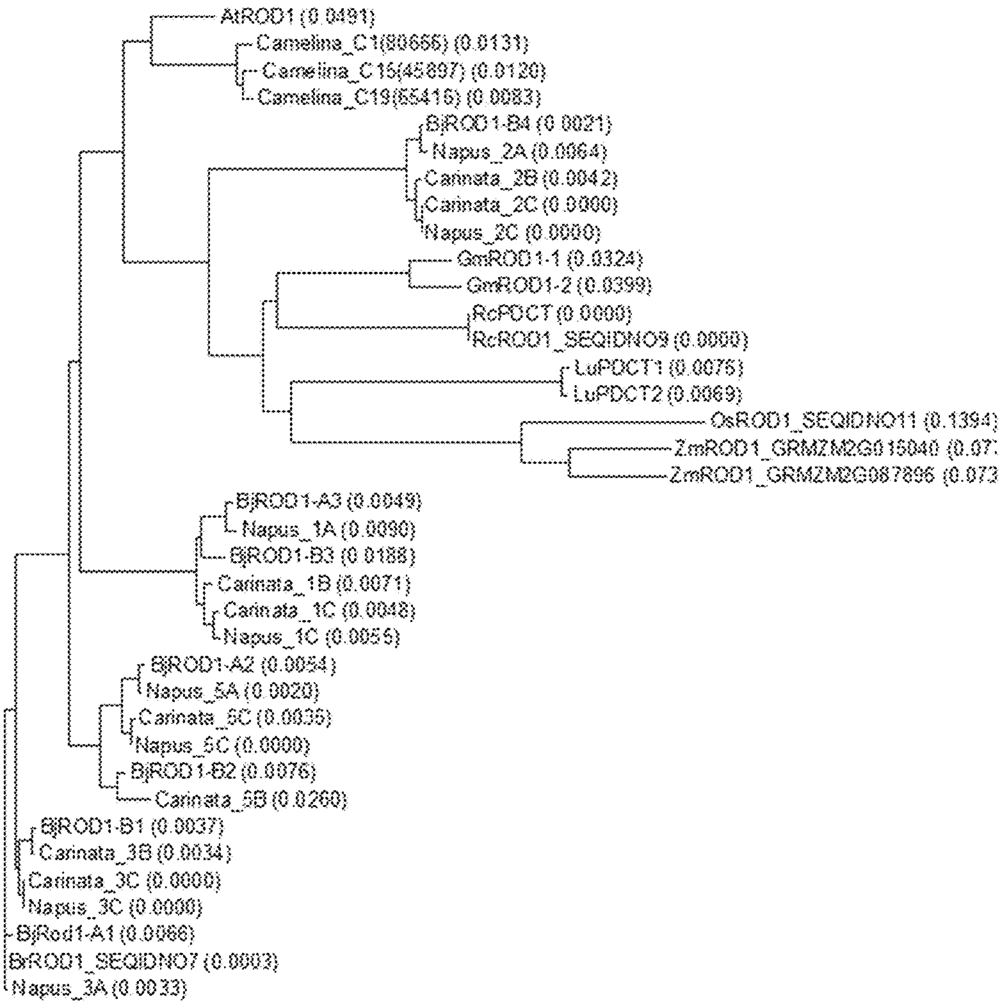
Figure 6B:
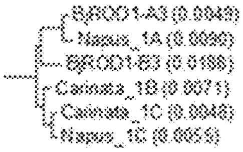
Figure 6C:
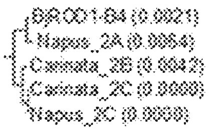
Figure 6D:
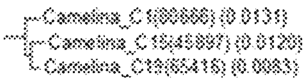
Figure 6E:
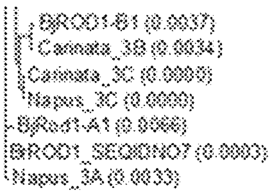
Figure 6F:
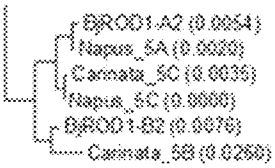
Figure 9A:
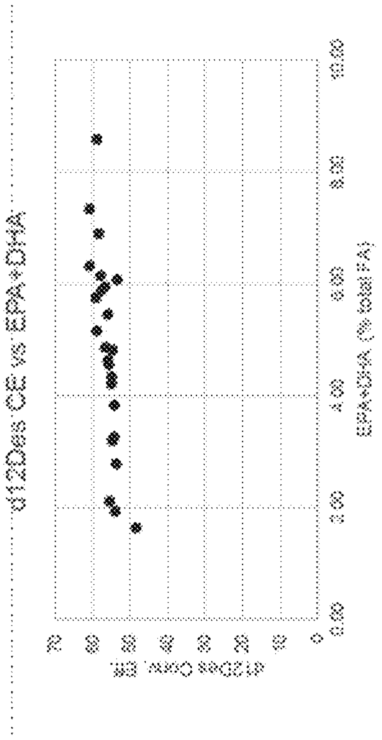
Figure 9B:
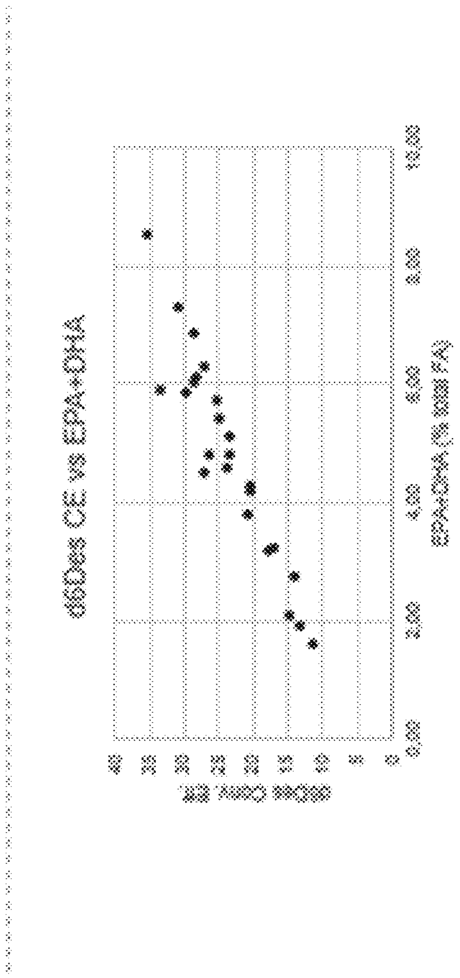
Figure 9C:
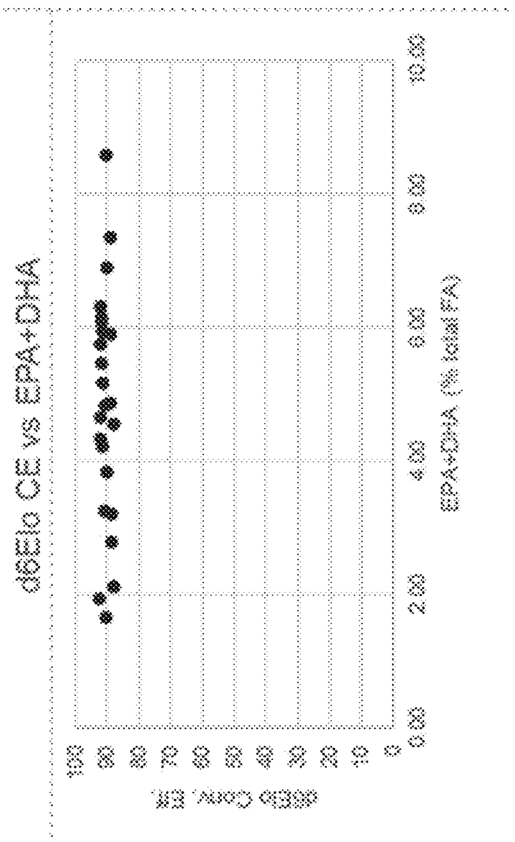
Figure 9D:
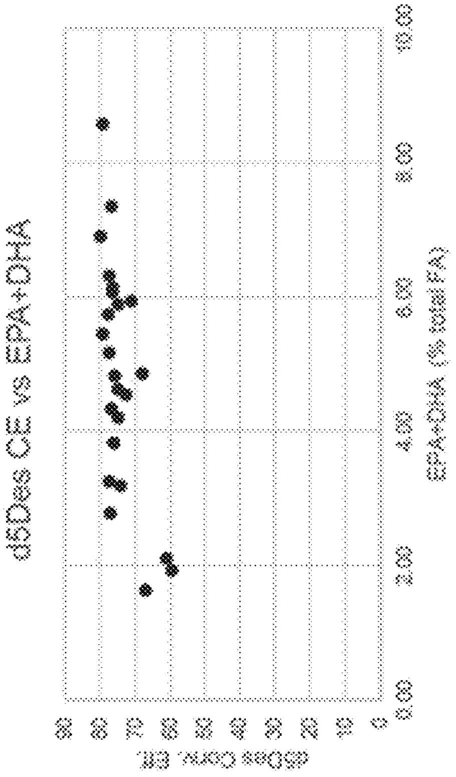
Figure 9E:
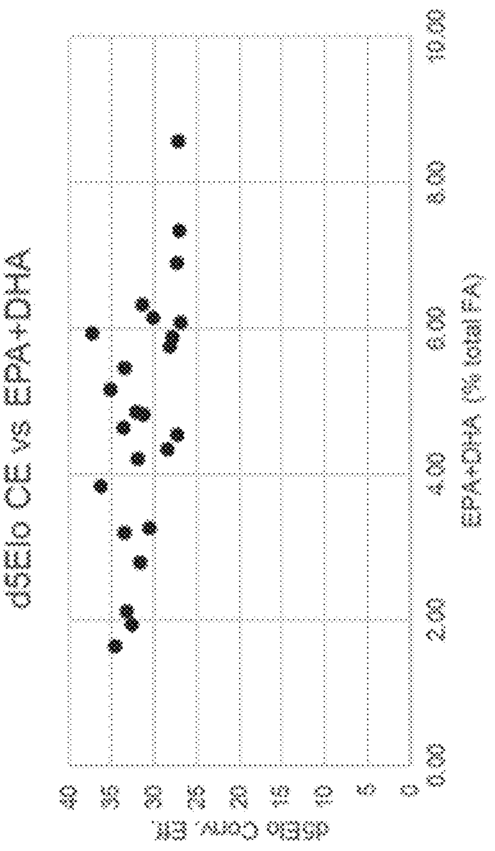
Figure 9F:
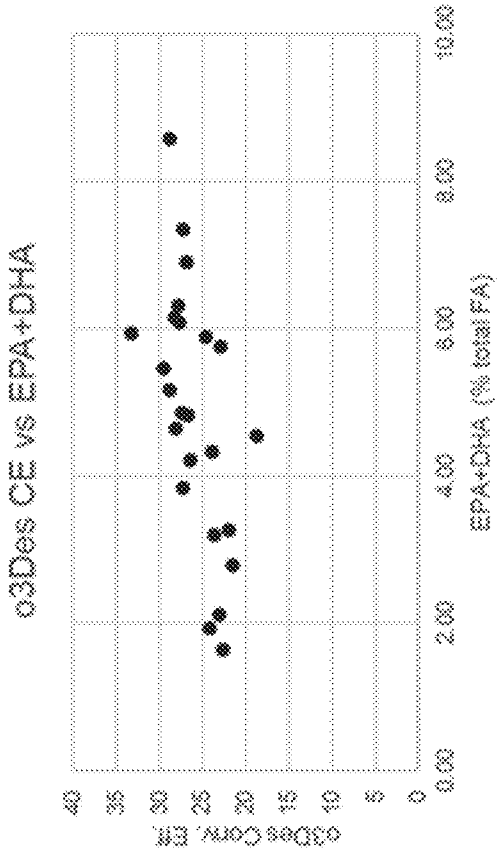
Figure 9G:
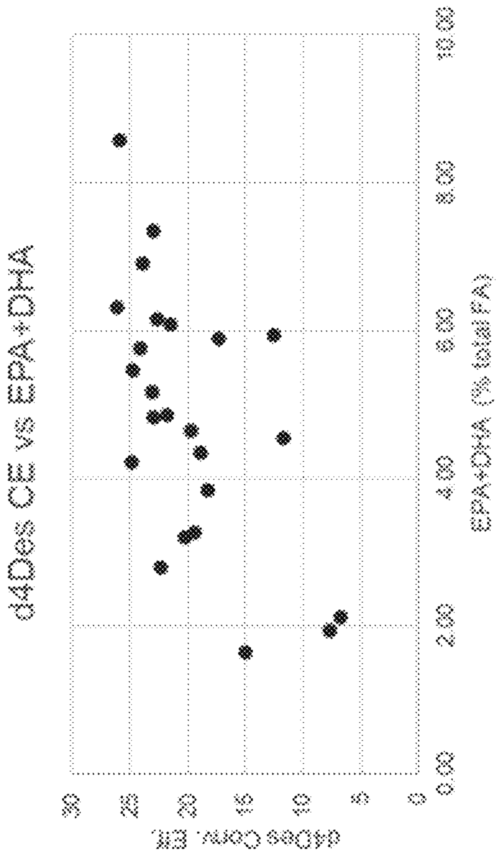

For example, in the method of the invention, the decreased activity of the PDCT3 can be achieved by reducing the activity of a PDCT as shown in FIG. 6E in the corresponding organism. Further, for example, the expression of more than one PDCT3 is decreased the PDCT3 shown in FIG. 6E is reduced, inhibited or the gene or a corresponding regulatory element is mutated For example, in the method of the invention, the decreased activity of the PDCT5 can be achieved by reducing the activity of a PDCT as shown in FIG. 6F in the corresponding organism. Further, for example, the expression of more than one PDCT5 is decreased if the PDCT5 shown in FIG. 6E is reduced, inhibited or the gene or a corresponding regulatory element is mutated For example, in the method of the invention, the increased activity of the PDCT1 can be achieved by expressing de novo or overexpressing a PDCT1. Further, for example, the activity of more than one PDCT1 is increased, overexpressing or expressing de novo the PDCT1 shown in FIG. 6B. Further, for example, the activity of more than one PDCT1 is increased, overexpressing or expressing de novo the PDCT1 shown in FIG. 6C. According to the method of the invention, for example, also a PDCT1 as shown in FIG. 6B and one as shown in FIG. 6C can be expressed or overexpressed to achieve the desired effect of the method.

For example, in the method of the invention, the increased activity of the PDCT19 can be achieved by expressing de novo or overexpressing a PDCT19. Further, for example, the activity of more than one PDCT19 is increased, overexpressing or expressing de novo the PDCT1 shown in FIG. 6D. According to the method of the invention, for example, also a PDCT1 as shown in FIG. 6B and one as shown in FIG. 6C can be expressed or overexpressed together with a PDCT shown in FIG. 6D to achieve the desired effect of the method.

Preferably, the gene that corresponds to the target organism, e.g. the organism in which the activity shall be increased, is overexpressed.

For example, a PDCT3 from *B. napus* as shown in FIG. 6D is reduced in its activity in the method of the present invention in *B. napus*. For example, a PDCT5 from *B. juncea* as shown in FIG. 6F is reduced in its activity in the method of the present invention in *B. juncea.*

The plant of the method of the present comprises a gene that encodes for the PDCT described herein as the PDCT of the invention, e.g. a PDCT3 or a PDCT5. The plant of the method of the present invention can for example be capable of expressing a PDCT as defined herein, in particular a PDCT3 and/or PDCT5, but the expression or activity is reduced, blocked, depleted, decreased or inhibited compared to the control or to the wild type. Further, the plant of the method of the present invention can also, for example not be capable of expressing the PDCT as defined herein, in particular a PDCT3 and/or PDCT5, as the expression is reduced, blocked, depleted, decreased or inhibited. The plant of the method of the present invention can also, for example not be capable of expressing an active PDCT as defined herein, in particular a PDCT3 and/or PDCT5, as the coding sequence was mutated and only a non-active PDCT or a PDCT3 and/or PDCT5 as defined herein with a reduced activity, e.g. with an reduced Delta-6 elongase increasing conversion rate is expressed. Other methods to reduced, blocked, depleted or inhibited the activity of a gene or protein are known to the person skilled in the art and comprise for example the expression of antibodies or inhibitors specifically binding to the protein and reducing, blocking, depleting or inhibiting the protein or its activity.

For example, the method of the invention comprises also increasing the expression, e.g. by a de novo expression with an expression construct encoding the corresponding PDCT, or by increasing the endogenous activity of at least one PDCT, whereby the PDCT is selected from the groups consisting of:

(a) a PDCT1 having at least 80% sequence identity with SEQ ID NO: 2, 4, 6, 8, 10, 12, 14, 16, 40, 42, 44, and/or 46;
(b) a PDCT1 encoded by a polynucleotide having at least 80% sequence identity with SEQ ID NO 1, 3, 5, 7, 9, 11, 13, 15, 39, 41, 43, and/or 45;
(c) a PDCT1 encoded by a polynucleotide that hybridizes under high stringency conditions with (i) a polynucleotide that encodes the amino acid sequence of SEQ ID NO: 2, 4, 6, 8, 10, 12, 14, 16, 40, 42, 44, and/or 46, or (ii) the full-length complement of (i);
(d) a variant of the PDCT1 of SEQ ID NO: 2, 4, 6, 8, 10, 12, 14, 16, 40, 42, 44, and/or 46 comprising a substitution, preferably a conservative substitution, deletion, and/or insertion at one or more positions and having PDCT1 activity;
(e) a PDCT1 encoded by a polynucleotide that differs from SEQ ID NO 1, 3, 5, 7, 9, 11, 13, 15, 39, 41, 43, and/or 45 due to the degeneracy of the genetic code;
(f) a fragment of the PDCT1 of (a), (b), (c), (d) or (e) having PDCT1 activity;
(g) a PDCT19 having at least 80% sequence identity with SEQ ID NO: 36, 38, and/or 48;
(h) a PDCT19 encoded by a polynucleotide having at least 80% sequence identity with SEQ ID NO: 35, 37, and/or 47;
(i) a PDCT19 encoded by a polynucleotide that hybridizes under high stringency conditions with (i) a polynucleotide that encodes the amino acid sequence of SEQ ID NO: 36, 38, and/or 48, or (ii) the full-length complement of (i);
(j) a variant of the PDCT19 of SEQ ID NO: 36, 38, and/or 48 comprising a substitution, preferably a conservative substitution, deletion, and/or insertion at one or more positions and having PDCT19 activity;
(k) a PDCT19 encoded by a polynucleotide that differs from SEQ ID NO: 35, 37, and/or 47 due to the degeneracy of the genetic code; and
(l) a fragment of the PDCT19 of (g), (h), (i), (j) or (k) having PDCT19 activity According to the present invention, unsaturated fatty acids preferably are polyunsaturated fatty acids, that is fatty acids comprising at least two, more preferably at least three and even more preferably at least or exactly 4 carbon-carbon double bonds. Unsaturated fatty acids including polyunsaturated fatty acids are generally known to the skilled person, important unsaturated fatty acids are categorised into a omega-3, omega-6 and omega-9 series, without any limitation intended. Unsaturated fatty acids of the omega-6 series include, for example, and without limitation, linoleic acid (18:2 n-6; LA), gamma-linolenic acid (18:3 n-6; GLA), di-homo-gamma-linolenic acid (C20: 3 n-6; DGLA), arachidonic acid (C20: 4 n-6; ARA), adrenic acid (also called docosatetraenoic acid or DTA; C22: 4 n-6) and docosapentaenoic acid (C22: 5 n-6). Unsaturated fatty acids of the omega-3 series include, for example and without limitation, alpha-linolenic acid (18:3 n-3, ALA), stearidonic acid (18:4 n-3; STA or SDA), eicosatrienoic acid (C20: 3 n-3; ETA), eicosatetraenoic acid (C20: 4 n-3; ETA), eicosapentaenoic acid (C20: 5 n-3; EPA), docosapentaenoic acid (C22: 5 n-3; DPA) and docosahexaenoic acid (C22: 6 n-3; DHA). Unsaturated fatty acids also include fatty acids with greater than 22 carbons and 4 or more double bonds, for example and without limitation, C28: 8 (n-3). Unsaturated fatty acids of the omega-9 series include, for example, and without limitation, mead acid (20:3 n-9; 5,8,11-eicosatrienoic acid), erucic acid (22:1 n-9; 13-docosenoic acid) and nervonic acid (24:1 n-9; 15-tetracosenoic acid). Further unsaturated fatty acids are eicosadienoic acid (C20: 2d11,14; EDA) and eicosatrienoic acid (20: 3d11, 14,17; ETrA).

In the method of the invention a number of VLC-PUFA and intermediates are produced that are non-naturally occurring in wild type crop plant, in particular not in oil seed crop plants, though they VLC-PUFA and intermediates may occur in various other organisms. These fatty acids include but are not limited to 18: 2n-9, GLA, SDA, 20: 2n-9, 20: 3n-9, 20:3 n-6, 20: 4n-6, 22: 2n-6, 22: 5n-6, 22: 4n-3, 22: 5n-3, and 22: 6n-3.

According to the present invention, the metabolic property preferably is the production and particularly preferably the yield of an omega-6 type and/or an omega-3 type unsaturated fatty acid. Such yield is preferably defined as the percentage of said fatty acid relative to the total fatty acids of an extract, preferably of a plant or seed oil. Thus, preferably the assay method of the present invention entails measuring the amount and/or concentration of an unsaturated fatty acid, preferably of an unsaturated fatty acid having at least 20 carbon atoms length, for example 18, 20 and 22 carbon atoms length, and belonging to the omiga-3 or omega-6 series.

Preferably, the DPA, DHA and/or EPA level is increased in lipids or oil or in an composition of fatty acids derived or isolated from the plant, plant cell or seed provided according to the method of the invention.

An increase in the level or the increase of a fatty acid or the increase of a combination of fatty acids or the increase of PUFAs or the increase of total PUFAs or similar expressions refer to an increase of the specific compound or the combination of compounds compared to a control. For example, the increase of said compound or combination of compound is an relative increase within the corresponding extract from plants, plant cells or plant seeds. According to the invention, the increase of a fatty acid or a combination of fatty acids, e.g. of a PUFA or of PUFAs, like vlcPUFAs, is measured in the oil or the fatty acids extracted from the plant, plant cell or plant seed in percent per volume or percent per weight, preferably percent of weight. For example, the content and composition of an extract from a plant, plant cell or plant seed or from plants, plant cells or plant seeds can be measured as shown in the examples.

"Total PUFA" as used in this invention refers to the level of GLA 18: 3n-6, SDA 18: 4n-3, DGLA 20: 3n-6, EtrA 20: 3n-3, ETA 20: 4n-3, ARA 20: 4n-6, EPA 20:5 n-3, DPA 22"5n-3, and DHA 22: 6n-3.

With the level of "total" or "new" PUFA is meant the level of GLA 18: 3n-6, SDA 18: 4n-3, DGLA 20: 3n-6, EtrA 20: 3n-3, ETA 20: 4n-3, ARA 20: 4n-6, EPA 20:5 n-3, DPA 22"5n-3, and DHA 22: 6n-3. For example, the term does not include (18: 2n-6) and ALA (18: 3n-3).

The amount and/or concentration is determined on a plant extract, preferably a plant oil or plant lipids. The term "lipids" refers to a complex mixture of molecules comprising compounds such as sterols, waxes, fat soluble vitamins such as tocopherols and carotenoid/retinoids, sphingolipids, phosphoglycerides, glycolipids such as glycosphingolipids, phospholipids such as phosphatidylethanolamine, phosphatidylcholine, phosphatidylserine, phosphatidylglycerol, phosphatidylinositol or diphosphatidylglycerol, monoacylglycerides, diacylglycerides, triacylglycerides or other fatty acid esters such as acetylcoenzyme A esters. "Lipids" can be obtained from biological samples, such as fungi, algae, plants, leaves, seeds, or extracts thereof, by solvent extraction using protocols well known to those skilled in the art (for example, as described in Bligh, E. G., and Dyer, J. J. (1959) Can J. Biochem. Physiol. 37:911-918).

The term "oil" refers to a fatty acid mixture comprising unsaturated and/or saturated fatty acids which are esterified to triglycerides. The oil may further comprise free fatty acids. Fatty acid content can be, e.g., determined by GC analysis after converting the fatty acids into the methyl esters by transesterification. The content of the various fatty acids in the oil or fat can vary, in particular depending on the source. It is known that most of the fatty acids in plant oil are esterified in triacylglycerides. In addition the oil of the invention may comprise other molecular species, such as monoacylglycerides, diacylglycerides, phospholipids, or any the molecules comprising lipids. Moreover, oil may comprise minor amounts of the polynucleotide or vector of the invention. Such low amounts, however, can be detected only by highly sensitive techniques such as PCR. Oil can be obtained by extraction of lipids from any lipid containing biological tissue and the amount of oil recovered is dependent on the amount of triacylglycerides present in the tissue. Extraction of oil from biological material can be achieved in a variety of ways, including solvent and mechanical extraction. Specifically, extraction of canola oil typically involves both solvent and mechanical extraction, the products of which are combined to form crude oil. The crude canola oil is further purified to remove phospholipids, free fatty acids, pigments and metals, and odiferous compounds by sequential degumming, refining, bleaching, and deoderorizing. The final product after these steps is a refined, bleached, and deodorized oil comprising predominantly fatty acids in the form of triglycerides.

The method of the present invention comprises the step of providing and/or producing a plant. According to the present invention, the term "plant" shall mean a plant or part thereof in any developmental stage. Particularly, the term "plant" herein is to be understood to indicate a callus, shoots, root, stem, branch, leaf, flower, pollen and/or seed, and/or any part thereof. The plant can be monocotyledonous or dicotyledonous and preferably is a crop plant. Crop plants include *Brassica* species, corn, alfalfa, sunflower, soybean, cotton, safflower, peanut, sorghum, wheat, millet and tobacco. The plant preferably is an oil plant. Preferred plants are of order Brassicales, particularly preferred of family Brassicaceae.

Even more preferred are plants of oil seed crops, e.g. *Camelina* sp., *Brassica* sp. e.g. *Camelina sativa, Brassica aucheri, Brassica balearica, Brassica barrelieri, Brassica carinata, Brassica carinata* x *Brassica napus, Brassica carinata* x *Brassica rapa, Brassica carinata* x *Brassica juncea, Brassica cretica, Brassica deflexa, Brassica desnottesii, Brassica drepanensis, Brassica elongata, Brassica fruticulosa, Brassica gravinae, Brassica hilarionis, Brassica incana, Brassica insularis, Brassica juncea, Brassica macrocarpa, Brassica maurorum, Brassica montana, Bras-*

*sica napus, Brassica napus* x *Brassica juncea, Brassica napus* x *Brassica nigra, Brassica nigra, Brassica oleracea, Brassica oxyrrhina, Brassica procumbens, Brassica rapa, Brassica repanda, Brassica rupestris, Brassica ruvo, Brassica souliei, Brassica spinescens, Brassica tournefortii* or *Brassica villosa.*

The plant can be provided by any appropriate means. For example, the plant can be provided by transforming a plant cell expressing the PDCT defined herein with a nucleic acid comprising a gene coding for inactive PDCT as defined herein or a corresponding PDCT with an decreased activity. For example, the plant can be provided by transforming a plant expressing the PDCT defined herein with an antisense RNA, microRNA, ribozyme encoding expression construct and reducing or inhibiting the expression of the native PDCT as described herein. For example, the plant can be provided by transforming a plant cell expressing the PDCT defined herein with an construct that inserts into the gene encoding the PDCT as defined herein and reducing or inhibiting the expression of the native PDCT as described herein. For example, the plant can be provided by mutating a plant cell expressing the PDCT defined herein with an construct that allows mutation, e.g. a site specific mutation, of the gene encoding the PDCT or the regulatory element that controls the transcription of the gene or the stability of the resulting RNA or the translation of the RNA of a gene encoding the PDCT as defined herein, for example reducing or inhibiting the expression of the native PDCT as described herein.

For example, the plant that is used in the method of the present invention is generally capable of expressing a PDCT as defined herein, in particular a PDCT3 or PDCT5, e.g. in form of the wild type or control.

For example, the plant is also capable of expressing a PDCT1 or PDCT 19 of the invention. According to the invention, the term "capable of expressing a gene product" means that a cell will produce the gene product provided that the growth conditions of the sale are sufficient for production of said gene product. For example, a plant is capable of expressing a PDCT, in particular a PDCT1 or a PDCT19 is a cell of said plant during any developmental stage of said plant will produce the corresponding PDCT.

For example, such transformed plant cell is planted and grown to a plant sufficiently developed for measuring the plant metabolic property. According to the invention, a plant can also be provided in the form of an offspring of such transformed plant. Such offspring may be produced vegetatively from material of a parent plant, or may be produced by crossing a plant with another plant, preferably by inbreeding.

According to the invention, the term "capable of expressing a gene product" means that a cell will produce the gene product provided that the growth conditions are sufficient for production of said gene product.

A PDCT having this desired sequence identity and/or sequence similarity and functionality is also called a PDCT of the present invention, PDCT used in the method of the invention or PDCT blocked, inhibited, inactivated, depleted or reduced in the method of the invention.

Preferably the PDCT3 and/or PDCT5 has 80% or higher identity to SEQ ID NO. 17, 19, 21, 23, 27, 29, 31, 49, 51, 53, 55, and/or 57. Preferably a PDCT3 has an identity of at least 80% to SEQ ID NO. 18, 22, or 24. Preferably, a PDCT5 has an identity of at least 80% to SEQ ID NO. 20, 26 or 28.

For a metabolic pathway for the production of unsaturated and polyunsaturated fatty acids, see for example FIG. 4 or FIG. 1 of WO2006100241.

Examples of PDCT referred to herein shown in the Examples, Figures and Tables, e.g. in Tables 5 or 6:

The action of a PDCT is shown in FIG. 5.

According to the invention, in the plant, plant seed, plant cell or part thereof a the activity or expression of the PDCT of the invention, in particular a PDCT3 and/or PDCT5, is reduced, blocked, depleted or inhibited, wherein said PDCT of the invention, in particular a PDCT3 and/or PDCT5 has at least, the PDCT3 and/or PDCT5 50, 70, 80, 85, 87, 88, 90, 91, 92, 92, 94, 95, 96, 97, 98, 99, or 100% sequence identity with 18, 20, 22, 24, 26, 28, 30, 32, 50, 52, 54, 56, 58, and/or 60. For example, the PDCT of said method has at least 50, 70, 80, 85, 87, 88, 90, 91, 92, 92, 94, 95, 96, 97, 98, 99, or 100% sequence identity with SEQ ID NO: 18, 22 and/or 26. Further, for example, the PDCT of said method has at least 50, 70, 80, 85, 87, 88, 90, 91, 92, 92, 94, 95, 96, 97, 98, 99, or 100% sequence identity with SEQ ID NO: 20, 26 and/or 28. Likewise, for example, the PDCT of said method has at least 50, 70, 80, 85, 87, 88, 90, 91, 92, 92, 94, 95, 96, 97, 98, 99, or 100% sequence identity with SEQ ID NO: 30, and/or 30, or 32, 50 and/or 54.

According to the invention, a nucleic acid sequence encoding a PDCT3 and/or PDCT5 can have 50, 70, 80, 85, 87, 88, 90, 91, 92, 92, 94, 95, 96, 97, 98, 99, or 100% sequence identity with SEQ ID NO: 18, 20, 22, 24, 26, 28, 30, 32, 50, 52, 54, 56, 58, and/or 60.

According to the invention, a PDCT19 can have 50, 70, 80, 85, 87, 88, 90, 91, 92, 92, 94, 95, 96, 97, 98, 99, or 100% sequence identity with SEQ ID NO: 36, 38, and/or 44.

According to the invention, a nucleic acid sequence encoding a PDCT19 can have 50, 70, 80, 85, 87, 88, 90, 91, 92, 92, 94, 95, 96, 97, 98, 99, or 100% sequence identity with SEQ ID NO: 35, 37, and/or 43.

According to the invention, the plant is capable of expressing a PDCT of the invention, in particular a PDCT1, wherein said PDCT of the invention, in particular a PDCT1 has at least, the PDCT1 50, 70, 80, 85, 87, 88, 90, 91, 92, 92, 94, 95, 96, 97, 98, 99, or 100% sequence identity with SEQ ID NO: 2, 4, 6, 8, 10, 12, 14, 16, 40, 42, 44, and/or 46.

According to the invention, a nucleic acid sequence encoding a PDCT1 can have 50, 70, 80, 85, 87, 88, 90, 91, 92, 92, 94, 95, 96, 97, 98, 99, or 100% sequence identity with SEQ ID NO: 1, 3, 5, 7, 9, 11, 13, 15, 39, 41, 43, and/or 45.

A gene coding for a PDCT1 or PDCT19 can be obtained by de novo synthesis. For example, for PDCT1 starting from any of the amino acid sequences SEQ ID NO: 2, 4, 6, 8, 10, 12, 14, 16 or 46, the skilled person can reverse-translate the selected sequence into a nucleic acid sequence and have the sequence synthesised. As described herein, the skilled person can also introduce one or more mutations, including insertions, substitutions and deletions to the amino acid sequence chosen or the corresponding nucleic acid sequence. For reverse translation, the skilled person can and should use nucleic acid codons such as to reflect codon frequency of the plant intended for expression of said PDCT. By using any of the amino acid sequences according to SEQ ID NO: 2, 4, 6, 8, 10, 12, 14, 16 or 46 as such or one or more mutations, the person can obtain using routine techniques and standard equipment, a PDCT having the beneficial properties described herein and exhibiting these beneficial properties in numerous plant species.

The amino acid sequence of the PDCT reduced, blocked, decreased, depleted or inhibited according to the method of the invention may be identical to any of the sequences according to SEQ ID NO: 18, 20, 22, 24, 26, 28, 30, 32, 50, 52, 54, 56, 58, and/or 60. However, in certain embodiments it is preferred that the amino acid sequence of the PDCT is not the sequence encoding a PDCT 1 and/or a PDCT19. Where the skilled person for any reason wants to avoid any one or more of the amino acid sequences encoding a PDCT1 or PDCT19 as described herein, the skilled person can use any of the remaining sequences of this set of sequences. However, the skilled person can also make up a new amino acid and corresponding nucleic acid sequence by selecting a base sequence from the set of amino acid sequences according to SEQ ID NO: 18, 20, 22, 24, 26, 28, 30, and/or 32 and introducing one or more mutations (insertions, substitutions and/or deletions) at appropriate positions of the base sequence to obtain a derived sequence. Generally, the skilled person will take into account that the higher the sequence identity and/or similarity between base sequence and derived sequence, the more will the corresponding derived PDCT resemble the PDCT activity that corresponds to the PDCT of the base sequence or the PDCT activity of the invention. Thus, if the skilled person uses a mutated PDCT according to the present invention and such mutated PDCT unexpectedly does not or does convey the benefits of a PDCT with the PDCT activity started with, the skilled person should reduce or increase the number of differences of the PDCT sequence to increase resemblance of any of the sequences according to SEQ ID NO: 18, 20, 22, 24, 26, 28, 30, 32, 50, 52, 54, 56, 58, and/or 60.

For substituting amino acids of a base sequence selected from any of the sequences without regard to the occurrence of amino acid in other of these sequences, the following applies, wherein letters indicate L amino acids using their common abbreviation and bracketed numbers indicate preference of replacement (higher numbers indicate higher preference), if a PDCT activity should be maintained: A may be replaced by any amino acid selected from S (1), C (0), G (0), T (0) or V (0). C may be replaced by A (0). D may be replaced by any amino acid selected from E (2), N (1), Q (0) or S (0). E may be replaced by any amino acid selected from D (2), Q (2), K (1), H (0), N (0), R (0) or S (0). F may be replaced by any amino acid selected from Y (3), W (1), I (0), L (0) or M (0). G may be replaced by any amino acid selected from A (0), N (0) or S (0). H may be replaced by any amino acid selected from Y (2), N (1), E (0), Q (0) or R (0). I may be replaced by any amino acid selected from V (3), L (2), M (1) or F (0). K may be replaced by any amino acid selected from R (2), E (1), Q (1), N (0) or S (0). L may be replaced by any amino acid selected from I (2), M (2), V (1) or F (0). M may be replaced by any amino acid selected from L (2), I (1), V (1), F (0) or Q (0). N may be replaced by any amino acid selected from D (1), H (1), S (1), E (0), G (0), K (0), Q (0), R (0) or T (0). Q may be replaced by any amino acid selected from E (2), K (1), R (1), D (0), H (0), M (0), N (0) or S (0). R may be replaced by any amino acid selected from K (2), Q (1), E (0), H (0) or N (0). S may be replaced by any amino acid selected from A (1), N (1), T (1), D (0), E (0), G (0), K (0) or Q (0). T may be replaced by any amino acid selected from S (1), A (0), N (0) or V (0). V may be replaced by any amino acid selected from I (3), L (1), M (1), A (0) or T (0). W may be replaced by any amino acid selected from Y (2) or F (1). Y may be replaced by any amino acid selected from F (3), H (2) or W (2).

If the activity shall not be maintained, the above preference of replacement (higher numbers indicate higher preference) may preferably not be applied or used to identify amino acids that can be used to reduce the activity.

Enzyme variants may be defined by their sequence identity when compared to a parent enzyme. Sequence identity usually is provided as "% sequence identity" or "% identity". To determine the percent-identity between two amino acid sequences in a first step a pairwise sequence alignment is generated between those two sequences, wherein the two sequences are aligned over their complete length (i.e., a pairwise global alignment). The alignment is generated with a program implementing the Needleman and Wunsch algorithm (J. Mol. Biol. (1979) 48, p. 443-453), preferably by using the program "NEEDLE" (The European Molecular Biology Open Software Suite (EMBOSS)) with the programs default parameters (gapopen=10.0, gapextend=0.5 and matrix=EBLOSUM62). The preferred alignment for the purpose of this invention is that alignment, from which the highest sequence identity can be determined.

The following example is meant to illustrate two nucleotide sequences, but the same calculations apply to protein sequences:

Seq A: AAGATACTG length: 9 bases

Seq B: GATCTGA length: 7 bases

Hence, the shorter sequence is sequence B.

Producing a pairwise global alignment which is showing both sequences over their complete lengths results in

```
Seq A: AAGATACTG-
         ||| |||
Seq B: --GAT-CTGA
```

The "|" symbol in the alignment indicates identical residues (which means bases for DNA or amino acids for proteins). The number of identical residues is 6.

The "-" symbol in the alignment indicates gaps. The number of gaps introduced by alignment within the Seq B is 1. The number of gaps introduced by alignment at borders of Seq B is 2, and at borders of Seq A is 1.

The alignment length showing the aligned sequences over their complete length is 10.

Producing a pairwise alignment which is showing the shorter sequence over its complete length according to the invention consequently results in:

```
Seq A: GATACTG-
       ||| |||
Seq B: GAT-CTGA
```

Producing a pairwise alignment which is showing sequence A over its complete length according to the invention consequently results in:

```
Seq A: AAGATACTG
         ||| |||
Seq B: --GAT-CTG
```

Producing a pairwise alignment which is showing sequence B over its complete length according to the invention consequently results in:

```
Seq A: GATACTG-
       ||| |||
Seq B: GAT-CTGA
```

The alignment length showing the shorter sequence over its complete length is 8 (one gap is present which is factored in the alignment length of the shorter sequence).

Accordingly, the alignment length showing Seq A over its complete length would be 9 (meaning Seq A is the sequence of the invention).

Accordingly, the alignment length showing Seq B over its complete length would be 8 (meaning Seq B is the sequence of the invention).

After aligning two sequences, in a second step, an identity value is determined from the alignment produced. For purposes of this description, percent identity is calculated by %-identity=(identical residues/length of the alignment region which is showing the two aligned sequences over their complete length)*100. Thus, sequence identity in relation to comparison of two amino acid sequences according to this embodiment is calculated by dividing the number of identical residues by the length of the alignment region which is showing the two aligned sequences over their complete length. This value is multiplied with 100 to give "%-identity". According to the example provided above, %-identity is: (6/10)* 100=60%.

In table 6, the identities between PDCTs used in the method of the invention and other PDCTs calculated as described herein are shown.

The PDCT reduced, blocked, inhibited, depleted or inactivated in the method of present invention preferably has at least 50% amino acid sequence identity to any of the sequences SEQ ID NO: 18, 20, 22, 24, 26, 28, 30, 32, 50, 52, 54, 56, 58, and/or 60. Most preferably, PDCTs reduced, blocked, inhibited, depleted or inactivated in the method of present invention has at least 50% amino acid sequence identity to sequence SEQ ID NO. 18, 22 and/or 24, and/or 20, 26 and/or 28. Preferably, the PDCT reduced, blocked, inhibited, depleted or inactivated in the method of the present invention has at least 55% amino acid sequence identity to any of the sequences SEQ ID NO: 18, 20, 22, 24, 26, 28, 30, 32, 50, 52, 54, 56, 58, and/or 60, wherein identity to SEQ ID NO. 18, 20, 22, 24, 26, and 28, are particularly preferred, even more preferably at least 65%, even more preferably at least 72%, even more preferably at least 78%, even more preferably at least 80%, even more preferably at least 82%, even more preferably at least 89%, even more preferably at least 91%, even more preferably at least 96%.

Preferably, the PDCT blocked, inhibited, depleted, decreased or inactivated in the method of present invention has not the sequence of a PDCT1 or PDCT19.

Preferably, the amino acid sequence of the PDCT blocked, inhibited, depleted or inactivated in the method of present invention differs from the SEQ ID 35, 37, and/or 47 amino acid sequences according to any of SEQ ID NO: 18, 20, 22, 24, 26, 28, 30, 32, 50, 52, 54, 56, 58, and/or 60 only at such one or more positions where according to FIG. 1 at least one of the amino acid sequences of SEQ ID NO. 18, 20, 22, 24, 26, 28, 30, 32, 50, 52, 54, 56, 58, and/or 60 differs from at least one other of the sequences SEQ ID NO. 18, 20, 22, 24, 26, 28, 30, 32, 50, 52, 54, 56, 58, and/or 60, preferably not allowing any amino acid insertion or deletion. FIG. 1 shows an alignment of the amino acid sequences of PDCT blocked, inhibited, depleted or inactivated in the method of the present invention. Preferably, the amino acid sequence of the PDCT blocked, inhibited, depleted or inactivated in the method of the invention can be thought to be the result of exchanging selected amino acids from one chosen base sequence of the sequences SEQ ID NO: 18, 20, 22, 24, 26, 28, 30, 32, 50, 52, 54, 56, 58, and/or 60 for the corresponding amino acid at the respective positions of any other of the sequences SEQ ID NO: 18, 20, 22, 24, 26, 28, 30, 32, 50, 52, 54, 56, 58, and/or 60. Also, preferably, any mutation should increase the similarity, or, even more preferably, the identity, of the amino acid sequence of the PDCT blocked, inhibited, depleted or inactivated in the method of the present invention to that of a sequence according to SEQ ID NO: 18, 20, 22, 24, 26, 28, 30, 32, 50, 52, 54, 56, 58, and/or 60 and reduce the similarity or, even more preferably, the identity, to an amino acid sequence according to SEQ ID NO: 18, 20, 22, 24, 26, 28, 30, 32, 50, 52, 54, 56, 58, and/or 60.

For the reasons indicated above, the PDCT blocked, inhibited, depleted or inactivated in the method of the present invention preferably consists of the amino acid sequence SEQ ID NO. 18, 20, 22, 24, 26, 28, 30, 32, 50, 52, 54, 56, 58, and/or 60. More preferably, the PDCT blocked, inhibited, depleted or inactivated in the method of the present invention does not differ from the amino acid sequence of SEQ ID NO. 18, 20, 22, 24, 26, 28, 30, 32, 50, 52, 54, 56, 58, and/or 60 by an insertion or deletion and thus only comprises one or more substitutions. Even more preferably, the PDCT blocked, inhibited, depleted or inactivated in the method of the present invention consists of an amino acid sequence that differs from SEQ ID NO. 18, 20, 22, 24, 26, 28, 30, 32, 50, 52, 54, 56, 58, and/or 60 only by amino acids found at the corresponding position of amino acid sequence SEQ ID NO. 18, 20, 22, 24, 26, 28, 30, 32, 50, 52, 54, 56, 58, and/or 60.

The plant of the present invention is further capable of expressing at least one or more enzymes of unsaturated fatty acid metabolism. Preferably, such enzymes are capable of using an unsaturated fatty acid of the omega-6 and/or, more preferably, of the omega-3 series as a substrate. Preferred activities of the enzymes are: desaturase, elongase, ACS, acylglycerol-3-phosphate acyltransferase (AGPAT), choline phosphotransferase (CPT), diacylglycerol acyltransferase (DGAT), glycerol-3-phosphate acyltransferase (GPAT), lysophosphatidate acyltransferase (LPAT), lysophosphatidylcholine acyltransferase (LPCAT), lysophosphatidylethanolamine acyltransferase (LPEAT), lysophospholipid acyltransferase (LPLAT), phosphatidate phosphatase (PAP), phospholipid:diacylglycerol acyltransferase (PDAT), phosphatidylcholine:diacylglycerol choline phosphotransferase (PDCT), particularly Delta-12 desaturase, Delta-8 desaturase, Delta-6 desaturase, Delta-5 desaturase, Delta-4 desaturase, Delta-9 elongase, Delta-6 elongase, Delta-5 elongase, omega-3 desaturase.

At least one of the enzymes is capable of using linoleic acid as substrate. Such enzymes are known to the skilled person as omega-3 desaturases, Delta-15 desaturases, Delta-9 desaturase and Delta-6 desaturases. It is possible that one or more enzymes of unsaturated fatty acid metabolism can have more than one activity. For example, it is common for omega-3 desaturases to be also Delta-15 desaturases and/or Delta-17 desaturases and/or Delta-19 desaturases. Further preferred enzymes of unsaturated fatty acid metabolic is our Delta-12 desaturases, omega-3 desaturases, Delta-6 desaturases, Delta-6 elongases, Delta-5 desaturases, Delta-5 elongase and Delta-4 desaturases. At least one of these enzymes is supposedly connected to a plant metabolic property. Preferably, the metabolic property is the presence and/or concentration of the product of the respective enzyme. Thus, preferably the plant metabolic property is the presence and/or concentration of any of GL a, SDA, EDA, ETrA, the GLA, EDTA, ARA, EPA, DTA, DPA and DHA, wherein particularly preferred are the concentration of ETA, DPA, EPA and DHA.

In the method of the present invention, the plant is capable of expressing at least one more enzyme of the unsaturated fatty acid metabolic pathway during the plant is grown.

"Growing" for the present invention means to nurture plant material, preferably a plant can use, embryo or seed, such that cells of said plant material can develop and preferably multiply, such that at least one cell of the developed plant material can be expected to exhibit the plant metabolic property. For example, where the expression of a gene coding for an enzyme of unsaturated fatty acid metabolism, for example a desaturase or elongates, is under the control of a tissue-specific promoter, the plant material is grown such that the corresponding tissue develops.

The plant metabolic property is then measured by any suitable means. For example, the concentration of fatty acids in the form of free fatty acids or in the form of mono-, di- or triglycerides can be measured from extracts of plant material, preferably of plant seeds and most preferably from seed oil.

The method of the present invention preferably is not performed only on one plant but on a group of plants. This way, the measured plant metabolic properties will be statistically more significant than measurements taken only on plant material of a single plant, for example a single seed. Even though assay methods of the present invention preferably are performed on plant groups, assay methods of the present invention performed on single plants are also useful and beneficial. Such methods allow for a fast screening plants and thus are particularly suitable for high throughput evaluation of genes and gene combinations coding for enzymes of unsaturated fatty acid metabolism.

According to the method of the invention, the activity of a PDCT which activity is increased in the method of the invention can be increased by de novo expression of the PDCT in the plant, plant cell or seed or by increasing the expression or activity of an endogenous PDCT.

The gene coding for the PDCT reduced, blocked, inhibited, depleted or inactivated in the method of the present invention or used in the method of the present invention preferably is operably linked to an expression control sequence to in the control or wild type cell allows constitutive or non-constitutive expression of said gene. Expression control sequences according to the present invention are known to the skilled person as promoters, transcription factor binding sites and regulatory nucleic acids like for example RNAi. Preferably, the expression control sequence directs expression of the gene in a tissue-specific manner. Where the plant is an oil seed plant, preferably of a *Brassica* species, expression of the gene preferably is specific to plant seeds in one or more of their developmental stages. According to the present invention, tissue-specific expression does not require the total absence of gene expression in any other tissue. However, tissue-specific expression for a selected tissue means that the maximum amount of mRNA transcript in this tissue is at least 2-fold, preferably at least 5-fold, even more preferably at least 10-fold, even more preferably at least 20-fold, even more preferably at least 50-fold and most preferably at least 100-fold the maximum amount of said mRNA in the other tissues. Furthermore, expression control sequences are known to the skilled person which allow induction or repression of expression by a signal applied by a user, for example application of an inductor like IPTG.

For example, in the method of the invention, the expression control sequence is mutated, e.g. by a site directed mutation, such that the expression of the PDCT3 and/PDCT5 is reduced, blocked, inhibited, depleted or inactivated.

The PDCT reduced, blocked, inhibited, depleted or inactivated in the method of the present invention or the PDCT or used in the method of the present invention can be present in the cell, the plant or seed of the method of the present invention as a single copy gene or in multiple gene copies.

The PDCT reduced, blocked, inhibited, depleted or inactivated in the method of the present invention or used in the method of the present invention preferably is natively, e.g. in the control or wild type expressed in the same plant cell also expressing the other at least one or more enzymes of unsaturated fatty acid metabolism. It is possible but not necessary that the PDCT1 or PDCT19 used in the method of the present invention is expressed at the same time as one, some or all of said other genes of unsaturated fatty acid metabolism.

The contribution from each desaturase and elongase gene present in the T-DNA to the amount of VLC-PUFA is difficult to assess, but it is possible to calculate conversion efficiencies for each pathway step, for example by using the equations shown in FIG. 7. The calculations are based on fatty acid composition of the tissue or oil in question and indicate the amount of product fatty acid (and downstream products) formed from the substrate of a particular enzyme. The conversion efficiencies are sometimes referred to as "apparent" conversion efficiencies because for some of the calculations it is recognized that the calculations do not take into account all factors that could be influencing the reaction. Nevertheless, conversion efficiency values can be used to assess contribution of each desaturase or elongase reaction to the overall production of VLC-PUFA. By comparing conversion efficiencies, one can compare the relative effectiveness of a given enzymatic step between different individual seeds, plants, bulk seed batches, events, *Brassica* germplasm, or transgenic constructs.

The activity of a PDCT can be measured as described in the Examples e.g. by expressing the PDCT in plants, as described in the examples.

Preferably, the activity of the PDCT3 and/or 5 is reduced in *C. sativa* or in B. species, e.g. in *B. napus* or *B. juncea.*

The resulting oil is enriched in ETA, preferably, in ETA, DPA, DHA and/or EPA. The method of the invention for example results preferably in an increase of the total PUFAs, compared to a control.

In one embodiment, in the method of the invention, the plant, plant cell, and/or seed, for example, expresses none, one or more Acyl-CoA dependent desaturase, e.g. an Acyl-CoA dependent Delta-4 desaturase, Delta-5 desaturase, Delta-6 Desaturase, Delta-12 Desaturase, and/or Omega-3 desaturase, for example a Phospholipid-dependent or an Acyl-CoA dependent Delta-6 desaturase as described herein. Preferably a Acyl-CoA dependent Destaurase, e.g. a Acyl-CoA Delta-6 desaturase is used in the method of the present invention.

Further, for example, in the method of the invention, the plant, plant cell, and/or seed, for example, expresses none, one or more phospholipid dependent desaturases.

According to the invention, for example, none, or one or more desaturase from the group above uses Acyl-CoA as substrate. So, for example, at least one desaturase uses phospholipids and one uses Acyl-CoA as substrate. Preferably, the Desaturase is selected from the group Delta-4 desaturase, Delta-5 desaturase, Delta-6 desaturase, omega.3 desaturase, or Delta-12 desaturase. So, for example, in the method of the present invention uses a Delta-6 desaturase with Acyl-CoA as substrate and a Delta-6 elongase, e.g. together with an another desaturase that uses Acyl-CoA as substrate. So, for example, in the method of the present invention uses a Delta-6 desaturase with Phospholipid as substrate and a Delta-6 elongase, e.g. together with an another desaturase that uses Acyl-CoA as substrate.

Preferably, at least one of the desaturases used in the method of the invention Acyl-CoA as substrate, in particular one desaturase selected from the groups consisting of Delta-4 desaturase, Delta-5 desaturase, Delta-6 desaturase, omega.3 desaturase, Delta 5/Delta 6-desaturase, Delta-8 desaturase or Delta-9 desaturase, Delta-8/9 desaturase, Delta-12 desaturase uses as substrate phospholipids.

Preferably, at least one desaturase from the group uses Acyl-CoA as substrate.

Thus, in the method of the invention, the plant, plant cell and/or seed, for example expresses Delta-4 desaturase, Delta-5 desaturase, Delta-6 Desaturase, Delta-12 Desaturase, and/or Omega-3 desaturase, whereby none, one or more desaturases use Acyl-CoA-activated fatty acids as substrate, and/or whereby none, one or more desaturases uses phospholipid activated fatty acids as substrate. Thus, in the method of the invention, the plant, plant cell and/or seed, for example expresses one or more Delta-4 desaturase, Delta-5 desaturase, Delta-6 Desaturase, Delta-12 Desaturase, and/or Omega-3 desaturase, that use Acyl-CoA-activated fatty acids as substrate, and one or more Delta-4 desaturase, Delta-5 desaturase, Delta-6 Desaturase, Delta-12 Desaturase, and/or Omega-3 desaturase, that use phospholipid-activated fatty acids as substrate So, for example, at least one desaturase uses phospholipids and one uses Acyl-CoA as substrate. Preferably, the desaturase is selected from the group Delta-4 desaturase, Delta-5 desaturase, Delta-6 desaturase, Omega.3 desaturase, or Delta-12 desaturase. So, for example, in the method of the present invention a Delta-6 desaturase uses phospholipids as substrate.

Preferably, at least one of the desaturases used in the method of the invention, in particular one desaturase selected from the groups consisting of Delta-4 desaturase, Delta-5 desaturase, Delta-6 desaturase, omega.3 desaturase, Delta 5/Delta 6-desaturase, Delta-8 desaturase or Delta-9 desaturase, Delta-8/9 desaturase, Delta-12 desaturase uses as substrate phospholipids. Preferably at least one desaturase from the group uses Acyl-CoA as substrate. So, in a embodiment, at least one desaturase uses phospholipids and one uses Acyl-CoA as substrate. Preferrably, the Desaturase is selected from the group Delta-4 desaturase, Delta-5 desaturase, Delta-6 desaturase, omega.3 desaturase, or Delta-12 desaturase Thus, the invention also provides a method of producing one or more desired unsaturated fatty acids in a plant, comprising growing a plant, in said plant the PDCT reduced, blocked, inhibited, depleted or inactivated according to the method of the present invention and one or more further genes to convert linoleic acid to said one or more desired unsaturated fatty acids. As indicated above, the one or more further genes coding for enzymes for the production of unsaturated fatty acids preferably comprise desaturases and elongases.

The invention also provides a nucleic acid comprising a gene coding for a PDCT reduced, blocked, inhibited, depleted or inactivated in the method of the present invention, wherein the gene does not code for a PDCT of any of the exact sequences SEQ ID NO. 18, 20, 22, 24, 26, 28, 30, 32, 50, 52, 54, 56, 58, and/or 60. Thus, the present invention provides a nucleic acid comprising a gene coding for a PDCT, wherein said PDCT has at least 50% total amino acid sequence identity to any of the sequences SEQ ID NO. 18, 20, 22, 24, 26, 28, 30, 32, 50, 52, 54, 56, 58, and/or 60 and/or at least 60%, 70%, 80; 90, 91, 92, 93, 94, 95, 96, 97, 98, or 99% total amino acid sequence similarity to any of the sequences SEQ ID NO. 18, 20, 22, 24, 26, 28, 30, 32, 50, 52, 54, 56, 58, and/or 60, but not the sequence encoding a PDCT of SEQ ID No. 18, 20, 22, 24, 26, 28, 30, 32, 50, 52, 54, 56, 58, and/or 60 and wherein the sequence is not any of the sequences encoding another PDCT, e.g. a PDCT1 or PDCT19.

The invention also provides a nucleic acid comprising a gene coding for a PDCT used in the method of the present invention, wherein the gene does not code for a PDCT of any of the exact sequences shown herein. Thus, the present invention provides a nucleic acid comprising a gene coding for a PDCT1 or 19, wherein said PDCT has at least 50% total amino acid sequence identity to any of the sequences encoding a PDCT1 or PDCT19 and/or at least 60%, 70%, 80; 90, 91, 92, 93, 94, 95, 96, 97, 98, or 99% total amino acid sequence similarity to any of the sequences encoding a PDCT1 or PDCT19, but not the sequence encoding a PDCT of SEQ ID No. 18, 20, 22, 24, 26, 28, 30, 32, 50, 52, 54, 56, 58, and/or 60 and wherein the sequence is not any of the sequences encoding a PDCT3 or PDCT5.

The invention also provides a nucleic acid comprising a gene coding for a PDCT described herein, e.g. a PDCT1 or 19, wherein the gene is operably linked to an expression control sequence, and wherein the expression control sequence is heterologous to said gene if the gene codes for any of the exact sequences or a complement thereof. Thus, the invention particularly provides combinations of promoters and genes not found in nature.

The nucleic acids of the present invention preferably are expression vectors transformation constructs or expression constructs useful for transforming a plant cell, preferably stable during plant or plant cell or seed development. Thus, the nucleic acids of the present invention facilitate to materialise the benefits conveyed by the present invention as described herein. Also, the invention provides purified PDCT polypeptides coded by any of the nucleic acids of the present invention as well as antibodies specifically binding the PDCT polypeptide of the invention, e.g. monoclonal Antibodies or fragments thereof, as long as the fragments specifically bind the PDCT of the invention. Further, the invention provides antisense RNA, ribozymes, microRNA molecules that comprise a fragment of the a polynucleotide encoding a PDCT3 or PDCT5 as described herein.

The present invention also relates to an antibody or a peptide that specifically bind to the polypeptide PDCT reduced, blocked, inhibited, depleted or inactivated in the method of the present invention, e.g. a PDCT3 and/or PDCT5 as described herein.

The antibody or peptide of the invention reduces, blocks, inhibited, depletes or inactivated the activity of the PDCT reduced, blocked, inhibited, depleted or inactivated in the method of the present invention, e.g. a PDCT3 and/or PDCT5 as described herein.

Further, the present invention relates to an antisense RNA, ribozyme, or microRNA that reduces, blocks, inhibits, depletes or inactivates the PDCT used in the method of the invention. For example the antisense RNA, ribozyme, or microRNA comprises (a) a nucleic acid sequence having at least 80% sequence identity to SEQ ID NO: 17, 19, 21, 23, 27, 29, 31, 49, 51, 53, 55, and/or 57;
(b) a nucleic acid sequence encoding a polypeptide having at least 80% sequence identity to SEQ ID NO: 17, 19, 21, 23, 27, 29, 31, 49, 51, 53, 55, and/or 57;
(c) a fragment of (a) or (b), or
(d) a nucleic acid sequence fully complementary to any of (a) to (c), whereby the antisense RNA, ribozyme, or microRNA, when expressed in a plant, plant cell or plant seed that comprises (a) a nucleic acid sequence having at least 80% sequence identity to SEQ ID NO: 17, 19, 21, 23, 27, 29, 31, 49, 51, 53, 55, and/or 57, wherein the nucleic acid encodes a polypeptide having PDCT3 and/or 5 activity;

(b) a nucleic acid sequence encoding a polypeptide having at least 80% sequence identity to SEQ ID NO: 17, 19, 21, 23, 27, 29, 31, 49, 51, 53, 55, and/or 57, wherein the polypeptide has PDCT3 and/or 5 activity;

(c) a fragment of (a) or (b), wherein the fragment encodes a polypeptide having PDCT3 and/or 5 activity;

or expresses a PDCT, wherein the PDCT is selected from the group consisting of:

a PDCT3 and/or PDCT5 having at least 90% sequence identity with SEQ ID NO: 18, 20, 22, 24, 26, 28, 30, 32, 50, 52, 54, 56, 58, and/or 60;

a PDCT3 and/or PDCT5 encoded by a polynucleotide having at least 90% sequence identity with SEQ ID NO: 17, 19, 21, 23, 27, 29, 31, 49, 51, 53, 55, and/or 57;

(c) PDCT3 and/or PDCT5 encoded by one or more polynucleotides that hybridize under high stringency conditions with (i) a polynucleotide that encodes the amino acid sequence of SEQ ID NO: 18, 20, 22, 24, 26, 28, 30, 32, 50, 52, 54, 56, 58, and/or 60, or (ii) the full-length complement of (i);

(d) variants of the PDCT3 and/or PDCT5 of SEQ ID NO: 18, 20, 22, 24, 26, 28, 30, 32, 50, 52, 54, 56, 58, and/or 60, comprising a substitution, preferably a conservative substitution, deletion, and/or insertion at one or more positions and having PDCT3 and/or PDCT5 activity, and (e) a PDCT3 and/or PDCT5 encoded by a polynucleotide that differs from SEQ ID NO: 17, 19, 21, 23, 27, 29, 31, 49, 51, 53, 55, and/or 57 due to the degeneracy of the genetic code and reduces the expression of said nucleic acid sequence or said PDCT2 and/or 5.

Further, the invention relates to an antisense RNA, ribozyme, or microRNA polynucleotides comprising a fragment of the PDCT3 polynucleotide of (a), (b), (c), or (d) that binds specifically to the polynucleotide of (a), (b), (c), or (d) or an antisense RNA, ribozyme, microRNA polynucleotide comprising a fragment of the PDCT5 polynucleotide of (a), (b), (c), or (d) that binds specifically to the polynucleotide of (a), (b), (c), or (d).

According to the invention, there is also provided a plant cell comprising a non-native gene coding for a PDCT of the present invention. Such plant cells can be obtained, as described above, by transformation of wild-type plant cells or offspring thereof, for example by crossing a plant comprising a gene coding for a PDCT of the invention with a plant not comprising such gene and selecting offspring, preferably seeds, which comprise said gene. This way it is easily possible to transfer the gene coding for a PDCT of the present invention from one germplasm to another. The plant cell of the present invention preferably comprises a gene coding for one of the preferred PDCT of the present invention to materialise the benefits conveyed by such preferred PDCT. Also as described above, the gene coding for the PDCT of the present invention preferably is operably linked to an expression control sequence, and it is particularly preferred that said expression control sequence directs expression to certain tissues and certain times of plant development, for example to developing seed tissue and the above indicated preferred times after flowering.

Preferably the plant cell, plant or seed used in the method of the invention is a *Camelia* species, or *Brassica* species, preferably *B. napus, B. juncea, B. carinata*, or *Camelina sativa.*

As the present invention provides an assay method which can, also be used for screening and comparison purposes, the present invention also provides a plant set comprising at least 2 plant groups, each consisting of one or more plants, wherein the plant or plants of each group are capable of expressing a PDCT used in the method present invention, and wherein the plant or plants of said groups comprise one or more genes coding for at least one or more enzymes of unsaturated fatty acid metabolism, of which enzymes at least one is capable of using linoleic acid as a substrate, and of which enzymes at least one is supposedly connected to a plant metabolic property, and wherein the plant or plants of said groups differ in the expression of at least one of the enzymes of unsaturated fatty acid metabolism. To differ in expression of at least one of the enzymes of unsaturated fatty acid metabolism, one gene present in the plant or plants of one group may be missing in the plant or plants of another group, or may be expressed at different times or in different tissues or in differing intensities. For example, the plants of 2 groups may both comprise a gene coding for a Delta-4 desaturase under the control of identical expression control sequences, but the Delta-4 desaturase nucleic acid sequences are derived from different organisms such that the amino acid sequences of the respective Delta-4 desaturases are unique for the plants of each of the groups. Instead of or additional to differing in the genes for Delta-4 desaturases, the groups can also differ in any other nucleic acid sequence coding for an enzyme of unsaturated fatty acid metabolism, included but not limited to omega-3 desaturases, Delta-6 desaturases, Delta-9 elongases, Delta-6 elongases, Delta-8 desaturases, Delta-5 desaturases and Delta-5 elongases.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in M. Green & J. Sambrook (2012) Molecular Cloning: a laboratory manual, 4th Edition Cold Spring Harbor Laboratory Press, CSH, New York; Ausubel et al., Current Protocols in Molecular Biology, Wiley Online Library; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York.

The term "cultivating" as used herein refers to maintaining and growing the transgenic plant under culture conditions which allow the cells to produce the said polyunsaturated fatty acids, i.e. the PUFAs and/or VLC-PUFAs referred to above. This implies that the polynucleotide of the present invention is expressed in the transgenic plant so that the desaturase, elongase as also the keto-acyl-CoA-synthase, keto-acyl-CoA-reductase, dehydratase and enoyl-CoA-reductase activity is present. Suitable culture conditions for cultivating the host cell are described in more detail below.

The term "obtaining" as used herein encompasses the provision of the cell culture including the host cells and the culture medium or the plant or plant part, particularly the seed, of the current invention, as well as the provision of purified or partially purified preparations thereof comprising the polyunsaturated fatty acids, preferably, ARA, EPA, DHA, in free or in CoA bound form, as membrane phospholipids or as triacylglyceride esters. More preferably, the PUFA and VLC-PUFA are to be obtained as triglyceride esters, e.g., in form of an oil. More details on purification techniques can be found elsewhere herein below.

The term "polynucleotide" according to the present invention refers to a desoxyribonucleic acid or ribonucleic acid. Unless stated otherwise, "polynucleotide" herein refers to a single strand of a DNA polynucleotide or to a double stranded DNA polynucleotide. The length of a polynucleotide is designated according to the invention by the specification of a number of basebairs ("bp") or nucleotides ("nt"). According to the invention, both specifications are used interchangeably, regardless whether or not the respective nucleic acid is a single or double stranded nucleic acid. Also, as polynucleotides are defined by their respective nucleotide sequence, the terms nucleotide/polynucleotide and nucleotide sequence/polynucleotide sequence are used interchangeably, thus that a reference to a nucleic acid sequence also is meant to define a nucleic acid comprising or consisting of a nucleic acid stretch the sequence of which is identical to the nucleic acid sequence.

In particular, the term "polynucleotide" as used in accordance with the present invention as far as it relates to a desaturase or elongase gene relates to a polynucleotide comprising a nucleic acid sequence which encodes a polypeptide having desaturase or elongase activity. Preferably, the polypeptide encoded by the polynucleotide of the present invention having desaturase, or elongase activity upon expression in a plant shall be capable of increasing the amount of PUFA and, in particular, VLC-PUFA in, e.g., seed oils or an entire plant or parts thereof. Whether an increase is statistically significant can be determined by statistical tests well known in the art including, e.g., Student's t-test with a confidentiality level of at least 90%, preferably of at least 95% and even more preferably of at least 98%. More preferably, the increase is an increase of the amount of triglycerides containing VLC-PUFA of at least 5%, at least 10%, at least 15%, at least 20% or at least 30% compared to wildtype control (preferably by weight), in particular compared to seeds, seed oil, extracted seed oil, crude oil, or refined oil from a wild-type control. Preferably, the VLC-PUFA referred to before is a polyunsaturated fatty acid having a C20, C22 or C24 fatty acid body, more preferably EPA or DHA. Lipid analysis of oil samples are shown in the accompanying Examples.

In the plants of the present invention, in particular in the oil obtained or obtainable from the plant of the present invention, the content of certain fatty as shall be decreased or, in particular, increased as compared to the oil obtained or obtainable from a control plant. In particular decreased or increased as compared to seeds, seed oil, crude oil, or refined oil from a control plant. The choice of suitable control plants is a routine part of an experimental setup and may include corresponding wild type plants or corresponding plants without the polynucleotides as encoding desaturases and elongase as referred to herein.

The control plant is typically of the same plant species or even of the same variety as the plant to be assessed. The control plant may also be a nullizygote of the plant to be assessed. Nullizygotes (or null control plants) are individuals missing the transgene by segregation. Further, control plants are grown under the same or essentially the same growing conditions to the growing conditions of the plants of the invention, i.e. in the vicinity of, and simultaneously with, the plants of the invention. A "control plant" as used herein preferably refers not only to whole plants, but also to plant parts, including seeds and seed parts. The control could also be the oil from a control plant.

Preferably, the control plant is an isogenic control plant. Thus, e.g. the control oil or seed shall be from an isogenic control plant.

The fatty acid esters with polyunsaturated C20- and/or C22-fatty acid molecules can be isolated in the form of an oil or lipid, for example, in the form of compounds such as sphingolipids, phosphoglycerides, lipids, glycolipids such as glycosphingolipids, phospholipids such as phosphatidylethanolamine, phosphatidylcholine, phosphatidylserine, phosphatidylglycerol, phosphatidylinositol or diphosphatidylglycerol, monoacylglycerides, diacylglycerides, triacylglycerides or other fatty acid esters such as the acetyl-coenzyme A esters which comprise the polyunsaturated fatty acids with at least two, three, four, five or six, preferably five or six, double bonds, from the organisms which were used for the preparation of the fatty acid esters. Preferably, they are isolated in the form of their diacylglycerides, triacylglycerides and/or in the form of phosphatidylcholine, especially preferably in the form of the triacylglycerides. In addition to these esters, the polyunsaturated fatty acids are also present in the non-human transgenic organisms or host cells, preferably in the plants, as free fatty acids or bound in other compounds. As a rule, the various abovementioned compounds (fatty acid esters and free fatty acids) are present in the organisms with an approximate distribution of 80 to 90% by weight of triglycerides, 2 to 5% by weight of diglycerides, 5 to 10% by weight of monoglycerides, 1 to 5% by weight of free fatty acids, 2 to 8% by weight of phospholipids, the total of the various compounds amounting to 100% by weight. In the process of the invention, the VLC-PUFAs which have been produced are produced in a content as for DHA of at least 5.5% by weight, at least 6% by weight, at least 7% by weight, advantageously at least 8% by weight, preferably at least 9% by weight, especially preferably at least 10.5% by weight, very especially preferably at least 20% by weight, as for EPA of at least 9.5% by weight, at least 10% by weight, at least 11% by weight, advantageously at least 12% by weight, preferably at least 13% by weight, especially preferably at least 14.5% by weight, very especially preferably at least 30% by weight based on the total fatty acids in the non-human transgenic organisms or the host cell referred to above. The fatty acids are, preferably, produced in bound form. It is possible, with the aid of the polynucleotides and polypeptides of the present invention, for these unsaturated fatty acids to be positioned at the sn1, sn2 and/or sn3 position of the triglycerides which are, preferably, to be produced.

In a method or manufacturing process of the present invention the polynucleotides and polypeptides of the present invention may be used with at least one further polynucleotide encoding an enzyme of the fatty acid or lipid biosynthesis. Preferred enzymes are in this context the desaturases and elongases as mentioned above, but also polynucleotide encoding an enzyme having delta-8-desaturase and/or delta-9-elongase activity. All these enzymes reflect the individual steps according to which the end products of the method of the present invention, for example EPA or DHA are produced from the starting compounds linoleic acid (C18:2) or linolenic acid (C18:3). As a rule, these compounds are not generated as essentially pure products. Rather, small traces of the precursors may be also present in the end product. If, for example, both linoleic acid and linolenic acid are present in the starting host cell, organism, or the starting plant, the end products, such as EPA or DHA, are present as mixtures. The precursors should advantageously not amount to more than 20% by weight, preferably not to more than 15% by weight, more preferably, not to more than 10% by weight, most preferably not to more than 5% by weight, based on the amount of the end product in question. Advantageously, only EPA or more preferably only DHA, bound or as free acids, is/are produced as end product(s) in the process of the invention in a host cell. If the compounds EPA and DHA are produced simultaneously, they are, preferably, produced in a ratio of at least 1:2 (DHA:EPA), more preferably, the ratios are at least 1:5 and, most preferably, 1:8. Fatty acid esters or fatty acid mixtures produced by the invention, preferably, comprise 6 to 15% of palmitic acid, 1 to 6% of stearic acid, 7-85% of oleic acid, 0.5 to 8% of vaccenic acid, 0.1 to 1% of arachidic acid, 7 to 25% of saturated fatty acids, 8 to 85% of monounsaturated fatty acids and 60 to 85% of polyunsaturated fatty acids, in each case based on 100% and on the total fatty acid content of the organisms. DHA as a preferred long chain polyunsaturated fatty acid is present in the fatty acid esters or fatty acid mixtures in a concentration of, preferably, at least 0.1; 0.2; 0.3; 0.4; 0.5; 0.6; 0.7; 0.8; 0.9 or 1%, based on the total fatty acid content.

Chemically pure VLC-PUFAs or fatty acid compositions can also be synthesized by the methods described herein. To this end, the fatty acids or the fatty acid compositions are isolated from a corresponding sample via extraction, distillation, crystallization, chromatography or a combination of these methods. These chemically pure fatty acids or fatty acid compositions are advantageous for applications in the food industry sector, the cosmetic sector and especially the pharmacological industry sector.

The terms “essentially”, “about”, “approximately”, “substantially” and the like in connection with an attribute or a value, particularly also define exactly the attribute or exactly the value, respectively. The term “substantially” in the context of the same functional activity or substantially the same function means a difference in function preferably within a range of 20%, more preferably within a range of 10%, most preferably within a range of 5% or less compared to the reference function. In context of formulations or compositions, the term “substantially” (e.g., “composition substantially consisting of compound X”) may be used herein as containing substantially the referenced compound having a given effect within the formulation or composition, and no further compound with such effect or at most amounts of such compounds which do not exhibit a measurable or relevant effect. The term “about” in the context of a given numeric value or range relates in particular to a value or range that is within 20%, within 10%, or within 5% of the value or range given. As used herein, the term “comprising” also encompasses the term “consisting of”.

The term “isolated” means that the material is substantially free from at least one other component with which it is naturally associated within its original environment. For example, a naturally-occurring polynucleotide, polypeptide, or enzyme present in a living animal is not isolated, but the same polynucleotide, polypeptide, or enzyme, separated from some or all of the coexisting materials in the natural system, is isolated. As further example, an isolated nucleic acid, e.g., a DNA or RNA molecule, is one that is not immediately contiguous with the 5' and 3' flanking sequences with which it normally is immediately contiguous when present in the naturally occurring genome of the organism from which it is derived. Such polynucleotides could be part of a vector, incorporated into a genome of a cell with an unrelated genetic background (or into the genome of a cell with an essentially similar genetic background, but at a site different from that at which it naturally occurs), or produced by PCR amplification or restriction enzyme digestion, or an RNA molecule produced by in vitro transcription, and/or such polynucleotides, polypeptides, or enzymes could be part of a composition, and still be isolated in that such vector or composition is not part of its natural environment.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in M. Green & J. Sambrook (2012) Molecular Cloning: a laboratory manual, 4th Edition Cold Spring Harbor Laboratory Press, CSH, New York; Ausubel et al., Current Protocols in Molecular Biology, Wiley Online Library; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York.

Unless otherwise noted, the terms used herein are to be understood according to conventional usage by those of ordinary skill in the relevant art. In addition to the definitions of terms provided herein, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement).

It is to be understood that as used in the specification and in the claims, “a” or “an” can mean one or more, depending upon the context in which it is used. Thus, for example, reference to “a cell” can mean that at least one cell can be utilized. It is to be understood that the terminology used herein is for the purpose of describing specific embodiments only and is not intended to be limiting.

If not stated otherwise herein, abbreviations and nomenclature, where employed, are deemed standard in the field and commonly used in professional journals such as those cited herein.

“Purified” means that the material is in a relatively pure state, e.g., at least about 90% pure, at least about 95% pure, or at least about 98% or 99% pure. Preferably “purified” means that the material is in a 100% pure state.

The term "non-naturally occurring" refers to a (poly) nucleotide, amino acid, (poly)peptide, enzyme, protein, cell, organism, or other material that is not present in its original environment or source, although it may be initially derived from its original environment or source and then reproduced by other means. Such non-naturally occurring (poly)nucleotide, amino acid, (poly)peptide, enzyme, protein, cell, organism, or other material may be structurally and/or functionally similar to or the same as its natural counterpart.

The term "native" (or "wildtype" or "endogenous") cell or organism and "native" (or wildtype or endogenous) polynucleotide or polypeptide refers to the cell or organism as found in nature and to the polynucleotide or polypeptide in question as found in a cell in its natural form and genetic environment, respectively (i.e., without there being any human intervention).

The term "heterologous" (or exogenous or foreign or recombinant) polypeptide is defined herein as:

a polypeptide that is not native to the host cell. The protein sequence of such a heterologous polypeptide is a synthetic, non-naturally occurring, "man made" protein sequence;

a polypeptide native to the host cell but structural modifications, e.g., deletions, substitutions, and/or insertions, are included as a result of manipulation of the DNA of the host cell by recombinant DNA techniques to alter the native polypeptide; or a polypeptide native to the host cell whose expression is quantitatively altered or whose expression is directed from a genomic location different from the native host cell as a result of manipulation of the DNA of the host cell by recombinant DNA techniques, e.g., a stronger promoter.

Descriptions b) and c), above, refer to a sequence in its natural form but not naturally expressed by the cell used for its production. The produced polypeptide is therefore more precisely defined as a "recombinantly expressed endogenous polypeptide", which is not in contradiction to the above definition but reflects the specific situation that it's not the sequence of a protein being synthetic or manipulated but the way the polypeptide molecule is produced.

Similarly, the term "heterologous" (or exogenous or foreign or recombinant) polynucleotide refers:

to a polynucleotide that is not native to the host cell;

a polynucleotide native to the host cell but structural modifications, e.g., deletions, substitutions, and/or insertions, are included as a result of manipulation of the DNA of the host cell by recombinant DNA techniques to alter the native polynucleotide;

a polynucleotide native to the host cell whose expression is quantitatively altered as a result of manipulation of the regulatory elements of the polynucleotide by recombinant DNA techniques, e.g., a stronger promoter; or a polynucleotide native to the host cell, but integrated not within its natural genetic environment as a result of genetic manipulation by recombinant DNA techniques.

With respect to two or more polynucleotide sequences or two or more amino acid sequences, the term "heterologous" is used to characterize that the two or more polynucleotide sequences or two or more amino acid sequences do not occur naturally in the specific combination with each other.

The term "gene" means the segment of DNA involved in producing a polypeptide chain; it includes regions preceding and following the coding region (leader and trailer) as well as intervening sequences (introns) between individual coding segments (exons).

The term "gene" means a segment of DNA containing hereditary information that is passed on from parent to offspring and that contributes to the phenotype of an organism. The influence of a gene on the form and function of an organism is mediated through the transcription into RNA (tRNA, rRNA, mRNA, non-coding RNA) and in the case of mRNA through translation into peptides and proteins.

The term hybridization according to this invention means, that hybridization must occur over the complete length of the sequence of the invention.

The term "hybridisation" as defined herein is a process wherein substantially complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting point (Tm) for the specific sequence at a defined ionic strength and pH. Medium stringency conditions are when the temperature is 20° C. below Tm, and high stringency conditions are when the temperature is 10° C. below Tm. High stringency hybridisation conditions are typically used for isolating hybridising sequences that have high sequence similarity to the target nucleic acid sequence. However, nucleic acids may deviate in sequence and still encode a substantially identical polypeptide, due to the degeneracy of the genetic code. Therefore, medium stringency hybridisation conditions may sometimes be needed to identify such nucleic acid molecules.

The "Tm" is the temperature under defined ionic strength and pH, at which 50% of the target sequence hybridises to a perfectly matched probe. The Tm is dependent upon the solution conditions and the base composition and length of the probe. For example, longer sequences hybridise specifically at higher temperatures. The maximum rate of hybridisation is obtained from about 16° C. up to 32° C. below Tm. The presence of monovalent cations in the hybridisation solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the Tm decreases about 1° C. per % base mismatch. The Tm may be calculated using the following equations, depending on the types of hybrids:

DNA-DNA hybrids (Meinkoth and Wahl, Anal. Biochem., 138:267-284, 1984):

Tm=81.5° C.+16.6xlog [Na+]a+0.41x % [G/Cb]−500x [Lc]−1−0.61x % formamide

DNA-RNA or RNA-RNA hybrids:

Tm=79.8+18.5 (log 10 [Na+]a)+0.58 (% G/Cb)+11.8 (% G/Cb)2−820/Lc oligo-DNA or oligo-RNAd hybrids:

For <20 nucleotides: Tm=2 (ln)

For 20-35 nucleotides: Tm=22+1.46 (ln)

a or for other monovalent cation, but only accurate in the 0.01-0.4 M range.

b only accurate for % GC in the 30% to 75% range.

c L=length of duplex in base pairs.

d Oligo, oligonucleotide; In, effective length of primer=2×(no. of G/C)+(no. of A/T).

Non-specific binding may be controlled using any one of a number of known techniques such as, for example, blocking the membrane with protein containing solutions, additions of heterologous RNA, DNA, and SDS to the hybridisation buffer, and treatment with Rnase. For non-related probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. A positive hybridisation gives a signal that is at least twice of that of the background. Generally, suitable stringent conditions for nucleic acid hybridisation assays or gene amplification detection procedures are as set forth above. More or less stringent conditions may also be selected. The skilled artisan is aware of various parameters which may be altered during washing and which will either maintain or change the stringency conditions.

For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC. The length of the hybrid is the anticipated length for the hybridising nucleic acid. When nucleic acids of known sequence are hybridised, the hybrid length may be determined by aligning the sequences and identifying the conserved regions described herein. 1×SSC is 0.15M NaCl and 15 mM sodium citrate; the hybridisation solution and wash solutions may additionally include 5×Denhardt's reagent, 0.5-1.0% SDS, 100 μg/ml denatured, fragmented salmon sperm DNA, 0.5% sodium pyrophosphate. Another example of high stringency conditions is hybridisation at 65° C. in 0.1×SSC comprising 0.1 SDS and optionally 5×Denhardt's reagent, 100 μg/ml denatured, fragmented salmon sperm DNA, 0.5% sodium pyrophosphate, followed by the washing at 65° C. in 0.3×SSC.

For the purposes of defining the level of stringency, reference can be made to Sambrook et al. (2001) Molecular Cloning: a laboratory manual, 3rd Edition, Cold Spring Harbor Laboratory Press, CSH, New York or to Current Protocols in Molecular Biology, John Wiley & Sons, N.Y. (1989 and yearly updates).

The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

A typical hybridisation experiment is done by an initial hybridisation step, which is followed by one to several washing steps. The solutions used for these steps may contain additional components, which are preventing the degradation of the analyzed sequences and/or prevent unspecific background binding of the probe, like EDTA, SDS, fragmented sperm DNA or similar reagents, which are known to a person skilled in the art (Sambrook et al. (2001) Molecular Cloning: a laboratory manual, 3rd Edition, Cold Spring Harbor Laboratory Press, CSH, New York or to Current Protocols in Molecular Biology, John Wiley & Sons, N.Y. (1989 and yearly updates).

A typical probe for a hybridisation experiment is for example generated by the random-primed-labeling method, which was initially developed by Feinberg and Vogelstein (Anal. Biochem., 132 (1), 6-13 (1983); Anal. Biochem., 137 (1), 266-7 (1984) and is based on the hybridisation of a mixture of all possible hexanucleotides to the DNA to be labeled. The labeled probe product will actually be a collection of fragments of variable length, typically ranging in sizes of 100-1000 nucleotides in length, with the highest fragment concentration typically around 200 to 400 bp. The actual size range of the probe fragments, which are finally used as probes for the hybridisation experiment, can for example also be influenced by the used labeling method parameter, subsequent purification of the generated probe (e.g. agarose gel), and the size of the used template DNA which is used for labeling (large templates can e.g. be restriction digested using a 4 bp cutter, e.g. HaeIII, prior labeling).

"Recombinant" (or transgenic) with regard to a cell or an organism means that the cell or organism contains an exogenous polynucleotide which is introduced by gene technology and with regard to a polynucleotide means all those constructions brought about by gene technology/recombinant DNA techniques in which either (a) the sequence of the polynucleotide or a part thereof, or (b) one or more genetic control sequences which are operably linked with the polynucleotide, for example a promoter, or (c) both a) and b)

are not located in their wildtype genetic environment or have been modified.

It shall further be noted that the term "isolated nucleic acid" or "isolated polypeptide" may in some instances be considered as a synonym for a "recombinant nucleic acid" or a "recombinant polypeptide", respectively and refers to a nucleic acid or polypeptide that is not located in its natural genetic environment or cellular environment, respectively, and/or that has been modified by recombinant methods. An isolated nucleic acid sequence or isolated nucleic acid molecule is one that is not in its native surrounding or its native nucleic acid neighborhood, yet it is physically and functionally connected to other nucleic acid sequences or nucleic acid molecules and is found as part of a nucleic acid construct, vector sequence or chromosome. Typically, the isolated nucleic acid is obtained by isolating RNA from cells under laboratory conditions and converting it in copy-DNA (cDNA).

The term "control" polypeptide or the "control" polynucleotide, e.g. for use in an assay to identify the polypeptide that can be used in the method of the invention, is defined herein to include all sequences effecting for the expression of a polynucleotide, including but not limited thereto, the expression of a polynucleotide encoding a polypeptide. Each control sequence may be native or foreign to the polynucleotide or native or foreign to each other. Such control sequences include, but are not limited to, a leader, polyadenylation sequence, propeptide sequence, promoter, 5'-UTR, ribosomal binding site (RBS, shine dalgarno sequence), 3'-UTR, signal peptide sequence, and transcription terminator. At a minimum, the control sequence includes a promoter and transcriptional start and stop signals.

The control plant is typically of the same plant species or even of the same variety as the plant to be assessed. The control plant may also be a nullizygote of the plant to be assessed. A nullizygote (or null control plant) is progeny of TO transformants and misses the transgene by segregation. Further, control plants are grown under equal growing conditions to the growing conditions of the plants of the invention, i.e. in the vicinity of, and simultaneously with, the plants of the invention. A "control plant" as used herein refers not only to whole plants, but also to plant parts, including seeds and seed parts.

The term "operably linked" means that the described components are in a relationship permitting them to function in their intended manner. For example, a regulatory sequence operably linked to a coding sequence is ligated in such a way that expression of the coding sequence is achieved under condition compatible with the control sequences.

Gene editing or genome editing is a type of genetic engineering in which DNA is inserted, replaced, or removed from a genome and which can be obtained by using a variety of techniques such as "gene shuffling" or "directed evolution" consisting of iterations of DNA shuffling followed by appropriate screening and/or selection to generate variants of nucleic acids or portions thereof encoding proteins having a modified biological activity (Castle et al., (2004) Science 304 (5674): 1151-4; U.S. Pat. Nos. 5,811,238 and 6,395, 547), or with "T-DNA activation" tagging (Hayashi et al. Science (1992) 1350-1353), where the resulting transgenic organisms show dominant phenotypes due to modified expression of genes close to the introduced promoter, or with "TILLING" (Targeted Induced Local Lesions In Genomes) and refers to a mutagenesis technology useful to generate and/or identify nucleic acids encoding proteins with modified expression and/or activity. TILLING also allows selection of organisms carrying such mutant variants. Methods for TILLING are well known in the art (McCallum et al., (2000) Nat Biotechnol 18:455-457; reviewed by Stemple (2004) Nat Rev Genet 5 (2): 145-50). Another technique uses artificially engineered nucleases like Zinc finger nucleases, Transcription Activator-Like Effector Nucleases (TALENs), the CRISPR/Cas system, and engineered meganuclease such as re-engineered homing endonucleases (Esvelt, K M.; Wang, H H. (2013), Mol Syst Biol 9 (1): 641; Tan, W S. et al. (2012), Adv Genet 80:37-97; Puchta, H.; Fauser, F. (2013), Int. J. Dev. Biol 57:629-637).

DNA and the proteins that they encoded can be modified using various techniques known in molecular biology to generate variant proteins or enzymes with new or altered properties. For example, random PCR mutagenesis, see, e.g., Rice (1992) Proc. Natl. Acad. Sci. USA 89:5467-5471; or, combinatorial multiple cassette mutagenesis, see, e.g., Crameri (1995) Biotechniques 18:194-196.

Alternatively, nucleic acids, e.g., genes, can be reassembled after random, or "stochastic," fragmentation, see, e.g., U.S. Pat. Nos. 6,291,242; 6,287,862; 6,287,861; 5,955, 358; 5,830,721; 5,824,514; 5,811,238; 5,605,793.

Alternatively, modifications, additions or deletions are introduced by error-prone PCR, shuffling, site-directed mutagenesis, assembly PCR, sexual PCR mutagenesis, in vivo mutagenesis (phage-assisted continuous evolution, in vivo continuous evolution), cassette mutagenesis, recursive ensemble mutagenesis, exponential ensemble mutagenesis, site-specific mutagenesis, gene reassembly, gene site saturation mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

Alternatively, "gene site saturation mutagenesis" or "GSSM" includes a method that uses degenerate oligonucleotide primers to introduce point mutations into a polynucleotide, as described in detail in U.S. Pat. Nos. 6,171,820 and 6,764,835.

Alternatively, Synthetic Ligation Reassembly (SLR) includes methods of ligating oligonucleotide building blocks together non-stochastically (as disclosed in, e.g., U.S. Pat. No. 6,537,776).

Alternatively, Tailored multi-site combinatorial assembly ("TMSCA") is a method of producing a plurality of progeny polynucleotides having different combinations of various mutations at multiple sites by using at least two mutagenic non-overlapping oligonucleotide primers in a single reaction. (as described in PCT Pub. No. WO 2009/018449).

The term "substrate specificity" reflects the range of substrates that can be catalytically converted by an enzyme.

"Enzyme properties" include, but are not limited to catalytic activity as such, substrate/cofactor specificity, product specificity, increased stability during the course of time, thermostability, pH stability, chemical stability, and improved stability under storage conditions.

"Enzymatic activity" means at least one catalytic effect exerted by an enzyme. In one embodiment, enzymatic activity is expressed as units per milligram of enzyme (specific activity) or molecules of substrate transformed per minute per molecule of enzyme (molecular activity). Enzymatic activity can be specified by the enzymes actual function, e.g. proteases exerting proteolytic activity by catalyzing hydrolytic cleavage of peptide bonds, lipases exerting lipolytic activity by hydrolytic cleavage of ester bonds, etc The term “recombinant organism” refers to a eukaryotic organism (yeast, fungus, alga, plant, animal) or to a prokaryotic microorganism (e.g., bacteria) which has been genetically altered, modified or engineered such that it exhibits an altered, modified or different genotype as compared to the wild-type organism which it was derived from. Preferably, the “recombinant organism” comprises an exogenous nucleic acid. “Recombinant organism”, “genetically modified organism” and “transgenic organism” are used herein interchangeably. The exogenous nucleic acid can be located on an extrachromosomal piece of DNA (such as plasmids) or can be integrated in the chromosomal DNA of the organism. In the case of a recombinant eukaryotic organism, it is understood as meaning that the nucleic acid(s) used are not present in, or originating from, the genome of said organism, or are present in the genome of said organism but not at their natural locus in the genome of said organism, it being possible for the nucleic acids to be expressed under the control of one or more endogenous and/or exogenous control element.

Host cells may be any cell selected from bacterial cells, yeast cells, fungal, algal or cyanobacterial cells, non-human animal or mammalian cells, or plant cells. The skilled artisan is well aware of the genetic elements that must be present on the genetic construct to successfully transform, select and propagate host cells containing the sequence of interest The term “plant” as used herein refers to a photosynthetic, eukaryotic multicellular organism. Plants encompass green algae (Chlorophyta), red algae (Rhodophyta), Glaucophyta, mosses and liverworts (bryophytes), seedless vascular plants (horsetails, club mosses, ferns) and seed plants (angiosperms and gymnosperms). The term “plant” encompasses whole plants, ancestors and progeny of the plants and plant parts, including seeds, shoots, stems, leaves, roots, flowers, and tissues and organs, wherein each of the aforementioned comprise the gene/nucleic acid of interest. The term “plant” also encompasses plant cells, suspension cultures, callus tissue, embryos, meristematic regions, gametophytes, sporophytes, pollen, microspores and propagules, again wherein each of the aforementioned comprises the gene/nucleic acid of interest.

The term “plant parts” as used herein encompasses seeds, shoots, stems, leaves, roots, flowers, and tissues and organs, plant cells, suspension cultures, callus tissue, embryos, meristematic regions, gametophytes, sporophytes, pollen, microspores and propagules “Propagule” is any kind of organ, tissue, or cell of a plant capable of developing into a complete plant. A propagule can be based on vegetative reproduction (also known as vegetative propagation, vegetative multiplication, or vegetative cloning) or sexual reproduction. A propagule can therefore be seeds or parts of the non-reproductive organs, like stem or leave. In particular, with respect to Poaceae, suitable propagules can also be sections of the stem, i.e., stem cuttings.

The terms “increase”, “improve” or “enhance” in the context of a yield-related trait are interchangeable and shall mean in the sense of the application at least a 3%, 4%, 5%, 6%, 7%, 8%, 9% or 10%, preferably at least 15% or 20%, more preferably 25%, 30%, 35% or 40% increase in the yield-related trait(s) (such as but not limited to more yield and/or growth) in comparison to control plants as defined herein.

The term “expression” or “gene expression” includes the transcription of a specific gene or specific genes or specific genetic construct. The term “expression” or “gene expression” in particular means the transcription of a gene or genes or genetic construct into structural RNA (rRNA, tRNA) or mRNA with or without subsequent translation of the latter into a protein. The process includes transcription of DNA and processing of the resulting mRNA product. Yet, the term “expression” as used herein may also include the translation of process of an mRNA molecule where a polypeptide is formed. Thus, the term “expression” may include the transcription process alone, the translation process alone, or both processes combined.

The term “increased expression”, “enhanced expression” or “overexpression” as used herein means any form of expression that is additional to the original wild-type expression level (which can be absence of expression or immeasurable expression as well). Reference herein to “increased expression”, “enhanced expression” or “overexpression” is taken to mean an increase in gene expression and/or, as far as referring to polypeptides, increased polypeptide levels and/or increased polypeptide activity, relative to control plants. The increase in expression, polypeptide levels or polypeptide activity is in increasing order of preference at least 5%, 10%, 20%, 30%, 40% or 50%, 60%, 70%, 80%, 85%, 90%, or 100% or even more compared to that of control plants.

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to increase expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present description so as to control the expression of the gene.

If polypeptide expression is desired, it is generally desirable to include a polyadenylation region at the 3'-end of a coding polynucleotide region.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8:4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

To obtain increased expression or overexpression of a polypeptide most commonly the nucleic acid encoding this polypeptide is overexpressed in sense orientation with a polyadenylation signal. Introns or other enhancing elements may be used in addition to a promoter suitable for driving expression with the intended expression pattern.

The term “vector” as used herein comprises any kind of construct suitable to carry foreign polynucleotide sequences for transfer to another cell, or for stable or transient expression within a given cell. The term “vector” as used herein encompasses any kind of cloning vehicles, such as but not limited to plasmids, phagemids, viral vectors (e.g., phages), bacteriophage, baculoviruses, cosmids, fosmids, artificial chromosomes, or and any other vectors specific for specific hosts of interest. Low copy number or high copy number vectors are also included. Foreign polynucleotide sequences usually comprise a coding sequence which may be referred to herein as “gene of interest”. The gene of interest may comprise introns and exons, depending on the kind of origin or destination of host cell.

Vectors thus are polynucleotide sequences-artificial in part or total or artificial in the arrangement of the genetic elements contained-capable of replication in a host cell and are used for introduction of a polynucleotide sequence of interest into a host cell or host organism (such as but, not limited to plasmids or viral polynucleotide sequences). A vector may be a construct or may comprise at least one construct, typically the vector comprises at least one expression cassette. A vector as used herein may provide segments for its transcription and translation upon transformation into a host cell or host cell organelles. Such additional segments may include regulatory nucleotide sequences, one or more origins of replication required for its maintenance and/or replication in a specific cell type, one or more selectable markers, a polyadenylation signal, a suitable site for the insertion of foreign coding sequences such as a multiple cloning site, etc. One example is when a vector is required to be maintained in a bacterial cell as an episomal genetic element (e.g. plasmid or cosmid molecule). Preferred origins of replication include, but are not limited to, the f1-ori and colE1. A vector may replicate without integrating into the genome of a host cell, e.g. as a plasmid in a bacterial host cell, or it may integrate part or all of its DNA into the genome of the host cell and thus lead to replication and expression of its DNA. The skilled artisan is well aware of the genetic elements that must be present on the genetic construct to successfully transform, select and propagate host cells containing the gene of interest.

Foreign nucleic acid may be introduced into a vector by means of cloning. Cloning may mean that by cleavage of the vector by suitable means and methods (e.g., restriction enzymes) e.g. within the multiple cloning site and the foreign nucleic acid comprising a coding sequence with appropriate means such as, e.g., restriction enzymes, fitting structures within the individual nucleic acids are created that enable the controlled fusion of said foreign nucleic acid and the vector.

Once introduced into the vector, the foreign nucleic acid comprising a coding sequence may be suitable to be introduced (transformed, transduced, transfected, etc.) into a host cell or host cell organelles. A cloning vector may be chosen for transport into a desired host cell or host cell organelles. A cloning vector may be chosen for expression of the foreign polynucleotide sequence in the host cell or host cell organelles. Suitability for expression normally requires that regulatory nucleotide sequences are operatively linked to the foreign polynucleotide sequence such that expression of the foreign polynucleotide sequence in the host cell or host cell organelle is possible. Such a vector may be called expression vector.

Expression vectors are generally derived from yeast or bacterial genomic or plasmid polynucleotide sequences, viral polynucleotide sequences, or artificial polynucleotide sequences, or may contain elements of two or more thereof. As already set forth, a vector may comprise one or more “origins of replication” which normally indicates a particular nucleotide sequence at which replication is initiated. Usually a origin of replication binds a protein complex that recognizes, unwinds, and begins to copy the polynucleotide sequence. Different origins of replication may be selected for different host cells or host cell organelles. The one skilled in the art is familiar with such a selection.

For the detection of the successful transfer of the nucleic acid sequences and/or selection of transgenic organisms or plants comprising these nucleic acids, it is advantageous to use marker genes (or reporter genes). Therefore, the vector may optionally comprise a selectable marker gene.

The term “terminator” encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene “Construct”, “genetic construct” or “expression cassette” (used interchangeably) as used herein, is a DNA molecule composed of at least one sequence of interest to be expressed, operably linked to one or more control sequences (at least to a promoter) as described herein. Typically, the expression cassette comprises three elements: a promoter sequence, an open reading frame, and a 3' untranslated region that, in eukaryotes, usually contains a polyadenylation site. Additional regulatory elements may include transcriptional as well as translational enhancers. An intron sequence may also be added to the 5' untranslated region (UTR) or in the coding sequence to increase the amount of the mature message that accumulates in the cytosol. The skilled artisan is well aware of the genetic elements that must be present in the expression cassette to be successfully expressed. Preferably, at least part of the DNA or the arrangement of the genetic elements forming the expression cassette is artificial. The expression cassette may be part of a vector or may be integrated into the genome of a host cell and replicated together with the genome of its host cell. The expression cassette is capable of increasing or decreasing the expression of DNA and/or protein of interest.

The term “functional linkage” or “operably linked” means that the described components are in a relationship permitting them to function in their intended manner. For example, a regulatory sequence operably linked to a coding sequence is ligated in such a way that expression of the coding sequence is achieved under conditions compatible with the control sequences. Further, with respect to regulatory elements, is to be understood as meaning the sequential arrangement of a regulatory element (e.g. a promoter) with a nucleic acid sequence to be expressed and, if appropriate, further regulatory elements (such as e.g., a terminator) in such a way that each of the regulatory elements can fulfil its intended function to allow, modify, facilitate or otherwise influence expression of said nucleic acid sequence. The expression may result, depending on the arrangement of the nucleic acid sequences, in sense or antisense RNA. Preferred arrangements are those in which the nucleic acid sequence to be expressed recombinantly is positioned behind the sequence acting as promoter, so that the two sequences are linked covalently to each other. In a preferred arrangement, the nucleic acid sequence to be transcribed is located behind the promoter in such a way that the transcription start is identical with the desired beginning of the RNA. Functional linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (NY); Silhavy et al. (1984) Experiments with Gene Fusions, Cold Spring Harbor Laboratory, Cold Spring Harbor (NY); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands; Plant Molecular Biology Labfax (1993) by R.D.D. Croy, published by BIOS Scientific Publications Ltd (UK) and Blackwell Scientific Publications (UK)). However, further sequences, which, for example, act as a linker with specific cleavage sites for restriction enzymes, or as a signal peptide, may also be positioned between the two sequences. The insertion of sequences may also lead to the expression of fusion proteins. Preferably, the expression construct, consisting of a linkage of a regulatory region for example a promoter and nucleic acid sequence to be expressed, can exist in a vector-integrated form and be inserted into a plant genome, for example by transformation.

The term "introduction" or "transformation" as referred to herein encompasses the transfer of an exogenous polynucleotide into a host cell, irrespective of the method used for transfer. That is, the term "transformation" as used herein is independent from vector, shuttle system, or host cell, and it not only relates to the polynucleotide transfer method of transformation as known in the art (cf., for example, Sambrook, J. et al. (1989) Molecular Cloning: A Laboratory Manual, 2nd Ed., Cold Spring Harbor Laboratory Press, Cold Spring Harbor, NY), but it encompasses any further kind polynucleotide transfer methods such as, but not limited to, transduction or transfection. Plant tissue capable of subsequent clonal propagation, whether by organogenesis or embryogenesis, may be transformed with a genetic construct and a whole plant regenerated therefrom). The particular tissue chosen will vary depending on the clonal propagation systems available for, and best suited to, the particular species being transformed. The polynucleotide may be transiently or stably introduced into a host cell and may be maintained non-integrated, for example, as a plasmid. "Stable transformation" may mean that the transformed cell or cell organelle passes the nucleic acid comprising the foreign coding sequence on to the next generations of the cell or cell organelles. Usually stable transformation is due to integration of nucleic acid comprising a foreign coding sequence into the chromosomes or as an episome (separate piece of nuclear DNA).

"Transient transformation" may mean that the cell or cell organelle once transformed expresses the foreign nucleic acid sequence for a certain time-mostly within one generation. Usually transient transformation is due to nucleic acid comprising a foreign nucleic acid sequence is not integrated into the chromosomes or as an episome.

Alternatively, it may be integrated into the host genome. The resulting transformed plant cell may then be used to regenerate a transformed plant in a manner known to persons skilled in the art.

Transformation methods may be selected from the calcium/polyethylene glycol method for protoplasts (Krens, F. A. et al., (1982) Nature 296, 72-74; Negrutiu I et al. (1987) Plant Mol Biol 8:363-373); electroporation of protoplasts (Shillito R. D. et al. (1985) Bio/Technol 3, 1099-1102); microinjection into plant material (Crossway A et al., (1986) Mol. Gen Genet 202:179-185); DNA or RNA-coated particle bombardment (Klein T M et al., (1987) Nature 327:70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds, on the intact plant or at least on the flower primordia, or to inoculate the plant meristem with agrobacteria. Methods for *Agrobacterium*-mediated transformation of rice include well known methods for rice transformation, such as those described in: European patent application EP 1198985 A1, Aldemita and Hodges (Planta 199:612-617, 1996); Chan et al. (Plant Mol Biol 22 (3): 491-506, 1993), Hiei et al. (Plant J 6 (2): 271-282, 1994). In the case of corn transformation, the preferred method is as described in either Ishida et al. (Nat. Biotechnol 14 (6): 745-50, 1996) or Frame et al. (Plant Physiol 129 (1): 13-22, 2002). Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

Cotyledonary petioles and hypocotyls of 5-6 day old young seedling are used as explants for tissue culture and transformed according to Babic et al. (1998, Plant Cell Rep 17:183-188). The commercial cultivar Westar (Agriculture Canada) is the standard variety used for transformation, but other varieties can also be used.

The terms "regulatory element", "control sequence" and "promoter" are all used interchangeably herein and are to be taken in a broad context to refer to regulatory nucleic acid sequences capable of effecting expression of the sequences to which they are associated. "Regulatory elements" or "regulatory nucleotide sequences" herein may mean pieces of nucleic acid which drive expression of a nucleic acid sequence. one upon transformation into a host cell or cell organelle had occurred. Regulatory nucleotide sequences may include any nucleotide sequence having a function or purpose individually and within a particular arrangement or grouping of other elements or sequences within the arrangement. Examples of regulatory nucleotide sequences include but are not limited to transcription control elements such as promoters, enhancers, and termination elements. Regulatory nucleotide sequences may be native (i.e. from the same gene) or foreign (i.e. from a different gene) to a nucleotide sequence to be expressed.

The term "promoter" typically refers to a nucleic acid control sequence located upstream from the transcriptional start of a gene and is involved in recognising and binding of RNA polymerase and other proteins, thereby directing transcription of an operably linked nucleic acid. "Promoter" herein may further include any nucleic acid sequence capable of driving transcription of a coding sequence. In particular, the term "promoter" as used herein may refer to a polynucleotide sequence generally described as the 5' regulator region of a gene, located proximal to the start codon. The transcription of one or more coding sequence is initiated at the promoter region. The term promoter may also include fragments of a promoter that are functional in initiating transcription of the gene. Promoter may also be called "transcription start site" (TSS).

Encompassed by the aforementioned terms are further transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner.

For example, enhancers as known in the art and as used herein are normally short DNA segments (e.g. 50-1500 bp) which may be bound by proteins such as transcription factors to increase the likelihood that transcription of a coding sequence will occur.

Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid molecule in a cell, tissue or organ. A promoter can be modified by one or more nucleotide substitution(s), insertion(s) and/or deletion(s) without interfering with functionality or activity, but it is also possible to increase the activity by modification of its sequence.

Further elements may be "transcription termination elements" which include pieces of nucleic acid sequences marking the end of a gene and mediating the transcriptional termination by providing signals within mRNA that initiates the release of the mRNA from the transcriptional complex. Transcriptional termination in prokaryotes usually is initiated by Rho-dependent or Rho-independent terminators. In eukaryotes transcription termination usually occurs through recognition of termination by proteins associated with RNA polymerase II.

A "plant promoter" comprises regulatory elements, which mediate the expression of a coding sequence segment in plant cells. Accordingly, a plant promoter need not be of plant origin, but may originate from viruses or microorganisms. For expression in plants, the nucleic acid molecule to be expressed must, as described herein, be linked operably to or comprise a suitable promoter which expresses the gene at the right point in time and with the required spatial expression pattern.

Functionally equivalents of a promoter have substantially the same strength and expression pattern as the original promoter. For the identification of functionally equivalent promoters, the promoter strength and/or expression pattern of a candidate promoter may be analysed for example by operably linking the promoter to a reporter gene and assaying the expression level and pattern of the reporter gene in various tissues of the plant. Suitable well-known reporter genes include for example beta-glucuronidase or beta-galactosidase. The promoter activity is assayed by measuring the enzymatic activity of the beta-glucuronidase or beta-galactosidase. The promoter strength and/or expression pattern may then be compared to that of a reference promoter (such as the one used in the methods described herein). Alternatively, promoter strength may be assayed by quantifying mRNA levels or by comparing mRNA levels of the nucleic acid used in the methods described herein, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6:986-994).

Constitutive Promoter

A "constitutive promoter" refers to a promoter that is transcriptionally active during most, but not necessarily all, phases of growth and development and under most environmental conditions, in at least one cell, tissue or organ.

A "ubiquitous promoter" is active in substantially all tissues or cells of an organism. A "developmentally-regulated promoter" is active during certain developmental stages or in parts of the plant that undergo developmental changes. Inducible promoter An "inducible promoter" has induced or increased transcription initiation in response to a chemical (for a review see Gatz 1997, Annu. Rev. Plant Physiol. Plant Mol. Biol., 48:89-108), environmental or physical stimulus, or may be "stress-inducible", i.e. activated when a plant is exposed to various stress conditions, or a "pathogen-inducible" i.e. activated when a plant is exposed to exposure to various pathogens. Organ-specific/Tissue-specific promoter An "organ-specific" or "tissue-specific promoter" is one that is capable of preferentially initiating transcription in certain organs or tissues, such as the leaves, roots, seed tissue etc. For example, a "root-specific promoter" is a promoter that is transcriptionally active predominantly in plant roots, substantially to the exclusion of any other parts of a plant, whilst still allowing for any leaky expression in these other plant parts. Promoters able to initiate transcription in certain cells only are referred to herein as "cell-specific". A "seed-specific promoter" is transcriptionally active predominantly in seed tissue, but not necessarily exclusively in seed tissue (in cases of leaky expression). The seed-specific promoter may be active during seed development and/or during germination. The seed specific promoter may be endosperm/aleurone/embryo specific. Examples of seed-specific promoters are given in Qing Qu and Takaiwa (Plant Biotechnol. J. 2, 113-125, 2004). A "green tissue-specific promoter" as defined herein is a promoter that is transcriptionally active predominantly in green tissue, substantially to the exclusion of any other parts of a plant, whilst still allowing for any leaky expression in these other plant parts.

Another example of a tissue-specific promoter is a meristem-specific promoter, which is transcriptionally active predominantly in meristematic tissue, substantially to the exclusion of any other parts of a plant, whilst still allowing for any leaky expression in these other plant parts.

An "intron" is a portion of non-coding DNA within a eukaryotic gene, which is removed from the primary gene transcript during RNA processing that generates mature and functional mRNA or other type of RNA.

Generally, the term "overexpression" as used herein comprises both, overexpression of polynucleotides (e.g., on the transcriptional level) and overexpression of polypeptides (e.g., on the translation level). In this context, the expression level of a polynucleotide can be easily assessed by the skilled person by methods known in the art, e.g., by quantitative RT-PCR (qRT-PCR), Northern Blot (for assessing the amount of expressed mRNA levels), Dot Blot, Microarray or the like (see, e.g., Sambrook, loc cit; Current Protocols in Molecular Biology, Update May 9, 2012, Print ISSN: 1934-3639, Online ISSN: 1934-3647). Preferably, the amount of expressed polynucleotide is measured by qRT-PCR.

The terms "reduction", "repression", "decrease" or "deletion" relate to a corresponding change of a property in an organism, a part of an organism such as a tissue, seed, root, tuber, fruit, leave, flower etc. or in a cell. Under "change of a property" it is understood that the activity, expression level or amount of a gene product or a metabolite content is changed in a specific volume or in a specific amount of protein relative to a corresponding volume or amount of protein of a control, reference or wild type. Preferably, the overall activity in the volume is reduced, decreased or deleted in cases if the reduction, decrease or deletion is related to the reduction, decrease or deletion of an activity of a gene product, independent whether the amount of gene product or the specific activity of the gene product or both is reduced, decreased or deleted or whether the amount, stability or translation efficacy of the nucleic acid sequence or gene encoding for the gene product is reduced, decreased or deleted.

The terms "reduction", "repression", "decrease" or "deletion" include the change of said property in only parts of the subject of the present invention, for example, the modification can be found in compartment of a cell, like an organelle, or in a part of a plant, including but not limited to tissue, seed, root, leave, tuber, fruit, flower etc. but is not detectable if the overall subject, i.e. complete cell or plant, is tested. Preferably, the "reduction", "repression", "decrease" or "deletion" is found cellular, thus the term "reduction, decrease or deletion of an activity" or "reduction, decrease or deletion of a metabolite content" relates to the cellular reduction, decrease or deletion compared to the wild type cell. In addition the terms "reduction", "repression", "decrease" or "deletion" include the change of said property only during different growth phases of the organism used in the inventive process, for example the reduction, repression, decrease or deletion takes place only during the seed growth or during blooming. Furthermore the terms include a transitional reduction, decrease or deletion for example because the used method, e.g. the antisense, RNAi, snRNA, dsRNA, siRNA, miRNA, ta-siRNA, cosuppression molecule, or ribozyme, is not stable integrated in the genome of the organism or the reduction, decrease, repression or deletion is under control of a regulatory or inducible element, e.g. a chemical or otherwise inducible promoter, and has therefore only a transient effect.

Accordingly, the term "reduction", "repression", "decrease" or "deletion" means that the specific activity of a gene product, an enzyme or other protein or a regulatory RNA as well as the amount of a compound or metabolite, e.g. of a polypeptide, a nucleic acid molecule, or an encoding mRNA or DNA, can be reduced, decreased or deleted in a specific volume. The terms "reduction", "repression", "decrease" or "deletion" include that the reason for said "reduction", "repression", "decrease" or "deletion" could be a chemical compound that is administered to the organism or part thereof.

Throughout the specification a deletion of the activity or of the expression of an expression product, e.g. of a protein as depicted in Table II means a total loss of the activity. The terms "reduction", "repression", or "decrease" are interchangeable. The term "reduction" shall include the terms "repression", "decrease" or "deletion" if not otherwise specified.

The term "reducing", "repressing", "decreasing" or "deleting" as used herein also comprises the term "debasing", "depleting", diminishing" or "bringing down".

Reduction is also understood as meaning the modification of the substrate specificity as can be expressed for example, by the kcat/Km value. In this context, the function or activity, e.g. the enzymatic activity or the "biological activity", is reduced by at least 10%, advantageously 20%, preferably 30%, especially preferably 40%, 50% or 60%, very especially preferably 70%, 80%, 85% or 90% or more, very especially preferably are 95%, more preferably are 99% or more in comparison to the control, reference or wild type. Most preferably the reduction, decrease or deletion in activity amounts to essentially 100%. Thus, a particularly advantageous embodiment is the inactivation of the function of a compound, e.g. a polypeptide or a nucleic acid molecule.

A "reference", "control" or "wild type" is in particular a cell, a tissue, an organ, a plant, or a part thereof, which was not produced according to the process of the invention.

Accordingly, the terms "wild type", "control" or "reference" are exchangeable and can be a cell or a part of organisms such as an organelle or tissue, or an organism, in particular a plant, which was not modified or treated according to the herein described process according to the invention. Accordingly, the cell or a part of organisms such as an organelle or a tissue, or an organism, in particular a plant used as wild type, control or reference corresponds to the cell, organism or part thereof as much as possible and is in any other property but in the result of the process of the invention as identical to the subject matter of the invention as possible. Thus, the wild type, control or reference is treated identically or as identical as possible, saying that only conditions or properties might be different which do not influence the quality of the tested property.

Preferably, any comparison is carried out under analogous conditions. The term "analogous conditions" means that all conditions such as, for example, culture or growing conditions, assay conditions (such as buffer composition, temperature, substrates, pathogen strain, concentrations and the like) are kept identical between the experiments to be compared.

The "reference", "control", or "wild type" is preferably a subject, e.g. an organelle, a cell, a tissue, an organism, in particular a plant, which was not modified or treated according to the herein described process of the invention and is in any other property as similar to the subject matter of the invention as possible. The reference, control or wild type is in its genome, transcriptome, proteome or metabolome as similar as possible to the subject of the present invention. Preferably, the term "reference-" "control-" or "wild type-"-organelle, -cell, -tissue or -organism, in particular plant, relates to an organelle, cell, tissue or organism, in particular plant, which is nearly genetically identical to the organelle, cell, tissue or organism, in particular plant, of the present invention or a part thereof preferably 95%, more preferred are 98%, even more preferred are 99.00%, in particular 99.10%, 99.30%, 99.50%, 99.70%, 99.90%, 99.99%, 99, 999% or more. Most preferable the "reference", "control", or "wild type" is preferably a subject, e.g. an organelle, a cell, a tissue, an organism, which is genetically identical to the organism, cell organelle used according to the process of the invention except that nucleic acid molecules or the gene product encoded by them are changed or modified according to the inventive process.

Preferably, the reference, control or wild type differs form the subject of the present invention only in the cellular activity of the polypeptide or RNA used in the process of the invention, e.g. as result of a reduction, decrease or deletion in the level of the nucleic acid molecule of the present invention or a reduction, decrease or deletion of the specific activity of the polypeptide or RNA used in the process of the invention, e.g. by the expression level or activity of protein or RNA, that means by reduction or inhibition of its biological activity and/or of its biochemical or genetical causes.

In one embodiment, the reduction, repression, decrease, deletion or modulation according to this invention can be conferred by the (e.g. transgenic) expression of a antisense nucleic acid molecule, an RNAi, a snRNA, a dsRNA, a siRNA, a miRNA, a ta-siRNA, a cosuppression molecule, a ribozyme or of an antibody, an inhibitor or of an other molecule inhibiting the expression or activity of the expression product of the nucleic acid molecule which activity is to be reduced, decreased or deleted in the process of the invention. E.g. the reduction, repression, decrease, deletion or modulation according to this invention can be conferred by the (e.g. transgenic) expression of a nucleic acid molecule comprising a polynucleotide encoding antisense nucleic acid molecule, RNAi, snRNA, dsRNA, siRNA, miRNA, ta-siRNA, a cosuppression molecule, ribozyme or of an antibody Against the nucleic acid molecule or the polypeptide which activity is to be reduced in the process of the invention.

In a further embodiment, the reduction, repression, decrease, deletion or modulation according to this invention can be to a stable mutation in the corresponding endogenous gene encoding the nucleic acid molecule to be reduced, decreased or deleted in the process of the invention.

In another embodiment, the reduction, repression, decrease, deletion or modulation according to this invention can be a modulation of the expression or of the behaviour of a gene conferring the expression of the polypeptide to be reduced, decreased, repressed or deleted according to the process of the invention An increase of the activity of the polypeptides used in the method of the invention can for example be achieved by overexpression of the corresponding PDCT.

Accordingly, in one embodiment, the process of the present invention comprises one or more of the following steps:

i) Inhibition, repression, inactivation or reduction of translation or transcription of,
ii) Destabilization of transcript stability or polypeptide stability of,
iii) Reduction of accumulation of,
iv) Inhibition, repression, inactivation or reduction of activity of transcript or polypeptide of, and/or
v) Reduction of the copy number of functional (e.g. expressed) genes of, a suitable compound, for example, of
a) a protein enabling, mediating or controlling the expression of a protein encoded by the nucleic acid molecule which activity is reduced in the process of invention or of the polypeptide which activity is reduced in the process of the invention, e.g. of a polypeptide comprising a polypeptide, a consensus sequence or a polypeptide motif of said PDCT3 and/or PDCT5;
b) a mRNA molecule enabling, mediating or controlling the expression of a protein to be reduced in the process of the invention or being encoded by the nucleic acid molecule which activity is reduced in the process of the invention, e.g. enabling, mediating or controlling the expression of a polypeptide comprising a polypeptide, a consensus sequence or a polypeptide motif as depicted in column 5 or 7, of Table II or IV, or of a polypeptide being encoded by a nucleic acid molecule comprising a polynucleotide encoding said PDCT3 and/or PDCT5,
c) an RNA molecule enabling, mediating or controlling the expression of a mRNA encoding a polypeptide which activity is reduced in the process of the invention, e.g. of a mRNA encoding a polypeptide comprising a polypeptide, a consensus sequence or a polypeptide motif of said PDCT3 and/or PDCT5;
d) an RNA molecule enabling, mediating or controlling the expression of an expression product of a nucleic acid molecule comprising the polynucleotide which activity is reduced in the process of the invention; e.g. of a nucleic acid molecule comprising a polynucleotide encoding said PDCT3 and/or PDCT5;
e) a mRNA encoding the polynucleotide or the polypeptide which activity is reduced in the process of the invention; e.g. of a nucleic acid molecule comprising a polynucleotide as depicted SEQ ID NO. 17, 19, 21, 23, 27, 29, 31, 49, 51, 53, 55, and/or 57 or of a mRNA enabling, mediating or controlling the expression of a polypeptide which activity is reduced in the process of the invention, the polypeptide depicted in SEQ ID No. 18, 20, 22, 24, 26, 28, 30, 32, 50, 52, 54, 56, 58, and/or 60,
f) a gene encoding an activator enabling the activation or increase of the expression of a nucleic acid molecule encoding a polypeptide encoded by the nucleic acid molecule which activity is reduced in the process of the invention or the polypeptide which activity is to be reduced in the process of the invention, e.g. a gene encoding an activator enabling the activation or increase of the expression of a polypeptide comprising a polypeptide, a consensus sequence or a polypeptide motif of PDCT3 and/or PDCT5 or of a nucleic acid molecule comprising a polynucleotide as encoding a PDCT3 and/or PDCT5; or
g) an endogenous gene encoding the polypeptide or the nucleic acid molecule which activity is reduced in the process of the invention, for example an endogenous gene encoding a polypeptide comprising a polypeptide, a consensus sequence or a polypeptide motif as of PDCT3 and/or PDCT5, or a nucleic acid molecule comprising a polynucleotide as encoding PDCT3 and/or PDCT5;

Accordingly, the
i) Inhibition, repression, inactivation or reduction of translation or transcription,
ii) Destabilization transcript stability or polypeptide stability,
iii) Reduction of accumulation,
iv) Inhibition, repression, inactivation or reduction of activation of transcript or polypeptide, and/or
v) reducing the copy number of functional (e.g. expressed) genes, can for example be mediated e.g. by adding or expressing an antisense molecule, cosuppression molecule, an antibody, ribozyme, siRNA, microRNA, ta-siRNA, a cosuppression molecule, or RNAi, by mutation or deletion of a gene sequence, expressing or improving the activity of a negative expression element or by other methods known to the person skilled in the art or mentioned herein. A polynucleotide, which activity is to be reduced in the process of the invention or one or more fragments thereof, can for example be expressed in antisense orientation. In another embodiment, a hairpin RNAi constructs is expressed. It is also advantageous to express simultaneously a sense and antisense RNA molecule of the nucleic acid molecule or polypeptide which activity is to be reduced in the method of the invention.

In one embodiment, the method of the present invention comprises for example one or more of the following steps a) stabilizing a protein conferring the decreased expression of a protein of the nucleic acid molecule or polypeptide which activity is reduced in the process of the invention;
b) stabilizing a mRNA or functional RNA conferring the decreased expression of a of the nucleic acid molecule or polypeptide which activity is reduced in the process of the invention;
c) increasing or stimulating the specific activity of a protein conferring the decreased expression of a of the nucleic acid molecule or polypeptide which activity is reduced in the process of the invention;
d) decreasing the specific activity of a protein conferring the increased expression of a of the nucleic acid molecule or polypeptide which activity is reduced in the process of the invention;
e) expressing a transgenic gene encoding a protein conferring the decreased expression of a nucleic acids molecule or polypeptide which activity is reduced in the process of the invention,
f) generating or increasing the expression of an endogenous or artificial transcription factor repressing the expression of a protein conferring the increased expression of the nucleic acid molecule or polypeptide which activity is reduced in the process of the invention;
g) generating or increasing the expression of an endogenous or artificial transcription factor mediating the expression of a protein conferring the decreased expression of the nucleic acid molecule or polypeptide which activity is reduced in the process of the invention;
h) reducing, repressing or deleting the expression of an endogenous or artificial transcription factor repressing the expression of a protein conferring the decreased expression of the nucleic acid molecule or polypeptide which activity is reduced in the process of the invention;
i) reducing, repressing or deleting the expression of an endogenous or artificial transcription factor mediating the expression of a protein conferring the increased expression of the nucleic acid molecule or polypeptide which activity is reduced in the process of the invention;
j) increasing the number of functional copies or expression of a gene conferring the decreased expression of the nucleic acid molecule or polypeptide which activity is reduced in the process of the invention,
k) increasing the activity of a repressor protein or a repressor RNA
l) Increasing the activity of a protein or RNA leading to a dominant negative phenotype of the protein which activity is reduced in the process of the invention;
m) expression of an antibody or aptamer, which binds to the nucleic acid molecule which activity is to be reduced in the process of the invention or the protein which activity is reduced in the process of the invention and thereby reducing, decreasing or deleting its activity;
n) expressing a repressor conferring the reduced, repressed, decreased or deleted expression of a protein encoded by the nucleic acid to be reduced in the process molecule of the invention or of the polypeptide which activity is reduced in the process of the invention, or increasing the inhibitory regulation of the polypeptide of the invention;
o) reducing or deleting the expression of the nucleic acid molecule which activity is reduced in the process of the invention or the polypeptide which activity is reduced in the process of the invention by adding one or more exogenous repression factors such as a inhibiting chemical compound to the organism or its medium or its feed, e.g. to the organism's water supply; or
p) modulating growth conditions of an organism in such a manner, that the expression or activity of a nucleic acid molecule encoding the protein which activity is reduced in the process of the invention or the protein itself is reduced, repressed, decreased or deleted. This can be achieved by e.g modulating light and/or nutrient conditions, which in terms modulated the expression of the gene or protein which activity is reduced in the process of the invention.

Others strategies and modifications and combinations of above strategies are well known to the person skilled in the art and are also embodiment of this invention. Above said can for example be achieved by adding positive expression or removing negative expression elements, e.g. homologous recombination can be used to either introduce positive or negative regulatory elements, like a 35S enhancer into a plant promoter, or to remove repressor elements from regulatory regions. Further gene conversion methods can be used to disrupt elements or to enhance the activity of repressor elements. Repressor elements can be randomly introduced in plants by T-DNA or transposon mutagenesis. Lines can be identified in which the repressor elements are integrated near to a gene encoding the nucleic acid molecule or polypeptide which activity is to be reduced in the process of the invention, the expression of which is thereby reduced, repressed or deleted. Furthermore mutations like point mutations can be introduced randomly by different mutagenesis methods and can be selected by specific methods such like TILLING (reviewed in Slade and Knauf, Transgenic Res. 2005, 14 (2), 109-115).

For example, an increase of the activity of a protein or RNA leading to a dominant negative phenotype of the protein which activity is reduced in the process of the invention can be achieved through the expression of a nucleic acid molecule encoding a protein, which has lost its biological activity but which binds to another protein in a multimeric complex thereby decreasing, repressing or deleting the activity of said complex or which binds for example as a transcription factor to DNA and thereby decreasing or deleting the activity of the translated protein.

The activity of the abovementioned proteins and/or polypeptide encoded by the nucleic acid molecule to be reduced in the process of the present invention can be reduced, repressed, decreased or deleted in various ways.

For example, the activity in an organism or in a part thereof, like a cell, is reduced, repressed or decreased via reducing or decreasing the gene product number, e.g. by reducing, repressing or decreasing the expression rate, like mutating the natural promoter to a lower activity, or by reducing, repressing or decreasing the stability of the mRNA expressed, thus reducing, repressing or decreasing the translation rate, and/or reducing, repressing or decreasing the stability of the gene product, thus increasing the proteins decay. Further, the activity or turnover of enzymes or channels or carriers, transcription factors, and similar active proteins can be influenced in such a manner that a reduction of the reaction rate or a modification (reduction, repression, decrease or deletion) of the affinity to the substrate results, is reached.

A mutation in the catalytic centre of a polypeptide or nucleic acid molecule which activity is reduced in the process of the invention, e.g. of an enzyme or a catalytic or regulatory RNA, can modulate the turn over rate of the enzyme, e.g. a knock out of an essential amino acid can lead to a reduced or complete knock out of the activity of the enzyme, or the deletion of regulator binding sites can reduce a positive regulation.

The specific activity of an enzyme of the present invention can be decreased such that the turn over rate is decreased or the binding of a co-factor is reduced. Reducing the stability of the encoding mRNA or the protein can also decrease the activity of a gene product. The reduction of the activity is also under the scope of the term "reduced, repressed, decreased or deleted activity". Besides this, advantageously the reduction of the activity in cis, eg. mutating the promoter including other cis-regulatory elements, or the transcribed or coding parts of the gene, inhibition can also be achieved in trans, eg. by transfactors like chimeric transcription factor, ribozymes, antisense RNAs, dsRNAs or dominant negative protein versions, which interfere with various stages of expression, eg the transcription, the translation or the activity of the protein or protein complex itself. Also epigenetic mechanisms like DNA modifications, DNA methylation, or DNA packaging might be recruited to inactivate or down regulate the nucleic acids of the invention or the encoded proteins.

The regulation of the abovementioned nucleic acid sequences may be modified so that gene expression is decreased. This reduction, repression, decrease or deletion (reduction, repression, decrease, deletion, inactivation or down-regulation shall be used as synonyms throughout the specification) can be achieved as mentioned above by all methods known to the skilled person, preferably by double-stranded RNA interference (dsRNAi), introduction of an antisense nucleic acid, a ribozyme, an antisense nucleic acid combined with a ribozyme, a nucleic acid encoding a co-suppressor, a nucleic acid encoding a dominant negative protein, DNA- or protein-binding factor or antibodies targeting said gene or -RNA or -proteins, RNA degradation inducing viral nucleic acids and expression systems, systems for inducing a homolog recombination of said genes, mutations in said genes or a combination of the above.

In general, an activity of a gene product in an organism or part thereof, in particular in a plant cell, a plant, or a plant tissue or a part thereof or in a microorganism can be decreased by decreasing the amount of the specific encoding mRNA or the corresponding protein in said organism or part thereof. "Amount of protein or mRNA" is understood as meaning the molecule number of polypeptides or mRNA molecules in an organism, a tissue, a cell or a cell compartment. "Decrease" in the amount of a protein means the quantitative decrease of the molecule number of said protein in an organism, a tissue, a cell or a cell compartment or part thereof—for example by one of the methods described herein below—in comparison to a wild type, control or reference.

Accordingly, in one further embodiment of the process of the invention the reduction, repression or deletion of the activity represented by the protein or nucleic acid molecule to be reduced in the process of the invention is achieved by at least one step selected from the group consisting of introducing an RNAi, snRNA, dsRNA, siRNA, miRNA, ta-siRNA, cosuppression molecule, or an antisense nucleic acid molecule, whereby the RNAi, snRNA, dsRNA, siRNA, miRNA, ta-siRNA, cosuppression molecule, or antisense nucleic acid molecule comprises a fragment of 17, 18, 19, 20, 21, 22, 23, 24 or 25 nucleotides (nt) or more, preferably of 25, 26, 27, 28, 29, 30, 31, 32, 33, 34, 35, 36, 37, 38, 39 or 40 nucleotides (nt) or more, more preferably of 50, 60, 70, 80, 90 or 100 nucleotides (nt) or more with an identity of at least 30% or more, preferably of 40, 50, 60, 65, 70, 75, 80, 85, 90, 95, 97, 98, 99 or most preferably of 100% to the nucleic acid molecule to be reduced according to the process of the invention or a nucleic acid molecule encoding the polypeptide to be reduced according to the process of the invention or to a nucleic acid molecule selected from a group defined in section (aa) to (ac);

b) introducing of a ribozyme which specifically cleaves the nucleic acid molecule to be reduced according to the process of the invention or a nucleic acid molecule encoding the polypeptide to be reduced according to the process of the invention or a nucleic acid molecule selected from a group defined in section (aa) to (ac);

c) introducing the RNAi, snRNA, dsRNA, siRNA, miRNA, ta-siRNA, cosuppression molecule, ribozyme, antibody, antisense nucleic acid molecule characterized in (a) and the ribozyme characterized in (b);

d) introducing of a sense nucleic acid molecule conferring the expression of the nucleic acid molecule to be reduced according to the process of the invention or a nucleic acid molecule encoding the polypeptide to be reduced according to the process of the invention or of a nucleic acid molecule selected from a group defined in section (aa) to (ac) for inducing a co-suppression of the endogenous expression product of the nucleic acid molecule to be reduced according to the process of the invention or a nucleic acid molecule encoding the polypeptide to be reduced according to the process of the invention or of a nucleic acid molecule selected from a group defined in section (aa) to (ac);

e) introducing a nucleic acid molecule comprising a polynucleotide conferring the expression of a dominant-negative mutant of a protein having the activity of a protein to be reduced according to the process of the invention or of a protein encoded by a nucleic acid molecule to be reduced according to the process of the invention or of a protein encoded by a nucleic acid molecule selected from a group defined in section (aa) to (ac);

f) introducing a nucleic acid molecule comprising a polynucleotide encoding a factor, which binds to a nucleic acid molecule comprising the nucleic acid molecule to be reduced according to the process of the invention or comprising a nucleic acid molecule encoding the polypeptide to be reduced according to the process of the invention or comprising a nucleic acid molecule selected from a group defined in section (aa) to (ac);

g) introducing a viral nucleic acid molecule conferring the decline of a RNA molecule comprising the nucleic acid molecule to be reduced according to the process of the invention or comprising a nucleic acid molecule encoding the polypeptide to be reduced according to the process of the invention or comprising a nucleic acid molecule selected from a group defined in section (aa) to (ac);

h) introducing a nucleic acid construct capable to recombinate with and silence, inactivate, repress or reduce the activity of an endogenous gene comprising the nucleic acid molecule to be reduced according to the process of the invention or comprising a nucleic acid molecule encoding the polypeptide to be reduced according to the process of the invention or comprising a nucleic acid molecule selected from a group defined in section (aa) to (ac);

i) introducing a non-silent mutation in an endogenous gene comprising the nucleic acid molecule to be reduced according to the process of the invention or comprising a nucleic acid molecule encoding the polypeptide to be reduced according to the process of the invention or comprising a nucleic acid molecule selected from a group defined in section (aa) to (ac); and/or j) introducing an expression construct conferring the expression of nucleic acid molecule characterized in any one of (a) to (i).

In this context, the expression level of a polypeptide can be easily assessed by the skilled person by methods known in the art, e.g., by Western Blot, ELISA, EIA, RIA, or the like (see, e.g., Sambrook, loc cit; Current Protocols in Molecular Biology, Update May 9, 2012, Print ISSN: 1934-3639, Online ISSN: 1934-3647). Preferably, the amount of expressed polypeptide is measured by Western Blot.

If not stated otherwise herein, abbreviations and nomenclature, where employed, are deemed standard in the field and commonly used in professional journals such as those cited herein.

EXAMPLES

Example 1: Materials and Methods

Cloning of Genes:

RNA from young root tissue of *B. napus, B. carinata* and *C. sativa* was reversed transcribed using Superscript III. Primers for cloning cDNAs were based on genomic sequence information from NCBI sequence databases (www.ncbi.nlm.nih.gov/) and naming of genes followed the information in these databases. The proofreading enzyme Phusion was used to clone cDNAs, which were transformed into pYes 2.1 prior to sequencing. Seven PDCT like genes were cloned from *B. napus*, originating from chromosome 1A, 1C, 2C, 3A, 3C, 5A and 5C. Seven genes were cloned from *B. carinata*, originating from chromosomes 1B, 1C, 2B, 3B, 3C, 5B and 5C. Three genes were cloned from *C. sativa*, originating from chromosomes 1, 15 and 19. Sequences of cDNAs and translation products are given in Table 1.

Example 2: Sequence Analysis

All clones were sequenced prior to transformation. The protein alignment and phylogenetic tree were constructed using the software program Vector NTI.

Example 3: Construction of Transformation Vectors and *Arabidopsis* Transformation Because the C genome genes from *B. carinata* and *B. napus* were identical or nearly identical, only C subgenome derived PDCT genes from *B. carinata* were used in further experiments. PDCT genes were cloned into the pUC-19 Napin-B vector to add the Napin promotor and OSC terminator, as described in Wu et al (2005). The genes including promotors and terminators were removed by restriction enzyme digestion and ligated to pUC19-ABC carrying the Thraustocytrium sp. delta 6 elongase (Sequence ID: KH273553.1) and the *P. irregulare* delta 6 desaturase (Sequence ID: AF419296.1). The three genes were removed from the vector by restriction enzyme digestion and ligated into the plant binary vector pSUN2-ASC. All vectors were analyzed by restriction digestion before transformation. Controls included an empty vector and a vector containing only the *P. irregulare* D6 desaturase and the PSE (tc) elongase. The *Arabidopsis* rod1 (At3g15820) mutant line (Lu et al. 2009), kindly provided by Chaofu Lu, was used as the *Arabidopsis* host plant. This mutant has a G to A mutation resulting in a premature stop codon in the phosphatidylcholine:diacylglycerol cholinephosphotransferase (PDCT) enzyme encoded by the *Arabidopsis* ROD1 gene (Lu et al. 2009). Four plants were tested by sequencing, which indicated all were homozygous for the relevant mutation, and seed was collected from these plants and used for transformation. Plant binary vectors were transformed into *Agrobacterium tumefaciens* strain GV3101-pMP90. The host plant was grown until the bolting stage and transformed using the floral dip method (Clough and Bent, 1998). Essentially, *Agrobacterium tumefaciens* carrying each vector was grown to mid-log stage, spun down and suspended to an OD600 of 0.8 in 5% sucrose solution containing 0.05% Silwet L-77, and plants were immersed in this solution for 2-3 minutes with gentle agitation. After maturity, seeds were sterilized and germinated on ½× MS selective medium containing 50 mg/L kanamycin for selection of transgenic plants. Positive plants were transplanted into soil and grown to maturity.

Example 4: GC Analysis

Twenty T2 seeds from positive T1 plants were used to extract fatty acids. Seeds were placed in a clean glass tube, 2 mL of 3M methanolic HCL was added to each tube, and capped tubes were incubated at 80° C. for 4 hours. After incubation, samples were cooled to room temperature, 1 mL of 0.9% NaCl and 2 mL of hexane was then added to each sample and vortexed. Samples were then centrifuged and the hexane (top) layer was removed and added to clean glass tubes. Samples were evaporated under nitrogen until dry. 80 μL of hexane was added to the tubes and vortexed briefly to resuspend the fatty acids. The solution was then moved to a collection vial containing a GC insert, and GC analysis was performed (Table 2).

The segregation of the transgene was tested by germinating 50-100 seeds on selective media, and testing the fit to a 3:1 hypothesis (Table 3). Seedling progeny of transgenic plants that segregated with a 3:1 ratio (consistent with expression of construct at a single locus) were used for further analysis. GC analysis of 20 seeds from 3-5 lines for each gene was conducted as described above, and fatty acid distribution was determined (Table 4).

Example 5: Results

The amino acid sequences of the 19 PDCT genes cloned in this study fell in 5 distinct groups (FIG. 1A-FIGS. 1B, 2 and 3). These groups consisted of the chromosome 1-derived sequences of *B. napus* and *B. carinata*, the chromosome 2 sequences of *B. napus* and *B. carinata*, the chromosome 3 sequences of *B. carinata* and *B. napus*, the chromosome 5 genes of *B. napus* and *B. carinata* and the three *C. sativa* sequences (FIG. 2). The amino acid translations of the C-subgenome derived genes of *B. carinata* and *B. napus* were identical or nearly identical, although there were differences in the cDNA sequences (FIG. 1A and FIG. 1B, Table 1). Most of the differences in amino acid sequences occurred in the N-terminal region of the translation products, while blocks of conserved amino acids were found throughout the middle and C-terminal regions (FIG. 1A and FIG. 1B). The Group 1 sequences were about 42 amino acids shorter than the other sequences in this area. The differences among the three *C. sativa* sequences occurred within the first 60 amino acids (FIG. 1A and FIG. 1B, FIG. 2).

The four subgenome A PDCT genes from *Brassica napus*, the four subgenome B and four subgenome C genes from *Brassica carinata*, and all three PDCT genes from *Camelina sativa* were co-expressed in the *Arabidopsis* rod1 mutant with the Δ6-desaturase from *Pythium irregulare* and the Δ6-elonagase from Thraustochytrium. The *Arabidopsis* rod1 mutant and a wild-type *Arabidopsis* line (with an active endogenous PDCT gene) were also transformed with the Δ6-desaturase from *Pythium irregulare* and the Δ6-elonagase from Thraustochytrium, and untransformed wild-type and ROD mutant lines were used for comparison.

Expression of the Δ6-desaturase and Δ6-elonagase will result in the production of the heterologous fatty acids γ-linolenic acid (GLA; 18:2 Δ11, 14), stearidonic acid (SDA; 18:3 Δ6, 9, 12, 15), di-homo γ-linolenic acid (DGLA; 20:3 Δ8, 11, 14) and eicosatetraenoic acid (ETA; 20:4 Δ8.11, 14, 17) in *Arabidopsis* seeds, as shown in FIG. 4. An active PDCT gene will lead to a decrease in the level of OA (18:1 Δ9) and an increase in the level(s) of LA (18:2Δ6, 9), ALA (18:3Δ6, 9, 15) and/or GLA, as shown in FIG. 5.

The presence of a mutation in the ROD1 gene of *Arabidopsis* has been shown to increase the percent of 18:1 in seed oil (Lu et al., 2009). The percentage of 18:1 in the untransformed rod1 mutant used in this study averaged 30.42%, while seed oil of the untransformed wild-type line contained 15.334% 18:1. Seed oil from *Arabidopsis* lines carrying group 1 and group 2 chromosome-derived PDCT genes had average 18:1 levels ranging from 25.72-31.12% (Table 2). This was comparable to the level in the ROD mutant lines transformed with only the Δ6-desaturase and Δ6-elonagase (average 30.732%). However, the levels in seeds carrying the subgenome 3A, 3B and 3C derived genes ranged from 14.959-15.871%. Levels in seeds carrying chromosome 5 derived PDCT genes ranged from 11.994-16.696%, and those in seeds carrying the *C. sativa* genes ranged from 13.288-14.050%. Thus, while the *Brassica napus* chromosome 3 and chromosome 5 derived genes, and the three *C. sativa* genes are able to compensate for the mutation in the *Arabidopsis* PDCT gene, the chromosome 1 and 2 derived genes appear to have little or no effect on 18:1 levels. This suggests that the chromosome 1 and 2 derived genes may have a different function and/or act on different substrates than the *Arabidopsis* PDCT gene.

Alignment of PDCT-like translation products from a range of species including *Triticum aestivum, Arabidopsis thaliana, Zea mays, Ricinus communis, Glycine max*, and *Linum usitatissimum* indicated that substitutions of highly conserved amino acids occurred throughout the *B. napus* chromosome 1 and chromosome 2 derived proteins. Using numbering based on the Arabidpsis ROD1 sequence as shown in the alignment in FIG. 1, *Brassica napus* chromosome-1 derived enzymes showed the following changes in conserved regions: position 102: M to T, between 104-105: insertion of E, and 225: H to Q. In addition to these changes in conserved regions, various differences occurred in the less conserved N-terminal region of the protein.

In the case of chromosome 2B and 2C derived proteins from *Brassica carinata* and *Brassica napus* respectively, a larger number of substitutions in conserved regions were detected. Using amino acid residue numbering based on the *Arabidopsis* ROD1 sequence, the following substitutions were detected 98: V/L to F, 101 F to V, 102 M to V, 106: Y to S, 141: L/V to G, 149-150: FV to LG, 158: L/V to A, 176: M to V, 186: S/A to C, 192: P to S, 211: L to Y, and 230: M/V to T. Notably, this threonine substitution at position 230 also occurred in most of the chromosome 1 group proteins, as did the M to T substitution at position 106.

In the untransformed *Arabidopsis* wild-type lines the decrease in 18:1 is compensated for by an increase in 18:2 compared to rod1 mutant plants (27.545% in wild-type versus 14.323% in ROD mutant; Table 2) although a slight increase in ALA also occurs (16.066 versus 14.323%). Transgenic lines carrying the elongase and desaturase genes plus chromosome-1 or 2 PDCT genes had LA levels of 8.314-12.165%, while lines carrying chromosome 3 and 5 derived PDCT genes had levels of 18.149-20.142%. The lines carrying the *C. sativa* genes had 18:2 levels of 11.324% (Chromosome 1 derived PDCT), 19.912% (C15) and 8.635% (C19). ALA levels were also comparatively low in lines carrying the *C. sativa* C1 (7.771%) and C19 (7.656%) genes, whereas lines containing the C15 genes had the highest average ALA content (14.826%). However, in lines carrying the Δ6-desaturase and the Δ6-elonagase along with the PDCT gene, the additional 18:2 produced in the presence of the PDCT gene may be used not only to produce ALA, but may also be used in the synthesis of GLA, DGLA, SDA and ETA (FIG. 4). The total levels of these fatty acids were highest in lines carrying the C1 (25.225%) and C19 (24.379%) PDCT genes, and these two lines also had the highest levels of GLA plus HGLA (22.183% and 21.094% respectively). The fatty acid profile of lines carrying the *C. sativa* C15 gene bore more of a resemblance to the group 5 and group 3 chromosomes, in that the total ALA plus SDA plus ETA (16%) was considerably higher than the total GLA plus HGLA (8.767%). Only in the C1 and C19 lines were total levels of GLA plus HGLA higher than total levels of ALA plus SDA plus ETA (Table 2). Thus, not only do the various PDCTs show differences in overall efficiency, but there also appears to be different substrate preferences among the genes. The *Camelina sativa* C1 and C19 proteins differed from the C15 protein in only a limited number of amino acids in the N-terminal region of the protein (FIG. 2). Position 3 was valine in C15 and alanine in C1 and C19. Position 4 was alanine in C15, whereas the similar amino acid residues serine and threonine were at position 4 in C1 and C19 respectively. A conserved histidine at position 20 in C1 and C19 was replaced by asparagine in C15, proline-valine residues at positions 35 to 36 in C1 and C19 were replaced with arginine-isoleucine in C15, and a threonine at position 41 was replaced with lysine in C15. Finally, C15 had an insertion of an amino acid (glycine) at position 63.

These differences indicated the importance of the N-terminal region of the PDCT enzyme in determining enzyme activity.

Potentially, inactivation of one or more *Camelina sativa* PDCT enzyme may modulate PDCT activity levels, and might also be beneficial in increasing the levels of specific fatty acids, or in pushing fatty acids towards the ω3 or ω6 pathway. Since *B. napus* and *B. carinata* each have four active PDCT genes, it should be possible to achieve a range in PDCT activity levels by combining active and inactive genes. Avoiding rapid transfer onto DAG may allow more efficient transfer to the acyl-CoA pool by the reverse reaction of plant LPCAT enzymes. The reverse reaction of LPCAT has been shown to play an important role in editing PC in plants, and plant LPCATs also show fatty acid selectivity (Lager et al., 2013) This may be of particular interest for the production of VLC-PUFAs, where rapid movement of fatty acids to the DAG pool and subsequently to TAG may not be desirable.

To ensure the differences in activities among the transgenic lines did not reflect differences in copy numbers of PDCT genes, the segregation ratio of T2 plants was checked (Table 3), and T3 seed from lines that fit a 3:1 segregation ratio was used for GC analysis. Results closely resembled those from the T2 generation (Table 4). 18:1 levels in lines carrying chromosome group 1 or 2 derived PDCT genes ranged from 31.26-31.41%, while levels in group 3 and 5 lines ranged from 12.17-14.59%. Levels in lines carrying the *C. sativa* genes ranged from 12.89 to 14.60%. LA levels in lines carrying group 1 and 2 chromosome genes ranged from 6.58-10.06%, while levels in the group of lines carrying chromosome 3 or 5 derived genes ranged from 15.58-23.54%. Levels in lines carrying C1, C15 and C19 PDCT genes were 11.53, 21.49 and 7.50%, respectively. Again, the low level of LA in C1 and C19 lines was due to the very high levels of GLA plus DGLA in these lines (20.85% in C1 and 23.11% in C19).

Example 6: Average Fatty Acid Composition (%) in Different Lipid Classes from Immature Seeds Thin-layer chromatography (TLC) analysis was performed on immature siliques (from plants homozygous for the desaturase and elongase transgenes) to measure the fatty acid profile in different lipid pools, namely, phosphatyidylcholine (PC), diacylglycerol (DAG), and triacylglycerol (TAG). Briefly, total lipids were extracted from immature siliques by rapid freezing and grinding of green siliques, followed by transferring approximately 500 mg of ground sample into a centrifuge tube with 3 ml of chloroform: methanol:formic acid (10:10:1, v/v/v) and storing overnight at −20° C. After centrifugation, the supernatant was collected, and the pellet was re-extracted with 1.1 ml chloroform:methanol:water (5:5:1, v/v/v). The extractions were combined and washed with 1.5 ml mL 0.2M H3PO4/1M KCl. Lipids in the chloroform phase were dried down, and re-dissolved in 0.2 ml of chloroform. After pre-running and drying the TLC plate, samples were run in hexane/diethyl ether/acetic acid (70:30:1). TAG and DAG were isolated and directly methylated with 3M methanolic HCL. Polar lipids were collected from the plate, extracted and resuspended in chloroform, then re-run in chloroform/methanol/acetic acid/ water (60:30:3:1) to separate PC. Bands were visualized by spraying with primulin solution and exposing to UV light. The appropriate silica bands were scraped from the TLC plate, and treated with 2 mL 3M methanolic HCL at 80° C., then analyzed by GC. All fatty acid data are presented as % relative and are shown in Table 7.

The data in Table 7 can be used to understand how the various PDCT genes influence the trafficking of fatty acids between different lipid pools. Table 7 shows the average fatty acid composition (%) in different lipid classes from immature seeds of *Arabidopsis* transformed with D6(Pi) desaturase+ Tc D6Elongase. 3C and 5C refers to data from plants with a knock out of PDCT3 and PDCT5, respectively.

The *Arabidopsis* rod1 mutant (CK mutant) and a wild-type *Arabidopsis* line (CK WT) (with an active endogenous PDCT gene) were also transformed with the Δ6-desaturase from *Pythium irregulare* and the Δ6-elonagase from Thraustochytrium, and untransformed wild-type (WT) and ROD mutant lines (Rod mut) were used for comparison.

TABLE 1

| Sequenzes: | | | |
|---|---|---|---|
| PDCT1 Polypeptide: | SEQ ID No.: 2, 4, 6, 8, 10, 12, 14, 16, 40, 42, 44, and/or 46 | | |
| PDCT1 Polynucleotide: | SEQ ID No.: 1, 3, 5, 7, 9, 11, 13, 15, 39, 41, 43, and/or 45 | | |
| PDCT19 Polypeptide: | SEQ ID No.: 36, 38, and/or 48 | | |
| PDCT19 Polynucleotide: | SEQ ID No.: 35, 37, and/or 47 | | |
| PDCT3/5 Polypeptide: | SEQ ID No.: 18, 20, 22, 24, 26, 28, 30, 32, 50, 52, 54, 56, 58, and/or 60 | | |
| PDCT19 Polynucleotide: | SEQ ID No.: 17, 19, 21, 23, 27, 29, 31, 49, 51, 53, 55, and/or 57 | | |
| Candiates of the PDCT1 that shall have the same activity as PDCT1: | | | |
| GmROD1-1 | 63 | 64 | PDCT1 candiate |
| GmROD1-2 | 65 | 66 | PDCT1 candiate |
| RcPDCT | 67 | 68 | PDCT1 candiate |
| RcROD1_SEQIDNO969 | 70 | | PDCT1 candiate |
| LuPDCT1 | 71 | 72 | PDCT1 candiate |
| LuPDCT2 | 73 | 74 | PDCT1 candiate |

TABLE 2

Average fatty acid composition (%) in seeds of PDCT + D6(Pi) desaturase+ Tc D6Elongase transgenic T2 Arabidopsis

| | 16:0 | 18:0 | 18:1 | 18:2 | GLA | 18:3 | 20:1 | HGLA | SDA | ETA | Total GLA HGLA SDA ETA | Total ALA SDA ETA | Total GLA HGLA |
|---|---|---|---|---|---|---|---|---|---|---|---|---|---|
| Napus 1A | 9.063 | 3.290 | 26.438 | 12.165 | 2.205 | 9.916 | 15.452 | 5.634 | 0.231 | 0.995 | 9.065 | 11.142 | 7.839 |
| Carinata 1C | 8.254 | 3.398 | 29.693 | 11.760 | 2.402 | 10.656 | 17.882 | 1.950 | 0.689 | 0.369 | 5.410 | 11.714 | 4.352 |
| Carinata 2B | 7.950 | 3.203 | 30.947 | 11.418 | 3.083 | 11.154 | 18.672 | 1.639 | 0.742 | 0.253 | 5.717 | 12.149 | 4.722 |
| Napus 2C | 8.045 | 3.239 | 29.547 | 11.834 | 3.903 | 10.586 | 17.472 | 1.703 | 0.898 | 0.237 | 6.741 | 11.721 | 5.606 |
| Napus 3A | 7.915 | 3.004 | 15.871 | 18.613 | 7.984 | 12.877 | 17.168 | 1.827 | 1.226 | 0.090 | 11.127 | 14.193 | 9.811 |
| Carinata 3B | 7.756 | 3.027 | 15.287 | 18.974 | 7.977 | 13.180 | 17.220 | 1.777 | 1.282 | 0.053 | 11.089 | 14.515 | 9.755 |
| Carinata 3C | 7.846 | 3.495 | 14.959 | 17.639 | 8.662 | 13.744 | 18.638 | 2.096 | 1.374 | 0.215 | 12.347 | 15.333 | 10.758 |
| Napus 5A | 7.606 | 3.286 | 16.696 | 18.657 | 6.467 | 14.627 | 18.890 | 1.192 | 1.092 | 0.065 | 8.816 | 15.784 | 7.659 |
| Carinata 5B | 8.031 | 3.244 | 15.025 | 18.149 | 9.193 | 12.762 | 16.790 | 2.481 | 1.493 | 0.155 | 13.322 | 14.410 | 11.674 |
| Carinata 5C | 8.429 | 2.905 | 11.994 | 20.812 | 9.901 | 11.717 | 15.036 | 2.453 | 1.365 | 0.102 | 13.821 | 13.184 | 12.354 |
| C1 (80666) | 9.126 | 3.440 | 13.288 | 11.324 | 14.380 | 7.771 | 15.141 | 7.803 | 2.063 | 0.980 | 25.225 | 10.813 | 22.183 |
| C15 (45897) | 8.196 | 3.489 | 14.367 | 19.912 | 7.366 | 14.826 | 18.397 | 1.401 | 1.158 | 0.016 | 9.941 | 16.000 | 8.767 |
| C19 (65416) | 7.830 | 3.454 | 14.050 | 8.635 | 14.658 | 7.656 | 15.746 | 6.436 | 2.440 | 0.844 | 24.379 | 10.940 | 21.094 |
| CK mutant | 8.936 | 3.290 | 30.732 | 11.866 | 3.172 | 11.105 | 17.449 | 1.905 | 0.602 | 0.198 | 5.877 | 11.905 | 5.077 |
| CK WT | 7.684 | 3.345 | 12.754 | 22.068 | 7.527 | 13.765 | 18.000 | 1.906 | 0.968 | 0.143 | 10.544 | 14.876 | 9.433 |
| WT | 7.335 | 3.284 | 15.334 | 27.545 | 0.000 | 16.066 | 18.071 | 0.000 | 0.000 | 0.000 | 0.000 | 16.066 | 0.000 |
| ROD mut | 7.619 | 3.123 | 30.420 | 14.332 | 0.000 | 15.158 | 19.276 | 0.000 | 0.000 | 0.000 | 0.000 | 15.158 | 0.000 |

CK mutant: PDCT mutant with D6(Pi) desaturase+ Tc D6Elongase
CK WT: WT Arabidopsis with D6(Pi) desaturase+ Tc D6Elongase
WT : Untransformed wild-type Arabidopsis
ROD mut: Untransformed Arabidopsis ROD mutant
Complete data in Appendix 1.

TABLE 3

Segregation ratios of $T_2$ generation to test goodness of fit to 3:1 ratio

| Group | Plant # | Resistant plant | Susceptible plant | Hypothesis Ratio | p value | Accept hypothesis |
|---|---|---|---|---|---|---|
| B. napus 1A | 2 | 50 | 0 | 63:1 | 0.312 | Accept |
| | 4 | 12 | 9 | 3:1 | 0.04 | No |
| | 5 | 71 | 19 | 3:1 | 0.46 | Accept |
| | 6 | 61 | 11 | 3:1 | 0.06 | Accept |
| | 7 | 20 | 45 | 3:1 | 0.249 | Accept |
| | 8 | 40 | 13 | 3:1 | 1 | Accept |
| | 9 | 41 | 26 | 3:1 | 0.012 | No |
| | 10 | 38 | 16 | 3:1 | 0.34 | Accept |
| | 11 | 40 | 16 | 3:1 | 0.537 | Accept |
| | 12 | 65 | 20 | 3:1 | 0.801 | Accept |
| | 13 | 67 | 18 | 3:1 | 0.451 | Accept |
| | 14 | 32 | 15 | 3:1 | 0.316 | Accept |
| | 15 | 50 | 9 | 3:1 | 0.073 | Accept |
| | 16 | 103 | 23 | 3:1 | 0.1 | Accept |
| | 17 | 54 | 19 | 3:1 | 0.786 | Accept |
| | 18 | 35 | 64 | 1:3 | 0.021 | No |
| | 19 | 54 | 18 | 3:1 | 1 | Accept |
| | 20 | 74 | 14 | 3:1 | 0.049 | No |
| | 21 | 22 | 8 | 3:1 | 1 | Accept |
| | 22 | 83 | 23 | 3:1 | 0.498 | Accept |
| | 23 | 52 | 17 | 3:1 | 1 | Accept |
| | 24 | 73 | 16 | 3:1 | 0.14 | Accept |

TABLE 3-continued

Segregation ratios of $T_2$ generation to test goodness of fit to 3:1 ratio

| Group | Plant # | Resistant plant | Susceptible plant | Hypothesis Ratio | p value | Accept hypothesis or not |
|---|---|---|---|---|---|---|
| B. carinata 2B | 1 | 72 | 20 | 3:1 | 0.47 | Accept |
| | 2 | 59 | 19 | 3:1 | 1 | Accept |
| | 3 | 73 | 23 | 3:1 | 0.814 | Accept |
| | 4 | 45 | 15 | 3:1 | 1 | Accept |
| | 5 | 99 | 5 | 15:1 | 0.674 | Accept |
| | 6 | 75 | 9 | 15:1 | 0.065 | Accept |
| | 7 | 103 | 11 | 15:1 | 0.119 | Accept |
| | 8 | 107 | 16 | 3:1 | 0.001 | No |
| | 9 | 98 | 12 | 15:1 | 0.051 | Accept |
| | 10 | 119 | 5 | 15:1 | 0.273 | Accept |
| | 12 | 50 | 0 | 63:1 | 0.312 | Accept |
| | 13 | 136 | 16 | 15:1 | 0.016 | No |
| | 14 | 113 | 19 | 3:1 | 0.005 | No |
| | 15 | 142 | 11 | 15:1 | 0.744 | Accept |
| | 16 | 50 | 5 | 15:1 | 0.235 | Accept |
| | 17 | 84 | 11 | 15:1 | 0.035 | No |
| | 18 | 88 | 29 | 3:1 | 1 | Accept |
| | 19 | 107 | 9 | 15:1 | 0.435 | Accept |
| | 20 | 105 | 10 | 15:1 | 0.242 | Accept |
| | 21 | 101 | 25 | 3:1 | 0.215 | Accept |
| | 22 | 76 | 3 | 15:1 | 0.355 | Accept |
| | 23 | 65 | 16 | 3:1 | 0.302 | Accept |
| | 24 | 51 | 21 | 3:1 | 0.414 | Accept |
| | 25 | 51 | 16 | 3:1 | 0.779 | Accept |
| B. napus 2C | 1 | 95 | 20 | 3:1 | 0.053 | Accept |
| | 2 | 55 | 17 | 3:1 | 0.785 | Accept |
| | 3 | 50 | 2 | 15:1 | 0.552 | Accept |
| | 4 | 120 | 12 | 15:1 | 0.145 | Accept |
| | 5 | 130 | 16 | 15:1 | 0.016 | No |
| | 6 | 160 | 14 | 15:1 | 0.35 | Accept |
| | 7 | 103 | 10 | 15:1 | 0.242 | Accept |
| | 8 | 60 | 19 | 3:1 | 0.796 | Accept |
| | 9 | 74 | 26 | 3:1 | 0.817 | Accept |
| | 10 | 58 | 25 | 3:1 | 0.313 | Accept |
| | 11 | 118 | 12 | 15:1 | 0.144 | Accept |
| | 12 | 98 | 2 | 63:1 | 1 | Accept |
| | 13 | 42 | 24 | 3:1 | 0.027 | No |
| | 14 | 71 | 1 | 63:1 | 1 | Accept |
| | 15 | 75 | 25 | 3:1 | 1 | Accept |
| | 16 | 38 | 29 | 3:1 | 0.001 | No |
| | 17 | 125 | 21 | 3:1 | 0.004 | No |
| | 18 | 143 | 35 | 3:1 | 0.118 | Accept |
| | 19 | 107 | 2 | 63:1 | 1 | Accept |
| | 20 | 81 | 23 | 3:1 | 0.497 | Accept |
| | 21 | 60 | 1 | 63:1 | 1 | Accept |
| | 22 | 92 | 1 | 63:1 | 1 | Accept |

| Group | Plant # | Resistant plant | Susceptible plant | Hypothesis Ratio | p value | Accept hypothesis |
|---|---|---|---|---|---|---|
| B. napus 3A | 1 | 67 | 12 | 3:1 | 0.038 | No |
| | 2 | 125 | 39 | 3:1 | 0.718 | Accept |
| | 3 | 29 | 26 | 3:1 | 0 | No |
| | 4 | 92 | 21 | 3:1 | 0.127 | Accept |
| | 5 | 67 | 20 | 3:1 | 0.622 | Accept |
| | 6 | 43 | 19 | 3:1 | 0.342 | Accept |
| | 7 | 55 | 26 | 3:1 | 0.236 | Accept |
| | 8 | 70 | 9 | 15:1 | 0.065 | Accept |
| | 9 | 60 | 7 | 15:1 | 0.122 | Accept |
| | 10 | 63 | 5 | 15:1 | 0.606 | Accept |
| | 11 | 60 | 18 | 3:1 | 0.792 | Accept |
| | 12 | 68 | 22 | 3:1 | 1 | Accept |
| | 13 | 56 | 29 | 3:1 | 0.044 | No |
| | 14 | 69 | 22 | 3:1 | 0.809 | Accept |
| | 15 | 70 | 2 | 63:1 | 0.314 | Accept |
| | 16 | 41 | 13 | 3:1 | 1 | Accept |
| | 17 | 53 | 3 | 15:1 | 1 | Accept |
| | 18 | 47 | 16 | 3:1 | 1 | Accept |
| | 19 | 77 | 13 | 3:1 | 0.027 | No |
| | 20 | 78 | 6 | 15:1 | 0.645 | Accept |
| | 21 | 90 | 15 | 3:1 | 0.013 | No |
| | 22 | 47 | 11 | 3:1 | 0.357 | Accept |
| | 23 | 35 | 11 | 3:1 | 1 | Accept |
| | 24 | 61 | 20 | 3:1 | 1 | Accept |

TABLE 3-continued

Segregation ratios of $T_2$ generation to test goodness of fit to 3:1 ratio

| Group | Plant # | Resistant plant | Susceptible plant | Hypothesis Ratio | p value | Accept hypothesis |
|---|---|---|---|---|---|---|
| B. carinata 3B | 3B-1 | 76 | 7 | 15:1 | 0.3562 | Accept |
| | 3B-2 | 56 | 23 | 3:1 | 0.4376 | Accept |
| | 3B-3 | 24 | 28 | 3:1 | <0.0001 | Reject |
| | 3B-4 | 58 | 15 | 3:1 | 0.415 | Accept |
| | 3B-5 | 27 | 45 | 3:1 | <0.0001 | Reject |
| | 3B-6 | 142 | 37 | 3:1 | 0.168 | Accept |
| | 3B-7 | 85 | 31 | 3:1 | 0.668 | Accept |
| | 3B-8 | 87 | 21 | 3:1 | 0.182 | Accept |
| | 3B-9 | 75 | 24 | 3:1 | 0.817 | Accept |
| | 3B-10 | 97 | 11 | 15:1 | 0.118 | Accept |
| | 3B-11 | 52 | 13 | 3:1 | 0.388 | Accept |
| | 3B-12 | 43 | 18 | 3:1 | 0.372 | Accept |
| | 3B-13 | 75 | 29 | 3:1 | 0.497 | Accept |
| | 3B-14 | 63 | 3 | 15:1 | 0.606 | Accept |
| | 3B-15 | 42 | 16 | 3:1 | 0.539 | Accept |
| | 3B-16 | 70 | 4 | 15:1 | 0.643 | Accept |
| | 3B-17 | 68 | 2 | 63:1 | 0.314 | Accept |
| | 3B-18 | 56 | 23 | 3:1 | 0.438 | Accept |
| | 3B-19 | 59 | 5 | 15:1 | 0.606 | Accept |
| | 3B-20 | 71 | 2 | 63:1 | 0.314 | Accept |
| | 3B-21 | 56 | 2 | 63:1 | 0.313 | Accept |
| | 3B-22 | 58 | 22 | 3:1 | 0.606 | Accept |
| | 3B-23 | 59 | 19 | 3:1 | 1 | Accept |
| | 3B-24 | 65 | 30 | 3:1 | 0.157 | Accept |
| B. carinata 3C | 1 | 128 | 2 | 63:1 | 1 | Accept |
| | 2 | 96 | 17 | 3:1 | 0.017 | No |
| | 5 | 78 | 24 | 3:1 | 0.818 | Accept |
| | 6 | 76 | 8 | 15:1 | 0.167 | Accept |
| | 7 | 50 | 5 | 15:1 | 0.235 | Accept |
| | 8 | 91 | 15 | 3:1 | 0.013 | No |
| | 9 | 75 | 10 | 15:1 | 0.021 | No |
| | 10 | 95 | 17 | 3:1 | 0.016 | No |
| | 11 | 97 | 13 | 15:1 | 0.019 | No |
| | 12 | 38 | 12 | 3:1 | 1 | Accept |
| | 13 | 80 | 10 | 15:1 | 0.091 | Accept |
| | 14 | 42 | 6 | 15:1 | 0.074 | Accept |
| | 15 | 77 | 17 | 3:1 | 0.15 | Accept |
| | 16 | 70 | 5 | 15:1 | 1 | Accept |
| | 17 | 120 | 1 | 63:1 | 0.476 | Accept |
| | 18 | 79 | 24 | 3:1 | 0.65 | Accept |
| | 19 | 61 | 15 | 3:1 | 0.289 | Accept |
| | 20 | 94 | 20 | 3:1 | 0.082 | Accept |
| | 21 | 59 | 13 | 3:1 | 0.174 | Accept |
| | 22 | 109 | 15 | 15:1 | 0.011 | No |
| | 23 | 49 | 19 | 3:1 | 0.575 | Accept |
| | 25 | 53 | 17 | 3:1 | 1 | Accept |
| | 34 | 65 | 22 | 3:1 | 1 | Accept |
| | 39 | 77 | 23 | 3:1 | 0.644 | Accept |
| | 24 | 58 | 1 | 63:1 | 1 | Accept |
| B. napus 5A | 5A-1 | 32 | 17 | 3:1 | 0.097 | Accept |
| | 5A-3 | 53 | 17 | 3:1 | 1 | Accept |
| | 5A-4 | 49 | 14 | 3:1 | 0.563 | Accept |
| | 5A-5 | 50 | 21 | 3:1 | 0.413 | Accept |
| | 5A-6 | 36 | 13 | 3:1 | 0.74 | Accept |
| | 5A-8 | 70 | 6 | 15:1 | 0.644 | Accept |
| | 5A-9 | 35 | 11 | 3:1 | 1 | Accept |
| | 5A--10 | 32 | 15 | 3:1 | 0.316 | Accept |
| | 5A-11 | 47 | 7 | 15:1 | 0.017 | Reject |
| | 5A-12 | 71 | 1 | 63:1 | 1 | Accept |
| | 5A-13 | 52 | 15 | 3:1 | 0.574 | Accept |
| | 5A-14 | 45 | 17 | 3:1 | 0.553 | Accept |
| | 5A-15 | 61 | 28 | 3:1 | 0.14 | Accept |
| | 5A-16 | 61 | 24 | 3:1 | 0.451 | Accept |
| | 5A-17 | 78 | 25 | 3:1 | 0.821 | Accept |
| | 5A-18 | 56 | 24 | 3:1 | 0.302 | Accept |
| | 5A-19 | 46 | 14 | 3:1 | 0.766 | Accept |
| | 5A-20 | 60 | 19 | 3:1 | 0.796 | Accept |
| | 5A-21 | 86 | 14 | 3:1 | 0.011 | Reject |
| | 5A-23 | 54 | 9 | 15:1 | 0.01 | Reject |
| | 5A-25 | 48 | 17 | 3:1 | 0.773 | Accept |
| | 5A-26 | 53 | 18 | 3:1 | 1 | Accept |

TABLE 3-continued

| Segregation ratios of $T_2$ generation to test goodness of fit to 3:1 ratio | | | | | | |
|---|---|---|---|---|---|---|
| | 5A-1 | 32 | 17 | 3:1 | 0.097 | Accept |
| | 5A-3 | 53 | 17 | 3:1 | 1 | Accept |
| | 5A-4 | 49 | 14 | 3:1 | 0.563 | Accept |
| | 5A-5 | 50 | 21 | 3:1 | 0.413 | Accept |
| B. carinata 5B | 5B-1 | 54 | 3 | 15:1 | 0.6041 | Accept |
| | 5B-2 | 49 | 15 | 3:1 | 0.7728 | Accept |
| | 5B-3 | 50 | 12 | 3:1 | 0.3737 | Accept |
| | 5B-4 | 59 | 20 | 3:1 | 1 | Accept |
| | 5B-5 | 76 | 29 | 3:1 | 0.4976 | Accept |
| | 5B-6 | 58 | 12 | 3:1 | 0.1634 | Accept |
| | 5B-7 | 68 | 21 | 3:1 | 0.806 | Accept |
| | 5B-8 | 67 | 22 | 3:1 | 1 | Accept |
| | 5B-9 | 74 | 18 | 3:1 | 0.229 | Accept |
| | 5B-10 | 112 | 26 | 3:1 | 0.114 | Accept |
| | 5B-11 | 48 | 20 | 3:1 | 0.401 | Accept |
| | 5B-12 | 53 | 21 | 3:1 | 0.416 | Accept |
| | 5B-13 | 57 | 24 | 3:1 | 0.303 | Accept |
| | 5B-14 | 63 | 16 | 3:1 | 0.301 | Accept |
| | 5B-15 | 107 | 9 | 15:1 | 0.435 | Accept |
| | 5B-16 | 99 | 32 | 3:1 | 0.84 | Accept |
| | 5B-17 | 56 | 14 | 3:1 | 0.403 | Accept |
| | 5B-18 | 56 | 19 | 3:1 | 1 | Accept |
| | 5B-19 | 42 | 23 | 3:1 | 0.044 | Reject |
| | 5B-20 | 125 | 7 | 15:1 | 0.715 | Accept |
| | 5B-21 | 26 | 29 | 3:1 | <0.0001 | Reject |
| | 5B-22 | 33 | 11 | 3:1 | 1 | Accept |
| | 5B-23 | 51 | 19 | 3:1 | 0.784 | Accept |
| B. carinata 5C | 5C-18 | 118 | 42 | 3:1 | 0.715 | Yes |
| | 5C-11 | 76 | 26 | 3:1 | 0.8179 | Yes |
| | 5C-15 | 114 | 101 | 3:1 | 0.0001 | No |
| | 5C-12 | 70 | 16 | 3:1 | 0.2095 | Yes |
| | 5C-2 | 52 | 17 | 3:1 | 1 | Yes |
| | 5C-10 | 79 | 3 | 15:1 | 0.356 | Yes |
| | 5C-26 | 88 | 13 | 3:1 | 0.0057 | No |
| | 5C-20 | 59 | 23 | 3:1 | 0.4404 | Yes |
| | 5C-25 | 60 | 16 | 3:1 | 0.4268 | Yes |
| | 5C-5 | 66 | 14 | 3:1 | 0.1213 | Yes |
| | 5C-19 | 45 | 6 | 3:1 | 0.0245 | No |
| | 5C-6 | 95 | 3 | 15:1 | 0.2062 | Yes |
| | 5C-16 | 93 | 94 | 3:1 | 0.0001 | No |
| | 5C-9 | 112 | 7 | 15:1 | 1 | Yes |
| | 5C-17 | 116 | 37 | 3:1 | 0.8516 | Yes |
| | 5C-8 | 156 | 58 | 3:1 | 0.529 | Yes |
| | 5C-13 | 72 | 43 | 3:1 | 0.0026 | No |
| | 5C-1 | 72 | 27 | 3:1 | 0.4817 | Yes |
| | 5C-7 | 140 | 124 | 3:1 | 0.0001 | No |
| | 5C-14 | 41 | 24 | 3:1 | 0.0213 | No |
| | 5C-3 | 64 | 33 | 3:1 | 0.0342 | No |
| Group | Plant # | Resistant | Susceptible | Hypothesis Ratio | p value | Accept hypothesis |
| C. sativa C1 | 80666-15 | 54 | 8 | 3:1 | 0.0684 | Yes |
| | 80666-20 | 50 | 12 | 3:1 | 0.3737 | Yes |
| | 80666-17 | 52 | 20 | 3:1 | 0.5862 | Yes |
| | 80666-13 | 48 | 18 | 3:1 | 0.5657 | Yes |
| | 80666-1 | 24 | 29 | 3:1 | 0.0001 | No |
| | 80666-3 | 39 | 32 | 3:1 | 0.0001 | No |
| | 80666-16 | 45 | 17 | 3:1 | 0.5531 | Yes |
| | 80666-19 | 55 | 18 | 3:1 | 1 | Yes |
| C. sativa C15 | 45897-16 | 68 | 17 | 3:1 | 0.3144 | Yes |
| | 45897-5 | 60 | 20 | 3:1 | 1 | Yes |
| | 45897-18 | 63 | 18 | 3:1 | 0.6063 | Yes |
| | 45897-8 | 82 | 6 | 15:1 | 0.6452 | Yes |
| | 45897-14 | 51 | 16 | 3:1 | 0.7789 | Yes |

TABLE 3-continued

| Segregation ratios of $T_2$ generation to test goodness of fit to 3:1 ratio | | | | | | |
|---|---|---|---|---|---|---|
| | 45897-1 | 53 | 8 | 3:1 | 0.0374 | No |
| | 45897-15 | 66 | 4 | 15:1 | 1 | Yes |
| | 45897-9 | 55 | 17 | 3:1 | 0.7855 | Yes |
| | 45897-13 | 81 | 19 | 3:1 | 0.1659 | Yes |
| | 45897-12 | 58 | 20 | 3:1 | 0.7919 | Yes |
| | 45897-11 | 58 | 30 | 3:1 | 0.0489 | No |
| | 45897-10 | 59 | 15 | 3:1 | 0.4163 | Yes |
| | 45897-6 | 58 | 17 | 3:1 | 0.5954 | Yes |
| | 45897-7 | 63 | 21 | 3:1 | 1 | Yes |
| | 45897-17 | 53 | 16 | 3:1 | 0.78 | Yes |
| | 45897-19 | 57 | 17 | 3:1 | 0.7864 | Yes |
| | 45897-2 | 56 | 11 | 3:1 | 0.0921 | Yes |
| | 45897-20 | 65 | 19 | 3:1 | 0.6143 | Yes |
| | 45897-3 | 64 | 1 | 63:1 | 1 | Yes |
| | 45897-4 | 63 | 15 | 3:1 | 0.2914 | Yes |
| C. sativa C19 | 65416-1 | 97 | 34 | 3:1 | 0.84 | Accept |
| | 65416-2 | 59 | 22 | 3:1 | 0.61 | Accept |
| | 65416-3 | 81 | 37 | 3:1 | 0.09 | Accept |
| | 65416-4 | 69 | 45 | 3:1 | 0.0002 | No |
| | 65416-5 | 174 | 47 | 3:1 | 0.213 | Accept |
| | 65416-6 | 176 | 37 | 3:1 | 0.01 | No |
| | 65416-7 | 99 | 19 | 3:1 | 0.03 | No |
| | 65416-8 | 123 | 26 | 3:1 | 0.04 | No |
| | 65416-9 | 110 | 18 | 15:1 | 0.0002 | No |
| | 65416-10 | 153 | 14 | 15:1 | 0.192 | Accept |
| | 65416-11 | 97 | 35 | 3:1 | 0.688 | Accept |
| | 65416-12 | 102 | 7 | 15:1 | 1 | Accept |
| | 65416-13 | 92 | 33 | 3:1 | 0.679 | Accept |
| | 65416-14 | 113 | 71 | 3:1 | 0 | No |
| | 65416-15 | 120 | 48 | 3:1 | 0.285 | Accept |
| | 65416-16 | 106 | 60 | 3:1 | 0.0006 | No |
| | 65416-17 | 203 | 63 | 3:1 | 0.67 | Accept |
| | 65416-19 | 165 | 52 | 3:1 | 0.75 | Accept |
| | 65416-20 | 40 | 11 | 3:1 | 0.52 | Accept |
| | 65416-21 | 261 | 78 | 3:1 | 0.38 | Accept |

TABLE 4

Average fatty acid composition (%) in transgenic T3 plants. Complete data in Appendix 2.

| LINE | 16:0 | 18:0 | 18:1 | 18:2 | GLA | 18:3 | 20:1 | DGLA | SDA | ETA | GLA DGLA SDA ETA | ALA SDA ETA | GLA DGLA |
|---|---|---|---|---|---|---|---|---|---|---|---|---|---|
| 1A | 8.96 ± 0.52 | 3.69 ± 0.15 | 31.64 ± 1.49 | 6.58 ± 0.99 | 3.40 ± 0.25 | 6.33 ± 0.54 | 17.08 ± 0.87 | 7.49 ± 0.85 | 0.55 ± 0.23 | 1.40 ± 0.22 | 12.83 | 8.27 | 10.89 |
| 1C | 8.38 ± 0.18 | 3.65 ± 0.09 | 32.33 ± 0.59 | 11.90 ± 3.22 | 3.11 ± 0.69 | 9.50 ± 1.22 | 18.67 ± 0.44 | 2.03 ± 0.92 | 0.91 ± 0.22 | 0.38 ± 0.26 | 6.43 | 10.78 | 5.15 |
| 2B | 8.44 ± 0.61 | 3.54 ± 0.15 | 30.31 ± 2.20 | 10.02 ± 2.27 | 4.07 ± 0.81 | 8.44 ± 2.00 | 17.74 ± 1.04 | 3.32 ± 2.22 | 0.79 ± 0.15 | 0.43 ± 0.37 | 8.61 | 9.66 | 7.39 |
| 20 | 8.36 ± 0.41 | 3.58 ± 0.22 | 31.10 ± 1.70 | 8.79 ± 2.63 | 3.80 ± 0.62 | 8.22 ± 2.67 | 18.15 ± 0.92 | 3.69 ± 2.99 | 0.80 ± 0.13 | 0.66 ± 0.56 | 8.96 | 9.69 | 7.50 |
| 3A | 8.25 ± 0.85 | 3.59 ± 0.54 | 13.86 ± 3.03 | 19.52 ± 1.92 | 8.00 ± 1.21 | 12.18 ± 1.50 | 17.82 ± 1.32 | 1.56 ± 0.63 | 1.09 ± 0.20 | 0.00 | 10.64 | 13.27 | 9.55 |
| 3B | 8.69 ± 0.32 | 3.25 ± 0.07 | 12.57 ± 1.82 | 18.48 ± 3.35 | 11.59 ± 2.99 | 12.28 ± 2.02 | 16.40 ± 0.82 | 1.25 ± 0.74 | 1.77 ± 0.92 | 0.00 | 14.60 | 14.05 | 12.83 |
| 3C | 8.13 ± 0.27 | 3.59 ± 0.07 | 14.32 ± 1.09 | 15.58 ± 4.40 | 11.53 ± 3.97 | 10.11 ± 2.36 | 17.74 ± 0.82 | 3.33 ± 3.08 | 1.63 ± 0.67 | 0.28 ± 0.48 | 16.77 | 12.02 | 14.86 |
| 5A | 8.33 ± 0.12 | 3.10 ± 0.12 | 12.15 ± 0.79 | 23.54 ± 6.02 | 8.90 ± 1.49 | 13.64 ± 0.59 | 16.45 ± 0.27 | 1.68 ± 0.69 | 1.18 ± 0.32 | 0.00 | 11.77 | 14.83 | 10.58 |
| 5B | 8.86 ± 0.36 | 3.28 ± 0.17 | 14.61 ± 8.96 | 15.65 ± 4.73 | 12.70 ± 1.84 | 10.67 ± 2.29 | 16.00 ± 1.13 | 1.71 ± 1.53 | 1.85 ± 0.31 | 0.01 ± 0.01 | 16.26 | 12.53 | 14.41 |
| 5C | 7.73 ± 0.24 | 2.95 ± 0.07 | 14.59 ± 1.10 | 22.07 ± 0.99 | 6.90 ± 1.20 | 13.85 ± 0.87 | 18.00 ± 0.43 | 0.87 ± 0.49 | 0.94 ± 0.18 | 0.00 | 8.70 | 14.79 | 7.76 |
| C1 | 7.82 ± 0.13 | 3.27 ± 0.15 | 12.89 ± 2.12 | 11.53 ± 7.13 | 15.07 ± 7.82 | 9.42 ± 3.98 | 17.21 ± 0.42 | 5.79 ± 3.13 | 2.40 ± 1.26 | 0.76 ± 0.51 | 24.02 | 12.58 | 20.85 |
| C15 | 7.96 ± 0.06 | 2.96 ± 0.06 | 13.35 ± 0.73 | 21.49 ± 0.44 | 8.29 ± 0.74 | 12.94 ± 0.43 | 17.49 ± 0.09 | 1.49 ± 0.39 | 1.11 ± 0.13 | 0.02 ± 0.04 | 10.91 | 14.07 | 9.78 |
| C19 | 7.70 ± 0.24 | 3.71 ± 0.17 | 14.60 ± 1.62 | 7.50 ± 0.89 | 16.99 ± 2.36 | 7.81 ± 0.74 | 16.96 ± 0.44 | 6.12 ± 0.67 | 2.57 ± 0.46 | 0.87 ± 0.14 | 26.55 | 11.25 | 23.11 |

TABLE 5

| PDCT Name | SEQ ID NA | SEQ ID AA | Activity | Organism |
|---|---|---|---|---|
| Napus_1A | 1 | 2 | PDCT1 | *Brasssica napus* |
| Napus_2A | 3 | 4 | PDCT1 | *Brasssica napus* |
| Carinata_1B | 5 | 6 | PDCT1 | *Brassica carinata* |
| Carinata_1C | 7 | 8 | PDCT1 | *Brassica carinata* |
| Carinata_2B | 9 | 10 | PDCT1 | *Brassica carinata* |
| Carinata_2C | 11 | 12 | PDCT1 | *Brassica carinata* |
| BjROD1-B4 | 13 | 14 | PDCT1 | *Brassica juncea* |
| BjROD1-A3 | 15 | 16 | PDCT1 | *Brassica juncea* |
| BjROD1-B3 | 39 | 40 | PDCT1 | *Brassica juncea* |
| Napus_1C | 41 | 42 | PDCT1 | *Brasssica napus* |
| Napus_2C | 43 | 44 | PDCT1 | *Brasssica napus* |
| Consensus PDCT1 | 45 | 46 | PDCT1 | Artificial |
| Napus_3A | 17 | 18 | PDCT3/5 | *Brasssica napus* |
| Napus_5A | 19 | 20 | PDCT3/5 | *Brasssica napus* |
| Carinata_3B | 21 | 22 | PDCT3/5 | *Brassica carinata* |
| Carinata_3C | 23 | 24 | PDCT3/5 | *Brassica carinata* |
| Carinata_5B | 25 | 26 | PDCT3/5 | *Brassica carinata* |
| Carinata_5C | 27 | 28 | PDCT3/5 | *Brassica carinata* |
| BjROD1-A2 | 29 | 30 | PDCT3/5 | *Brassica juncea* |
| BjROD1-B2 | 31 | 32 | PDCT3/5 | *Brassica juncea* |
| BjROD1-B1 | 49 | 50 | PDCT3/5 | *Brassica juncea* |
| BjROD1-A1 | 51 | 52 | PDCT3/5 | *Brassica juncea* |
| BrROD1_SEQIDNO7 | 53 | 54 | PDCT3/5 | *Brassica rapa* |
| Napus_5C | 55 | 56 | PDCT3/5 | *Brasssica napus* |
| Napus_3C | 57 | 58 | PDCT3/5 | *Brasssica napus* |
| Consensus PDCT3/5 | 59 | 60 | PDCT3/5 | Artificial |
| Camelina_C15(45897) | 33 | 34 | PDCT15 | *Camelina sativa* |
| Camelina_C19(65416) | 35 | 36 | PDCT19 | *Camelina sativa* |
| Camelina_C1(80666) | 37 | 38 | PDCT19 | *Camelina sativa* |
| Consensus PDCT19 | 47 | 48 | PCDT19 | Artificial |
| AtRodD1 | 61 | 62 | | *Arabidopsis thaliana* |
| GmROD1-1 | 63 | 64 | PDCT1 candiate | Glycine max |
| GmROD1-2 | 65 | 66 | PDCT1 candiate | Glycine max |
| RcPDCT | 67 | 68 | PDCT1 candiate | *Ricinis communis* |

TABLE 5-continued

| PDCT Name | SEQ ID NA | SEQ ID AA | Activity | Organism |
|---|---|---|---|---|
| RcROD1_SEQIDNO9 | 69 | 70 | PDCT1 candiate | *Ricinis communis* |
| LuPDCT1 | 71 | 72 | PDCT1 candiate | *Linum usitatissimum* |
| LuPDCT2 | 73 | 74 | PDCT1 candiate | *Linum usitatissimum* |
| OsROD1_SEQIDNO 11 | 75 | 76 | / | *Oryza sativa* |
| ZmROD1_GRMZM2G015040 | 77 | 78 | / | *Zea mays* |
| ZmROD1_GRMZM2G087896 | 78 | 80 | / | *Zea mays* |

TABLE 6

| Seq_1 | Seq_2 | Needle Protein Identity % Default settings |
|---|---|---|
| ATRODD1 | ATRODD1 | 100 |
| ATRODD1 | BJROD1-A1 | 78.8 |
| ATRODD1 | BJROD1-A2 | 76.1 |
| ATRODD1 | BJROD1-A3 | 72.7 |
| ATRODD1 | BJROD1-B1 | 78.5 |
| ATRODD1 | BJROD1-B2 | 78.1 |
| ATRODD1 | BJROD1-B3 | 73.7 |
| ATRODD1 | BJROD1-B4 | 55.5 |
| ATRODD1 | BRROD1_ SEQIDNO7 | 78.8 |
| ATRODD1 | CAMELINA_ C1(80666) | 86.1 |
| ATRODD1 | CAMELINA_ C15(45897) | 85.8 |
| ATRODD1 | CAMELINA_ C19(65416) | 86.2 |
| ATRODD1 | CARINATA_1B | 73.7 |
| ATRODD1 | CARINATA_1C | 74 |
| ATRODD1 | CARINATA_2B | 55.5 |
| ATRODD1 | CARINATA_2C | 55.5 |
| ATRODD1 | CARINATA_3B | 78.5 |
| ATRODD1 | CARINATA_3C | 78.8 |
| ATRODD1 | CARINATA_5B | 80.5 |
| ATRODD1 | CARINATA_5C | 79.8 |
| ATRODD1 | GMROD1-1 | 60.7 |
| ATRODD1 | GMROD1-2 | 58.1 |
| ATRODD1 | LUPDCT1 | 54.6 |
| ATRODD1 | LUPDCT2 | 54.2 |
| ATRODD1 | NAPUS_1A | 72.7 |
| ATRODD1 | NAPUS_1C | 73.7 |
| ATRODD1 | NAPUS_2A | 55.5 |
| ATRODD1 | NAPUS_2C | 55.1 |
| ATRODD1 | NAPUS_3A | 79.2 |
| ATRODD1 | NAPUS_3C | 78.8 |
| ATRODD1 | NAPUS_5A | 79.7 |
| ATRODD1 | NAPUS_5C | 80.1 |
| ATRODD1 | OSROD1_ SEQIDNO 11 | 45.5 |
| ATRODD1 | RCPDCT | 58.7 |
| ATRODD1 | RCROD1_ SEQIDNO9 | 58.7 |
| ATRODD1 | ZMROD1_ GRMZM2G015040 | 44.4 |
| ATRODD1 | ZMROD1 GRMZM2G087896 | 42.9 |
| BJROD1-A1 | ATRODD1 | 78.8 |
| BJROD1-A1 | BJROD1-A1 | 100 |
| BJROD1-A1 | BJROD1-A2 | 82.6 |
| BJROD1-A1 | BJROD1-A3 | 77.8 |
| BJROD1-A1 | BJROD1-B1 | 96.8 |
| BJROD1-A1 | BJROD1-B2 | 83.7 |
| BJROD1-A1 | BJROD1-B3 | 77.8 |
| BJROD1-A1 | BJROD1-B4 | 57.1 |
| BJROD1-A1 | BRROD1_ SEQIDNO7 | 99.3 |
| BJROD1-A1 | CAMELINA_ C1(80666) | 76.8 |

TABLE 6-continued

| Seq_1 | Seq_2 | Needle Protein Identity % Default settings |
|---|---|---|
| BJROD1-A1 | CAMELINA_ C15(45897) | 76.5 |
| BJROD1-A1 | CAMELINA_ C19(65416) | 76.5 |
| BJROD1-A1 | CARINATA_1B | 77.8 |
| BJROD1-A1 | CARINATA_1C | 78.8 |
| BJROD1-A1 | CARINATA_2B | 57.1 |
| BJROD1-A1 | CARINATA_2C | 57.1 |
| BJROD1-A1 | CARINATA_3B | 96.8 |
| BJROD1-A1 | CARINATA_3C | 97.9 |
| BJROD1-A1 | CARINATA_5B | 87.1 |
| BJROD1-A1 | CARINATA_5C | 86.5 |
| BJROD1-A1 | GMROD1-1 | 62.4 |
| BJROD1-A1 | GMROD1-2 | 62.8 |
| BJROD1-A1 | LUPDCT1 | 54.5 |
| BJROD1-A1 | LUPDCT2 | 54.5 |
| BJROD1-A1 | NAPUS_1A | 77.1 |
| BJROD1-A1 | NAPUS_1C | 78.5 |
| BJROD1-A1 | NAPUS_2A | 57.1 |
| BJROD1-A1 | NAPUS_2C | 56.8 |
| BJROD1-A1 | NAPUS_3A | 98.2 |
| BJROD1-A1 | NAPUS_3C | 97.9 |
| BJROD1-A1 | NAPUS_5A | 86.5 |
| BJROD1-A1 | NAPUS_5C | 86.8 |
| BJROD1-A1 | OSROD1_ SEQIDNO 11 | 45.3 |
| BJROD1-A1 | RCPDCT | 58.6 |
| BJROD1-A1 | RCROD1_ SEQIDNO9 | 58.6 |
| BJROD1-A1 | ZMROD1_ GRMZM2G015040 | 45.3 |
| BJROD1-A1 | ZMROD1 GRMZM2G087896 | 44.1 |
| BJROD1-A2 | ATRODD1 | 76.1 |
| BJROD1-A2 | BJROD1-A1 | 82.6 |
| BJROD1-A2 | BJROD1-A2 | 100 |
| BJROD1-A2 | BJROD1-A3 | 77.2 |
| BJROD1-A2 | BJROD1-B1 | 83.3 |
| BJROD1-A2 | BJROD1-B2 | 87 |
| BJROD1-A2 | BJROD1-B3 | 77.9 |
| BJROD1-A2 | BJROD1-B4 | 55.4 |
| BJROD1-A2 | BRROD1_ SEQIDNO7 | 83 |
| BJROD1-A2 | CAMELINA_ C1(80666) | 71.7 |
| BJROD1-A2 | CAMELINA_ C15(45897) | 71.9 |
| BJROD1-A2 | CAMELINA_ C19(65416) | 72.5 |
| BJROD1-A2 | CARINATA_1B | 77.9 |
| BJROD1-A2 | CARINATA_1C | 78.3 |
| BJROD1-A2 | CARINATA_2B | 55.4 |
| BJROD1-A2 | CARINATA_2C | 55.4 |
| BJROD1-A2 | CARINATA_3B | 83.3 |
| BJROD1-A2 | CARINATA_3C | 83 |
| BJROD1-A2 | CARINATA_5B | 88.8 |
| BJROD1-A2 | CARINATA_5C | 93.3 |
| BJROD1-A2 | GMROD1-1 | 62.1 |

TABLE 6-continued

| Seq_1 | Seq_2 | Needle Protein Identity % Default settings |
|---|---|---|
| BJROD1-A2 | GMROD1-2 | 57.5 |
| BJROD1-A2 | LUPDCT1 | 51.5 |
| BJROD1-A2 | LUPDCT2 | 51.5 |
| BJROD1-A2 | NAPUS_1A | 76.6 |
| BJROD1-A2 | NAPUS_1C | 77.9 |
| BJROD1-A2 | NAPUS_2A | 55.4 |
| BJROD1-A2 | NAPUS_2C | 55.1 |
| BJROD1-A2 | NAPUS_3A | 81.7 |
| BJROD1-A2 | NAPUS_3C | 83 |
| BJROD1-A2 | NAPUS_5A | 95.4 |
| BJROD1-A2 | NAPUS_5C | 93.6 |
| BJROD1-A2 | OSROD1_ SEQIDNO 11 | 42.2 |
| BJROD1-A2 | RCPDCT | 59.7 |
| BJROD1-A2 | RCROD1_ SEQIDNO9 | 59.7 |
| BJROD1-A2 | ZMROD1 GRMZM2G015040 | 45.1 |
| BJROD1-A2 | ZMROD1 GRMZM2G087896 | 45.6 |
| BJROD1-A3 | ATRODD1 | 72.7 |
| BJROD1-A3 | BJROD1-A1 | 77.8 |
| BJROD1-A3 | BJROD1-A2 | 77.2 |
| BJROD1-A3 | BJROD1-A3 | 100 |
| BJROD1-A3 | BJROD1-B1 | 78.5 |
| BJROD1-A3 | BJROD1-B2 | 76.1 |
| BJROD1-A3 | BJROD1-B3 | 95.8 |
| BJROD1-A3 | BJROD1-B4 | 55.4 |
| BJROD1-A3 | BRROD1_ SEQIDNO7 | 78.5 |
| BJROD1-A3 | CAMELINA_ C1(80666) | 69.1 |
| BJROD1-A3 | CAMELINA_ C15(45897) | 69.5 |
| BJROD1-A3 | CAMELINA_ C19(65416) | 69.5 |
| BJROD1-A3 | CARINATA_1B | 95.8 |
| BJROD1-A3 | CARINATA_1C | 94.5 |
| BJROD1-A3 | CARINATA_2B | 55 |
| BJROD1-A3 | CARINATA_2C | 55.4 |
| BJROD1-A3 | CARINATA_3B | 78.8 |
| BJROD1-A3 | CARINATA_3C | 78.8 |
| BJROD1-A3 | CARINATA_5B | 79.3 |
| BJROD1-A3 | CARINATA_5C | 78.2 |
| BJROD1-A3 | GMROD1-1 | 60.2 |
| BJROD1-A3 | GMROD1-2 | 54.4 |
| BJROD1-A3 | LUPDCT1 | 52.5 |
| BJROD1-A3 | LUPDCT2 | 53.4 |
| BJROD1-A3 | NAPUS_1A | 98.6 |
| BJROD1-A3 | NAPUS_1C | 95.5 |
| BJROD1-A3 | NAPUS_2A | 55.4 |
| BJROD1-A3 | NAPUS_2C | 55 |
| BJROD1-A3 | NAPUS_3A | 78.3 |
| BJROD1-A3 | NAPUS_3C | 78.8 |
| BJROD1-A3 | NAPUS_5A | 78.2 |
| BJROD1-A3 | NAPUS_5C | 78.5 |
| BJROD1-A3 | OSROD1_ SEQIDNO 11 | 41.8 |
| BJROD1-A3 | RCPDCT | 57 |
| BJROD1-A3 | RCROD1 SEQIDNO9 | 57 |
| BJROD1-A3 | ZMROD1 GRMZM2G015040 | 43.7 |
| BJROD1-A3 | ZMROD1 GRMZM2G087896 | 42.7 |
| BJROD1-B1 | ATRODD1 | 78.5 |
| BJROD1-B1 | BJROD1-A1 | 96.8 |
| BJROD1-B1 | BJROD1-A2 | 83.3 |
| BJROD1-B1 | BJROD1-A3 | 78.5 |
| BJROD1-B1 | BJROD1-B1 | 100 |
| BJROD1-B1 | BJROD1-B2 | 83.3 |
| BJROD1-B1 | BJROD1-B3 | 78.5 |
| BJROD1-B1 | BJROD1-B4 | 56.8 |

TABLE 6-continued

| Seq_1 | Seq_2 | Needle Protein Identity % Default settings |
|---|---|---|
| BJROD1-B1 | BRROD1_ SEQIDNO7 | 97.5 |
| BJROD1-B1 | CAMELINA_ C1(80666) | 76.5 |
| BJROD1-B1 | CAMELINA_ C15(45897) | 75.8 |
| BJROD1-B1 | CAMELINA_ C19(65416) | 75.8 |
| BJROD1-B1 | CARINATA_1B | 78.5 |
| BJROD1-B1 | CARINATA_1C | 79.2 |
| BJROD1-B1 | CARINATA_2B | 56.8 |
| BJROD1-B1 | CARINATA_2C | 56.8 |
| BJROD1-B1 | CARINATA_3B | 99.3 |
| BJROD1-B1 | CARINATA_3C | 98.2 |
| BJROD1-B1 | CARINATA_5B | 86.8 |
| BJROD1-B1 | CARINATA_5C | 86.8 |
| BJROD1-B1 | GMROD1-1 | 61.5 |
| BJROD1-B1 | GMROD1-2 | 62.8 |
| BJROD1-B1 | LUPDCT1 | 53.9 |
| BJROD1-B1 | LUPDCT2 | 53.9 |
| BJROD1-B1 | NAPUS_1A | 77.8 |
| BJROD1-B1 | NAPUS_1C | 79.2 |
| BJROD1-B1 | NAPUS_2A | 56.8 |
| BJROD1-B1 | NAPUS_2C | 56.4 |
| BJROD1-B1 | NAPUS_3A | 96.8 |
| BJROD1-B1 | NAPUS_3C | 98.2 |
| BJROD1-B1 | NAPUS_5A | 86.8 |
| BJROD1-B1 | NAPUS_5C | 87.2 |
| BJROD1-B1 | OSROD1 SEQIDNO 11 | 43.8 |
| BJROD1-B1 | RCPDCT | 60.8 |
| BJROD1-B1 | RCROD1_ SEQIDNO9 | 60.8 |
| BJROD1-B1 | ZMROD1_ GRMZM2G015040 | 45.8 |
| BJROD1-B1 | ZMROD1 GRMZM2G087896 | 44.1 |
| BJROD1-B2 | ATRODD1 | 78.1 |
| BJROD1-B2 | BJROD1-A1 | 83.7 |
| BJROD1-B2 | BJROD1-A2 | 87 |
| BJROD1-B2 | BJROD1-A3 | 76.1 |
| BJROD1-B2 | BJROD1-B1 | 83.3 |
| BJROD1-B2 | BJROD1-B2 | 100 |
| BJROD1-B2 | BJROD1-B3 | 77.5 |
| BJROD1-B2 | BJROD1-B4 | 56.1 |
| BJROD1-B2 | BRROD1_ SEQIDNO7 | 84 |
| BJROD1-B2 | CAMELINA_ C1(80666) | 75.1 |
| BJROD1-B2 | CAMELINA_ C15(45897) | 75.2 |
| BJROD1-B2 | CAMELINA_ C19(65416) | 75.2 |
| BJROD1-B2 | CARINATA_1B | 77.1 |
| BJROD1-B2 | CARINATA_1C | 77.5 |
| BJROD1-B2 | CARINATA_2B | 58.9 |
| BJROD1-B2 | CARINATA_2C | 56.1 |
| BJROD1-B2 | CARINATA_3B | 83.3 |
| BJROD1-B2 | CARINATA_3C | 85.2 |
| BJROD1-B2 | CARINATA_5B | 93.3 |
| BJROD1-B2 | CARINATA_5C | 91.2 |
| BJROD1-B2 | GMROD1-1 | 64.1 |
| BJROD1-B2 | GMROD1-2 | 65 |
| BJROD1-B2 | LUPDCT1 | 53.8 |
| BJROD1-B2 | LUPDCT2 | 53.8 |
| BJROD1-B2 | NAPUS_1A | 75.4 |
| BJROD1-B2 | NAPUS_1C | 77.1 |
| BJROD1-B2 | NAPUS_2A | 56.1 |
| BJROD1-B2 | NAPUS_2C | 55.7 |
| BJROD1-B2 | NAPUS_3A | 84.2 |
| BJROD1-B2 | NAPUS_3C | 85.2 |
| BJROD1-B2 | NAPUS_5A | 90.8 |
| BJROD1-B2 | NAPUS_5C | 91.5 |

TABLE 6-continued

| Seq_1 | Seq_2 | Needle Protein Identity % Default settings |
|---|---|---|
| BJROD1-B2 | OSROD1 SEQIDNO 11 | 41.3 |
| BJROD1-B2 | RCPDCT | 59.1 |
| BJROD1-B2 | RCROD1_ SEQIDNO9 | 59.1 |
| BJROD1-B2 | ZMROD1_ GRMZM2G015040 | 47.1 |
| BJROD1-B2 | ZMROD1 GRMZM2G087896 | 45.6 |
| BJROD1-B3 | ATRODD1 | 73.7 |
| BJROD1-B3 | BJROD1-A1 | 77.8 |
| BJROD1-B3 | BJROD1-A2 | 77.9 |
| BJROD1-B3 | BJROD1-A3 | 95.8 |
| BJROD1-B3 | BJROD1-B1 | 78.5 |
| BJROD1-B3 | BJROD1-B2 | 77.5 |
| BJROD1-B3 | BJROD1-B3 | 100 |
| BJROD1-B3 | BJROD1-B4 | 56.1 |
| BJROD1-B3 | BRROD1_ SEQIDNO7 | 78.5 |
| BJROD1-B3 | CAMELINA_ C1(80666) | 70.4 |
| BJROD1-B3 | CAMELINA_ C15(45897) | 70.2 |
| BJROD1-B3 | CAMELINA_ C19(65416) | 70.9 |
| BJROD1-B3 | CARINATA_1B | 98.6 |
| BJROD1-B3 | CARINATA_1C | 94.5 |
| BJROD1-B3 | CARINATA_2B | 55.4 |
| BJROD1-B3 | CARINATA_2C | 56.4 |
| BJROD1-B3 | CARINATA_3B | 78.8 |
| BJROD1-B3 | CARINATA_5B | 80.2 |
| BJROD1-B3 | CARINATA_5C | 78.8 |
| BJROD1-B3 | GMROD1-1 | 61.5 |
| BJROD1-B3 | GMROD1-2 | 52.7 |
| BJROD1-B3 | LUPDCT1 | 53.3 |
| BJROD1-B3 | LUPDCT2 | 53.6 |
| BJROD1-B3 | NAPUS_1A | 95.2 |
| BJROD1-B3 | NAPUS_1C | 95.5 |
| BJROD1-B3 | NAPUS_2A | 56.1 |
| BJROD1-B3 | NAPUS_2C | 55.7 |
| BJROD1-B3 | NAPUS_3A | 78.3 |
| BJROD1-B3 | NAPUS_3C | 78.8 |
| BJROD1-B3 | NAPUS_5A | 78.9 |
| BJROD1-B3 | NAPUS_5C | 79.2 |
| BJROD1-B3 | OSROD1 SEQIDNO 11 | 43.2 |
| BJROD1-B3 | RCPDCT | 57.6 |
| BJROD1-B3 | RCROD1_ SEQIDNO9 | 57.6 |
| BJROD1-B3 | ZMROD1 GRMZM2G015040 | 44 |
| BJROD1-B3 | ZMROD1 GRMZM2G087896 | 44.7 |
| BJROD1-B4 | ATRODD1 | 55.5 |
| BJROD1-B4 | BJROD1-A1 | 57.1 |
| BJROD1-B4 | BJROD1-A2 | 55.4 |
| BJROD1-B4 | BJROD1-A3 | 55.4 |
| BJROD1-B4 | BJROD1-B1 | 56.8 |
| BJROD1-B4 | BJROD1-B2 | 59 |
| BJROD1-B4 | BJROD1-B3 | 56.1 |
| BJROD1-B4 | BJROD1-B4 | 100 |
| BJROD1-B4 | BRROD1_ SEQIDNO7 | 57.1 |
| BJROD1-B4 | CAMELINA_ C1(80666) | 55.4 |
| BJROD1-B4 | CAMELINA_ C15(45897) | 55.2 |
| BJROD1-B4 | CAMELINA_ C19(65416) | 55.2 |
| BJROD1-B4 | CARINATA_1B | 56.4 |
| BJROD1-B4 | CARINATA_1C | 55.4 |
| BJROD1-B4 | CARINATA_2B | 97.4 |
| BJROD1-B4 | CARINATA_2C | 98.3 |
| BJROD1-B4 | CARINATA_3B | 57.1 |
| BJROD1-B4 | CARINATA_3C | 56.8 |
| BJROD1-B4 | CARINATA_5B | 58.2 |
| BJROD1-B4 | CARINATA_5C | 55.5 |
| BJROD1-B4 | GMROD1-1 | 54.9 |
| BJROD1-B4 | GMROD1-2 | 53.5 |
| BJROD1-B4 | LUPDCT1 | 48.4 |
| BJROD1-B4 | LUPDCT2 | 48.4 |
| BJROD1-B4 | NAPUS_1A | 55.4 |
| BJROD1-B4 | NAPUS_1C | 55.7 |
| BJROD1-B4 | NAPUS_2A | 99.6 |
| BJROD1-B4 | NAPUS_2C | 99.1 |
| BJROD1-B4 | NAPUS_3A | 57.4 |
| BJROD1-B4 | NAPUS_3C | 56.8 |
| BJROD1-B4 | NAPUS_5A | 55.5 |
| BJROD1-B4 | NAPUS_5C | 55.5 |
| BJROD1-B4 | OSROD1_ SEQIDNO 11 | 37.7 |
| BJROD1-B4 | RCPDCT | 51.6 |
| BJROD1-B4 | RCROD1_ SEQIDNO9 | 51.6 |
| BJROD1-B4 | ZMROD1 GRMZM2G015040 | 44.6 |
| BJROD1-B4 | ZMROD1 GRMZM2G087896 | 45.1 |
| BRROD1_ SEQIDNO7 | ATRODD1 | 78.8 |
| BRROD1_ SEQIDNO7 | BJROD1-A1 | 99.3 |
| BRROD1_ SEQIDNO7 | BJROD1-A2 | 83 |
| BRROD1_ SEQIDNO7 | BJROD1-A3 | 78.5 |
| BRROD1_ SEQIDNO7 | BJROD1-B1 | 97.5 |
| BRROD1_ SEQIDNO7 | BJROD1-B2 | 84 |
| BRROD1_ SEQIDNO7 | BJROD1-B3 | 78.5 |
| BRROD1_ SEQIDNO7 | BJROD1-B4 | 57.1 |
| BRROD1_ SEQIDNO7 | BRROD1_ SEQIDNO7 | 100 |
| BRROD1_ SEQIDNO7 | CAMELINA_ C1(80666) | 76.8 |
| BRROD1_ SEQIDNO7 | CAMELINA_ C15(45897) | 76.5 |
| BRROD1_ SEQIDNO7 | CAMELINA_ C19(65416) | 76.5 |
| BRROD1_ SEQIDNO7 | CARINATA_1B | 78.5 |
| BRROD1_ SEQIDNO7 | CARINATA_1C | 79.5 |
| BRROD1_ SEQIDNO7 | CARINATA_2B | 57.1 |
| BRROD1_ SEQIDNO7 | CARINATA_2C | 57.1 |
| BRROD1_ SEQIDNO7 | CARINATA_3B | 97.5 |
| BRROD1_ SEQIDNO7 | CARINATA_3C | 98.6 |
| BRROD1_ SEQIDNO7 | CARINATA_5B | 87.5 |
| BRROD1_ SEQIDNO7 | CARINATA_5C | 86.8 |
| BRROD1_ SEQIDNO7 | GMROD1-1 | 61.2 |
| BRROD1_ SEQIDNO7 | GMROD1-2 | 63.1 |
| BRROD1_ SEQIDNO7 | LUPDCT1 | 54.5 |
| BRROD1_ SEQIDNO7 | LUPDCT2 | 54.5 |

TABLE 6-continued

| Seq_1 | Seq_2 | Needle Protein Identity % Default settings |
|---|---|---|
| BRROD1_ SEQIDNO7 | NAPUS_1A | 77.8 |
| BRROD1_ SEQIDNO7 | NAPUS_1C | 79.2 |
| BRROD1_ SEQIDNO7 | NAPUS_2A | 57.1 |
| BRROD1_ SEQIDNO7 | NAPUS_2C | 56.8 |
| BRROD1_ SEQIDNO7 | NAPUS_3A | 98.9 |
| BRROD1_ SEQIDNO7 | NAPUS_3C | 98.6 |
| BRROD1_ SEQIDNO7 | NAPUS_5A | 86.8 |
| BRROD1_ SEQIDNO7 | NAPUS_5C | 87.2 |
| BRROD1_ SEQIDNO7 | OSROD1_ SEQIDNO 11 | 41.4 |
| BRROD1_ SEQIDNO7 | RCPDCT | 60.8 |
| BRROD1_ SEQIDNO7 | RCROD1_ SEQIDNO9 | 60.8 |
| BRROD1_ SEQIDNO7 | ZMROD1 GRMZM2G015040 | 46.2 |
| BRROD1_ SEQIDNO7 | ZMROD1 GRMZM2G087896 | 44.1 |
| CAMELINA_ C1(80666) | ATRODD1 | 86.1 |
| CAMELINA_ C1(80666) | BJROD1-A1 | 76.8 |
| CAMELINA_ C1(80666) | BJROD1-A2 | 71.7 |
| CAMELINA_ C1(80666) | BJROD1-A3 | 69.1 |
| CAMELINA_ C1(80666) | BJROD1-B1 | 76.5 |
| CAMELINA_ C1(80666) | BJROD1-B2 | 75.1 |
| CAMELINA_ C1(80666) | BJROD1-B3 | 70.4 |
| CAMELINA_ C1(80666) | BJROD1-B4 | 55.4 |
| CAMELINA_ C1(80666) | BRROD1_ SEQIDNO7 | 76.8 |
| CAMELINA_ C1(80666) | CAMELINA_ C1(80666) | 100 |
| CAMELINA_ C1(80666) | CAMELINA_ C15(45897) | 96.6 |
| CAMELINA_ C1(80666) | CAMELINA_ C19(65416) | 98 |
| CAMELINA_ C1(80666) | CARINATA_1B | 70.4 |
| CAMELINA_ C1(80666) | CARINATA_1C | 71.1 |
| CAMELINA_ C1(80666) | CARINATA_2B | 55.4 |
| CAMELINA_ C1(80666) | CARINATA_2C | 55.4 |
| CAMELINA_ C1(80666) | CARINATA_3B | 76.5 |
| CAMELINA_ C1(80666) | CARINATA_3C | 76.8 |
| CAMELINA_ C1(80666) | CARINATA_5B | 77.1 |
| CAMELINA_ C1(80666) | CARINATA_5C | 75.7 |
| CAMELINA_ C1(80666) | GMROD1-1 | 60.8 |
| CAMELINA_ C1(80666) | GMROD1-2 | 60.1 |
| CAMELINA_ C1(80666) | LUPDCT1 | 55 |

TABLE 6-continued

| Seq_1 | Seq_2 | Needle Protein Identity % Default settings |
|---|---|---|
| CAMELINA_ C1(80666) | LUPDCT2 | 55.3 |
| CAMELINA_ C1(80666) | NAPUS_1A | 69.1 |
| CAMELINA_ C1(80666) | NAPUS_1C | 70.8 |
| CAMELINA_ C1(80666) | NAPUS_2A | 55.4 |
| CAMELINA_ C1(80666) | NAPUS_2C | 55.1 |
| CAMELINA_ C1(80666) | NAPUS_3A | 76.9 |
| CAMELINA_ C1(80666) | NAPUS_3C | 76.8 |
| CAMELINA_ C1(80666) | NAPUS_5A | 75.3 |
| CAMELINA_ C1(80666) | NAPUS_5C | 76 |
| CAMELINA_ C1(80666) | OSROD1 SEQIDNO 11 | 43.8 |
| CAMELINA_ C1(80666) | RCPDCT | 55.4 |
| CAMELINA_ C1(80666) | RCROD1 SEQIDNO9 | 55.4 |
| CAMELINA_ C1(80666) | ZMROD1 GRMZM2G015040 | 45.1 |
| CAMELINA_ C1(80666) | ZMROD1 GRMZM2G087896 | 47 |
| CAMELINA_ C15(45897) | ATRODD1 | 85.8 |
| CAMELINA_ C15(45897) | BJROD1-A1 | 76.5 |
| CAMELINA_ C15(45897) | BJROD1-A2 | 71.9 |
| CAMELINA_ C15(45897) | BJROD1-A3 | 69.5 |
| CAMELINA_ C15(45897) | BJROD1-B1 | 75.8 |
| CAMELINA_ C15(45897) | BJROD1-B2 | 75.2 |
| CAMELINA_ C15(45897) | BJROD1-B3 | 70.2 |
| CAMELINA_ C15(45897) | BJROD1-B4 | 55.2 |
| CAMELINA_ C15(45897) | BRROD1_ SEQIDNO7 | 76.5 |
| CAMELINA_ C15(45897) | CAMELINA_ C1(80666) | 96.6 |
| CAMELINA_ C15(45897) | CAMELINA_ C15(45897) | 100 |
| CAMELINA_ C15(45897) | CAMELINA_ C19(65416) | 97.3 |
| CAMELINA_ C15(45897) | CARINATA_1B | 70.2 |
| CAMELINA_ C15(45897) | CARINATA_1C | 70.9 |
| CAMELINA_ C15(45897) | CARINATA_2B | 55.2 |
| CAMELINA_ C15(45897) | CARINATA_2C | 55.2 |
| CAMELINA_ C15(45897) | CARINATA_3B | 75.8 |
| CAMELINA_ C15(45897) | CARINATA_3C | 76.2 |
| CAMELINA_ C15(45897) | CARINATA_5B | 76.8 |
| CAMELINA_ C15(45897) | CARINATA_5C | 76.6 |
| CAMELINA_ C15(45897) | GMROD1-1 | 61 |
| CAMELINA_ C15(45897) | GMROD1-2 | 60.7 |

TABLE 6-continued

| Seq_1 | Seq_2 | Needle Protein Identity % Default settings |
|---|---|---|
| CAMELINA_ C15(45897) | LUPDCT1 | 53.9 |
| CAMELINA_ C15(45897) | LUPDCT2 | 54.2 |
| CAMELINA_ C15(45897) | NAPUS_1A | 69.5 |
| CAMELINA_ C15(45897) | NAPUS_1C | 70.5 |
| CAMELINA_ C15(45897) | NAPUS_2A | 55.2 |
| CAMELINA_ C15(45897) | NAPUS_2C | 54.9 |
| CAMELINA_ C15(45897) | NAPUS_3A | 76.5 |
| CAMELINA_ C15(45897) | NAPUS_3C | 76.2 |
| CAMELINA_ C15(45897) | NAPUS_5A | 75.6 |
| CAMELINA_ C15(45897) | NAPUS_5C | 76.9 |
| CAMELINA_ C15(45897) | OSROD1 SEQIDNO 11 | 45.4 |
| CAMELINA_ C15(45897) | RCPDCT | 59.8 |
| CAMELINA_ C15(45897) | RCROD1_ SEQIDNO9 | 59.8 |
| CAMELINA_ C15(45897) | ZMROD1 GRMZM2G015040 | 45 |
| CAMELINA_ C15(45897) | ZMROD1 GRMZM2G087896 | 46.5 |
| CAMELINA_ C19(65416) | ATRODD1 | 86.2 |
| CAMELINA_ C19(65416) | BJROD1-A1 | 76.5 |
| CAMELINA_ C19(65416) | BJROD1-A2 | 72.5 |
| CAMELINA_ C19(65416) | BJROD1-A3 | 69.5 |
| CAMELINA_ C19(65416) | BJROD1-B1 | 75.8 |
| CAMELINA_ C19(65416) | BJROD1-B2 | 75.2 |
| CAMELINA_ C19(65416) | BJROD1-B3 | 70.9 |
| CAMELINA_ C19(65416) | BJROD1-B4 | 55.2 |
| CAMELINA_ C19(65416) | BRROD1_ SEQIDNO7 | 76.5 |
| CAMELINA_ C19(65416) | CAMELINA_ C1(80666) | 98 |
| CAMELINA_ C19(65416) | CAMELINA_ C15(45897) | 97.3 |
| CAMELINA_ C19(65416) | CAMELINA_ C19(65416) | 100 |
| CAMELINA_ C19(65416) | CARINATA_1B | 70.9 |
| CAMELINA_ C19(65416) | CARINATA_1C | 71.5 |
| CAMELINA_ C19(65416) | CARINATA_2B | 55.2 |
| CAMELINA_ C19(65416) | CARINATA_2C | 55.2 |
| CAMELINA_ C19(65416) | CARINATA_3B | 75.8 |
| CAMELINA_ C19(65416) | CARINATA_3C | 76.5 |
| CAMELINA_ C19(65416) | CARINATA_5B | 76.8 |
| CAMELINA_ C19(65416) | CARINATA_5C | 76.1 |
| CAMELINA_ C19(65416) | GMROD1-1 | 60.3 |
| CAMELINA_ C19(65416) | GMROD1-2 | 60.5 |
| CAMELINA_ C19(65416) | LUPDCT1 | 52.6 |
| CAMELINA_ C19(65416) | LUPDCT2 | 55.3 |
| CAMELINA_ C19(65416) | NAPUS_1A | 69.5 |
| CAMELINA_ C19(65416) | NAPUS_1C | 71.2 |
| CAMELINA_ C19(65416) | NAPUS_2A | 55.2 |
| CAMELINA_ C19(65416) | NAPUS_2C | 54.9 |
| CAMELINA_ C19(65416) | NAPUS_3A | 77.2 |
| CAMELINA_ C19(65416) | NAPUS_3C | 76.5 |
| CAMELINA_ C19(65416) | NAPUS_5A | 76.2 |
| CAMELINA_ C19(65416) | NAPUS_5C | 76.4 |
| CAMELINA_ C19(65416) | OSROD1 SEQIDNO 11 | 43.9 |
| CAMELINA_ C19(65416) | RCPDCT | 59.9 |
| CAMELINA_ C19(65416) | RCROD1_ SEQIDNO9 | 59.9 |
| CAMELINA_ C19(65416) | ZMROD1 GRMZM2G015040 | 43.8 |
| CAMELINA_ C19(65416) | ZMROD1 GRMZM2G087896 | 47.7 |
| CARINATA_1B | ATRODD1 | 73.7 |
| CARINATA_1B | BJROD1-A1 | 77.8 |
| CARINATA_1B | BJROD1-A2 | 77.9 |
| CARINATA_1B | BJROD1-A3 | 95.8 |
| CARINATA_1B | BJROD1-B1 | 78.5 |
| CARINATA_1B | BJROD1-B2 | 77.1 |
| CARINATA_1B | BJROD1-B3 | 98.6 |
| CARINATA_1B | BJROD1-B4 | 56.4 |
| CARINATA_1B | BRROD1_ SEQIDNO7 | 78.5 |
| CARINATA_1B | CAMELINA_ C1(80666) | 70.4 |
| CARINATA_1B | CAMELINA_ C15(45897) | 70.2 |
| CARINATA_1B | CAMELINA_ C19(65416) | 70.9 |
| CARINATA_1B | CARINATA_1B | 100 |
| CARINATA_1B | CARINATA_1C | 93.8 |
| CARINATA_1B | CARINATA_2B | 56.4 |
| CARINATA_1B | CARINATA_2C | 56.7 |
| CARINATA_1B | CARINATA_3B | 78.8 |
| CARINATA_1B | CARINATA_3C | 78.8 |
| CARINATA_1B | CARINATA_5B | 80.2 |
| CARINATA_1B | CARINATA_5C | 78.8 |
| CARINATA_1B | GMROD1-1 | 61.1 |
| CARINATA_1B | GMROD1-2 | 55.3 |
| CARINATA_1B | LUPDCT1 | 54.1 |
| CARINATA_1B | LUPDCT2 | 54.5 |
| CARINATA_1B | NAPUS_1A | 94.5 |
| CARINATA_1B | NAPUS_1C | 94.8 |
| CARINATA_1B | NAPUS_2A | 56.4 |
| CARINATA_1B | NAPUS_2C | 56.1 |
| CARINATA_1B | NAPUS_3A | 78.3 |
| CARINATA_1B | NAPUS_3C | 78.8 |
| CARINATA_1B | NAPUS_5A | 78.9 |
| CARINATA_1B | NAPUS_5C | 79.2 |
| CARINATA_1B | OSROD1_ SEQIDNO 11 | 42.3 |
| CARINATA_1B | RCPDCT | 57.6 |
| CARINATA_1B | RCROD1 SEQIDNO9 | 57.6 |

TABLE 6-continued

| Seq_1 | Seq_2 | Needle Protein Identity % Default settings |
|---|---|---|
| CARINATA_1B | ZMROD1 GRMZM2G015040 | 44 |
| CARINATA_1B | ZMROD1 GRMZM2G087896 | 44.7 |
| CARINATA_1C | ATRODD1 | 74 |
| CARINATA_1C | BJROD1-A1 | 78.8 |
| CARINATA_1C | BJROD1-A2 | 78.3 |
| CARINATA_1C | BJROD1-A3 | 94.5 |
| CARINATA_1C | BJROD1-B1 | 79.2 |
| CARINATA_1C | BJROD1-B2 | 77.5 |
| CARINATA_1C | BJROD1-B3 | 94.5 |
| CARINATA_1C | BJROD1-B4 | 55.4 |
| CARINATA_1C | BRROD1_ SEQIDNO7 | 79.5 |
| CARINATA_1C | CAMELINA_ C1(80666) | 71.1 |
| CARINATA_1C | CAMELINA_ C15(45897) | 70.9 |
| CARINATA_1C | CAMELINA_ C19(65416) | 71.5 |
| CARINATA_1C | CARINATA_1B | 93.8 |
| CARINATA_1C | CARINATA_1C | 100 |
| CARINATA_1C | CARINATA_2B | 55.4 |
| CARINATA_1C | CARINATA_2C | 55.7 |
| CARINATA_1C | CARINATA_3B | 79.5 |
| CARINATA_1C | CARINATA_3C | 79.9 |
| CARINATA_1C | CARINATA_5B | 80.3 |
| CARINATA_1C | CARINATA_5C | 79.2 |
| CARINATA_1C | GMROD1-1 | 60.3 |
| CARINATA_1C | GMROD1-2 | 52.9 |
| CARINATA_1C | LUPDCT1 | 53.3 |
| CARINATA_1C | LUPDCT2 | 53.6 |
| CARINATA_1C | NAPUS_1A | 95.5 |
| CARINATA_1C | NAPUS_1C | 99 |
| CARINATA_1C | NAPUS_2A | 55.4 |
| CARINATA_1C | NAPUS_2C | 55 |
| CARINATA_1C | NAPUS_3A | 79.3 |
| CARINATA_1C | NAPUS_3C | 79.9 |
| CARINATA_1C | NAPUS_5A | 79.3 |
| CARINATA_1C | NAPUS_5C | 79.5 |
| CARINATA_1C | OSROD1 SEQIDNO 11 | 41.7 |
| CARINATA_1C | RCPDCT | 57.9 |
| CARINATA_1C | RCROD1 SEQIDNO9 | 57.9 |
| CARINATA_1C | ZMROD1 GRMZM2G015040 | 42.9 |
| CARINATA_1C | ZMROD1 GRMZM2G087896 | 42.7 |
| CARINATA_2B | ATRODD1 | 55.5 |
| CARINATA_2B | BJROD1-A1 | 57.1 |
| CARINATA_2B | BJROD1-A2 | 55.4 |
| CARINATA_2B | BJROD1-A3 | 55 |
| CARINATA_2B | BJROD1-B1 | 56.8 |
| CARINATA_2B | BJROD1-B2 | 58.9 |
| CARINATA_2B | BJROD1-B3 | 55.4 |
| CARINATA_2B | BJROD1-B4 | 97.4 |
| CARINATA_2B | BRROD1_ SEQIDNO7 | 57.1 |
| CARINATA_2B | CAMELINA_ C1(80666) | 55.4 |
| CARINATA_2B | CAMELINA_ C15(45897) | 55.2 |
| CARINATA_2B | CAMELINA_ C19(65416) | 55.2 |
| CARINATA_2B | CARINATA_1B | 56.4 |
| CARINATA_2B | CARINATA_1C | 55.4 |
| CARINATA_2B | CARINATA_2B | 100 |
| CARINATA_2B | CARINATA_2C | 99.1 |
| CARINATA_2B | CARINATA_3B | 57.1 |
| CARINATA_2B | CARINATA_3C | 56.8 |
| CARINATA_2B | CARINATA_5B | 58.2 |
| CARINATA_2B | CARINATA_5C | 55.5 |

TABLE 6-continued

| Seq_1 | Seq_2 | Needle Protein Identity % Default settings |
|---|---|---|
| CARINATA_2B | GMROD1-1 | 55.7 |
| CARINATA_2B | GMROD1-2 | 54.6 |
| CARINATA_2B | LUPDCT1 | 49.3 |
| CARINATA_2B | LUPDCT2 | 49.3 |
| CARINATA_2B | NAPUS_1A | 55 |
| CARINATA_2B | NAPUS_1C | 55.7 |
| CARINATA_2B | NAPUS_2A | 97 |
| CARINATA_2B | NAPUS_2C | 96.6 |
| CARINATA_2B | NAPUS_3A | 57.4 |
| CARINATA_2B | NAPUS_3C | 56.8 |
| CARINATA_2B | NAPUS_5A | 55.5 |
| CARINATA_2B | NAPUS_5C | 55.5 |
| CARINATA_2B | OSROD1_ SEQIDNO 11 | 38.1 |
| CARINATA_2B | RCPDCT | 52.3 |
| CARINATA_2B | RCROD1_ SEQIDNO9 | 52.3 |
| CARINATA_2B | ZMROD1_ GRMZM2G015040 | 44.9 |
| CARINATA_2B | ZMROD1_ GRMZM2G087896 | 44.2 |
| CARINATA_2C | ATRODD1 | 55.5 |
| CARINATA_2C | BJROD1-A1 | 57.1 |
| CARINATA_2C | BJROD1-A2 | 55.4 |
| CARINATA_2C | BJROD1-A3 | 55.4 |
| CARINATA_2C | BJROD1-B1 | 56.8 |
| CARINATA_2C | BJROD1-B2 | 59 |
| CARINATA_2C | BJROD1-B3 | 56.4 |
| CARINATA_2C | BJROD1-B4 | 98.3 |
| CARINATA_2C | BRROD1_ SEQIDNO7 | 57.1 |
| CARINATA_2C | CAMELINA_ C1(80666) | 55.4 |
| CARINATA_2C | CAMELINA_ C15(45897) | 55.2 |
| CARINATA_2C | CAMELINA_ C19(65416) | 55.2 |
| CARINATA_2C | CARINATA_1B | 56.7 |
| CARINATA_2C | CARINATA_1C | 55.7 |
| CARINATA_2C | CARINATA_2B | 99.1 |
| CARINATA_2C | CARINATA_2C | 100 |
| CARINATA_2C | CARINATA_3B | 57.1 |
| CARINATA_2C | CARINATA_3C | 56.8 |
| CARINATA_2C | CARINATA_5B | 58.2 |
| CARINATA_2C | CARINATA_5C | 55.5 |
| CARINATA_2C | GMROD1-1 | 55.3 |
| CARINATA_2C | GMROD1-2 | 53.9 |
| CARINATA_2C | LUPDCT1 | 48.7 |
| CARINATA_2C | LUPDCT2 | 48.7 |
| CARINATA_2C | NAPUS_1A | 55.4 |
| CARINATA_2C | NAPUS_1C | 56.1 |
| CARINATA_2C | NAPUS_2A | 97.9 |
| CARINATA_2C | NAPUS_2C | 97.4 |
| CARINATA_2C | NAPUS_3A | 57.4 |
| CARINATA_2C | NAPUS_3C | 56.8 |
| CARINATA_2C | NAPUS_5A | 55.5 |
| CARINATA_2C | NAPUS_5C | 55.5 |
| CARINATA_2C | OSROD1 SEQIDNO 11 | 38.1 |
| CARINATA_2C | RCPDCT | 51.9 |
| CARINATA_2C | RCROD1 SEQIDNO9 | 51.9 |
| CARINATA_2C | ZMROD1 GRMZM2G015040 | 45.3 |
| CARINATA_2C | ZMROD1 GRMZM2G087896 | 46.2 |
| CARINATA_3B | ATRODD1 | 78.5 |
| CARINATA_3B | BJROD1-A1 | 96.8 |
| CARINATA_3B | BJROD1-A2 | 83.3 |
| CARINATA_3B | BJROD1-A3 | 78.8 |
| CARINATA_3B | BJROD1-B1 | 99.3 |
| CARINATA_3B | BJROD1-B2 | 83.3 |
| CARINATA_3B | BJROD1-B3 | 78.8 |

TABLE 6-continued

| Seq_1 | Seq_2 | Needle Protein Identity % Default settings |
|---|---|---|
| CARINATA_3B | BJROD1-B4 | 57.1 |
| CARINATA_3B | BRROD1_ SEQIDNO7 | 97.5 |
| CARINATA_3B | CAMELINA_ C1(80666) | 76.5 |
| CARINATA_3B | CAMELINA_ C15(45897) | 75.8 |
| CARINATA_3B | CAMELINA_ C19(65416) | 75.8 |
| CARINATA_3B | CARINATA_1B | 78.8 |
| CARINATA_3B | CARINATA_1C | 79.5 |
| CARINATA_3B | CARINATA_2B | 57.1 |
| CARINATA_3B | CARINATA_2C | 57.1 |
| CARINATA_3B | CARINATA_3B | 100 |
| CARINATA_3B | CARINATA_3C | 98.2 |
| CARINATA_3B | CARINATA_5B | 86.8 |
| CARINATA_3B | CARINATA_5C | 86.8 |
| CARINATA_3B | GMROD1-1 | 61.9 |
| CARINATA_3B | GMROD1-2 | 63.1 |
| CARINATA_3B | LUPDCT1 | 54.2 |
| CARINATA_3B | LUPDCT2 | 54.2 |
| CARINATA_3B | NAPUS_1A | 78.2 |
| CARINATA_3B | NAPUS_1C | 79.5 |
| CARINATA_3B | NAPUS_2A | 57.1 |
| CARINATA_3B | NAPUS_2C | 56.8 |
| CARINATA_3B | NAPUS_3A | 96.8 |
| CARINATA_3B | NAPUS_3C | 98.2 |
| CARINATA_3B | NAPUS_5A | 86.8 |
| CARINATA_3B | NAPUS_5C | 87.2 |
| CARINATA_3B | OSROD1_ SEQIDNO 11 | 44.1 |
| CARINATA_3B | RCPDCT | 61.1 |
| CARINATA_3B | RCROD1_ SEQIDNO9 | 61.1 |
| CARINATA_3B | ZMROD1_ GRMZM2G015040 | 46.4 |
| CARINATA_3B | ZMROD1 GRMZM2G087896 | 44.4 |
| CARINATA_3C | ATRODD1 | 78.8 |
| CARINATA_3C | BJROD1-A1 | 97.9 |
| CARINATA_3C | BJROD1-A2 | 83 |
| CARINATA_3C | BJROD1-A3 | 78.8 |
| CARINATA_3C | BJROD1-B1 | 98.2 |
| CARINATA_3C | BJROD1-B2 | 85.2 |
| CARINATA_3C | BJROD1-B3 | 78.8 |
| CARINATA_3C | BJROD1-B4 | 56.8 |
| CARINATA_3C | BRROD1_ SEQIDNO7 | 98.6 |
| CARINATA_3C | CAMELINA_ C1(80666) | 76.8 |
| CARINATA_3C | CAMELINA_ C15(45897) | 76.2 |
| CARINATA_3C | CAMELINA_ C19(65416) | 76.5 |
| CARINATA_3C | CARINATA_1B | 78.8 |
| CARINATA_3C | CARINATA_1C | 79.9 |
| CARINATA_3C | CARINATA_2B | 56.8 |
| CARINATA_3C | CARINATA_2C | 56.8 |
| CARINATA_3C | CARINATA_3B | 98.2 |
| CARINATA_3C | CARINATA_3C | 100 |
| CARINATA_3C | CARINATA_5B | 87.1 |
| CARINATA_3C | CARINATA_5C | 86.8 |
| CARINATA_3C | GMROD1-1 | 61.9 |
| CARINATA_3C | GMROD1-2 | 63.1 |
| CARINATA_3C | LUPDCT1 | 54.5 |
| CARINATA_3C | LUPDCT2 | 54.5 |
| CARINATA_3C | NAPUS_1A | 78.2 |
| CARINATA_3C | NAPUS_1C | 79.5 |
| CARINATA_3C | NAPUS_2A | 56.8 |
| CARINATA_3C | NAPUS_2C | 56.4 |
| CARINATA_3C | NAPUS_3A | 98.2 |
| CARINATA_3C | NAPUS_3C | 100 |
| CARINATA_3C | NAPUS_5A | 86.8 |

TABLE 6-continued

| Seq_1 | Seq_2 | Needle Protein Identity % Default settings |
|---|---|---|
| CARINATA_3C | NAPUS_5C | 87.2 |
| CARINATA_3C | OSROD1_ SEQIDNO 11 | 44.9 |
| CARINATA_3C | RCPDCT | 60.8 |
| CARINATA_3C | RCROD1_ SEQIDNO9 | 60.8 |
| CARINATA_3C | ZMROD1 GRMZM2G015040 | 45.8 |
| CARINATA_3C | ZMROD1 GRMZM2G087896 | 44.4 |
| CARINATA_5B | ATRODD1 | 80.5 |
| CARINATA_5B | BJROD1-A1 | 87.1 |
| CARINATA_5B | BJROD1-A2 | 88.8 |
| CARINATA_5B | BJROD1-A3 | 79.3 |
| CARINATA_5B | BJROD1-B1 | 86.8 |
| CARINATA_5B | BJROD1-B2 | 93.3 |
| CARINATA_5B | BJROD1-B3 | 80.2 |
| CARINATA_5B | BJROD1-B4 | 58.2 |
| CARINATA_5B | BRROD1_ SEQIDNO7 | 87.5 |
| CARINATA_5B | CAMELINA_ C1(80666) | 77.1 |
| CARINATA_5B | CAMELINA_ C15(45897) | 76.8 |
| CARINATA_5B | CAMELINA_ C19(65416) | 76.8 |
| CARINATA_5B | CARINATA_1B | 80.2 |
| CARINATA_5B | CARINATA_1C | 80.3 |
| CARINATA_5B | CARINATA_2B | 58.2 |
| CARINATA_5B | CARINATA_2C | 58.2 |
| CARINATA_5B | CARINATA_3B | 86.8 |
| CARINATA_5B | CARINATA_3C | 87.1 |
| CARINATA_5B | CARINATA_5B | 100 |
| CARINATA_5B | CARINATA_5C | 93.7 |
| CARINATA_5B | GMROD1-1 | 61.7 |
| CARINATA_5B | GMROD1-2 | 61.2 |
| CARINATA_5B | LUPDCT1 | 54.1 |
| CARINATA_5B | LUPDCT2 | 54.1 |
| CARINATA_5B | NAPUS_1A | 78.6 |
| CARINATA_5B | NAPUS_1C | 79.9 |
| CARINATA_5B | NAPUS_2A | 58.2 |
| CARINATA_5B | NAPUS_2C | 57.8 |
| CARINATA_5B | NAPUS_3A | 86.5 |
| CARINATA_5B | NAPUS_3C | 87.1 |
| CARINATA_5B | NAPUS_5A | 92.7 |
| CARINATA_5B | NAPUS_5C | 94.1 |
| CARINATA_5B | OSROD1_ SEQIDNO 11 | 42.6 |
| CARINATA_5B | RCPDCT | 59.9 |
| CARINATA_5B | RCROD1_ SEQIDNO9 | 59.9 |
| CARINATA_5B | ZMROD1 GRMZM2G015040 | 46.4 |
| CARINATA_5B | ZMROD1_ GRMZM2G087896 | 45.8 |
| CARINATA_5C | ATRODD1 | 79.8 |
| CARINATA_5C | BJROD1-A1 | 86.5 |
| CARINATA_5C | BJROD1-A2 | 93.3 |
| CARINATA_5C | BJROD1-A3 | 78.2 |
| CARINATA_5C | BJROD1-B1 | 86.8 |
| CARINATA_5C | BJROD1-B2 | 91.2 |
| CARINATA_5C | BJROD1-B3 | 78.8 |
| CARINATA_5C | BJROD1-B4 | 55.5 |
| CARINATA_5C | BRROD1_ SEQIDNO7 | 86.8 |
| CARINATA_5C | CAMELINA_ C1(80666) | 75.7 |
| CARINATA_5C | CAMELINA_ C15(45897) | 76.6 |
| CARINATA_5C | CAMELINA_ C19(65416) | 76.1 |
| CARINATA_5C | CARINATA_1B | 78.8 |
| CARINATA_5C | CARINATA_1C | 79.2 |

TABLE 6-continued

| Seq_1 | Seq_2 | Needle Protein Identity % Default settings |
|---|---|---|
| CARINATA_5C | CARINATA_2B | 55.5 |
| CARINATA_5C | CARINATA_2C | 55.5 |
| CARINATA_5C | CARINATA_3B | 86.8 |
| CARINATA_5C | CARINATA_3C | 86.8 |
| CARINATA_5C | CARINATA_5B | 93.7 |
| CARINATA_5C | CARINATA_5C | 100 |
| CARINATA_5C | GMROD1-1 | 60.3 |
| CARINATA_5C | GMROD1-2 | 61.1 |
| CARINATA_5C | LUPDCT1 | 51.7 |
| CARINATA_5C | LUPDCT2 | 51.7 |
| CARINATA_5C | NAPUS_1A | 77.5 |
| CARINATA_5C | NAPUS_1C | 78.8 |
| CARINATA_5C | NAPUS_2A | 55.5 |
| CARINATA_5C | NAPUS_2C | 55.1 |
| CARINATA_5C | NAPUS_3A | 85.5 |
| CARINATA_5C | NAPUS_3C | 86.8 |
| CARINATA_5C | NAPUS_5A | 97.5 |
| CARINATA_5C | NAPUS_5C | 99.6 |
| CARINATA_5C | OSROD1_ SEQIDNO 11 | 42.5 |
| CARINATA_5C | RCPDCT | 59.9 |
| CARINATA_5C | RCROD1_ SEQIDNO9 | 59.9 |
| CARINATA_5C | ZMROD1 GRMZM2G015040 | 46.4 |
| CARINATA_5C | ZMROD1 GRMZM2G087896 | 44.8 |
| GMROD1-1 | ATRODD1 | 60.7 |
| GMROD1-1 | BJROD1-A1 | 62.4 |
| GMROD1-1 | BJROD1-A2 | 62.1 |
| GMROD1-1 | BJROD1-A3 | 60.2 |
| GMROD1-1 | BJROD1-B1 | 61.5 |
| GMROD1-1 | BJROD1-B2 | 64.1 |
| GMROD1-1 | BJROD1-B3 | 61.5 |
| GMROD1-1 | BJROD1-B4 | 54.9 |
| GMROD1-1 | BRROD1_ SEQIDNO7 | 61.2 |
| GMROD1-1 | CAMELINA_ C1(80666) | 60.8 |
| GMROD1-1 | CAMELINA_ C15(45897) | 61 |
| GMROD1-1 | CAMELINA_ C19(65416) | 60.3 |
| GMROD1-1 | CARINATA_1B | 61.1 |
| GMROD1-1 | CARINATA_1C | 60.3 |
| GMROD1-1 | CARINATA_2B | 55.7 |
| GMROD1-1 | CARINATA_2C | 55.3 |
| GMROD1-1 | CARINATA_3B | 61.9 |
| GMROD1-1 | CARINATA_3C | 61.9 |
| GMROD1-1 | CARINATA_5B | 61.7 |
| GMROD1-1 | CARINATA_5C | 60.3 |
| GMROD1-1 | GMROD1-1 | 100 |
| GMROD1-1 | GMROD1-2 | 86.3 |
| GMROD1-1 | LUPDCT1 | 60.1 |
| GMROD1-1 | LUPDCT2 | 60.1 |
| GMROD1-1 | NAPUS_1A | 60.5 |
| GMROD1-1 | NAPUS_1C | 60.3 |
| GMROD1-1 | NAPUS_2A | 54.9 |
| GMROD1-1 | NAPUS_2C | 54.6 |
| GMROD1-1 | NAPUS_3A | 61.2 |
| GMROD1-1 | NAPUS_3C | 61.9 |
| GMROD1-1 | NAPUS_5A | 62.3 |
| GMROD1-1 | NAPUS_5C | 60.3 |
| GMROD1-1 | OSROD1_ SEQIDNO 11 | 47.1 |
| GMROD1-1 | RCPDCT | 68.2 |
| GMROD1-1 | RCROD1_ SEQIDNO9 | 68.2 |
| GMROD1-1 | ZMROD1 GRMZM2G015040 | 51.4 |
| GMROD1-1 | ZMROD1 GRMZM2G087896 | 53.1 |

TABLE 6-continued

| Seq_1 | Seq_2 | Needle Protein Identity % Default settings |
|---|---|---|
| GMROD1-2 | ATRODD1 | 58.1 |
| GMROD1-2 | BJROD1-A1 | 62.8 |
| GMROD1-2 | BJROD1-A2 | 57.5 |
| GMROD1-2 | BJROD1-A3 | 54.4 |
| GMROD1-2 | BJROD1-B1 | 62.8 |
| GMROD1-2 | BJROD1-B2 | 65 |
| GMROD1-2 | BJROD1-B3 | 52.7 |
| GMROD1-2 | BJROD1-B4 | 53.5 |
| GMROD1-2 | BRROD1_ SEQIDNO7 | 63.1 |
| GMROD1-2 | CAMELINA_ C1(80666) | 60.1 |
| GMROD1-2 | CAMELINA_ C15(45897) | 60.7 |
| GMROD1-2 | CAMELINA_ C19(65416) | 60.5 |
| GMROD1-2 | CARINATA_1B | 55.3 |
| GMROD1-2 | CARINATA_1C | 52.9 |
| GMROD1-2 | CARINATA_2B | 54.6 |
| GMROD1-2 | CARINATA_2C | 53.9 |
| GMROD1-2 | CARINATA_3B | 63.1 |
| GMROD1-2 | CARINATA_3C | 63.1 |
| GMROD1-2 | CARINATA_5B | 61.2 |
| GMROD1-2 | CARINATA_5C | 61.1 |
| GMROD1-2 | GMROD1-1 | 86.3 |
| GMROD1-2 | GMROD1-2 | 100 |
| GMROD1-2 | LUPDCT1 | 56.1 |
| GMROD1-2 | LUPDCT2 | 56.1 |
| GMROD1-2 | NAPUS_1A | 54.4 |
| GMROD1-2 | NAPUS_1C | 52.9 |
| GMROD1-2 | NAPUS_2A | 53.5 |
| GMROD1-2 | NAPUS_2C | 53.2 |
| GMROD1-2 | NAPUS_3A | 62.7 |
| GMROD1-2 | NAPUS_3C | 63.1 |
| GMROD1-2 | NAPUS_5A | 61 |
| GMROD1-2 | NAPUS_5C | 61.1 |
| GMROD1-2 | OSROD1 SEQIDNO 11 | 46.5 |
| GMROD1-2 | RCPDCT | 59.3 |
| GMROD1-2 | RCROD1_ SEQIDNO9 | 59.3 |
| GMROD1-2 | ZMROD1 GRMZM2G015040 | 50.9 |
| GMROD1-2 | ZMROD1 GRMZM2G087896 | 49 |
| LUPDCT1 | ATRODD1 | 54.6 |
| LUPDCT1 | BJROD1-A1 | 54.5 |
| LUPDCT1 | BJROD1-A2 | 51.5 |
| LUPDCT1 | BJROD1-A3 | 52.5 |
| LUPDCT1 | BJROD1-B1 | 53.9 |
| LUPDCT1 | BJROD1-B2 | 53.8 |
| LUPDCT1 | BJROD1-B3 | 53.3 |
| LUPDCT1 | BJROD1-B4 | 48.4 |
| LUPDCT1 | BRROD1_ SEQIDNO7 | 54.5 |
| LUPDCT1 | CAMELINA_ C1(80666) | 55 |
| LUPDCT1 | CAMELINA_ C15(45897) | 53.9 |
| LUPDCT1 | CAMELINA_ C19(65416) | 52.6 |
| LUPDCT1 | CARINATA_1B | 54.1 |
| LUPDCT1 | CARINATA_1C | 53.3 |
| LUPDCT1 | CARINATA_2B | 49.3 |
| LUPDCT1 | CARINATA_2C | 48.7 |
| LUPDCT1 | CARINATA_3B | 54.2 |
| LUPDCT1 | CARINATA_3C | 54.5 |
| LUPDCT1 | CARINATA_5B | 54.1 |
| LUPDCT1 | CARINATA_5C | 51.7 |
| LUPDCT1 | GMROD1-1 | 60.1 |
| LUPDCT1 | GMROD1-2 | 56.1 |
| LUPDCT1 | LUPDCT1 | 100 |
| LUPDCT1 | LUPDCT2 | 98.6 |

TABLE 6-continued

| Seq_1 | Seq_2 | Needle Protein Identity % Default settings |
|---|---|---|
| LUPDCT1 | NAPUS_1A | 52.9 |
| LUPDCT1 | NAPUS_1C | 53.3 |
| LUPDCT1 | NAPUS_2A | 48.4 |
| LUPDCT1 | NAPUS_2C | 48 |
| LUPDCT1 | NAPUS_3A | 54.9 |
| LUPDCT1 | NAPUS_3C | 54.5 |
| LUPDCT1 | NAPUS_5A | 52 |
| LUPDCT1 | NAPUS_5C | 52 |
| LUPDCT1 | OSROD1_ SEQIDNO 11 | 45.9 |
| LUPDCT1 | RCPDCT | 59.2 |
| LUPDCT1 | RCROD1 SEQIDNO9 | 59.2 |
| LUPDCT1 | ZMROD1 GRMZM2G015040 | 48.1 |
| LUPDCT1 | ZMROD1 GRMZM2G087896 | 49 |
| LUPDCT2 | ATRODD1 | 54.2 |
| LUPDCT2 | BJROD1-A1 | 54.5 |
| LUPDCT2 | BJROD1-A2 | 51.5 |
| LUPDCT2 | BJROD1-A3 | 53.4 |
| LUPDCT2 | BJROD1-B1 | 53.9 |
| LUPDCT2 | BJROD1-B2 | 53.8 |
| LUPDCT2 | BJROD1-B3 | 53.6 |
| LUPDCT2 | BJROD1-B4 | 48.4 |
| LUPDCT2 | BRROD1_ SEQIDNO7 | 54.5 |
| LUPDCT2 | CAMELINA_ C1(80666) | 55.3 |
| LUPDCT2 | CAMELINA_ C15(45897) | 54.2 |
| LUPDCT2 | CAMELINA_ C19(65416) | 55.3 |
| LUPDCT2 | CARINATA_1B | 54.5 |
| LUPDCT2 | CARINATA_1C | 53.6 |
| LUPDCT2 | CARINATA_2B | 49.3 |
| LUPDCT2 | CARINATA_2C | 48.7 |
| LUPDCT2 | CARINATA_3B | 54.2 |
| LUPDCT2 | CARINATA_3C | 54.5 |
| LUPDCT2 | CARINATA_5B | 54.1 |
| LUPDCT2 | CARINATA_5C | 51.7 |
| LUPDCT2 | GMROD1-1 | 60.1 |
| LUPDCT2 | GMROD1-2 | 56.1 |
| LUPDCT2 | LUPDCT1 | 98.6 |
| LUPDCT2 | LUPDCT2 | 100 |
| LUPDCT2 | NAPUS_1A | 53.8 |
| LUPDCT2 | NAPUS_1C | 53.6 |
| LUPDCT2 | NAPUS_2A | 48.4 |
| LUPDCT2 | NAPUS_2C | 48 |
| LUPDCT2 | NAPUS_3A | 54.9 |
| LUPDCT2 | NAPUS_3C | 54.5 |
| LUPDCT2 | NAPUS_5A | 52 |
| LUPDCT2 | NAPUS_5C | 52 |
| LUPDCT2 | OSROD1_ SEQIDNO 11 | 46.3 |
| LUPDCT2 | RCPDCT | 59.2 |
| LUPDCT2 | RCROD1_ SEQIDNO9 | 59.2 |
| LUPDCT2 | ZMROD1 GRMZM2G015040 | 47.8 |
| LUPDCT2 | ZMROD1_ GRMZM2G087896 | 48.6 |
| NAPUS_1A | ATRODD1 | 72.7 |
| NAPUS_1A | BJROD1-A1 | 77.1 |
| NAPUS_1A | BJROD1-A2 | 76.6 |
| NAPUS_1A | BJROD1-A3 | 98.6 |
| NAPUS_1A | BJROD1-B1 | 77.8 |
| NAPUS_1A | BJROD1-B2 | 75.4 |
| NAPUS_1A | BJROD1-B3 | 95.2 |
| NAPUS_1A | BJROD1-B4 | 55.4 |
| NAPUS_1A | BRROD1 SEQIDNO7 | 77.8 |

TABLE 6-continued

| Seq_1 | Seq_2 | Needle Protein Identity % Default settings |
|---|---|---|
| NAPUS_1A | CAMELINA_ C1(80666) | 69.1 |
| NAPUS_1A | CAMELINA_ C15(45897) | 69.5 |
| NAPUS_1A | CAMELINA_ C19(65416) | 69.5 |
| NAPUS_1A | CARINATA_1B | 94.5 |
| NAPUS_1A | CARINATA_1C | 95.5 |
| NAPUS_1A | CARINATA_2B | 55 |
| NAPUS_1A | CARINATA_2C | 55.4 |
| NAPUS_1A | CARINATA_3C | 78.2 |
| NAPUS_1A | CARINATA_5B | 78.6 |
| NAPUS_1A | CARINATA_5C | 77.5 |
| NAPUS_1A | GMROD1-1 | 60.5 |
| NAPUS_1A | GMROD1-2 | 54.4 |
| NAPUS_1A | LUPDCT1 | 52.9 |
| NAPUS_1A | LUPDCT2 | 53.8 |
| NAPUS_1A | NAPUS_1A | 100 |
| NAPUS_1A | NAPUS_1C | 96.5 |
| NAPUS_1A | NAPUS_2A | 55.4 |
| NAPUS_1A | NAPUS_2C | 55 |
| NAPUS_1A | NAPUS_3A | 77.6 |
| NAPUS_1A | NAPUS_3C | 78.2 |
| NAPUS_1A | NAPUS_5A | 77.6 |
| NAPUS_1A | NAPUS_5C | 77.8 |
| NAPUS_1A | OSROD1 SEQIDNO 11 | 42.4 |
| NAPUS_1A | RCPDCT | 57.3 |
| NAPUS_1A | RCROD1_ SEQIDNO9 | 57.3 |
| NAPUS_1A | ZMROD1 GRMZM2G015040 | 44 |
| NAPUS_1A | ZMROD1 GRMZM2G087896 | 43 |
| NAPUS_1C | ATRODD1 | 73.7 |
| NAPUS_1C | BJROD1-A1 | 78.5 |
| NAPUS_1C | BJROD1-A2 | 77.9 |
| NAPUS_1C | BJROD1-A3 | 95.5 |
| NAPUS_1C | BJROD1-B1 | 79.2 |
| NAPUS_1C | BJROD1-B2 | 77.1 |
| NAPUS_1C | BJROD1-B3 | 95.5 |
| NAPUS_1C | BJROD1-B4 | 55.7 |
| NAPUS_1C | BRROD1 SEQIDNO7 | 79.2 |
| NAPUS_1C | CAMELINA_ C1(80666) | 70.8 |
| NAPUS_1C | CAMELINA_ C15(45897) | 70.5 |
| NAPUS_1C | CAMELINA_ C19(65416) | 71.2 |
| NAPUS_1C | CARINATA_1B | 94.8 |
| NAPUS_1C | CARINATA_1C | 99 |
| NAPUS_1C | CARINATA_2B | 55.7 |
| NAPUS_1C | CARINATA_2C | 56.1 |
| NAPUS_1C | CARINATA_3B | 79.5 |
| NAPUS_1C | CARINATA_3C | 79.5 |
| NAPUS_1C | CARINATA_5B | 79.9 |
| NAPUS_1C | CARINATA_5C | 78.8 |
| NAPUS_1C | GMROD1-1 | 60.3 |
| NAPUS_1C | GMROD1-2 | 52.9 |
| NAPUS_1C | LUPDCT1 | 53.3 |
| NAPUS_1C | LUPDCT2 | 53.6 |
| NAPUS_1C | NAPUS_1A | 96.5 |
| NAPUS_1C | NAPUS_1C | 100 |
| NAPUS_1C | NAPUS_2A | 55.7 |
| NAPUS_1C | NAPUS_2C | 55.4 |
| NAPUS_1C | NAPUS_3A | 79 |
| NAPUS_1C | NAPUS_3C | 79.5 |

TABLE 6-continued

| Seq_1 | Seq_2 | Needle Protein Identity % Default settings |
|---|---|---|
| NAPUS_1C | NAPUS_5A | 78.9 |
| NAPUS_1C | NAPUS_5C | 79.2 |
| NAPUS_1C | OSROD1 SEQIDNO 11 | 42 |
| NAPUS_1C | RCPDCT | 57.9 |
| NAPUS_1C | RCROD1_ SEQIDNO9 | 57.9 |
| NAPUS_1C | ZMROD1 GRMZM2G015040 | 43.3 |
| NAPUS_1C | ZMROD1 GRMZM2G087896 | 43 |
| NAPUS_2A | ATRODD1 | 55.5 |
| NAPUS_2A | BJROD1-A1 | 57.1 |
| NAPUS_2A | BJROD1-A2 | 55.4 |
| NAPUS_2A | BJROD1-A3 | 55.4 |
| NAPUS_2A | BJROD1-B1 | 56.8 |
| NAPUS_2A | BJROD1-B2 | 59 |
| NAPUS_2A | BJROD1-B3 | 56.1 |
| NAPUS_2A | BJROD1-B4 | 99.6 |
| NAPUS_2A | BRROD1_ SEQIDNO7 | 57.1 |
| NAPUS_2A | CAMELINA_ C1(80666) | 55.4 |
| NAPUS_2A | CAMELINA_ C15(45897) | 55.2 |
| NAPUS_2A | CAMELINA_ C19(65416) | 55.2 |
| NAPUS_2A | CARINATA_1B | 56.4 |
| NAPUS_2A | CARINATA_1C | 55.4 |
| NAPUS_2A | CARINATA_2B | 97 |
| NAPUS_2A | CARINATA_2C | 97.9 |
| NAPUS_2A | CARINATA_3B | 57.1 |
| NAPUS_2A | CARINATA_3C | 56.8 |
| NAPUS_2A | CARINATA_5B | 58.2 |
| NAPUS_2A | CARINATA_5C | 55.5 |
| NAPUS_2A | GMROD1-1 | 54.9 |
| NAPUS_2A | GMROD1-2 | 53.5 |
| NAPUS_2A | LUPDCT1 | 48.4 |
| NAPUS_2A | LUPDCT2 | 48.4 |
| NAPUS_2A | NAPUS_1A | 55.4 |
| NAPUS_2A | NAPUS_1C | 55.7 |
| NAPUS_2A | NAPUS_2A | 100 |
| NAPUS_2A | NAPUS_2C | 99.6 |
| NAPUS_2A | NAPUS_3A | 57.4 |
| NAPUS_2A | NAPUS_3C | 56.8 |
| NAPUS_2A | NAPUS_5A | 55.5 |
| NAPUS_2A | NAPUS_5C | 55.5 |
| NAPUS_2A | OSROD1_ SEQIDNO 11 | 38.1 |
| NAPUS_2A | RCPDCT | 51.6 |
| NAPUS_2A | RCROD1_ SEQIDNO9 | 51.6 |
| NAPUS_2A | ZMROD1 GRMZM2G015040 | 44.9 |
| NAPUS_2A | ZMROD1 GRMZM2G087896 | 45.5 |
| NAPUS_2C | ATRODD1 | 55.1 |
| NAPUS_2C | BJROD1-A1 | 56.8 |
| NAPUS_2C | BJROD1-A2 | 55.1 |
| NAPUS_2C | BJROD1-A3 | 55 |
| NAPUS_2C | BJROD1-B1 | 56.4 |
| NAPUS_2C | BJROD1-B2 | 58.6 |
| NAPUS_2C | BJROD1-B3 | 55.7 |
| NAPUS_2C | BJROD1-B4 | 99.1 |
| NAPUS_2C | BRROD1_ SEQIDNO7 | 56.8 |
| NAPUS_2C | CAMELINA_ C1(80666) | 55.1 |
| NAPUS_2C | CAMELINA_ C15(45897) | 54.9 |
| NAPUS_2C | CAMELINA_ C19(65416) | 54.9 |

TABLE 6-continued

| Seq_1 | Seq_2 | Needle Protein Identity % Default settings |
|---|---|---|
| NAPUS_2C | CARINATA_1B | 56.1 |
| NAPUS_2C | CARINATA_1C | 55 |
| NAPUS_2C | CARINATA_2B | 96.6 |
| NAPUS_2C | CARINATA_2C | 97.4 |
| NAPUS_2C | CARINATA_3B | 56.8 |
| NAPUS_2C | CARINATA_3C | 56.4 |
| NAPUS_2C | CARINATA_5B | 57.8 |
| NAPUS_2C | CARINATA_5C | 55.1 |
| NAPUS_2C | GMROD1-1 | 54.6 |
| NAPUS_2C | GMROD1-2 | 53.2 |
| NAPUS_2C | LUPDCT1 | 48 |
| NAPUS_2C | LUPDCT2 | 48 |
| NAPUS_2C | NAPUS_1A | 55 |
| NAPUS_2C | NAPUS_1C | 55.4 |
| NAPUS_2C | NAPUS_2A | 99.6 |
| NAPUS_2C | NAPUS_2C | 100 |
| NAPUS_2C | NAPUS_3A | 57.1 |
| NAPUS_2C | NAPUS_3C | 56.4 |
| NAPUS_2C | NAPUS_5A | 55.1 |
| NAPUS_2C | NAPUS_5C | 55.1 |
| NAPUS_2C | OSROD1_ SEQIDNO 11 | 38.1 |
| NAPUS_2C | RCPDCT | 51.2 |
| NAPUS_2C | RCROD1_ SEQIDNO9 | 51.2 |
| NAPUS_2C | ZMROD1 GRMZM2G015040 | 44.6 |
| NAPUS_2C | ZMROD1 GRMZM2G087896 | 45.1 |
| NAPUS_3A | ATRODD1 | 79.2 |
| NAPUS_3A | BJROD1-A1 | 98.2 |
| NAPUS_3A | BJROD1-A2 | 81.7 |
| NAPUS_3A | BJROD1-A3 | 78.3 |
| NAPUS_3A | BJROD1-B1 | 96.8 |
| NAPUS_3A | BJROD1-B2 | 84.2 |
| NAPUS_3A | BJROD1-B3 | 78.3 |
| NAPUS_3A | BJROD1-B4 | 57.4 |
| NAPUS_3A | BRROD1_SEQID NO7 | 98.9 |
| NAPUS_3A | CAMELINA_C1(8 0666) | 76.9 |
| NAPUS_3A | CAMELINA_C15( 45897) | 76.5 |
| NAPUS_3A | CAMELINA_C19( 65416) | 77.2 |
| NAPUS_3A | CARINATA_1B | 78.3 |
| NAPUS_3A | CARINATA_1C | 79.3 |
| NAPUS_3A | CARINATA_2B | 57.4 |
| NAPUS_3A | CARINATA_2C | 57.4 |
| NAPUS_3A | CARINATA_3B | 96.8 |
| NAPUS_3A | CARINATA_3C | 98.2 |
| NAPUS_3A | CARINATA_5B | 86.5 |
| NAPUS_3A | CARINATA_5C | 85.5 |
| NAPUS_3A | GMROD1-1 | 61.2 |
| NAPUS_3A | GMROD1-2 | 62.7 |
| NAPUS_3A | LUPDCT1 | 54.9 |
| NAPUS_3A | LUPDCT2 | 54.9 |
| NAPUS_3A | NAPUS_1A | 77.6 |
| NAPUS_3A | NAPUS_1C | 79 |
| NAPUS_3A | NAPUS_2A | 57.4 |
| NAPUS_3A | NAPUS_2C | 57.1 |
| NAPUS_3A | NAPUS_3A | 100 |
| NAPUS_3A | NAPUS_3C | 98.2 |
| NAPUS_3A | NAPUS_5A | 85.5 |
| NAPUS_3A | NAPUS_5C | 85.9 |
| NAPUS_3A | OSROD1_ SEQIDNO 11 | 44.6 |
| NAPUS_3A | RCPDCT | 61 |
| NAPUS_3A | RCROD1_ SEQIDNO9 | 61 |
| NAPUS_3A | ZMROD1 GRMZM2G015040 | 45.9 |

TABLE 6-continued

| Seq_1 | Seq_2 | Needle Protein Identity % Default settings |
|---|---|---|
| NAPUS_3A | ZMROD1 GRMZ M2G087896 | 43.8 |
| NAPUS_3C | ATRODD1 | 78.8 |
| NAPUS_3C | BJROD1-A1 | 97.9 |
| NAPUS_3C | BJROD1-A2 | 83 |
| NAPUS_3C | BJROD1-A3 | 78.8 |
| NAPUS_3C | BJROD1-B1 | 98.2 |
| NAPUS_3C | BJROD1-B2 | 85.2 |
| NAPUS_3C | BJROD1-B3 | 78.8 |
| NAPUS_3C | BJROD1-B4 | 56.8 |
| NAPUS_3C | BRROD1_ SEQIDNO7 | 98.6 |
| NAPUS_3C | CAMELINA_ C1(80666) | 76.8 |
| NAPUS_3C | CAMELINA_ C15(45897) | 76.2 |
| NAPUS_3C | CAMELINA_ C19(65416) | 76.5 |
| NAPUS_3C | CARINATA_1B | 78.8 |
| NAPUS_3C | CARINATA_1C | 79.9 |
| NAPUS_3C | CARINATA_2B | 56.8 |
| NAPUS_3C | CARINATA_2C | 56.8 |
| NAPUS_3C | CARINATA_3B | 98.2 |
| NAPUS_3C | CARINATA_3C | 100 |
| NAPUS_3C | CARINATA_5B | 87.1 |
| NAPUS_3C | CARINATA_5C | 86.8 |
| NAPUS_3C | GMROD1-1 | 61.9 |
| NAPUS_3C | GMROD1-2 | 63.1 |
| NAPUS_3C | LUPDCT1 | 54.5 |
| NAPUS_3C | LUPDCT2 | 54.5 |
| NAPUS_3C | NAPUS_1A | 78.2 |
| NAPUS_3C | NAPUS_1C | 79.5 |
| NAPUS_3C | NAPUS_2A | 56.8 |
| NAPUS_3C | NAPUS_2C | 56.4 |
| NAPUS_3C | NAPUS_3A | 98.2 |
| NAPUS_3C | NAPUS_3C | 100 |
| NAPUS_3C | NAPUS_5A | 86.8 |
| NAPUS_3C | NAPUS_5C | 87.2 |
| NAPUS_3C | OSROD1_SEQID NO 11 | 44.9 |
| NAPUS_3C | RCPDCT | 60.8 |
| NAPUS_3C | RCROD1_SEQID NO9 | 60.8 |
| NAPUS_3C | ZMROD1 GRMZ M2G015040 | 45.8 |
| NAPUS_3C | ZMROD1 GRMZ M2G087896 | 44.4 |
| NAPUS_5A | ATRODD1 | 79.7 |
| NAPUS_5A | BJROD1-A1 | 86.5 |
| NAPUS_5A | BJROD1-A2 | 95.4 |
| NAPUS_5A | BJROD1-A3 | 78.2 |
| NAPUS_5A | BJROD1-B1 | 86.8 |
| NAPUS_5A | BJROD1-B2 | 90.8 |
| NAPUS_5A | BJROD1-B3 | 78.9 |
| NAPUS_5A | BJROD1-B4 | 55.5 |
| NAPUS_5A | BRROD1_ SEQIDNO7 | 86.8 |
| NAPUS_5A | CAMELINA_ C1(80666) | 75.3 |
| NAPUS_5A | CAMELINA_ C15(45897) | 75.6 |
| NAPUS_5A | CAC19(MELINA_ 65416) | 76.2 |
| NAPUS_5A | CARINATA_1B | 78.9 |
| NAPUS_5A | CARINATA_1C | 79.3 |
| NAPUS_5A | CARINATA_2B | 55.5 |
| NAPUS_5A | CARINATA_2C | 55.5 |
| NAPUS_5A | CARINATA_3B | 86.8 |
| NAPUS_5A | CARINATA_3C | 86.8 |
| NAPUS_5A | CARINATA_5B | 92.7 |
| NAPUS_5A | CARINATA_5C | 97.5 |
| NAPUS_5A | GMROD1-1 | 62.3 |
| NAPUS_5A | GMROD1-2 | 61 |
| NAPUS_5A | LUPDCT1 | 52 |
| NAPUS_5A | LUPDCT2 | 52 |
| NAPUS_5A | NAPUS_1A | 77.6 |
| NAPUS_5A | NAPUS_1C | 78.9 |
| NAPUS_5A | NAPUS_2A | 55.5 |
| NAPUS_5A | NAPUS_2C | 55.1 |
| NAPUS_5A | NAPUS_3A | 85.5 |
| NAPUS_5A | NAPUS_3C | 86.8 |
| NAPUS_5A | NAPUS_5A | 100 |
| NAPUS_5A | NAPUS_5C | 97.9 |
| NAPUS_5A | OSROD1 SEQIDNO 11 | 42.2 |
| NAPUS_5A | RCPDCT | 60.2 |
| NAPUS_5A | RCROD1 SEQIDNO9 | 60.2 |
| NAPUS_5A | ZMROD1 GRMZM2G015040 | 45.2 |
| NAPUS_5A | ZMROD1 GRMZM2G087896 | 45.6 |
| NAPUS_5C | ATRODD1 | 80.1 |
| NAPUS_5C | BJROD1-A1 | 86.8 |
| NAPUS_5C | BJROD1-A2 | 93.6 |
| NAPUS_5C | BJROD1-A3 | 78.5 |
| NAPUS_5C | BJROD1-B1 | 87.2 |
| NAPUS_5C | BJROD1-B2 | 91.5 |
| NAPUS_5C | BJROD1-B3 | 79.2 |
| NAPUS_5C | BJROD1-B4 | 55.5 |
| NAPUS_5C | BRROD1_ SEQIDNO7 | 87.2 |
| NAPUS_5C | CAMELINA_ C1(80666) | 76 |
| NAPUS_5C | CAMELINA_ C15(45897) | 76.9 |
| NAPUS_5C | CAMELINA_ C19(65416) | 76.4 |
| NAPUS_5C | CARINATA_1B | 79.2 |
| NAPUS_5C | CARINATA_1C | 79.5 |
| NAPUS_5C | CARINATA_2B | 55.5 |
| NAPUS_5C | CARINATA_2C | 55.5 |
| NAPUS_5C | CARINATA_3B | 87.2 |
| NAPUS_5C | CARINATA_3C | 87.2 |
| NAPUS_5C | CARINATA_5B | 94.1 |
| NAPUS_5C | CARINATA_5C | 99.6 |
| NAPUS_5C | GMROD1-1 | 60.3 |
| NAPUS_5C | GMROD1-2 | 61.1 |
| NAPUS_5C | LUPDCT1 | 52 |
| NAPUS_5C | LUPDCT2 | 52 |
| NAPUS_5C | NAPUS_1A | 77.8 |
| NAPUS_5C | NAPUS_1C | 79.2 |
| NAPUS_5C | NAPUS_2A | 55.5 |
| NAPUS_5C | NAPUS_2C | 55.1 |
| NAPUS_5C | NAPUS_3A | 85.9 |
| NAPUS_5C | NAPUS_3C | 87.2 |
| NAPUS_5C | NAPUS_5A | 97.9 |
| NAPUS_5C | NAPUS_5C | 100 |
| NAPUS_5C | OSROD1 SEQIDNO 11 | 42.5 |
| NAPUS_5C | RCPDCT | 59.9 |
| NAPUS_5C | RCROD1_ SEQIDNO9 | 59.9 |
| NAPUS_5C | ZMROD1 GRMZM2G015040 | 46.4 |
| NAPUS_5C | ZMROD1 GRMZM2G087896 | 44.8 |
| OSROD1_ SEQIDNO 11 | ATRODD1 | 45.5 |
| OSROD1 SEQIDNO 11 | BJROD1-A1 | 45.3 |
| OSROD1_ SEQID NO 11 | BJROD1-A2 | 42.2 |
| OSROD1_ SEQID NO 11 | BJROD1-A3 | 41.8 |

TABLE 6-continued

| Seq_1 | Seq_2 | Needle Protein Identity % Default settings |
|---|---|---|
| OSROD1_ SEQID NO 11 | BJROD1-B1 | 43.8 |
| OSROD1_ SEQID NO 11 | BJROD1-B2 | 41.3 |
| OSROD1_ SEQID NO 11 | BJROD1-B3 | 43.2 |
| OSROD1_ SEQID NO 11 | BJROD1-B4 | 37.7 |
| OSROD1_ SEQID NO 11 | BRROD1_ SEQIDNO7 | 41.4 |
| OSROD1_ SEQID NO 11 | CAMELINA_ C1(80666) | 43.8 |
| OSROD1_ SEQID NO 11 | CAMELINA_ C15(45897) | 45.4 |
| OSROD1_ SEQID NO 11 | CAMELINA C19(65416) | 43.9 |
| OSROD1_ SEQID NO 11 | CARINATA_1B | 42.3 |
| OSROD1_ SEQID NO 11 | CARINATA_1C | 41.7 |
| OSROD1_ SEQID NO 11 | CARINATA_2B | 38.1 |
| OSROD1_ SEQID NO 11 | CARINATA_2C | 38.1 |
| OSROD1_ SEQID NO 11 | CARINATA_3B | 44.1 |
| OSROD1_ SEQID NO 11 | CARINATA_3C | 44.9 |
| OSROD1_ SEQID NO 11 | CARINATA_5B | 42.6 |
| OSROD1_ SEQID NO 11 | CARINATA_5C | 42.5 |
| OSROD1_ SEQID NO 11 | GMROD1-1 | 47.1 |
| OSROD1_ SEQID NO 11 | GMROD1-2 | 46.5 |
| OSROD1_ SEQID NO 11 | LUPDCT1 | 45.9 |
| OSROD1_ SEQID NO 11 | LUPDCT2 | 46.3 |
| OSROD1_ SEQID NO 11 | NAPUS_1A | 42.4 |
| OSROD1_ SEQID NO 11 | NAPUS_1C | 42 |
| OSROD1_ SEQID NO 11 | NAPUS_2A | 38.1 |
| OSROD1_ SEQID NO 11 | NAPUS_2C | 38.1 |
| OSROD1_ SEQID NO 11 | NAPUS_3A | 44.6 |
| OSROD1_ SEQID NO 11 | NAPUS_3C | 44.9 |
| OSROD1_ SEQID NO 11 | NAPUS_5A | 42.2 |
| OSROD1_ SEQID NO 11 | NAPUS_5C | 42.5 |
| OSROD1_ SEQID NO 11 | OSROD1_ SEQID NO 11 | 100 |
| OSROD1_ SEQID NO 11 | RCPDCT | 48.9 |
| OSROD1_ SEQID NO 11 | RCROD1_ SEQIDNO9 | 48.9 |
| OSROD1_ SEQID NO 11 | ZMROD1 GRMZM2G015040 | 69.1 |
| OSROD1_ SEQID NO 11 | ZMROD1 GRMZM2G087896 | 68.9 |
| RCPDCT | ATRODD1 | 58.7 |
| RCPDCT | BJROD1-A1 | 58.6 |
| RCPDCT | BJROD1-A2 | 59.7 |
| RCPDCT | BJROD1-A3 | 57 |
| RCPDCT | BJROD1-B1 | 60.8 |
| RCPDCT | BJROD1-B2 | 59.1 |
| RCPDCT | BJROD1-B3 | 57.6 |

TABLE 6-continued

| Seq_1 | Seq_2 | Needle Protein Identity % Default settings |
|---|---|---|
| RCPDCT | BJROD1-B4 | 51.6 |
| RCPDCT | BRROD1_ SEQIDNO7 | 60.8 |
| RCPDCT | CAMELINA_ C1(80666) | 55.4 |
| RCPDCT | CAMELINA_ C15(45897) | 59.8 |
| RCPDCT | CAMELINA_ C19(65416) | 59.9 |
| RCPDCT | CARINATA_1B | 57.6 |
| RCPDCT | CARINATA_1C | 57.9 |
| RCPDCT | CARINATA_2B | 52.3 |
| RCPDCT | CARINATA_2C | 51.9 |
| RCPDCT | CARINATA_3B | 61.1 |
| RCPDCT | CARINATA_3C | 60.8 |
| RCPDCT | CARINATA_5B | 59.9 |
| RCPDCT | CARINATA_5C | 59.9 |
| RCPDCT | GMROD1-1 | 68.2 |
| RCPDCT | GMROD1-2 | 59.3 |
| RCPDCT | LUPDCT1 | 59.2 |
| RCPDCT | LUPDCT2 | 59.2 |
| RCPDCT | NAPUS_1A | 57.3 |
| RCPDCT | NAPUS_1C | 57.9 |
| RCPDCT | NAPUS_2A | 51.6 |
| RCPDCT | NAPUS_2C | 51.2 |
| RCPDCT | NAPUS_3A | 61 |
| RCPDCT | NAPUS_3C | 60.8 |
| RCPDCT | NAPUS_5A | 60.2 |
| RCPDCT | NAPUS_5C | 59.9 |
| RCPDCT | OSROD1 SEQIDNO 11 | 48.9 |
| RCPDCT | RCPDCT | 100 |
| RCPDCT | RCROD1 SEQIDNO9 | 100 |
| RCPDCT | ZMROD1 GRMZM2G015040 | 51.3 |
| RCPDCT | ZMROD1_ GRMZM2G087896 | 48.2 |
| RCROD1_ SEQIDNO9 | ATRODD1 | 58.7 |
| RCROD1_ SEQIDNO9 | BJROD1-A1 | 58.6 |
| RCROD1_ SEQIDNO9 | BJROD1-A2 | 59.7 |
| RCROD1_ SEQIDNO9 | BJROD1-A3 | 57 |
| RCROD1_ SEQIDNO9 | BJROD1-B1 | 60.8 |
| RCROD1_ SEQIDNO9 | BJROD1-B2 | 59.1 |
| RCROD1_ SEQIDNO9 | BJROD1-B3 | 57.6 |
| RCROD1_ SEQIDNO9 | BJROD1-B4 | 51.6 |
| RCROD1_ SEQIDNO9 | BRROD1 SEQIDNO7 | 60.8 |
| RCROD1_ SEQIDNO9 | CAMELINA_ C1(80666) | 55.4 |
| RCROD1_ SEQIDNO9 | CAMELINA_ C15(45897) | 59.8 |
| RCROD1_ SEQIDNO9 | CAMELINA_ C19(65416) | 59.9 |
| RCROD1_ SEQIDNO9 | CARINATA_1B | 57.6 |
| RCROD1_ SEQIDNO9 | CARINATA_1C | 57.9 |
| RCROD1_ SEQIDNO9 | CARINATA_2B | 52.3 |
| RCROD1_ SEQIDNO9 | CARINATA_2C | 51.9 |
| RCROD1_ SEQIDNO9 | CARINATA_3B | 61.1 |

TABLE 6-continued

| Seq_1 | Seq_2 | Needle Protein Identity % Default settings |
|---|---|---|
| RCROD1_ SEQIDNO9 | CARINATA_3C | 60.8 |
| RCROD1_ SEQIDNO9 | CARINATA_5B | 59.9 |
| RCROD1_ SEQIDNO9 | CARINATA_5C | 59.9 |
| RCROD1_ SEQIDNO9 | GMROD1-1 | 68.2 |
| RCROD1_ SEQIDNO9 | GMROD1-2 | 59.3 |
| RCROD1_ SEQIDNO9 | LUPDCT1 | 59.2 |
| RCROD1_ SEQIDNO9 | LUPDCT2 | 59.2 |
| RCROD1_ SEQIDNO9 | NAPUS_1A | 57.3 |
| RCROD1_ SEQIDNO9 | NAPUS_1C | 57.9 |
| RCROD1_ SEQIDNO9 | NAPUS_2A | 51.6 |
| RCROD1_ SEQIDNO9 | NAPUS_2C | 51.2 |
| RCROD1_ SEQIDNO9 | NAPUS_3A | 61 |
| RCROD1_ SEQIDNO9 | NAPUS_3C | 60.8 |
| RCROD1_ SEQIDNO9 | NAPUS_5A | 60.2 |
| RCROD1_ SEQIDNO9 | NAPUS_5C | 59.9 |
| RCROD1_ SEQIDNO9 | OSROD1_ SEQIDNO 11 | 48.9 |
| RCROD1_ SEQIDNO9 | RCPDCT | 100 |
| RCROD1_ SEQIDNO9 | RCROD1_ SEQIDNO9 | 100 |
| RCROD1_ SEQIDNO9 | ZMROD1 GRMZM2G015040 | 51.3 |
| RCROD1_ SEQIDNO9 | ZMROD1 GRMZM2G087896 | 48.2 |
| ZMROD1_ GRMZM2G015040 | ATRODD1 | 44.4 |
| ZMROD1_ GRMZM2G015040 | BJROD1-A1 | 45.3 |
| ZMROD1_ GRMZM2G015040 | BJROD1-A2 | 45.1 |
| ZMROD1_ GRMZM2G015040 | BJROD1-A3 | 43.7 |
| ZMROD1_ GRMZM2G015040 | BJROD1-B1 | 45.8 |
| ZMROD1_ GRMZM2G015040 | BJROD1-B2 | 47.1 |
| ZMROD1_ GRMZM2G015040 | BJROD1-B3 | 44 |
| ZMROD1_ GRMZM2G015040 | BJROD1-B4 | 44.6 |
| ZMROD1_ GRMZM2G015040 | BRROD1_SEQID NO7 | 46.2 |
| ZMROD1_ GRMZM2G015040 | CAMELINA_ C1(80666) | 45.1 |
| ZMROD1_ GRMZM2G015040 | CAMELINA_ C15(45897) | 45 |
| ZMROD1_ GRMZM2G015040 | CAMELINA_ C19(65416) | 43.8 |
| ZMROD1_ GRMZM2G015040 | CARINATA_1B | 44 |
| ZMROD1_ GRMZM2G015040 | CARINATA_1C | 42.9 |
| ZMROD1_ GRMZM2G015040 | CARINATA_2B | 44.9 |
| ZMROD1_ GRMZM2G015040 | CARINATA_2C | 45.3 |

TABLE 6-continued

| Seq_1 | Seq_2 | Needle Protein Identity % Default settings |
|---|---|---|
| ZMROD1_ GRMZM2G015040 | CARINATA_3B | 46.4 |
| ZMROD1_ GRMZM2G015040 | CARINATA_3C | 45.8 |
| ZMROD1_ GRMZM2G015040 | CARINATA_5B | 46.4 |
| ZMROD1_ GRMZM2G015040 | CARINATA_5C | 46.4 |
| ZMROD1_ GRMZM2G015040 | GMROD1-1 | 51.4 |
| ZMROD1_ GRMZM2G015040 | GMROD1-2 | 50.9 |
| ZMROD1_ GRMZM2G015040 | LUPDCT1 | 48.1 |
| ZMROD1_ GRMZM2G015040 | LUPDCT2 | 47.8 |
| ZMROD1_ GRMZM2G015040 | NAPUS_1A | 44 |
| ZMROD1_ GRMZM2G015040 | NAPUS_1C | 43.3 |
| ZMROD1_ GRMZM2G015040 | NAPUS_2A | 44.9 |
| ZMROD1_ GRMZM2G015040 | NAPUS_2C | 44.6 |
| ZMROD1_ GRMZM2G015040 | NAPUS_3A | 45.9 |
| ZMROD1_ GRMZM2G015040 | NAPUS_3C | 45.8 |
| ZMROD1_ GRMZM2G015040 | NAPUS_5A | 45.2 |
| ZMROD1_ GRMZM2G015040 | NAPUS_5C | 46.4 |
| ZMROD1_ GRMZM2G015040 | OSROD1_ SEQIDNO 11 | 69.1 |
| ZMROD1_ GRMZM2G015040 | RCPDCT | 51.3 |
| ZMROD1_ GRMZM2G015040 | RCROD1_ SEQIDNO9 | 51.3 |
| ZMROD1_ GRMZM2G015040 | ZMROD1 GRMZM2G015040 | 100 |
| ZMROD1_ GRMZM2G015040 | ZMROD1 GRMZM2G087896 | 83.9 |
| ZMROD1 GRMZM2G087896 | ATRODD1 | 42.9 |
| ZMROD1 GRMZM2G087896 | BJROD1-A1 | 44.1 |
| ZMROD1 GRMZM2G087896 | BJROD1-A2 | 45.6 |
| ZMROD1 GRMZM2G087896 | BJROD1-A3 | 42.7 |
| ZMROD1 GRMZM2G087896 | BJROD1-B1 | 44.1 |
| ZMROD1 GRMZM2G087896 | BJROD1-B2 | 45.6 |
| ZMROD1 GRMZM2G087896 | BJROD1-B3 | 44.7 |
| ZMROD1 GRMZM2G087896 | BJROD1-B4 | 43.6 |
| ZMROD1 GRMZM2G087896 | BRROD1_SEQID NO7 | 44.1 |
| ZMROD1 GRMZM2G087896 | CAMELINA_ C1(80666) | 47 |
| ZMROD1 GRMZM2G087896 | CAMELINA_ C15(45897) | 46.5 |
| ZMROD1 GRMZM2G087896 | CAMELINA_ C19(65416) | 47.7 |
| ZMROD1 GRMZM2G087896 | CARINATA_1B | 44.7 |
| ZMROD1 GRMZM2G087896 | CARINATA_1C | 42.7 |
| ZMROD1 GRMZM2G087896 | CARINATA_2B | 44.2 |

TABLE 6-continued

| Seq_1 | Seq_2 | Needle Protein Identity % Default settings |
|---|---|---|
| ZMROD1 GRMZM2G087896 | CARINATA_2C | 44.7 |
| ZMROD1 GRMZM2G087896 | CARINATA_3B | 44.4 |
| ZMROD1 GRMZM2G087896 | CARINATA_3C | 44.4 |
| ZMROD1 GRMZM2G087896 | CARINATA_5B | 45.8 |
| ZMROD1 GRMZM2G087896 | CARINATA_5C | 44.8 |
| ZMROD1 GRMZM2G087896 | GMROD1-1 | 53.1 |
| ZMROD1 GRMZM2G087896 | GMROD1-2 | 49 |
| ZMROD1 GRMZM2G087896 | LUPDCT1 | 49 |
| ZMROD1 GRMZM2G087896 | LUPDCT2 | 48.6 |
| ZMROD1 GRMZM2G087896 | NAPUS_1A | 43 |
| ZMROD1 GRMZM2G087896 | NAPUS_1C | 43 |

TABLE 6-continued

| Seq_1 | Seq_2 | Needle Protein Identity % Default settings |
|---|---|---|
| ZMROD1 GRMZM2G087896 | NAPUS_2A | 44 |
| ZMROD1 GRMZM2G087896 | NAPUS_2C | 43.6 |
| ZMROD1 GRMZM2G087896 | NAPUS_3A | 43.8 |
| ZMROD1 GRMZM2G087896 | NAPUS_3C | 44.4 |
| ZMROD1 GRMZM2G087896 | NAPUS_5A | 45.6 |
| ZMROD1 GRMZM2G087896 | NAPUS_5C | 44.8 |
| ZMROD1 GRMZM2G087896 | OSROD1_ SEQIDNO 11 | 68.9 |
| ZMROD1 GRMZM2G087896 | RCPDCT | 48.2 |
| ZMROD1 GRMZM2G087896 | RCROD1 SEQIDNO9 | 48.2 |
| ZMROD1 GRMZM2G087896 | ZMROD1 GRMZM2G015040 | 83.9 |
| ZMROD1 GRMZM2G087896 | ZMROD1 GRMZM2G087896 | 100 |

TABLE 7

| Average fatty acid composition (%) in different lipid classes from immature seeds | | | | | | | | | | | | |
|---|---|---|---|---|---|---|---|---|---|---|---|---|
| | 16:0 | 18:0 | 18:1 | 18:2 | GLA | 18:3 | SDA | 20:0 | 20:1 | 20:2 | DGLA | 22:1 |
| TAG | | | | | | | | | | | | |
| 3C | 10.3 | 5.0 | 18.7 | 15.2 | 17.3 | 7.2 | 2.3 | 2.4 | 15.2 | 1.1 | 3.6 | 1.3 |
| 5C | 10.7 | 5.5 | 26.2 | 19.2 | 12.5 | 7.5 | 1.1 | 2.1 | 11.9 | 0.8 | 1.0 | 1.1 |
| CK mutant | 10.6 | 4.9 | 36.8 | 17.6 | 1.7 | 6.7 | 0.1 | 2.0 | 15.0 | 0.5 | 1.8 | 1.5 |
| CK WT | 9.4 | 4.7 | 19.5 | 22.0 | 11.6 | 7.9 | 1.6 | 2.2 | 16.6 | 1.2 | 1.2 | 1.4 |
| WT | 8.8 | 4.4 | 22.2 | 31.2 | 0.0 | 11.3 | 0.0 | 2.2 | 16.6 | 1.5 | 0.0 | 1.6 |
| Rod mut | 10.2 | 4.5 | 31.4 | 20.9 | 0.0 | 10.2 | 0.0 | 2.6 | 16.7 | 0.7 | 0.0 | 2.2 |
| PC | | | | | | | | | | | | |
| 3C | 19.0 | 2.8 | 6.1 | 37.5 | 6.8 | 23.0 | 1.1 | 0.1 | 1.2 | 1.0 | 1.0 | 0.2 |
| 5C | 21.3 | 2.5 | 2.9 | 46.1 | 3.3 | 21.8 | 0.4 | 0.0 | 0.3 | 0.9 | 0.0 | 0.1 |
| CK mutant | 18.1 | 1.8 | 3.4 | 46.7 | 2.7 | 25.3 | 0.3 | 0.0 | 0.2 | 0.9 | 0.1 | 0.2 |
| CK WT | 27.3 | 3.6 | 4.0 | 40.0 | 3.9 | 18.3 | 0.5 | 0.0 | 0.7 | 0.9 | 0.2 | 0.0 |
| WT | 22.6 | 2.6 | 5.8 | 45.9 | 0.0 | 20.6 | 0.0 | 0.0 | 1.1 | 0.9 | 0.0 | 0.0 |
| Rod mut | 18.2 | 2.0 | 2.8 | 48.2 | 0.0 | 27.5 | 0.0 | 0.0 | 0.0 | 0.9 | 0.0 | 0.0 |
| DAG | | | | | | | | | | | | |
| 3C | 21.8 | 16.6 | 12.2 | 10.5 | 8.7 | 7.5 | 0.0 | 4.7 | 9.9 | 0.0 | 2.7 | 5.3 |
| 5C | 24.6 | 14.4 | 11.4 | 13.7 | 7.1 | 6.8 | 0.0 | 6.6 | 6.0 | 0.0 | 0.0 | 9.2 |
| CK mutant | 19.9 | 10.3 | 32.9 | 16.2 | 1.1 | 5.0 | 0.0 | 3.2 | 10.4 | 0.0 | 0.0 | 0.8 |
| CK WT | 17.9 | 5.2 | 13.6 | 35.6 | 7.8 | 10.9 | 0.0 | 1.7 | 5.1 | 0.0 | 0.8 | 1.4 |
| WT | 17.1 | 7.2 | 24.4 | 34.1 | 0.0 | 5.9 | 0.0 | 2.4 | 6.7 | 0.0 | 0.0 | 2.2 |
| Rod mut | 18.2 | 9.7 | 25.1 | 19.2 | 0.0 | 7.3 | 0.0 | 5.2 | 9.9 | 0.0 | 0.0 | 5.4 |

REFERENCES

Philip D. Bates, Abdelhak Fatihi, Anna R. Snapp, Anders S. Carlsson, John Browse, Chaofu Lu (2012) Acyl Editing and Headgroup Exchange Are the Major Mechanisms That Direct Polyunsaturated Fatty Acid Flux into Triacylglycerols. Plant Physiology 160 (3), 1530-1539

Clough S J, Bent A F. Floral dip: a simplified method forAgrobacterium-mediated transformation of *Arabidopsis thaliana*. The plant journal. 1998 Dec. 1; 16 (6): 735-43.

Genet T, Labuschagne M T, Hugo A. Capillary gas chromatography analysis of Ethiopian mustard to determine variability of fatty acid composition. Journal of the Science of Food and Agriculture. 2004 Oct. 1; 84 (13): 1663-70.

Iskandarov U, Kim H J, Cahoon E B. *Camelina*: an emerging oilseed platform for advanced biofuels and bio-based materials. InPlants and BioEnergy 2014 (pp. 131-140). Springer New York Lager I, Yilmaz J L, Zhou X R, Jasieniecka K, Kazachkov M, Wang P, Zou J, Weselake R, Smith M A, Bayon S, Dyer J M. Plant acyl-CoA: lysophosphatidylcholine acyltransferases (LPCATs) have different specificities in their forward and reverse reactions. Journal of Biological Chemistry. 2013 Dec. 27; 288 (52): 36902-14.

Lu C, Xin Z, Ren Z, Miquel M. An enzyme regulating triacylglycerol composition is encoded by the ROD1 gene of *Arabidopsis*. Proceedings of the National Academy of Sciences. 2009 Nov. 3; 106 (44): 18837-42.

Liu J W, Huang Y S, DeMichele S, Bergana M, E Jr Bobik, Hastilow C, Chuang L T, Mukerji P, Knutzon D (2001) Evaluation of the seed oils from a canola plant genetically transformed to produce high levels of gamma-linolenic acid. In: Huang Y S, Ziboh V A (eds) Gamma-linolenic acid: recent advances in biotechnology and clinical applications. AOCS Press, Champaign, IL, pp 61-71

Petrie, J. R., Shrestha, P., Zhou, X. R., Mansour, M. P., Li, Q., Belide, S., Nichols, P. D. and Singh, S. P. (2012) Metabolic engineering of seeds with fish oil-like levels of DHA. PLOS ONE, 7, e49165.

Ruiz-Lopez N, Haslam R P, Napier J A, Sayanova O. Successful high-level accumulation of fish oil omega-3 long-chain polyunsaturated fatty acids in a transgenic oilseed crop. The Plant Journal. 2014 Jan. 1; 77 (2): 198-208.

Singer S D, Weselake R J, Rahman H. Development and characterization of low α-linolenic acid *Brassica oleracea* lines bearing a novel mutation in a 'class a' FATTY ACID DESATURASE 3 gene. BMC genetics. 2014 Aug. 29; 15 (1): 94.

Ursin V M. Modification of plant lipids for human health: development of functional land-based omega-3 fatty acids. The Journal of nutrition. 2003 Dec. 1; 133 (12): 4271-4.

Venegas-Caleron, Monica; Sayanova, Olga; Napier, Johnathan A. (2010) An alternative to fish oils: Metabolic engineering of oil-seed crops to produce omega-3 long chain polyunsaturated fatty acids. Progress In Lipid Research 49 (2), 108-119.

Aruna D Wickramarathna, Rodrigo M P Siloto, Elzbieta Mietkiewska, Stacy D Singer, Xue Pan, Randall J Weselake (2015) Heterologous expression of flax PHOSPHOLIPID:DIACYLGLYCEROL CHOLINEPHOSPHOTRANSFERASE (PDCT) increases polyunsaturated fatty acid content in yeast and *Arabidopsis* seeds. BMC Biotechnology 15 article 63

Wu G, Truksa M, Datla N, Vrinten P, Bauer J, Zank T, Cirpus P, Heinz E, Qiu X. Stepwise engineering to produce high yields of very long-chain polyunsaturated fatty acids in plants. Nature biotechnology. 2005 August; 23 (8): 1013

The invention claimed is:

1. A method for increasing the delta-6 elongase conversion efficiency in an oil crop plant of a *Brassica* species that produces very long chain polyunsaturated fatty acids (vlcPUFAs) and expresses a delta-6 elongase, comprising:

providing an oil crop plant of a *Brassica* species that expresses a delta-6 elongase and a delta-6 desaturase and that has decreased activity, compared to a control plant, of one or more phosphotidylcholine:diacylglycerol cholinephosphotransferase (PDCT) selected from the group consisting of:

(a) PDCT3 and/or PDCT5 having at least 80% sequence identity with SEQ ID NO: 18, 20, 22, 24, 26, 28, 30, 32, 50, 52, 54, 56, 58, and/or 60;

(b) PDCT3 and/or PDCT5 encoded by a polynucleotide having at least 80% sequence identity with SEQ ID NO: 17, 19, 21, 23, 27, 29, 31, 49, 51, 53, 55, 57 and/or 59; and (c) PDCT3 and/or PDCT5 encoded by a polynucleotide that differs from SEQ ID NO: 17, 19, 21, 23, 27, 29, 31, 49, 51, 53, 55, 57 and/or 59 due to the degeneracy of the genetic code wherein the plant produces docosahexaenoic acid (DHA), eicosapentaenoic acid (EPA), and docosapentaenoic acid (DPA).

2. The method of claim 1, wherein the plant comprises an oil that is characterized by an i. Increased ETA level ii. Reduced ALA level, iii. Reduced GLA level iv. Reduced SDA level, v. The level of the 18:2 fatty acid fraction in % (w/w) in the triacylglycerol (TAG) composition is higher than the 18:2 fatty acid level in % (w/w) in the diacylglyerol (DAG) fraction, vi. The level of the 20:0 fatty acid in % (w/w) in the diacylglyerol fraction is higher than the 20:0 fatty acid level in % (w/w) in the triacylglycerol fraction vii. The level of the 22:1 fatty acid in % (w/w) in the diacylglyerol (DAG) fraction is higher than the 22:1 level in % (w/w) in the triacylglycerol fraction and/or viii. Reduced 18:1 fatty acid level;

compared to a control, and, optionally, comprising the further step of isolating the oil from the plant or a part thereof, the plant cell, and/or the plant seed.

3. The method of claim 1, wherein the plant is a *B. napus* plant, and wherein the plant has decreased activity of one or more PDCT selected from the group consisting of:

(a) a PDCT3 having at least 90% sequence identity with SEQ ID NO: 18 or 22 or 24;

(b) a PDCT5 having at least 90% sequence identity with SEQ ID NO: 20 or 26 or 28;

(c) a PDCT3 encoded by a polynucleotide having at least 90% sequence identity with SEQ ID NO: 17 or 21 or 23;

(d) a PDCT5 encoded by a polynucleotide having at least 90% sequence identity with SEQ ID NO: 19 or 25 or 27;

(e) a PDCT3 encoded by a polynucleotide that differs from SEQ ID NO: 17 or 21 or 23 due to the degeneracy of the genetic code; and (f) a PDCT5 encoded by a polynucleotide that differs from SEQ ID NO: 19 or 25 or 27 due to the degeneracy of the genetic code.

4. The method of claim 1, wherein the plant is a *B. carinata* plant, and wherein the plant has decreased activity of one or more PDCT selected from the group consisting of:

(e) a PDCT3 having at least 90% sequence identity with SEQ ID NO: 18 or 22 or 24;

(f) a PDCT5 having at least 90% sequence identity with SEQ ID NO: 20 or 26 or 28;

(g) a PDCT3 encoded by a polynucleotide having at least 90% sequence identity with SEQ ID NO: 17 or 21 or 23;

(h) a PDCT5 encoded by a polynucleotide having at least 90% sequence identity with SEQ ID NO: 19 or 25 or 27;

(i) a PDCT3 encoded by a polynucleotide that differs from SEQ ID NO: 17 or 21 or 23 due to the degeneracy of the genetic code; and (j) a PDCT5 encoded by a polynucleotide that differs from SEQ ID NO: 19 or 25 or 27 due to the degeneracy of the genetic code.

5. The method of claim 1, wherein the plant is a *B. juncea* plant, and wherein the plant has decreased activity of one or more PDCT selected from the group consisting of:

(a) PDCT3 and/or PDCT5 having at least 80% sequence identity with SEQ ID NO: 18, 20, 22, 24, 26, 28, 30, 32, 50, 52, 54, 56, 58, and/or 60;

(b) PDCT3 and/or PDCT5 encoded by a polynucleotide having at least 80% sequence identity with SEQ ID NO: 17, 19, 21, 23, 27, 29, 31, 49, 51, 53, 55, 57 and/or 59; and (c) PDCT3 and/or PDCT5 encoded by a polynucleotide that differs from SEQ ID NO: 17, 19, 21, 23, 27, 29, 31, 49, 51, 53, 55, 57 and/or 59 due to the degeneracy of the genetic code.

* * * * *